United States Patent
Ono et al.

(10) Patent No.: US 8,022,091 B2
(45) Date of Patent: Sep. 20, 2011

(54) TRIAZOLE DERIVATIVE

(75) Inventors: Naoya Ono, Toshima-ku (JP); Tetsuo Takayama, Toshima-ku (JP); Fumiyasu Shiozawa, Toshima-ku (JP); Hironori Katakai, Toshima-ku (JP); Tetsuya Yabuuchi, Toshima-ku (JP); Tomomi Ota, Toshima-ku (JP); Makoto Yagi, Toshima-ku (JP); Masakazu Sato, Toshima-ku (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/278,054

(22) PCT Filed: Feb. 5, 2007

(86) PCT No.: PCT/JP2007/051951
§ 371 (c)(1),
(2), (4) Date: Aug. 1, 2008

(87) PCT Pub. No.: WO2007/089018
PCT Pub. Date: Aug. 9, 2007

(65) Prior Publication Data
US 2010/0041655 A1 Feb. 18, 2010

(30) Foreign Application Priority Data
Feb. 3, 2006 (JP) .................................. 2006-027799

(51) Int. Cl.
*A01N 43/64* (2006.01)
*A61K 31/41* (2006.01)
*C07D 249/12* (2006.01)

(52) U.S. Cl. ..................................... 514/384; 548/264.2
(58) Field of Classification Search ............... 548/264.2; 514/384
See application file for complete search history.

(56) References Cited

U.S. PATENT DOCUMENTS

| | | | |
|---|---|---|---|
| 5,516,783 A | 5/1996 | Whittaker et al. | |
| 5,910,506 A | 6/1999 | Sugimoto et al. | |
| 2003/0229125 A1 | 12/2003 | Haaf et al. | |
| 2005/0124654 A1 | 6/2005 | Groneberg et al. | |
| 2007/0232682 A1 | 10/2007 | Beard et al. | |
| 2009/0131438 A1 | 5/2009 | Ono et al. | |
| 2009/0182144 A1 | 7/2009 | Ono et al. | |

FOREIGN PATENT DOCUMENTS

| | | |
|---|---|---|
| EP | 0786455 A1 | 7/1997 |
| EP | 786455 A1 | 7/1997 |
| EP | 1 798 226 A1 | 6/2007 |
| JP | 5-194412 A | 8/1993 |
| JP | 2002-212070 A | 7/2002 |
| JP | 2002-332278 A | 11/2002 |
| JP | 2003-137894 A | 5/2003 |
| JP | 2003137894 A | 5/2003 |
| JP | 2003/530388 A | 10/2003 |
| JP | 2004/532276 A | 10/2004 |
| WO | 96/10019 A1 | 4/1996 |
| WO | 01/77089 A1 | 10/2001 |
| WO | 02/18395 A1 | 3/2002 |
| WO | 0218395 A1 | 3/2002 |
| WO | 02/100853 A1 | 12/2002 |
| WO | 03/000679 A2 | 1/2003 |
| WO | 03/073986 A2 | 9/2003 |
| WO | 03/074008 A2 | 9/2003 |
| WO | 03073986 A2 | 9/2003 |
| WO | 03074008 A2 | 9/2003 |
| WO | 03/097028 A1 | 11/2003 |
| WO | 03097028 A1 | 11/2003 |
| WO | 03/105771 A2 | 12/2003 |
| WO | 2004/024673 A1 | 3/2004 |

(Continued)

OTHER PUBLICATIONS

Gehlen et. al., Justus Liebigs Annalen der Chemie, 1962, Paedagogischen Hochschule, vol. 651, English language STN Abstract.*
Brzozowski, Acta Poloniae Pharmaceutica, 1995, Polish Pharmaceutical Society, vol. 52, No. 2, pp. 91-101.*
Van Brocklyn et. al., Cancer Letters, 2003, Elsevier, vol. 199, pp. 53-60.*
International Search Report dated Sep. 22, 2008, as issued in International Application No. PCT/JP2008/063851.

(Continued)

*Primary Examiner* — Sreeni Padmanabhan
*Assistant Examiner* — Sarah Pihonak
(74) *Attorney, Agent, or Firm* — Sughrue Mion, PLLC

(57) ABSTRACT

An object of the present invention is to provide a compound having an action of inhibiting binding between S1P and its receptor, Edg-1 (S1P$_1$), and is useful as a pharmaceutical compound. A compound or a pharmaceutically acceptable salt thereof, which compound is represented by the formula below

[Formula 1]

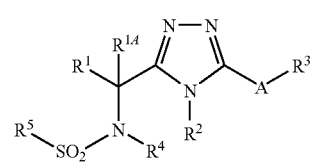

(where A represents an oxygen atom, a sulfur atom, a group represented by Formula —SO—, a group represented by Formula —SO$_2$—, or the like, $R^1$ represents a hydrogen atom, an alkyl group having 1-6 carbon atoms, or the like, $R^{1A}$ represents a hydrogen atom or the like, $R^2$ represents an alkyl group having 1-6 carbon atoms, a cycloalkyl group having 3-6 carbon atoms, or the like, $R^3$ represents an aryl group, $R^4$ represents a hydrogen atom or an alkyl group having 1-6 carbon atoms and optionally substituted with a carboxyl group, and $R^5$ represents an alkyl group having 1-10 carbon atoms, a cycloalkyl group having 3-8 carbon atoms, an aryl group which is optionally substituted, or the like).

14 Claims, No Drawings

FOREIGN PATENT DOCUMENTS

| | | |
|---|---|---|
| WO | 2004/074257 A1 | 9/2004 |
| WO | 2004/089367 A1 | 10/2004 |
| WO | 2004/103279 A2 | 12/2004 |
| WO | 2005/123677 A1 | 12/2005 |
| WO | 2006/013948 A1 | 2/2006 |
| WO | 2006013948 A1 | 2/2006 |
| WO | 2006/097489 A1 | 9/2006 |
| WO | 2007/083089 A1 | 7/2007 |
| WO | 2007083089 A1 | 7/2007 |
| WO | 2007/091570 A1 | 8/2007 |
| WO | 2007/112322 A2 | 10/2007 |
| WO | 2007/122401 A1 | 11/2007 |
| WO | 2007/129019 A1 | 11/2007 |
| WO | 2007122401 A1 | 11/2007 |
| WO | 2007129019 A1 | 11/2007 |

OTHER PUBLICATIONS

J. Clemens, et al., "Synthesis of *Para*-Alkyl Aryl Amide Analogues of Sphingosine-1-phosphate: Discovery of Potent S1P Receptor Agonists", Bioorganic & Medicinal Chemistry Letters, vol. 13, pp. 3401-3404, 2003.

M. Sanna, et al., "Sphingosine 1-Phosphate (S1P) Receptor Subtypes S1P$_1$ and S1P$_3$, Respectively, Regulate Lymphocyte Recirculation and Heart Rate", The Journal of Biological Chemistry, vol. 279, No. 14, pp. 13839-13848, Apr. 2, 2004.

Von Heinz Gehlen, et al; Zur Kenntnis der 2-Amino-1,3,4-oxdiazole. X 3-Xlkoxy-1,2,4-Triazole Durch Alkoholyse von 2-Amino-1,3,4-Oxdiazolen; Liebigs Ann. Chem. 651, 137 (1962); pp. 137-141 (with an English translation).

M. Germana Sanna et al., "Sphingosine I-Phosphate (S1P) Receptor Subtypes S1P$_1$ and S1P$_3$, Respectively, Regulate Lymphocyte Recirculation and Heart Rate", The Journal of Biological Chemistry, vol. 279, No. 14, Issue of Apr. 2, pp. 13839-13848, 2004.

Jeremy J. Clemens et al., "Synthesis of *Para*-Alkyl Aryl Amide Analogues of Sphingosine-I-phosphate: Discovery of Potent S1P Receptor Agonists", Bioorganic & Medicinal Chemistry Letters, 13 (2003) 3401-3404.

Guofeng Jia, et al., "Syntheses of Some New 4-Amino-5-(N-methyl-arylsulfonamido)methyl-1,2,4-triazole-3-thiones and Their Derivatives", Heteroatom Chemistry, vol. 7, No. 4, pp. 263-267, 1996.

H. Gehlen, et al., "2-Amino-1, 3,4-oxidiazoles. VII. Formation of 2-amino-5-aminoalkyl-1, 3,4-oxidiazoles and their conversion into 1,2,4-triazoles and triazolones", Justus Liebigs Annalen der Chemi. vol. 651, pp. 128-132, Sep. 23, 1962 with Full English language translation.

H. Gehlen, et al., "2-Amino-1, 3,4-oxidiazoles. VIII. Formation of 2-amino-5-aminoalkyl-1,3,4-oxidiazoles and their conversion into 1,2,4-triazoles and triazolones", Chemical Abstracts, Database Accession No. 57:16892, Justus Liebigs Annalen der Chemie, vol. 651, pp. 128-132, 1962.

Supplemental European Search Report dated Oct. 13, 2009, issued in European Application No. 07708069.5.

H. Gehlen, et al., "2-Amino-1, 3,4-oxidiazoles. VII. Formation of 2-amino-5-aminoalkyl-1, 3,4-oxidiazoles and their conversion into 1,2,4-triazoles and triazolones", Justus Liebigs Annalen der Chemi. vol. 651, pp. 128-132, Sep. 23, 1961, with Full English language translation.

Gehlen, H., et al., 2-Amino-1,3,4-oxadiazoles. IX. Oxidation of Aldehyde Semicarbazones to 2-amino-1, 3,4-oxadiazoles and Their Conversion Into 1-acylsemicarbazides, Justus Liebigs Annalen Der Chemi, vol. 651, pp. 133-136, 1962.

Extended European Search Report issued Nov. 23, 2010 from the European Patent Office in a counterpart European Application No. 07713881.6 of the co-pending U.S. Appl. No. 12/278,477.

Hla, Timothy, "Physiological and Pathological Actions of Sphingosine 1-Phosphate", 15 Sem. Cell & Dev. Bio. 513 (2004).

\* cited by examiner

TRIAZOLE DERIVATIVE

TECHNICAL FIELD

The present invention relates to novel triazole derivatives which have an inhibitory effect on the binding between sphingosine-1-phosphate having various physiological actions and its receptor Edg-1 (Endothelial differentiation gene receptor type-1, S1P1). The present invention also relates to pharmaceutical preparations comprising these compounds as active ingredients, and synthetic intermediates for these compounds.

BACKGROUND ART

Sphingosine-1-phosphate (hereinafter referred to as "S1P") is a physiologically active lipid which is generated when sphingolipids (typified by sphingomyelin) are metabolized in cells. S1P is known to have a wide variety of actions such as cell differentiation induction, cell growth stimulation, cell motility inhibition and apoptosis inhibition, and is also known to show physiological actions such as angiogenesis, bradycardia induction, inflammatory cell activation and platelet activation (Non-patent Document 1).

As SIP receptors, the following 5 subtypes have been reported: Edg-1(S1P1), Edg-3(S1P3), Edg-5(S1P2), Edg-6 (S1P4) and Edg-8(S1P5) (Non-patent Document 2).

Among these subtypes, Edg-1(S1P1) is highly expressed in immunocytes (e.g., T cells, dendritic cells) and vascular endothelial cells, suggesting that Edg-1(S1P1) contributes deeply to S1P-stimulated T cell migration (Non-patent Document 3), mast cell migration (Non-patent Document 4), T and B cell egress from lymphoid organs (Non-patent Document 5) and angiogenesis (Non-patent Document 6), and is involved in autoimmune diseases such as Crohn's disease, irritable colitis, Sjogren's syndrome, multiple sclerosis and systemic lupus erythematosus, as well as other diseases such as rheumatoid arthritis, asthma, atopic dermatitis, rejection after organ transplantation, cancer, retinopathy, psoriasis, osteoarthritis, age-related macular degeneration, etc.

Thus, ligands for Edg-1(S1P1) would be effective for treatment or prevention of these diseases.

Edg-1(S1P1) ligands previously known include certain types of thiophene derivatives (Non-patent Document 7), phosphoric acid derivatives (Patent Documents 1 and 2, Non-patent Documents 8 and 9) and thiazolidine derivatives (Patent Document 3), carboxylic acid derivatives (Patent Documents 4, 5, 6 and 8, Non-patent Documents 10 and 11), amino group-containing derivatives (Patent Document 7), and pyrrole derivatives (Patent Document 9).

Patent Document 1: WO2002-18395
Patent Document 2: JP 2003-137894 A
Patent Document 3: JP 2002-332278 A
Patent Document 4: WO2002-092068
Patent Document 5: WO2003-105771
Patent Document 6: WO2004-058149
Patent Document 7: WO2004-103279
Patent Document 8: WO2005-1058848
Patent Document 9: WO2005-123677
Non-patent Document 1: J Biol. Chem. 2004, 279: 20555, FASEB J 2002, 16: 625, Proceedings of the Japanese Society for Immunology 2003, 33: 2-J-W30-20-P
Non-patent Document 2: Pharmacol Res 2003, 47: 401
Non-patent Document 3: FASEB J 2002, 16:1874
Non-patent Document 4: J Exp Med 2004, 199: 959
Non-patent Document 5: Nature 2004, 427: 355
Non-patent Document 6: J Clin Invest 2000, 106: 951, Biocchim Biophys Acta 2002, 1582: 222
Non-patent Document 7: J Biol Chem 2004, 279: 13839
Non-patent Document 8: Bioorg Med Chem Lett 2003, 13: 3401
Non-patent Document 9: J Med. Chem. 2004, 47: 6662
Non-patent Document 10: J Med. Chem. 2005, 48: 6169
Non-patent Document 11: J Biol. Chem. 2005; 280: 9833

DISCLOSURE OF THE INVENTION

Problems to be Solved by the Invention

The present invention has as an object to provide a compound with a new skeletal structure, which compound has an action of inhibiting binding between S1P and its receptor Edg-1 ($S1P_1$) and is useful as a pharmaceutical product.

Means for Solving the Problems

The inventors of the present invention have diligently studied in an attempt to find ligand compounds for Edg-1 ($S1P_1$). As a result, they find that the object is attained with a triazole derivative of Formula (I) below or a pharmaceutically acceptable salt thereof (a feature is that $R^3$ in the formula is an optionally substituted aryl group). This finding has led to the accomplishment of the present invention. The triazole derivative of Formula (I) below with this feature is a completely new compound. Although compounds having an alkyl group corresponding to $R^3$ of Formula (I) are commercially available from Bionet as reagents, they differ in structure from that of the compound of the subject application, and pharmaceutical use of the compounds of Bionet has not been known at all.

The following are embodiments of the triazole derivatives of Formula (I) and compounds of Formula (II), which are intermediates of the triazole derivatives (hereinafter, all of them will be referred to as "compounds of the present invention").

1. A compound represented by Formula (I)

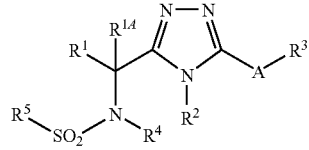

[Formula 1]

or a pharmaceutically acceptable salt thereof, wherein
A represents:
  an oxygen atom,
  a sulfur atom,
  a group represented by Formula —SO—,
  a group represented by Formula —$SO_2$—,
  a group represented by Formula —$CH_2$—, or
  a group represented by Formula —$NR^6$—, wherein $R^6$ represents a hydrogen atom or an alkyl group having from 1 to 6 carbon atoms;
$R^1$ represents;
  a hydrogen atom,
  an alkyl group having from 1 to 6 carbon atoms and optionally substituted with a substituent(s) selected from the group consisting of:
    a hydroxyl group,
    a halogen atom, an alkoxy group having from 1 to 6 carbon atoms, said alkoxy group optionally substituted with a phenyl group, and a phenyl group, optionally substituted with a substituent(s) selected from the group consisting of a halogen atom and an alkyl group having from 1 to 6 carbon atoms, a cycloalkyl group having from 3 to 8 carbon atoms, an alkenyl group having from 2 to 8 carbon atoms, an alkynyl group having from 2 to 8 carbon atoms, or a phenyl group;

$R^{1A}$ represents:

a hydrogen atom or an alkyl group having from 1 to 6 carbon atoms;

$R^1$ and $R^{1A}$ optionally form, together with a carbon atom to which said $R^1$ and $R^{1A}$ are attached, a cycloalkyl group having from 3 to 6 carbon atoms;

$R^2$ represents:

a hydrogen atom, an alkyl group having from 1 to 6 carbon atoms, an alkenyl group having from 2 to 8 carbon atoms, an alkynyl group having from 2 to 8 carbon atoms, or a cycloalkyl group having from 3 to 6 carbon atoms;

$R^3$ represents an optionally substituted aryl group;

$R^4$ represents:

a hydrogen atom or an alkyl group having from 1 to 6 carbon atoms and optionally substituted with a carboxyl group;

$R^5$ represents:

(i) an alkyl group having from 1 to 10 carbon atoms, (ii) an alkyl group having from 1 to 10 carbon atoms and substituted with 1 to 2 substituents selected from the group consisting of:

a cycloalkyl group having from 3 to 8 carbon atoms, a pyridyl group, and a phenyl group, a phenoxy group, and a naphthyl group, each optionally substituted with 1 to 2 substituents selected from the group consisting of a halogen atom and an alkoxy group having from 1 to 6 carbon atoms, (iii) a cycloalkyl group having from 3 to 8 carbon atoms, (iv) an alkenyl group having from 2 to 8 carbon atoms, (v) an alkenyl group having from 2 to 8 carbon atoms and substituted with a phenyl group, (vi) an alkynyl group having from 2 to 8 carbon atoms, (vii) an alkynyl group having from 2 to 8 carbon atoms and substituted with a phenyl group, or (viii) an optionally substituted aryl group.

2. The compound of Embodiment 1, or a pharmaceutically acceptable salt thereof, wherein, in Formula (I):

$R^1$ represents:

a hydrogen atom, an alkyl group having from 1 to 6 carbon atoms, an alkyl group having from 1 to 6 carbon atoms and substituted with a phenyl group, a cycloalkyl group having from 3 to 8 carbon atoms, an alkenyl group having from 2 to 8 carbon atoms, an alkynyl group having from 2 to 8 carbon atoms, or a phenyl group;

$R^{1A}$ represents a hydrogen atom;

$R^2$ represents:

an alkyl group having from 1 to 6 carbon atoms, an alkenyl group having from 2 to 8 carbon atoms, an alkynyl group having from 2 to 8 carbon atoms, or a cycloalkyl group having from 3 to 6 carbon atoms;

$R^4$ represents:

a hydrogen atom, or an alkyl group having from 1 to 6 carbon atoms;

$R^5$ represents:

(i) an alkyl group having from 1 to 10 carbon atoms, (ii) an alkyl group having from 1 to 10 carbon atoms and substituted with 1 to 2 substituents selected from the group consisting of:

a cycloalkyl group having from 3 to 8 carbon atoms, a phenyl group, a naphthyl group, a pyridyl group, and a phenyl group substituted with 1 to 2 substituents selected from the group consisting of a halogen atom and an alkoxy group having from 1 to 6 carbon atoms, (iii) a cycloalkyl group having from 3 to 8 carbon atoms, (iv) an alkenyl group having from 2 to 8 carbon atoms, (v) an alkenyl group having from 2 to 8 carbon atoms and substituted with a phenyl group, (vi) an alkynyl group having from 2 to 8 carbon atoms, (vii) an alkynyl group having from 2 to 8 carbon atoms and substituted with a phenyl group, or (viii) an optionally substituted aryl group.

3. The compound of Embodiment 1 or 2, or a pharmaceutically acceptable salt thereof, wherein A is an oxygen atom or a group represented by Formula —$NR^6$—.

4. The compound of Embodiment 1 or 2, or a pharmaceutically acceptable salt thereof, wherein A is an oxygen atom.

5. The compound of Embodiment 1 or 2, or a pharmaceutically acceptable salt thereof, wherein A is a group represented by Formula —NH—.

6. The compound of any one of Embodiments 1 and 3-5, or a pharmaceutically acceptable salt thereof, wherein:

$R^1$ represents an alkyl group having from 1 to 6 carbon atoms and optionally substituted with a substituent(s) selected from the group consisting of:

a hydroxyl group, a halogen atom, an alkoxy group having from 1 to 6 carbon atoms, said alkoxy group optionally substituted with a phenyl group; and a phenyl group, optionally substituted with a substituent(s) selected from the group consisting of a halogen atom and an alkyl group having from 1 to 6 carbon atoms;

$R^{1A}$ represents:

a hydrogen atom; or an alkyl group having from 1 to 6 carbon atoms; and $R^1$ and $R^{1A}$ optionally form, together with a carbon atom to which said $R^1$ and $R^{1A}$ are attached, a cycloalkyl group having from 3 to 6 carbon atoms.

7. The compound of any one of Embodiments 1 and 3-5, or a pharmaceutically acceptable salt thereof, wherein:

$R^1$ is:

an alkyl group having from 1 to 6 carbon atoms and optionally substituted with a halogen atom(s), or a benzyl group optionally substituted with a substituent(s) selected from the group consisting of a halogen atom and an alkyl group having from 1 to 6 carbon atoms: and $R^{1A}$ is a hydrogen atom.

8. The compound of any one of Embodiments 1-5, or a pharmaceutically acceptable salt thereof, wherein $R^1$ is a methyl group or an ethyl group, and $R^{1A}$ is a hydrogen atom.

9. The compound of any one of Embodiments 1-8, or a pharmaceutically acceptable salt thereof, wherein $R^4$ is a hydrogen atom.

10. The compound of any one of Embodiments 1-9, or a pharmaceutically acceptable salt thereof, wherein $R^2$ is an alkyl group having from 1 to 6 carbon atoms, or a cycloalkyl group having from 3 to 6 carbon atoms.

11. The compound of any one of Embodiments 1-9, or a pharmaceutically acceptable salt thereof, wherein $R^2$ is an ethyl group or a cyclopropyl group.

12. The compound of any one of Embodiments 1 and 3-11, or a pharmaceutically acceptable salt thereof, wherein $R^5$ is:
(i) an alkyl group having from 1 to 10 carbon atoms,
(ii) an alkyl group having from 1 to 10 carbon atoms and substituted with 1 to 2 substituents selected from the group consisting of:
a cycloalkyl group having from 3 to 8 carbon atoms,
a pyridyl group, and
a phenyl group, a phenoxy group, and a naphthyl group, each optionally substituted with 1 to 2 substituents selected from the group consisting of a halogen atom and an alkoxy group having from 1 to 6 carbon atoms;
(iii) an alkenyl group having from 2 to 8 carbon atoms and optionally substituted with a phenyl group, or
(iv) a phenyl group, a naphthyl group, a thienyl group, a pyrrolyl group, a pyrazolyl group, a pyridyl group, a furanyl group, a benzothienyl group, an isoquinolinyl, an isoxazolyl group, a thiazolyl group, a benzothiadiazolyl group, a benzoxadiazolyl group, a dihydrobenzodioxepinyl group, a dihydrobenzodioxynyl group, a benzodioxolyl group, a dihydrobenzofuranyl group, an indanyl group, an uracil group, a coumaryl group, a chromanyl group, a dihydroindolyl group, a tetrahydronaphthyl group, or a tetrahydroisoquinolinyl group, each optionally substituted with 1 to 5 substituents selected from the group consisting of:
an alkyl group having from 1 to 6 carbon atoms and optionally substituted with a fluorine atom(s),
an alkenyl group having from 2 to 8 carbon atoms,
a halogen atom,
an alkoxy group having from 1 to 6 carbon atoms and optionally substituted with a fluorine atom(s),
a pyrazolyl group, an oxazolyl group, an isoxazolyl group, a thiadiazolyl group, and a pyrimidinyl group, each optionally substituted with a substituent(s) selected from Group X consisting of a methyl group, a trifluoromethyl group, a halogen atom, and a methylsulfanyl group,
an alkylthio group having from 1 to 6 carbon atoms,
an alkylsulfonyl group having from 1 to 6 carbon atoms,
a benzenesulfonyl group,
a morpholinosulfonyl group,
a morpholinocarbonylamino group,
an aminosulfonyl group,
an alkoxycarbonyl group having from 2 to 10 carbon atoms,
a morpholino group optionally substituted with an alkyl group(s) having from 1 to 6 carbon atoms
a phenyl group optionally substituted with an alkoxy group(s) having from 1 to 6 carbon atoms,
a phenoxy group,
a pyridinecarbonyl group,
a pyridineoxy group,
a cyano group,
an alkanoyl group having from 2 to 7 carbon atoms and optionally substituted with a fluorine atom(s), and
an alkanoylamino group having from 2 to 7 carbon atoms.
13. The compound of any one of Embodiments 1-11, or a pharmaceutically acceptable salt thereof, wherein $R^5$ is:
an alkyl group having from 1 to 10 carbon atoms and substituted with a cycloalkyl group having from 3 to 8 carbon atoms,
an alkyl group having from 1 to 10 carbon atoms and substituted with a naphthyl group,
an alkenyl group having from 2 to 8 carbon atoms and substituted with a phenyl group,
a phenyl group or a naphthyl group, each optionally substituted with 1 to 5 substituents selected from the group consisting of:
an alkyl group having from 1 to 6 carbon atoms;
a halogen atom,
an alkoxy group having from 1 to 6 carbon atoms;
a trifluoromethoxy group,
a difluoromethoxy group,
a trifluoromethyl group,
an alkenyl group having from 1 to 6 carbon atoms,
an alkylsulfonyl group having from 1 to 6 carbon atoms,
an alkanoyl group having from 2 to 7 carbon atoms,
an alkoxycarbonyl group having from 2 to 7 carbon atoms, and
a cyano group,
a pyrrolyl group optionally substituted with a substituent(s) selected from the group consisting of an alkyl group having from 1 to 6 carbon atoms and a methoxycarbonyl group;
a furanyl group optionally selected from a substituent(s) selected from the group consisting of an alkyl group having from 1 to 6 carbon atoms, a trifluoromethyl group, and a halogen atom;
a thienyl group optionally substituted with a substituent (s) selected from the group consisting of an alkyl group having from 1 to 6 carbon atoms, a trifluoromethyl group, a thiadiazolyl group, an oxazolyl group, and a halogen atom; or
a benzothienyl group, a dihydrobenzodioxepinyl group, a benzodioxolyl group, a dihydrobenzodioxynyl group, a dihydrobenzofuranyl group, a tetrahydronaphthyl group, an indanyl group, a thiadiazolyl group, a benzoxadiazolyl group, or a benzothiadiazolyl group, each optionally substituted with a substituent(s) selected from the group consisting of an alkyl group having from 1 to 6 carbon atoms and a halogen atom.
14. The compound of any one of Embodiments 1-11, or a pharmaceutically acceptable salt thereof, wherein $R^5$ is:
an alkyl group having from 1 to 6 carbon atoms and substituted with a naphthyl group,
an alkenyl group having from 2 to 6 carbon atoms and substituted with a phenyl group;
an unsubstituted phenyl group,
a phenyl group substituted with 1 to 5 substituents selected from the group consisting of a methyl group, a methoxy group, and a halogen atom,
a phenyl group substituted with 1 to 3 substituents selected from the group consisting of:
an alkyl group having from 1 to 6 carbon atoms,
a halogen atom,
a methoxy group,
a trifluoromethoxy group,
a difluoromethoxy group,
a trifluoromethyl group,
an alkenyl group having from 1 to 6 carbon atoms,
a methylsulfonyl group,
an acetyl group,
a methoxycarbonyl group, and
a cyano group,
said phenyl group substituted at either 3 or 4 position or both;
a naphthyl group optionally substituted with a substituent(s) selected from the group consisting of:
a halogen atom,
an alkyl group having from 1 to 6 carbon atoms,
a cyano group, and
an alkylsulfonyl group having from 1 to 6 carbon atoms, or
a benzothienyl group, a benzoxadiazolyl group, a benzodioxolyl group, a dihydrobenzodioxynyl group, a dihydrobenzofuranyl group, an indanyl group, or a benzothiadiazolyl group, each optionally substituted with a substituent(s) selected from the group consisting of an alkyl group having from 1 to 6 carbon atoms and a halogen atom.

15. The compound of any one of Embodiments 1-11, or a pharmaceutically acceptable salt thereof, wherein $R^5$ is:
   a phenyl group substituted at 3 and 4 positions each with a halogen atom, or
   a naphthyl group optionally substituted with a substituent(s) selected from the group consisting of a halogen atom, an alkyl group having from 1 to 6 carbon atoms, and a cyano group.

16. The compound of any one of Embodiments 1-15, or a pharmaceutically acceptable salt thereof, wherein $R^3$ is a phenyl group, a naphthyl group, a pyrazolyl group, a pyridyl group, an indolyl group, a benzothiazolyl group, a benzothiadiazolyl group, a pyrazolopyrimidinyl group, a quinolinyl group, an isoquinolinyl group, a benzothienyl group, or a dihydroquinolinonyl group, each optionally substituted with 1 to 3 substituents selected from the group consisting of the following substituents:
   an alkyl group having from 1 to 6 carbon atoms and optionally substituted with a fluorine atom(s),
   a cycloalkyl group having from 3 to 8 carbon atoms,
   a halogen atom,
   an alkoxy group having from 1 to 6 carbon atoms, said alkoxy group optionally substituted with a substituent(s) selected from the group consisting of a fluorine atom, a phenyl group, an amino group substituted with two alkyl groups each having from 1 to 4 carbon atoms, and a morpholino group;
   a phenoxy group,
   a phenyl group,
   a carboxyl group,
   an alkoxycarbonyl group having from 2 to 10 carbon atoms,
   a hydroxyl group,
   a monocylic saturated hydrocarbon group having from 2 to 7 carbon atoms and having a nitrogen atom(s) as a ring atom(s), said saturated hydrocarbon group optionally substituted with an alkyl group(s) having from 1 to 6 carbon atoms,
   a nitrogen-containing monocylic unsaturated hydrocarbon group,
   a morpholinyl group optionally substituted with an alkyl group(s) having from 1 to 6 carbon atoms,
   a piperazino group optionally substituted with a substituent(s) selected from the group consisting of:
      an alkyl group having from 1 to 6 carbon atoms, said alkyl group optionally substituted with an amino group optionally substituted with one or two alkyl groups each having from 1 to 6 carbon atoms, a morpholino group, a hydroxyl group, or an alkoxy group having from 1 to 6 carbon atoms,
      a formyl group,
      an alkanoyl group having from 2 to 7 carbon atoms,
      a carbamoyl group optionally substituted with one or two alkyl groups each having from 1 to 4 carbon atoms,
      an aminosulfonyl group optionally substituted with one or two alkyl groups each having from 1 to 6 carbon atoms, and
      an alkylsulfonyl group having from 1 to 6 carbon atoms, and
      Formula $-NR^7R^8$, wherein:
      $R^7$ and $R^8$ each represent:
      a hydrogen atom,
      an alkyl group having from 1 to 6 carbon atoms, said alkyl group optionally substituted with an amino group optionally substituted with one or two alkyl groups each having from 1 to 6 carbon atoms, a hydroxyl group, or an alkoxy group having from 1 to 6 carbon atoms,
   an alkanoyl group having from 1 to 6 carbon atoms,
   a carbamoyl group optionally substituted with one or two alkyl groups each having from 1 to 4 carbon atoms,
   a morpholinocarbonyl group,
   an aminosulfonyl group optionally substituted with one or two alkyl groups each having from 1 to 6 carbon atoms, or
   an alkylsulfonyl group having from 1 to 6 carbon atoms, or
   $R^7$ and $R^8$ optionally form, together with the nitrogen atom to which said $R^7$ and $R^8$ are attached, a 3- to 8-membered saturated hydrocarbon ring, said ring optionally substituted with a substituent(s) selected from the group consisting of a dimethylenedioxy group, an oxo group, and a hydroxyl group.

17. The compound of any one of Embodiments 1-15, or a pharmaceutically acceptable salt thereof, wherein $R^3$ is:
   a 2-naphthyl group, optionally substituted with a substituent(s) selected from the group consisting of a halogen atom and an alkyl group having from 1 to 6 carbon atoms,
   a 3-pyrazolyl group, optionally substituted with a substituent(s) selected from the group consisting of an alkyl group having from 1 to 6 carbon atoms, a trifluoromethyl group, and a halogen atom, or
   a 5-benzothiazolyl group, a 5-benzothiadiazolyl group, a 7-dihydroquinolinonyl group, a 7-isoquinolinyl group, a 7-quinolinyl group, a 3-pyridyl group, or an indolyl group, each optionally substituted with an alkyl group(s) having from 1 to 6 carbon atoms,
   an unsubstituted phenyl group, or
   a substituted phenyl group (A), (B), or (C) below:
   (A) a phenyl group substituted at 4 position with a substituent selected from the group consisting of:
      an alkyl group having from 1 to 6 carbon atoms,
      a cycloalkyl group having from 3 to 8 carbon atoms,
      an alkoxy group having from 1 to 6 carbon atoms, said alkoxy group optionally substituted with a substituent(s) selected from the group consisting of an amino group substituted with two alkyl groups each having from 1 to 4 carbon atoms, a morpholino group, and a phenyl group,
      a halogen atom,
      a trifluoromethoxy group,
      a phenoxy group,
      a phenyl group,
      a 1-pyrrolyl group, and
      $-NR^AR^B$, wherein each of $R^A$ and $R^B$ is an alkyl group having from 1 to 6 carbon atoms, or $R^A$ and $R^B$ optionally form, together with the nitrogen atom to which said $R^A$ and $R^B$ are attached, a 3- to 5-membered saturated hydrocarbon ring,
   wherein said phenyl group substituted at 4 position is further optionally substituted at 3 position with a substituent selected from the group consisting of an alkyl group having from 1 to 6 carbon atoms, a halogen atom, and an alkoxy group having from 1 to 6 carbon atoms;
   (B) a phenyl group substituted at 3 position with a substituent selected from the group consisting of:
      a hydroxyl group,
      an alkyl group having from 1 to 6 carbon atoms, and
      an alkoxy group having from 1 to 6 carbon atoms, said alkoxy group optionally substituted with a substituent(s) selected from the group consisting of an amino group substituted with two alkyl groups each having from 1 to 4 carbon atoms, a morpholino group, and a phenyl group, wherein said phenyl group substituted at 3 position is further optionally substituted with one or two alkyl groups each having from 1 to 6 carbon atoms, or is further optionally substituted at 4 position with a halogen atom; and (C) a phenyl group substituted at 3 position with a substituent selected from the group consisting of nitrogen-containing groups (i)-(v) below, said phenyl group further optionally substituted at 4 position with a halogen atom:
  (i) a monocylic saturated hydrocarbon group having from 2 to 7 carbon atoms and having a nitrogen atom(s) as a ring atom(s), said saturated hydrocarbon group optionally substituted with an alkyl group(s) having from 1 to 6 carbon atoms,
  (ii) a nitrogen-containing monocylic unsaturated hydrocarbon group,
  (iii) a morpholinyl group optionally substituted with an alkyl group(s) having from 1 to 6 carbon atoms,
  (iv) a piperazino group, optionally substituted with an alkanoyl group having from 2 to 7 carbon atoms or an alkyl group having from 1 to 6 carbon atoms and optionally substituted with a substituent(s) selected from the group consisting of:
    an amino group substituted with two alkyl groups each having from 1 to 4 carbon atoms, and
    a morpholino group, and
  (v) Formula —NR$^7$R$^8$, wherein:
    R$^7$ and R$^8$ each represent:
    a hydrogen atom,
    an alkyl group having from 1 to 6 carbon atoms, said alkyl group optionally substituted with an amino group optionally substituted with one or two alkyl groups each having from 1 to 6 carbon atoms, a morpholino group, a hydroxyl group, or an alkoxy group having from 1 to 6 carbon atoms,
    an alkanoyl group having from 1 to 6 carbon atoms,
    a carbamoyl group optionally substituted with one or two alkyl groups each having from 1 to 4 carbon atoms,
    a morpholinocarbonyl group,
    an aminosulfonyl group optionally substituted with one or two alkyl groups each having from 1 to 6 carbon atoms, or
    an alkylsulfonyl group having from 1 to 6 carbon atoms, or
  R$^7$ and R$^8$ optionally form, together with the nitrogen atom to which said R$^7$ and R$^8$ are attached, a 3- to 8-membered saturated hydrocarbon ring, said ring optionally substituted with a substituent(s) selected from the group consisting of a dimethylenedioxy group, an oxo group, and a hydroxyl group.

18. The compound of any one of Embodiments 1-15, or a pharmaceutically acceptable salt thereof, wherein R$^3$ is a phenyl group substituted at 3 position with a substituent selected from the group consisting of nitrogen-containing groups (i)-(v) below, said phenyl group further optionally substituted at 4 position with a halogen atom:
  (i) a monocylic saturated hydrocarbon group having from 2 to 7 carbon atoms and having a nitrogen atom(s) as a ring atom(s), said saturated hydrocarbon group optionally substituted with an alkyl group(s) having from 1 to 6 carbon atoms,
  (ii) a nitrogen-containing monocylic unsaturated hydrocarbon group,
  (iii) a morpholinyl group optionally substituted with an alkyl group(s) having from 1 to 6 carbon atoms,
  (iv) a piperazino group, optionally substituted with an alkanoyl group having from 2 to 7 carbon atoms or an alkyl group having from 1 to 6 carbon atoms and optionally substituted with a substituent(s) selected from the group consisting of:
    an amino group substituted with two alkyl groups each having from 1 to 4 carbon atoms, and
    a morpholino group, and
  (v) Formula —NR$^7$R$^8$, wherein:
    R$^7$ and R$^8$ each represent:
    a hydrogen atom,
    an alkyl group having from 1 to 6 carbon atoms, said alkyl group optionally substituted with an amino group optionally substituted with one or two alkyl groups each having from 1 to 6 carbon atoms, a morpholino group, a hydroxyl group, or an alkoxy group having from 1 to 6 carbon atoms,
    an alkanoyl group having from 1 to 6 carbon atoms,
    a carbamoyl group optionally substituted with one or two alkyl groups each having from 1 to 4 carbon atoms,
    a morpholinocarbonyl group,
    an aminosulfonyl group optionally substituted with one or two alkyl groups each having from 1 to 6 carbon atoms,
    or an alkylsulfonyl group having from 1 to 6 carbon atoms, or
  R$^7$ and R$^8$ optionally form, together with the nitrogen atom to which said R$^7$ and R$^8$ are attached, a 3- to 8-membered saturated hydrocarbon ring, said ring optionally substituted with a substituent(s) selected from the group consisting of a dimethylenedioxy group, an oxo group, and a hydroxyl group.

19. The compound of any one of Embodiments 1-15, or a pharmaceutically acceptable salt thereof, wherein R$^3$ is a phenyl group substituted at 4 position with a fluorine atom or a chlorine atom.

20. The compound of any one of Embodiments 1-15, or a pharmaceutically acceptable salt thereof, wherein R$^3$ is a 6-indolyl group.

21. A pharmaceutical preparation, comprising the compound of any one of Embodiments 1-20 or a pharmaceutically acceptable salt thereof.

22. The pharmaceutical preparation of Embodiment 21, which is for treatment of an autoimmune disease, such as Crohn disease, hypersensitivity colitis, Sjogren's syndrome, multiple sclerosis, and systemic lupus erythematosus, rheumatoid arthritis, asthma, atopic dermatitis, organ transplant rejection, cancer, retinopathy, psoriasis, osteoarthritis, or age-related macular degeneration.

23. A compound represented by Formula (II)

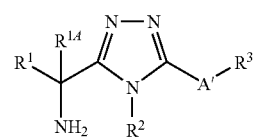

[Formula 2]

or a salt thereof, wherein R$^1$, R$^{1A}$, R$^2$, and R$^3$ are as defined in Embodiment 1, and A' represents an oxygen atom or NH.

24. The compound of Embodiment 23, or a salt thereof, wherein, in Formula (II):
A' represents an oxygen atom;
R$^1$ represents:
  a hydrogen atom,
  an alkyl group having from 1 to 6 carbon atoms, an alkyl group having from 1 to 6 carbon atoms and substituted with a phenyl group,
  a cycloalkyl group having from 3 to 8 carbon atoms, an alkenyl group having from 2 to 8 carbon atoms,
an alkynyl, group having from 2 to 8 carbon atoms, or
a phenyl group;
$R^{1A}$ represents a hydrogen atom; and
$R^2$ represents;
an alkyl group having from 1 to 6 carbon atoms,
an alkenyl group having from 2 to 8 carbon atoms,
an alkynyl group having from 2 to 8 carbon atoms, or
a cycloalkyl group having from 3 to 6 carbon atoms.

25. The compound of Embodiment 23, or a salt thereof, wherein, in Formula (II):
A' represents NH;
$R^1$ represents:
a hydrogen atom,
an alkyl group having from 1 to 6 carbon atoms,
an alkyl group having from 1 to 6 carbon atoms and substituted with a phenyl group,
a cycloalkyl group having from 3 to 8 carbon atoms,
an alkenyl group having from 2 to 8 carbon atoms,
an alkynyl group having from 2 to 8 carbon atoms, or
a phenyl group;
$R^{1A}$ represents a hydrogen atom; and
$R^2$ represents:
an alkyl group having from 1 to 6 carbon atoms,
an alkenyl group having from 2 to 8 carbon atoms,
an alkynyl group having from 2 to 8 carbon atoms, or
a cycloalkyl group having from 3 to 6 carbon atoms.

26. The compound of Embodiment 23, or a salt thereof, wherein:
$R^1$ represents an alkyl group having from 1 to 6 carbon atoms and optionally substituted with a substituent(s) selected from the group consisting of:
a hydroxyl group,
a halogen atom,
an alkoxy group having from 1 to 6 carbon atoms, said alkoxy group optionally substituted with a phenyl group, and
a phenyl group, optionally substituted with a substituent(s) selected from the group consisting of a halogen atom and an alkyl group having from 1 to 6 carbon atoms;
$R^{1A}$ represents a hydrogen atom or an alkyl group having from 1 to 6 carbon atoms; and
$R^1$ and $R^{1A}$ optionally form, together with a carbon atom to which said $R^1$ and $R^{1A}$ are attached, a cycloalkyl group having from 3 to 6 carbon atoms.

27. The compound of Embodiment 23, or a salt thereof, wherein:
$R^1$ is an alkyl group having from 1 to 6 carbon atoms and optionally substituted with a halogen atom(s), or a benzyl group optionally substituted with a substituent(s) selected from the group consisting of a halogen atom and an alkyl group having from 1 to 6 carbon atoms; and
$R^{1A}$ is a hydrogen atom.

28. The compound of any one of Embodiments 23-25, or a salt thereof, wherein $R^1$ is a methyl group or an ethyl group, and $R^{1A}$ is a hydrogen atom.

29. The compound of any one of Embodiments 23-28, or a salt thereof, wherein $R^2$ is an alkyl group having from 1 to 6 carbon atoms, or a cycloalkyl group having from 3 to 8 carbon atoms.

30. The compound of any one of Embodiments 23-28, or a salt thereof, wherein $R^2$ is an ethyl group or a cyclopropyl group.

31. The compound of any one of Embodiments 23-30, or a salt thereof, wherein;
$R^3$ is a phenyl group, a naphthyl group, a pyrazolyl group, a pyridyl group, an indolyl group, a benzothiazolyl group, a benzothiadiazolyl group, a pyrazolopyrimidinyl group, a quinolinyl group, an isoquinolinyl group, a benzothienyl group, or a dihydroquinolinonyl group, each optionally substituted with 1 to 3 substituents selected from the group consisting of the following substituents:
an alkyl group having from 1 to 6 carbon atoms and optionally substituted with a fluorine atom(s),
a cycloalkyl group having from 3 to 8 carbon atoms,
a halogen atom,
an alkoxy group having from 1 to 6 carbon atoms, said alkoxy group optionally substituted with a substituent(s) selected from the group consisting of a fluorine atom, a phenyl group, an amino group substituted with two alkyl groups each having from 1 to 4 carbon atoms, and a morpholino group,
a phenoxy group,
a phenyl group,
a carboxyl group,
an alkoxycarbonyl group having from 2 to 10 carbon atoms,
a hydroxyl, group,
a monocylic saturated hydrocarbon group having from 2 to 7 carbon atoms and having a nitrogen atom(s) as a ring atom(s), said saturated hydrocarbon group optionally substituted with an alkyl group(s) having from 1 to 6 carbon atoms;
a nitrogen-containing monocylic unsaturated hydrocarbon group,
a morpholinyl group optionally substituted with an alkyl group(s) having from 1 to 6 carbon atoms,
a piperazino group optionally substituted with a substituent(s) selected from the group consisting of:
an alkyl group having from 1 to 6 carbon atoms, said alkyl group optionally substituted with an amino group optionally substituted with one or two alkyl groups each having from 1 to 6 carbon atoms, a morpholino group, a hydroxyl group, or an alkoxy group having from 1 to 6 carbon atoms,
a formyl group,
an alkanoyl group having from 2 to 7 carbon atoms,
a carbamoyl group optionally substituted with one or two alkyl groups each having from 1 to 4 carbon atoms,
an aminosulfonyl group optionally substituted with one or two alkyl groups each having from 1 to 6 carbon atoms, and
an alkylsulfonyl group having from 1 to 6 carbon atoms; and
Formula $-NR^7R^8$, wherein:
$R^7$ and $R^8$ each represent:
a hydrogen atom,
an alkyl group having from 1 to 6 carbon atoms, said alkyl group optionally substituted with an amino group optionally substituted with one or two alkyl groups each having from 1 to 6 carbon atoms, a hydroxyl group, or an alkoxy group having from 1 to 6 carbon atoms,
an alkanoyl group having from 1 to 6 carbon atoms,
a carbamoyl group optionally substituted with one or two alkyl groups each having from 1 to 4 carbon atoms,
a morpholinocarbonyl group,
an aminosulfonyl group optionally substituted with one or two alkyl groups each having from 1 to 6 carbon atoms, or
an alkylsulfonyl group having from 1 to 6 carbon atoms, or
$R^7$ and $R^8$ optionally form, together with the nitrogen atom to which said $R^7$ and $R^8$ are attached, a 3- to 8-membered saturated hydrocarbon ring, said ring optionally substituted with a substituent(s) selected from the group consisting of a dimethylenedioxy group, an oxo group, and a hydroxyl group.

32. The compound of any one of Embodiments 23-30, or a salt thereof, wherein $R^3$ is:
   a 2-naphthyl group, optionally substituted with a substituent(s) selected from the group consisting of a halogen atom and an alkyl group having from 1 to 6 carbon atoms;
   a 3-pyrazolyl group, optionally substituted with a substituent(s) selected from the group consisting of an alkyl group having from 1 to 6 carbon atoms, a trifluoromethyl group, and a halogen atom;
   a 5-benzothiazolyl group, a 5-benzothiadiazolyl group, a 7-dihydroquinolinonyl group, a 7-isoquinolinyl group, a 7-quinolinyl group, a 3-pyridyl group, or an indolyl group, each optionally substituted with an alkyl group(s) having from 1 to 6 carbon atoms;
   an unsubstituted phenyl group; or
   a substituted phenyl group (A), (B), or (C) below:
   (A) a phenyl group substituted at 4 position with a substituent selected from the group consisting of:
      an alkyl group having from 1 to 6 carbon atoms,
      a cycloalkyl group having from 3 to 8 carbon atoms,
      an alkoxy group having from 1 to 6 carbon atoms, said alkoxy group optionally substituted with a substituent(s) selected from the group consisting of an amino group substituted with two alkyl groups each having from 1 to 4 carbon atoms, a morpholino group, and a phenyl group,
      a halogen atom,
      a trifluoromethoxy group,
      a phenoxy group,
      a phenyl group,
      a 1-pyrrolyl group, and
      —$NR^A R^B$, wherein each of $R^A$ and $R^B$ is an alkyl group having from 1 to 6 carbon atoms, or $R^A$ and $R^B$ optionally form, together with the nitrogen atom to which said $R^A$ and $R^B$ are attached, a 3- to 5-membered saturated hydrocarbon ring,
   wherein said phenyl group substituted at 4 position is further optionally substituted at 3 position with a substituent selected from the group consisting of an alkyl group having from 1 to 6 carbon atoms, a halogen atom, and an alkoxy group having from 1 to 6 carbon atoms;
   (B) a phenyl group substituted at 3 position with a substituent selected from the group consisting of:
      a hydroxyl group,
      an alkyl group having from 1 to 6 carbon atoms, and
      an alkoxy group having from 1 to 6 carbon atoms, said alkoxy group optionally substituted with a substituent(s) selected from the group consisting of an amino group substituted with two alkyl groups each having from 1 to 4 carbon atoms, a morpholino group, and a phenyl group,
   wherein said phenyl group substituted at 3 position is further optionally substituted with one or two alkyl groups each having from 1 to 6 carbon atoms, or is further optionally substituted at 4 position with a halogen atom; and
   (C) a phenyl group substituted at 3 position with a substituent selected from the group consisting of nitrogen-containing groups (i)-(v) below, said phenyl group further optionally substituted at 4 position with a halogen atom:
      (i) a monocylic saturated hydrocarbon group having from 2 to 7 carbon atoms and having a nitrogen atom(s) as a ring atom(s), said saturated hydrocarbon group optionally substituted with an alkyl group(s) having from 1 to 6 carbon atoms,
      (ii) a nitrogen-containing monocylic unsaturated hydrocarbon group,
      (iii) a morpholinyl group optionally substituted with an alkyl group(s) having from 1 to 6 carbon atoms,
      (iv) a piperazino group, optionally substituted with an alkanoyl group having from 2 to 7 carbon atoms or an alkyl group having from 1 to 6 carbon atoms and optionally substituted with a substituent(s) selected from the group consisting of:
         an amino group substituted with two alkyl groups each having from 1 to 4 carbon atoms; and
         a morpholino group, and
      (v) Formula —$NR^7 R^8$, wherein;
         $R^7$ and $R^8$ each represent:
            a hydrogen atom,
            an alkyl group having from 1 to 6 carbon atoms, said alkyl group optionally substituted with an amino group optionally substituted with one or two alkyl groups each having from 1 to 6 carbon atoms, a morpholino group, a hydroxyl group, or an alkoxy group having from 1 to 6 carbon atoms;
            an alkanoyl group having from 1 to 6 carbon atoms,
            a carbamoyl group optionally substituted with one or two alkyl groups each having from 1 to 4 carbon atoms,
            a morpholinocarbonyl group,
            an aminosulfonyl group optionally substituted with one or two alkyl groups each having from 1 to 6 carbon atoms, or
            an alkylsulfonyl group having from 1 to 6 carbon atoms, or
         $R^7$ and $R^8$ optionally form, together with the nitrogen atom to which said $R^7$ and $R^8$ are attached, a 3- to 8-membered saturated hydrocarbon ring, said ring optionally substituted with a substituent(s) selected from the group consisting of a dimethylenedioxy group, an oxo group, and a hydroxyl group.

The present invention is described in detail as follows.

The term "halogen atoms means a fluorine atom, a chlorine atom, a bromine atom, or an iodine atom.

The term "alkyl group having from 1 to 6 carbon atoms" refers to a linear or branched alkyl group containing 1 to 6 carbon atoms. Examples include a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, and a n-hexyl group.

The term "cycloalkyl group having from 3 to 8 carbon atoms" refers to a cycloalkyl group containing 3 to 8 carbon atoms. Examples include a cyclopropyl group, a cyclobutyl group, a cyclopentyl group, and a cyclohexyl group.

The term "alkenyl group having from 2 to 8 carbon atoms" refers to a linear or branched alkenyl group containing 2 to 8 carbon atoms. Examples include a vinyl group, an allyl group, a 1-propenyl group, an isopropenyl group, a 1-butenyl group, a 2-butenyl group, a 3-butenyl group, a 1,3-butadienyl group, a 2-methylallyl group, a 2-methyl-propenyl group, a 2-pentenyl group, and a 3-methyl-but-2-enyl group.

The term "alkynyl group having from 2 to 8 carbon atoms" refers to a linear or branched alkynyl group containing 2 to 8 carbon atoms. Examples include an ethynyl group, a 2-propynyl group, a 2-butynyl group, a 1-methyl-prop-2-ynyl group, a 2-pentynyl group, and a 4-pentynyl group.

The term "alkoxy group having from 1 to 6 carbon atoms" refers to a linear or branched alkoxy group containing 1 to 6 carbon atoms. Examples include a methoxy group, an ethoxy group, a propoxy group, an isopropoxy group, a butoxy group, an isobutoxy group, a sec-butoxy group, a tert-butoxy group, a pentyloxy group, and a hexyloxy group.

The term "alkyl group having from 1 to 10 carbon atoms" refers to a linear or branched alkyl group containing 1 to 10 carbon atoms. Examples include a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, a n-hexyl group, a n-heptyl group, a n-octyl group, and a n-hexadecyl group.

The term "alkylthio group having from 1 to 6 carbon atoms" refers to a linear or branched alkylthio group containing 1 to 6 carbon atoms. Examples include a methylthio group, an ethylthio group, a propylthio group, an isopropylthio group, a butylthio group, an isobutylthio group, a pentylthio group, and a hexylthio group.

The term "alkylsulfonyl group having from 1 to 6 carbon atoms" refers to a linear or branched alkylsulfonyl group containing 1 to 6 carbon atoms. Examples include a methanesulfonyl group, an ethanesulfonyl group, a propane-2-sulfonyl group, and a hexanesulfonyl group.

The term "alkoxycarbonyl group having from 2 to 10 carbon atoms" refers to a linear or branched alkoxycarbonyl group containing 2 to 10 carbon atoms. Examples include alkanoyl group having from 2 to 7 carbon atoms such as a methoxycarbonyl group, an ethoxycarbonyl group and a t-butoxycarbonyl group, as well as an octyloxycarbonyl group.

The term "alkanoyl group having from 2 to 7 carbon atoms" refers to a linear or branched alkanoyl group containing 2 to 7 carbon atoms. Examples include an acetyl group, a propanoyl group, a butanoyl group, and a hexanoyl group.

The term "alkanoyl group having from 1 to 6 carbon atoms" refers to a linear or branched alkanoyl group containing 1 to 6 carbon atoms. Examples include a formyl group, an acetyl group, a propanoyl group, and a butanoyl group.

The phrase "amino group optionally substituted with one or two alkyl groups each having from 1 to 6 carbon atoms" is intended to include, for example, an amino group, a methylamino group, an ethylamino group, an isopropylamino group, a hexylamino group, a dimethylamino group, a diethylamino group, a diisopropylamino group, and a dihexylamino group.

The phrase "aminosulfonyl group optionally substituted with one or two alkyl groups each having from 1 to 6 carbon atoms" is intended to include, for example, a sulfamoyl group, a dimethylaminosulfonyl group, and a diethylaminosulfonyl group.

The phrase "carbamoyl group optionally substituted with an alkyl group(s) having from 1 to 4 carbon atoms" is intended to include a carbamoyl group, a methylcarbamoyl group, an ethylcarbamoyl group, and a propylcarbamoyl group.

The phrase "piperazino group which may be substituted" or "optionally substituted piperazino group" refers to a piperazino group which may be substituted (preferably on its nitrogen atom) with a substituent(s) selected from the group consisting of an alkyl group having 1-6 carbon atoms (wherein said alkyl group may be substituted with an amino group which may be substituted with one or two alkyl groups each having 1-6 carbon atoms, a morpholino group, a hydroxyl group, or an alkoxy group having 1-6 carbon atoms), a formyl group, an alkanoyl group having 2-7 carbon atoms, a carbamoyl group which may be substituted with one or two alkyl groups each having 1-4 carbon atoms, an aminosulfonyl group optionally substituted with one or two alkyl groups each having 1-6 carbon atoms, and an alkylsulfonyl group having 1-6 carbon atoms. Specific examples include a piperazino group, a methylpiperazino group, an isopropylpiperazino group, a dimethylaminoethylpiperazino group, and an acetylpiperazino group.

The term "monocylic saturated hydrocarbon group having from 2 to 7 carbon atoms and having a nitrogen atom(s) as a ring atom(s)" means a 3- to 9-membered monocylic saturated hydrocarbon group containing one or two nitrogen atoms as ring-forming atoms and substituted at a ring carbon atom. Examples of the monocylic saturated hydrocarbon group include aziridinyl groups, azetidinyl groups, pyrrolidinyl groups, and piperidinyl groups (e.g., 4-piperidinyl groups).

The term "nitrogen-containing monocyclic unsaturated hydrocarbon group" refers to a 5- or 6-membered unsaturated ring containing 1 to 3 nitrogen atoms as its ring members. Examples include a pyrrolyl group (e.g., a pyrrol-1-yl group), an imidazol-1-yl group (e.g., an imidazolyl group), a pyrazolyl group, a triazol-4-yl group (e.g., a [1,2,4]triazol-4-yl group), and a pyridyl group.

The 3- to 5-membered saturated hydrocarbon ring formed by $R^A$ and $R^B$ together with the nitrogen atom to which $R^A$ and $R^B$ are attached is intended to include an aziridinyl group, an azetidinyl group, and a pyrrolidinyl group.

The 3- to 8-membered saturated hydrocarbon ring formed by $R^7$ and $R^8$ (or $R^C$ and $R^D$) together with the nitrogen atom to which $R^7$ and $R^8$ (or $R^C$ and $R^D$) are attached is intended to include an aziridinyl group, an azetidinyl group, a pyrrolidinyl group, and a piperidinyl group.

The term "aryl group" as used herein refers to an aromatic hydrocarbon group, a partially saturated aromatic hydrocarbon group, an aromatic heterocyclic group, or a partially saturated aromatic heterocyclic ring. The aromatic hydrocarbon group refers to, for example, an aromatic hydrocarbon group containing 6-14 carbon atoms, including a phenyl group, a naphthyl group, and an anthryl group.

The partially saturated aromatic hydrocarbon group refers to a group obtained by partial saturation of a polycyclic aromatic hydrocarbon group having 6-14 carbon atoms. Examples include a tetrahydronaphthyl group and an indanyl group.

The aromatic heterocyclic group refers to a monocylic or polycyclic aromatic heterocyclic group containing 2-13 carbon atoms and having 1-6 hetero atoms (e.g., oxygen, sulfur and/or nitrogen atoms). Examples include a thienyl group, a furanyl group, a pyrrolyl group, an isothiazolyl group, an isoxazolyl group, a pyrazolyl group, a thiazolyl group, an oxazolyl group, an imidazolyl group, a pyridyl group, a pyridazinyl group, a pyrimidinyl group, a pyrazinyl group, a benzothienyl group, a benzofuranyl group, an indolyl group, a benzothiazolyl group, a benzoxazolyl group, a benzimidazolyl group, a quinolinyl group, an isoquinolinyl group, a benzoxadiazolyl group, a benzothiadiazolyl group, and a pyrazolopyrimidinyl group (e.g., a 5,7-dimethyl-pyrazolo[1,5-a]pyrimidin-2-yl group).

The partially saturated aromatic heterocyclic ring refers to a heterocyclic ring obtained by partial saturation of a polycyclic aromatic heterocyclic group. Such a heterocyclic ring may be substituted with an oxo group. Examples include a dihydroquinolinonyl group:

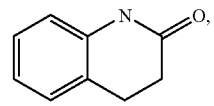

[Formula 3]

a dihydrobenzofuranyl group, a dihydrobenzodioxinyl group, a dihydrobenzodioxepinyl group, a benzodioxolyl group, a dihydrobenzoxazolyl group, and a dihydrobenzoxazinyl group, In a case where such an aryl group is substituted, substituents for the aryl group include those listed below and the aryl group can be substituted with 1 to 5 of these substituents:

a halogen atom, a cyano group, a nitro group, a sulfamoyl group, a hydroxyl group, a carboxyl group, an alkyl group having 1-6 carbon atoms, a trifluoromethyl group, a methoxycarbonylethyl group, an alkoxy group having 1-6 carbon atoms (the alkoxy group is optionally substituted with a phenyl group, an alkylamino group having 1-6 carbon atoms, a dialkylamino group having 2-12 carbon atoms, or a morpholino group), a trifluoromethoxy group, a difluoromethoxy group, a cyanoethoxy group, an alkenyl group having 2-8 carbon atoms, an alkynyl group having 2-8 carbon atoms, a cycloalkyl group having 3-8 carbon atoms, an alkanoyl group having 2-7 carbon atoms, a trifluoroacetyl group, an alkoxycarbonyl group having 2-10 carbon atoms, a phenyl group (the phenyl group is optionally substituted with an alkanoyl group having 2-7 carbon atoms or an alkoxy group having 1-6 carbon atoms), a phenoxy group optionally substituted with an alkoxy group having 1-6 carbon atoms, a pyrazolyl group, a 1-methyl-5-trifluoromethyl-1H-pyrazol-3-yl group, a methylpyrimidinyl group, a 2-methylsulfanyl-pyrimidin-4-yl groups, an oxazolyl group (e.g., oxazol-5-yl group), an isooxazol-5-yl group, a 5-trifluoromethyl-isooxazol-3-yl group, a pyridyloxy group (e.g., 4-pyridyloxy group), a pyridinecarbonyl group, a benzoyl group, a pyrrolyl group (e.g., pyrrol-1-yl group), an imidazolyl group (e.g., imidazol-1-yl group), a thiazolyl group, a [1,2,3]thiadiazol-4-yl group, a triazolyl group (e.g., [1,2,4]triazol-4-yl group), an alkylthio group having 1-6 carbon atoms (e.g., methylthio group), an alkylsulfonyl group having 1-6 carbon atoms (e.g., methanesulfonyl group), a benzenesulfonyl group, a pyrrolidinesulfonyl group, a morpholinylsulfonyl group, a 4-piperidinyl group optionally substituted with an alkyl group having 1-6 carbon atoms, a morpholino group optionally substituted with an alkyl group having 1-6 carbon atoms, a piperazino group substituted with an alkyl group having 1-6 carbon atoms or an alkyl group having 1-6 carbon atoms and substituted with a dimethylamino group, or a group represented by Formula —$NR^7R^8$, where $R^7$ and $R^8$ each represent a hydrogen atom, an alkyl group having 1-6 carbon atoms (the alkyl group is optionally substituted with an alkoxy group having 1-6 carbon atoms or a dimethylamino group), an alkanoyl group having 1-6 carbon atoms, a carbamoyl group, a carbamoyl group substituted with an alkyl group(s) having 1-4 carbon atoms, a morpholinocarbonyl group, a dimethylaminosulfonyl group, or an alkylsulfonyl group having 1-6 carbon atoms, or $R^7$ and $R^8$ optionally form, together with the nitrogen atom to which $R^7$ and $R^8$ are attached, to form a 3- to 8-membered saturated hydrocarbon ring, which ring is optionally substituted with a dimethylenedioxy group, an oxo group, or a hydroxyl group, (e.g., acetamide groups, dimethylamino groups, methylureido groups, butylureido groups, trimethylureido groups, morpholinylcarbonylamino), a methoxyethylureido group, a pyridylethoxycarbonylamino group.

The term "pharmaceutically acceptable salt" refers to a salt with an alkali metal, an alkaline earth metal, ammonium or an alkylammonium, or a salt with a mineral acid or an organic acid. Examples include a sodium salt, a potassium salt, a calcium salt, an ammonium salt, an aluminum salt, a triethylammonium salt, an acetate salt, a propionate salt, a butyrate salt, a formate salt, a trifluoroacetate salt, a maleate salt, a tartrate salt, a citrate salt, a stearate salt, a succinate salt, an ethylsuccinate salt, a lactobionate salt, a gluconate salt, a glucoheptate salt, a benzoate salt, a methanesulfonate salt, an ethanesulfonate salt, a 2-hydroxyethanesulfonate salt, a benzenesulfonate salt, a paratoluenesulfonate salt, a lauryl sulfate salt, a malate salt, an aspartate salt, a glutamate salt, an adipate salt, a salt with cysteine, a salt with N-acetylcysteine, a hydrochloride salt, a hydrobromide salt, a phosphate salt, a sulfate salt, a hydroiodide salt, a nicotinate salt, an oxalate salt, a picrate salt, a thiocyanate salt, an undecanoate salt, a salt with an acrylate polymer, and a salt with a carboxyvinyl polymer.

The compounds of the present invention may have stereoisomers including optical isomers, diastereoisomers and geometrical isomers. All of these stereoisomers and mixtures thereof also fall within the scope of the present invention. Some of the compounds and intermediates of the present invention may also exist, e.g., as keto-enol tautomers.

As shown in Test Example below, the compounds of the present invention show strong activity in an action of inhibiting binding between S1P and its receptor, Edg-1 (S1P1). Thus, the compounds are expected to have preventive or therapeutic effects on autoimmune diseases, such as Crohn disease, hypersensitivity colitis, Sjogren's syndrome, multiple sclerosis, and systemic lupus erythematosus, and diseases such as rheumatoid arthritis, asthma, atopic dermatitis, organ transplant rejection, cancer, retinopathy, psoriasis, osteoarthritis, and age-related macular degeneration.

Preferred embodiments of the compound of the present invention are described as follows.

A preferred example of A is an oxygen atom or —$NR^6$— (it is preferable that $R^6$ be hydrogen). A more preferred example of A is an oxygen atom.

A preferred example of $R^1$ is an alkyl group having 1-6 carbon atoms which may be substituted with a halogen atom(s), or a benzyl group which may be substituted with a substituent(s) selected from the group consisting of a halogen atom and an alkyl group having 1-6 carbon atoms. More preferred is a methyl group, an ethyl group, or a benzyl group which may be substituted with a halogen atom(s), and even more preferred is a methyl group.

A preferred example of $R^{1.4}$ is a hydrogen atom.

Preferred examples of $R^2$ are an ethyl group and a cyclopropyl group.

A preferred example of $R^4$ is a hydrogen atom.

In a preferred embodiment, $R^3$ is: a optionally substituted phenyl group; a 2-naphthyl group (the naphthyl group is optionally substituted with a substituent(s) selected from the group consisting of a halogen atom and an alkyl group having 1-6 carbon atoms); a 3-pyrazolyl group (the pyrazolyl group is optionally substituted with a substituent(s) selected from the group consisting of an alkyl group having 1-6 carbon atoms (preferably a methyl group), a trifluoromethyl group, and a halogen atom); or a 5-benzothiazolyl group, a 5-benzothiadiazolyl group, a 7-dihydroquinolinonyl group, a 7-isoquinolinyl group, a 7-quinolinyl group, a 3-pyridyl group, or an indolyl group (preferably a 6-indolyl group), each optionally substituted with an alkyl group(s) having 1-6 carbon atoms (preferably a methyl group).

The "optionally substituted phenyl group" in the preferred embodiment of $R^3$ includes unsubstituted phenyl groups and substituted phenyl groups (A)-(C) below:

(A) a phenyl group substituted at 4 position with a substituent selected from the group consisting of an alkyl group having 1-6 carbon atoms, a cycloalkyl group having 3-8 carbon atoms, an alkoxy group having 1-6 carbon atoms (the alkoxy group is optionally substituted with a substituent(s) selected from the group consisting of an amino group substituted with two alkyl groups each having 1-4 carbon atoms, a morpholino group, and a phenyl group), a halogen atom, a trifluoromethoxy group, a phenoxy group, a phenyl group, a 1-pyrrolyl group, and —NR$^A$R$^B$ (R$^A$ and R$^B$ are alkyl groups each having 1-6 carbon atoms, or R$^A$ and R$^B$ optionally form, together with the nitrogen atom to which R$^A$ and R$^B$ are attached, a 3- to 5-membered saturated hydrocarbon ring), which phenyl group substituted at 4 position is optionally further substituted at 3 position with a substituent selected from the group consisting of an alkyl group having 1-6 carbon atoms, a halogen atom, and an alkoxy group having 1-6 carbon atoms;

(B) a phenyl group substituted at 3 position with a substituent selected from the group consisting of a hydroxyl group, an alkyl group having 1-6 carbon atoms, and an alkoxy group having 1-6 carbon atoms (the alkoxy group is optionally substituted with a substituent(s) selected from the group consisting of an amino group substituted with two alkyl groups each having 1-4 carbon atoms, a morpholino group, and a phenyl group), which phenyl group substituted at 3 position is optionally further substituted with one or two alkyl groups each having 1-6 carbon atoms, or is optionally further substituted at 4 position with a halogen atom; and (C) a phenyl group substituted at 3 position with a substituent selected from the group consisting of nitrogen-containing groups (i)-(v) below and, in some cases, optionally further substituted at 4 position with a halogen atom, which nitrogen-containing groups preferably have a tertiary nitrogen and are attached to the phenyl group at a nitrogen atom:

(i) a monocylic saturated hydrocarbon group having 2-7 carbon atoms, having a nitrogen atom(s) as a ring atom(s), and substituted with a phenyl group at a carbon atom (the saturated hydrocarbon group is optionally substituted with an alkyl group(s) having 1-6 carbon atoms) (e.g., a piperidinyl group optionally substituted with an alkyl group(s) having 1-6 carbon atoms, such as a 4-piperidinyl group);

(ii) a nitrogen-containing monocylic unsaturated hydrocarbon group (e.g., a pyrrolyl group, an imidazolyl group);

(iii) a morpholinyl group optionally substituted with an alkyl group(s) having 1-6 carbon atoms, such as a morpholino group;

(iv) an optionally substituted piperazino group (e.g., a piperazino group optionally substituted (preferably on a nitrogen atom constituting a ring) with a substituent(s) selected from the group consisting of an alkyl group having 1-6 carbon atoms (the alkyl group is optionally substituted with a substituent(s) selected from the group consisting of an amino group substituted with two alkyl groups each having 1-4 carbon atoms, and a morpholino group), and an alkanoyl group having 2-7 carbon atoms); and (v) Formula —NR$^7$R$^8$, in which R$^7$ and R$^8$ each represent a hydrogen atom, an alkyl group having 1-6 carbon atoms (the alkyl group is optionally substituted with an amino group optionally substituted with one or two alkyl groups each having 1-6 carbon atoms, a morpholino group, a hydroxyl group, or an alkoxy group having 1-6 carbon atoms), an alkanoyl group having 1-6 carbon atoms, a carbamoyl group optionally substituted with one or two alkyl groups each having 1-4 carbon atoms, a morpholinocarbonyl group, an aminosulfonyl group optionally substituted with one or two alkyl groups each having 1-6 carbon atoms, or an alkylsulfonyl group having 1-6 carbon atoms, or R$^7$ and R$^8$ optionally form, together with the nitrogen atom to which R$^7$ and R$^8$ are attached, a 3- to 8-membered saturated hydrocarbon ring, which ring is optionally substituted with a substituent(s) selected from the group consisting of a dimethylenedioxy group, an oxo group, and a hydroxyl group.

It is preferable that Formula —NR$^7$R$^8$ in item (v) above be —NR$^C$R$^D$ as defined below.

R$^C$ and R$^D$ each represent a hydrogen atom, an alkyl group having 1-6 carbon atoms (the alkyl group is optionally substituted with an amino group optionally substituted with one or two alkyl groups each having 1-4 carbon atoms, a hydroxyl group, or an alkoxy group having 1-4 carbon atoms), a formyl group, an acetyl group, an aminocarbonyl group, a dimethylaminosulfonyl group, or a methylsulfonyl group, or R$^C$ and R$^D$ optionally form, together with the nitrogen atom to which R$^C$ and R$^D$ are attached, a 3- to 8-membered saturated hydrocarbon ring, which ring is optionally substituted with a substituent(s) selected from the group consisting of a dimethylenedioxy group, an oxo group, and a hydroxyl group.

In an especially preferred embodiment, R$^3$ is a phenyl group substituted at 4 position with a fluorine atom or a chlorine atom, a 6-indolyl group, and nitrogen-containing groups (i), (iv), and (v) shown in item (C) above, which phenyl group substituted with a substituent selected from the above group is optionally further substituted at 4 position with a halogen atom.

In a preferred embodiment, R$^5$ is: an alkyl group having 1-10 carbon atoms (preferably 1-6 carbon atoms) and substituted with a cycloalkyl group having 3-8 carbon atoms; an alkyl group having 1-10 carbon atoms (preferably 1-6 carbon atoms) and substituted with a naphthyl group; an alkenyl group having 2-8 carbon atoms (preferably 2-6 carbon atoms) and substituted with a phenyl group; a phenyl group or a naphthyl group (preferably 2-naphthyl group) each optionally substituted with 1-5 substituents selected from the group consisting of an alkyl group having 1-6 carbon atoms, a halogen atom, an alkoxy group having 1-6 carbon atoms, a trifluoromethoxy group, a difluoromethoxy group, a trifluoromethyl group, an alkenyl group having 1-6 carbon atoms, an alkylsulfonyl group having 1-6 carbon atoms, an alkanoyl group having 2-7 carbon atoms, an alkoxycarbonyl group having 2-7 carbon atoms, and a cyano group; a pyrrolyl group optionally substituted with a substituent(s) selected from the group consisting of an alkyl group having 1-6 carbon atoms (preferably a methyl group) and a methoxycarbonyl group; a furanyl group optionally substituted with a substituent(s) selected from the group consisting of an alkyl group having 1-6 carbon atoms (preferably a methyl group), a trifluoromethyl group, and a halogen atom; a thienyl group optionally substituted with a substituent(s) selected from the group consisting of an alkyl group having 1-6 carbon atoms (preferably a methyl group), a trifluoromethyl group, a thiadiazolyl group, an oxazolyl group, and a halogen atom; or a benzothienyl group (preferably a 2-benzothienyl group), a phenyl group condensed with a 5- to 7-membered saturated hydrocarbon ring which may contain one or two oxygen atoms as ring-forming atoms (e.g., a dihydrobenzodioxepinyl group, a benzodioxolyl group, a dihydrobenzodioxynyl group, a dihydrobenzofuranyl group, a tetrahydronaphthyl group, an indanyl group), a thiadiazolyl group, a benzoxadiazolyl group, or a benzothiadiazolyl group (preferably 5-benzothiadiazolyl groups), each optionally substituted with a substituent(s) selected from the group consisting of an alkyl group having 1-6 carbon atoms (preferably a methyl group) and a halogen atom.

In a preferred embodiment of R$^5$, examples of the "phenyl group which is optionally substituted" include an unsubstituted phenyl group, a phenyl group substituted with 1-5 substituents selected from the group consisting of an alkyl group having 1-6 carbon atoms (preferably a methyl group), an alkoxy group having 1-6 carbon atoms (preferably a methoxy group), and a halogen atom, and a phenyl group substituted at either 3 or 4 position or both and substituted with 1-3 substituents selected from the group consisting of an alkyl group having 1-6 carbon atoms, a halogen atom, an alkoxy group having 1-6 carbon atoms (preferably a methoxy group), a trifluoromethoxy group, a difluoromethoxy group, a trifluoromethyl group, an alkenyl group having 1-6 carbon atoms, an alkylsulfonyl group having 1-6 carbon atoms (preferably a methylsulfonyl group), a methoxycarbonyl group, an acetyl group, and a cyano group, preferably a halogen atom, a methyl group, and a methoxy group, and more preferably a halogen atom.

In a preferred embodiment of $R^5$, an example of the "naphthyl group which is optionally substituted" is a naphthyl group optionally substituted with a substituent(s) (preferably 1-3 substituents) selected from the group consisting of a halogen atom, an alkyl group having 1-6 carbon atoms (preferably a methyl group), a cyano group, and an alkylsulfonyl group having 1-6 carbon atoms (preferably a methylsulfonyl group). More preferably, it is a naphthyl group optionally substituted with a substituent(s) selected from the group consisting of a halogen atom, an alkyl group having 1-6 carbon atoms (preferably a methyl group), and a cyano group. Examples in a case of a 2-naphthyl group include an unsubstituted 2-naphthyl group and a 2-naphthyl group substituted with a substituent(s) selected from the group consisting of an alkyl group having 1-6 carbon atoms (substituted at any position, preferably at 5, 7 and/or 8 position) and other substituents (substituted at 5, 7 and/or 8 position). Examples in a case of a 1-naphthyl group include an unsubstituted 1-naphthyl group and a 1-naphthyl group substituted with a substituent(s) selected from the group consisting of an alkyl group having 1-6 carbon atoms (substituted at any position) and other substituents, preferably a halogen atom (substituted preferably at 4 position).

In an especially preferred embodiment, $R^5$ is a phenyl group substituted at 3 and 4 positions with a halogen atom, an unsubstituted 2-naphthyl group, and a 2-naphthyl group substituted at 5, 7 and/or 8 position with a substituent(s) selected from the group consisting of a halogen atom, an alkyl group having 1-6 carbon atoms (preferably a methyl group), and a cyano group.

The following are combinations of $R^3$ and $R^5$ that are especially preferred. In a case in which $R^3$ is a phenyl group substituted at 4 position with a fluorine atom or a chlorine atom, $R^5$ is: an alkyl group having 1-10 carbon atoms (preferably 1-6 carbon atoms) and substituted with a naphthyl group; an alkenyl group having 2-8 carbon atoms (preferably 2-6 carbon atoms) and substituted with a phenyl group; a substituted phenyl group (e.g., a phenyl group substituted with 1-5 methyl groups, a phenyl group substituted at either 3 or 4 position or both and substituted with 1-3 substituents selected from the group consisting of an alkyl group having 1-6 a carbon atom (preferably a methyl group, an ethyl group, a propyl group), a halogen atom, a methoxy group, a trifluoromethoxy group, a difluoromethoxy group, a trifluoromethyl group, an alkenyl group having 1-6 carbon atoms (preferably a vinyl group), a methoxycarbonyl group, an acetyl group, and a cyano group; a benzothienyl group; a naphthyl group optionally substituted with a substituent(s) selected from the group consisting of a halogen atom, an alkyl group having 1-6 carbon atoms (preferably a methyl group), a cyano group, and an alkylsulfonyl group having 1-6 carbon atoms (preferably a methylsulfonyl group); a pyrrolyl group optionally substituted with a substituent(s) selected from the group consisting of a methyl group and a methoxycarbonyl group; a thienyl group substituted with an alkyl group(s) having 1-6 carbon atoms (preferably a methyl group); a benzodioxolyl group; a dihydrobenzodioxynyl group; a dihydrobenzofuranyl group; a tetrahydronaphthyl group; an indanyl group; or a benzothiadiazolyl group (preferably a 5-benzothiadiazolyl group).

In a case in which $R^3$ is a 6-indolyl group, $R^5$ is: an alkyl group having 1-10 carbon atoms (preferably 1-6 carbon atoms) and substituted with a naphthyl group; an alkenyl group having 2-8 carbon atoms (preferably 2-6 carbon atoms) and substituted with a phenyl group; a phenyl group which is optionally substituted (e.g., an unsubstituted phenyl group, a phenyl group substituted with 1-5 methyl groups, a phenyl group substituted at either 3 or 4 position or both and substituted with 1-3 substituents selected from the group consisting of an alkyl group having 1-6 carbon atoms (preferably a methyl group, an ethyl group, a propyl group), a halogen atom, a methoxy group, a trifluoromethoxy group, a difluoromethoxy group, a trifluoromethyl group, an alkenyl group having 1-6 carbon atoms (preferably a vinyl group), a methoxycarbonyl group, an acetyl group, and a cyano group); a benzothienyl group; a naphthyl group optionally substituted with a substituent(s) selected from the group consisting of a halogen atom, an alkyl group having 1-6 carbon atoms (preferably a methyl group), a cyano group, and an alkylsulfonyl group having 1-6 carbon atoms (preferably a methylsulfonyl group); a pyrrolyl group optionally substituted with a substituent(s) selected from the group consisting of an alkyl group having 1-6 carbon atoms (preferably a methyl group) and a methoxycarbonyl group: or a benzodioxolyl group, a dihydrobenzodioxynyl group, a dihydrobenzofuranyl group, a tetrahydronaphtyl group, an indanyl group, or a benzothiadiazolyl group (preferably, 5-benzothiadiazolyl group), each optionally substituted with a substituent(s) selected from the group consisting of an alkyl group having 1-6 carbon atoms (preferably a methyl group) and a halogen atom.

In a case in which $R^3$ is of the embodiment shown in item (C) above, $R^5$ is: an alkyl group having 1-6 carbon atoms and substituted with a cycloalkyl group having 3-8 carbon atoms: an alkyl group having 1-10 carbon atoms (preferably 1-6 carbon atoms) and substituted with a naphthyl group; an alkenyl group having 2-8 carbon atoms (preferably 2-6 carbon atoms) and substituted with a phenyl group; a optionally substituted phenyl group (e.g., an unsubstituted phenyl group, a phenyl group substituted with 1-5 substituents selected from the group consisting of an alkyl group having 1-6 carbon atoms (preferably a methyl group) and a halogen atom, a phenyl group substituted at 3 or 4 position or both and substituted with 1-3 substituents selected from the group consisting of an alkyl group having 1-6 carbon atoms, a halogen atom, a methoxy group, a trifluoromethoxy group, a difluoromethoxy group, a trifluoromethyl group, an alkenyl group having 1-6 carbon atoms, an alkylsulfonyl group having 1-6 carbon atoms (preferably a methylsulfonyl group), a methoxycarbonyl group, an acetyl group, and a cyano group; a naphthyl group optionally substituted with a substituent(s) selected from the group consisting of a halogen atom, an alkyl group having 1-6 carbon atoms (preferably a methyl group), a cyano group, and an alkylsulfonyl group having 1-6 carbon atoms (preferably a methylsulfonyl group); a pyrrolyl group optionally substituted with a substituent(s) selected from the group consisting of an alkyl group having 1-6 carbon atoms (preferably a methyl group) and a methoxycarbonyl group; a thienyl group optionally substituted with a substituent(s) selected from the group consisting of an alkyl group having 1-6 carbon atoms (preferably a methyl group), a trifluoromethyl group, a thiadiazolyl group, an oxazolyl group, and a halogen atom; a furanyl group optionally substituted with a substituent(s) selected from the group consisting of an alkyl group having 1-6 carbon atoms (preferably a methyl group), a trifluoromethyl group, and a halogen atom; or a benzothienyl group, a benzodioxolyl group, a dihydrobenzodioxynyl group, a dihydrobenzofuranyl group, a tetrahydronaphthyl group, an indanyl group, a thiadiazolyl group (preferably a 5-thiadiazolyl group), a benzoxadiazolyl group, or a benzothiadiazolyl group (preferably a 5-benzothiadiazolyl group), each optionally substituted with a substituent(s) selected from the group consisting of an alkyl group having 1-6 carbon atoms (preferably a methyl group) and a halogen atom.

A preferred optically-active compound of the present compound having $R^{1A}$ being a hydrogen atom has the structure below.

[Formula 4]

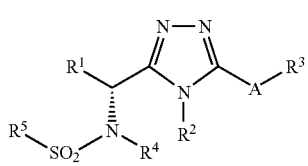

The compound of the present invention can be synthesized by, for instance, the method described below.

(Scheme 1)

[Formula 5]

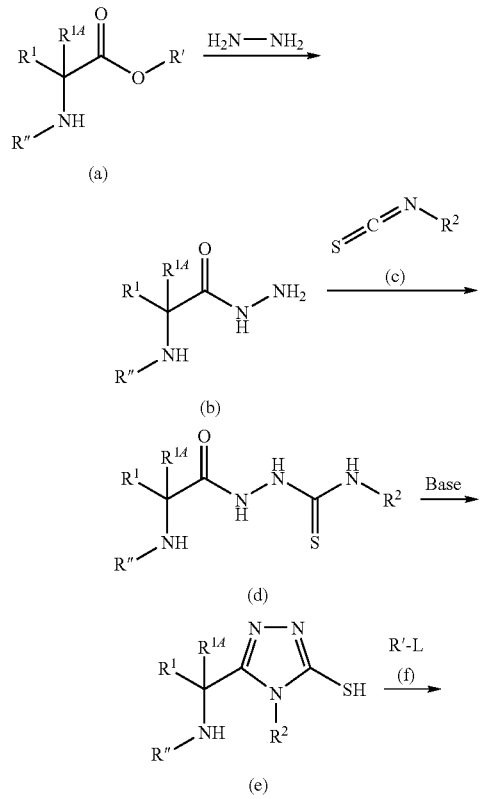

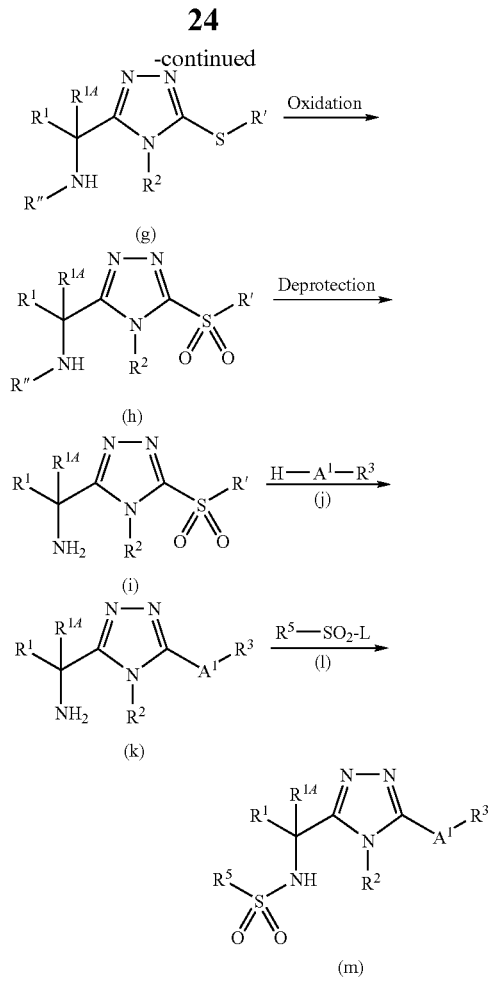

(where $R^1$, $R^{1A}$, $R^2$, $R^3$, and $R^5$ are as defined above, R' represents an alkyl group having 1-6 carbon atoms, R" represents a protecting group for an amino group, which protecting group is stable under a basic condition (e.g., a t-butoxycarbonyl group, a benzyloxycarbonyl group), L represents a leaving group (e.g., a halogen atom, such as a chlorine atom, a bromine atom, and an iodine atom, an alkylsulfonyloxy group, such as an a methanesulfonyloxy group and a p-toluenesulfonyloxy group, an arylsulfonyloxy group, a 2-oxo-1-oxazolyl group), and $A^1$ represents an oxygen atom, a sulfur atom, or a group represented by —$NR^6$—, where $R^6$ represents a hydrogen atom or an alkyl group having 1-6 carbon atoms.)

In the present invention, a compound having A being an oxygen atom, a sulfur atom, or a group represented by —$NR^6$— can be synthesized by, for instance, the method shown in Scheme 1.

The compound represented by Formula (b) can be obtained by allowing the compound represented by Formula (a) to react with hydrazine in a solvent or in the absence of a solvent. The amount of the hydrazine used is generally 1-30 equivalent weight with respect to Compound (a), preferably 5-30 equivalent weight. A solvent to be used when it is necessary is not particularly limited, as long as it is inert. Examples of the solvent to be used include alcohols such as methanol and ethanol. The reaction temperature is generally a room temperature to a solvent reflux temperature. The reaction time is generally 12-24 hours, but it depends on the reaction temperature and starting compounds.

The compound represented by Formula (d) can be obtained by allowing the compound represented by Formula (b) to react with the compound represented by Formula (c) in a solvent or in the absence of a solvent. The amount of the compound represented by Formula (c) to be used is generally 1-3 equivalent weight with respect to the compound represented by Formula (b), preferably 1.1-1.5 equivalent weight. A solvent to be used when it is necessary is not particularly limited, as long as it is inert. For instance, alcohols, such as methanol and ethanol, and halogenated hydrocarbons, such as dichloromethane and chloroform, are preferably used. The reaction temperature is generally a room temperature to a solvent reflux temperature. The reaction time is generally 30 minutes to 24 hours, but it depends on the reaction temperature and starting compounds.

The compound represented by Formula (e) can be obtained by allowing the compound of Formula (d) to react with a base in a solvent or in the absence of a solvent to cyclize. The base to be used includes alkali metal hydroxides such as NaOH and KOH, and alkali metal salts such as $NaHCO_3$ and $K_2CO_3$. The amount of the base used is 1-10 equivalent weight with respect to the compound represented by Formula (d), preferably 1.1-1.5 equivalent weight. If a solvent is necessary, the following can be used as the solvent: water, alcohols such as methanol and ethanol, ethers such as dioxane and tetrahydrofuran (THF), and mixed solvents thereof. The reaction temperature is generally a room temperature to a solvent reflux temperature. The reaction time is generally a period of 30 minutes to 24 hours, but it depends on the reaction temperature and starting compounds.

The compound represented by Formula (g) can be obtained by allowing, in a solvent or in the absence of a solvent, the compound represented by Formula (e) to react with the compound represented by Formula (f) in the presence of a base. The amount of the compound represented by Formula (f) to be used is generally 1-5 equivalent weight, preferably 1.1-1.5 equivalent weight, with respect to the compound represented by Formula (e). The base to be used includes alkali metal hydroxides, such as NaOH and KOH, alkali metal salts, such as $NaHCO_3$ and $K_2CO_3$, and amines, such as triethylamine, diisopropylethylamine, and diisopropylamine. The amount of the base used is 1-10 equivalent weight with respect to the compound represented by Formula (e), preferably 1.0-3.0 equivalent weight. The reaction temperature is 0° C. to a solvent reflux temperature, preferably 0° C. to a room temperature. A solvent to be used when it is necessary is not particularly limited, as long as it is inert. Examples of the solvent to be used include water, ethers such as dioxane and THF, dimethylformamide (DMF), N,N'-dimethylacetamide (DMA), N,N'-dimethylpropyleneurea (DMPU), hexamethylphosphoramide (HMPA), and mixed solvents thereof. The reaction time is generally a period of 30 minutes to 24 hours, but it depends on the reaction temperature and starting compounds.

The compound represented by Formula (h) can be obtained by allowing the compound represented by Formula (g) to react with an oxidant in a solvent. Examples of the solvent to be used include organic peroxyacids such as m-chloroperbenzoic acid, magnesium monoperphthalate hexahydrate, peroxyacetic acid, and peroxyformic acid, inorganic or organic peroxides such as hydrogen peroxide, hydrogen peroxide urea adduct/phthalic anhydride, tert-butylhydroperoxide, and cumenehydroperoxide, sodium periodate, Oxone (registered trademark), N-bromosuccinimide, N-chlorosuccinimide, chloramine-T, hypochlorite tert-butyl, iodobenzene diacetate, and bromine-1,4-diazabicyclo[2,2,2]octane addition complex. The amount of the oxidant used is 2-10 equivalent weight with respect to the compound represented by Formula (g), preferably 2-3 equivalent weight. A solvent to be used when it is necessary is not particularly limited, as long as it is inert. Examples of the solvent to be used include halogenated hydrocarbons such as methylene chloride and chloroform. The reaction temperature is 0° C. to a solvent reflux temperature, preferably 0° C.-40° C. The reaction time is generally a period of 30 minutes to 24 hours, but it depends on the reaction temperature and starting compound.

The compound represented by Formula (i) or a salt of the compound can be obtained by subjecting the compound represented by Formula (h) to deprotection of an amino group in a solvent under a conventional condition, e.g., allowing it to react with an acid. Examples of the acid used include inorganic acids (e.g., hydrochloric acid, hydrobromic acid, hydroiodic acid, sulfuric acid, nitric acid) and organic acids (e.g., trifluoroacetic acid, p-toluenesulfonic acid, methanesulfonic acid). The amount of the acid used is 1-50 equivalent weight with respect to the compound represented by Formula (h). The reaction temperature is 0° C. to a solvent ref lux temperature, preferably a room temperature to 40° C. A solvent to be used when it is necessary is not particularly limited, as long as it is inert. Examples of the solvent to be used include halogenated hydrocarbons such as methylene chloride and chloroform. The reaction time is generally a period of 30 minutes to 24 hours, but it depends on the reaction temperature and starting compound.

The compound represented by Formula (k) or a pharmaceutically acceptable salt of the compound can be obtained by allowing, in a solvent or in the absence of a solvent, the compound represented by Formula (i) to react with the compound represented by Formula (j) (where $A^1$ represents an oxygen atom, a sulfur atom, or a group represented by Formula $—NR^6—$, and $R^3$ is as defined above) in the presence of a base and, when necessary, forming a salt. The amount of the compound of Formula (j) to be used is generally 1-5 equivalent weight with respect to the compound represented by Formula (i), preferably 1-3 equivalent weight. Examples of the base used include alkali metal salts, such as sodium carbonate, potassium carbonate, cesium carbonate, sodium hydrogen carbonate, potassium hydrogen carbonate, sodium hydroxide, dimsyl sodium, sodium hydride, sodium amide, tert-butoxypotassium, and tert-butoxysodium, amines, such as triethylamine, diisopropylamine, pyrrolidine, and piperidine, sodium acetate, and potassium acetate. The amount of the base used is generally 1-10 equivalent weight with respect to the compound represented by Formula (i), preferably 1-3 equivalent weight. The reaction temperature is 0° C. to a solvent reflux temperature, and it can be carried out under ordinary pressure, increased pressure, microwave irradiation, or the like. The reaction solvent to be used includes ethers such as dioxane and THF, DMF, DMA, DMPU, HMPA, or the like, or mixed solvents thereof. The reaction time is generally a period of 1-12 hours, but it depends on the reaction temperature and starting compound.

The compound represented by Formula (m) or a pharmaceutically acceptable salt of the compound can be obtained by allowing, in a solvent or in the absence of a solvent, the compound represented by Formula (k) to react with the compound represented by Formula (l) in the presence of a base and, when necessary, forming a salt. The amount of the compound represented by Formula (l) used is 1-5 equivalent weight with respect to the compound represented by Formula (k), preferably 1-1.2 equivalent weight. The base to be used includes alkali metal hydroxides, such as NaOH and KOH, alkali metal salts, such as $NaHCO_3$ and $K_2CO_3$, or amines, such as triethylamine, diisopropylethylamine, and diisopropylamine. The amount of the base used is 1-10 equivalent weight with respect to the compound represented by Formula (k), preferably 1.0-3.0 equivalent weight. The reaction temperature is 0° C. to a solvent reflux temperature, preferably 0° C. to a room temperature. A solvent to be used when it is necessary is not particularly limited, as long as it is inert. Examples of the solvent to be used include halogenated hydrocarbons such as methylene chloride and chloroform, ethers such as dioxane and THF, and mixed solvents thereof. The reaction time is generally a period of 30 minutes to 24 hours, but it depends on the reaction temperature and starting compound.

(Scheme 2)

[Formula 6]

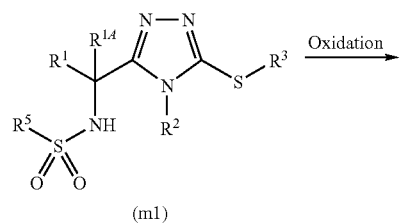

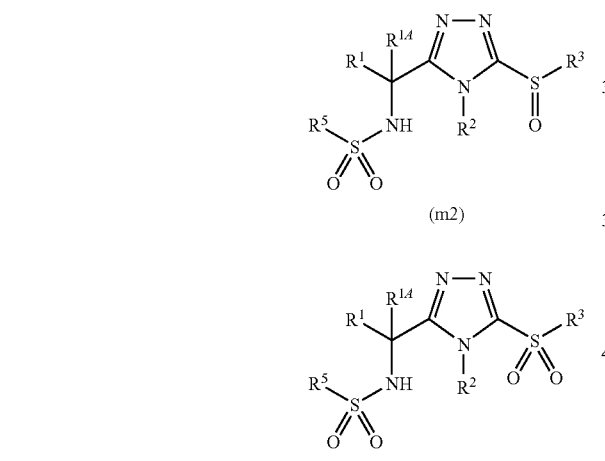

(Scheme 3)

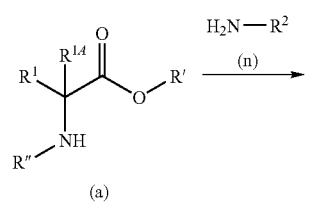

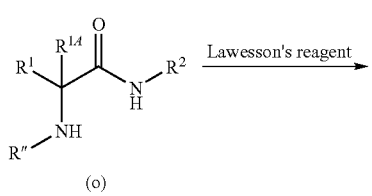

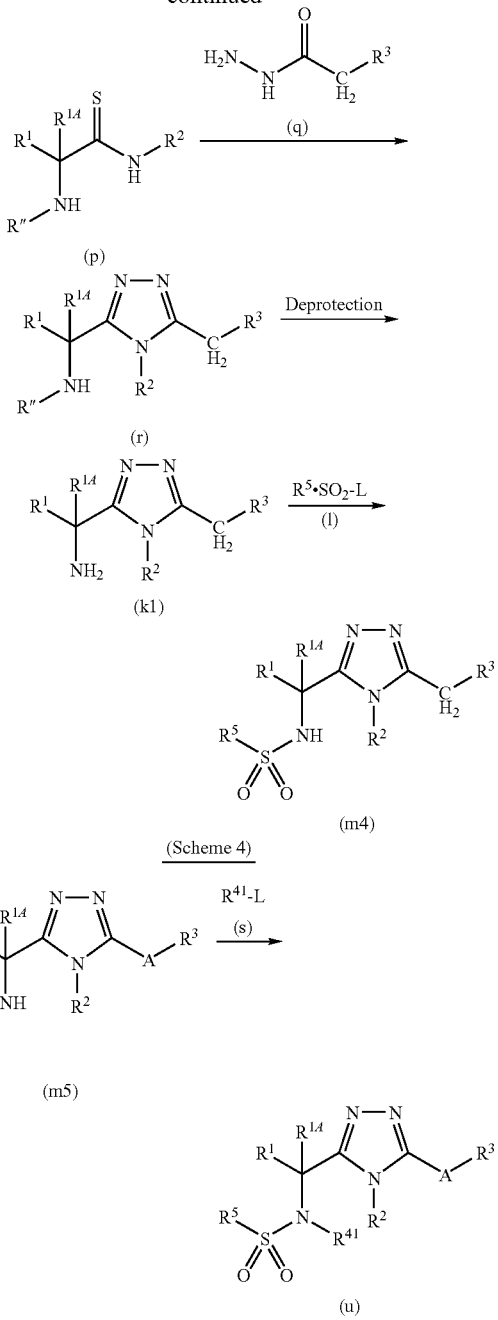

(where $R^1$, $R^{14}$, $R^2$, $R^3$, $R^4$, $R^5$, R', R", A, and L are as defined above, and $R^{41}$ is the same as $R^4$ excluding the hydrogen atom).

In the present invention, a compound having A represented by Formula —SO— or Formula —SO$_2$— can be synthesized by the method shown in Scheme 2.

The compound represented by Formula (m2), the compound represented by Formula (m3), or pharmaceutically acceptable salts of the compounds can be obtained by allowing, among the compounds obtained in Scheme 1 and represented by Formula (m), the compound represented by Formula (m1) having $A^1$ being a sulfur atom to react with an oxidant and, when necessary, forming a salt. Examples of the oxidant to be used include organic peroxyacids such as m-chloroperbenzoic acid, magnesium monoperphthalate hexahydrate, peroxyacetic acid, and peroxyformic acid, inorganic or organic peroxides such as hydrogen peroxide, hydrogen peroxide urea adduct/phthalic anhydride, tert-butylhydroperoxide, and cumenehydroperoxide, sodium periodate, Oxone (registered trademark), N-bromosuccinimide, N-chlorosuccinimide, chloramine-T, hypochlorite tert-butyl, iodobenzene diacetate, and bromine-1,4-diazabicyclo[2,2,2]octane addition complex. The amount of the oxidant used is 1-10 equivalent weight with respect to the compound represented by Formula (m1), preferably 1-3 equivalent weight. A solvent to be used when it is necessary is not particularly limited, as long as it is inert. Examples of the solvent to be used include halogenated hydrocarbons such as methylene chloride and chloroform. The reaction temperature is $-78°$ C. to a solvent ref lux temperature, preferably $0°$-$40°$ C. The reaction time is generally a period of 30 minutes to 24 hours, but it depends on the reaction temperature and starting compound.

In the present invention, a compound having A represented by —$CH_2$— can be synthesized by the method shown in Scheme 3.

The compound represented by Formula (o) can be obtained by allowing the compound represented by Formula (a) to react with the compound represented by Formula (n) ($R^2$ is as defined above) in a solvent or in the absence of a solvent. The amount of the compound represented by Formula (n) to be used is 1-10 equivalent weight with respect to the compound represented by Formula (a), preferably 1-1.2 equivalent weight. A solvent to be used when it is necessary is not particularly limited, as long as it is inert. Examples of the solvent to be used include alcohols such as methanol and ethanol. The reaction temperature is generally a room temperature to a solvent reflux temperature, preferably a room temperature to $50°$ C. The reaction time is generally a period of 12-24 hours, but it depends on the reaction temperature and starting compound.

The compound represented by Formula (p) can be obtained by allowing the compound represented by Formula (o) to react with a Lawesson's reagent in a solvent or in the absence of a solvent. The amount of the Lawesson's reagent used is 1-5 equivalent weight with respect to the compound represented by Formula (o), preferably 1-1.2 equivalent weight. The reaction solvent to be used includes ethers such as dioxane and THF, and mixed solvents thereof. The reaction temperature is a room temperature to a solvent reflux temperature, preferably a room temperature to $50°$ C. The reaction time is generally 1-12 hours, but it depends on the reaction temperature and starting compounds.

The compound represented by Formula (r) can be obtained by allowing the compound represented by Formula (p) to react with the compound represented by Formula (q) in the presence of a mercury compound. The amount of the compound represented by Formula (q) to be used is 1-10 equivalent weight with respect to the compound represented by Formula (p), preferably 1-1.2 equivalent weight. Examples of the mercury compound include $HgCl_2$ and $Hg(OAc)_2$. The amount of the mercury compound used is 1-10 equivalent weight with respect to the compound represented by Formula (p), preferably 1-1.2 equivalent weight. The solvent to be used includes acetonitrile, THF, dioxane, and the like. The reaction temperature is a room temperature to a solvent reflux temperature, preferably a room temperature to $50°$ C. The reaction time is generally a period of 12-48 hours, but it depends on the reaction temperature and starting compound.

The compound represented by Formula (k1) or a salt of the compound can be obtained by subjecting the compound represented by Formula (r) to deprotection of an amino group in a solvent under a conventional condition, e.g., allowing it to react with an acid. Examples of the acid include inorganic acids (e.g., hydrochloric acid, hydrobromic acid, hydroiodic acid, sulfuric acid, nitric acid) and organic acids (e.g., trifluoroacetic acid, p-toluenesulfonic acid, methanesulfonic acid). The amount of the acid used is 1-50 equivalent weight with respect to the compound represented by Formula (r). The reaction temperature is $0°$ C. to a solvent reflux temperature, preferably a room temperature to $40°$ C. A solvent to be used when it is necessary is not particularly limited, as long as it is inert. Examples of the solvent to be used include halogenated hydrocarbons such as methylene chloride and chloroform. The reaction time is generally a period of 30 minutes to 24 hours, but it depends on the reaction temperature and starting compound.

The compound represented by Formula (m4) or a pharmaceutically acceptable salt of the compound can be obtained by allowing, in a solvent or in the absence of a solvent, the compound represented by Formula (k1) to react with the compound represented by Formula (l) in the presence of a base and, when necessary, forming a salt. The amount of the compound represented by Formula (l) to be used is 1-5 equivalent weight with respect to the compound represented by Formula (k1), preferably 1-1.2 equivalent weight. The base to be used includes alkali metal hydroxides, such as NaOH and KOH, alkali metal salts, such as $NaHCO_3$ and $K_2CO_3$, and amines, such as triethylamine, diisopropylethylamine, and diisopropylamine. The amount of the base is 1-10 equivalent weight, preferably 1.0-3.0 equivalent weight. The reaction temperature is $0°$ C. to a solvent reflux temperature, preferably $0°$ C. to a room temperature. A solvent to be used when it is necessary is not particularly limited, as long as it is inert. Examples of the solvent to be used include halogenated hydrocarbons such as methylene chloride and chloroform, ethers such as dioxane and THF, and mixed solvents thereof. The reaction time is generally a period of 30 minutes to 24 hours, but it depends on the reaction temperature and starting compound.

The compound represented by Formula (u) or a pharmaceutically acceptable salt of the compound can be obtained by allowing, in a solvent or in the absence of a solvent, the compound represented by Formula (m5) to react with the compound represented by Formula (s) in the presence of a base and, when necessary, forming a salt. The amount of the compound represented by Formula (s) to be used is generally 1-10 equivalent weight with respect to the compound represented by Formula (m5), preferably 1.1-1.5 equivalent weight. The base to be used includes alkali metal hydroxides, such as NaOH and KOH, alkali metal salts, such as $NaHCO_3$ and $K_2CO_3$, and amines, such as triethylamine, diisopropylethylamine, and diisopropylamine. The amount of the base used is 1-10 equivalent weight with respect to the compound represented by Formula (m5), preferably 1.0-3.0 equivalent weight. The reaction temperature is $0°$ C. to a solvent reflux temperature, preferably $0°$ C. to a room temperature. A solvent to be used when it is necessary is not particularly limited, as long as it is inert. Examples of the solvent to be used include water, ethers such as dioxane and THF, dimethylformamide (DMF), N,N'-dimethylacetamide (DMA), N,N'-dimethylpropyleneurea (DMPU), hexamethylphosphoramide (HMPA), and mixed solvents thereof. The reaction time is generally a period of 30 minutes to 24 hours, but it depends on the reaction temperature and starting compound.

Further, a functional group can be introduced to $R^3$ by carrying out protection, deprotection, functional group transformation in the process described above.

For use as pharmaceutical preparations, the compounds of the present invention may be supplemented with commonly used excipients, extenders, pH regulators, solubilizers and so on, and then formulated using standard techniques into tablets, granules, pills, capsules, powders, solutions, suspensions, injections, etc. The pharmaceutical preparations thus obtained can be administered as oral or parenteral formulations.

The compound of the present invention can be administered to an adult patient at a dose of 1-1000 mg per day in several separated doses. This dosage can be increased or reduced according to a type of a disease, an age, a weight, and a symptom of a patient, or the like.

Advantageous Effect of the Invention

As the Test Example described below shows, it is found that the compounds of the present invention are strong Edg-1 (S1P$_1$) ligands.

BEST MODE FOR CARRYING OUT THE INVENTION

The following describes the present invention in more detail, with reference to Examples and the Test Example.

Example 1

3,4-Dichloro-N-{(R)-1-[4-ethyl-5-(4-fluorophenoxy)-4H-[1,2,4]-triazol-3-yl]ethyl}benzenesulfonamide (Compound 12)

[Formula 7]

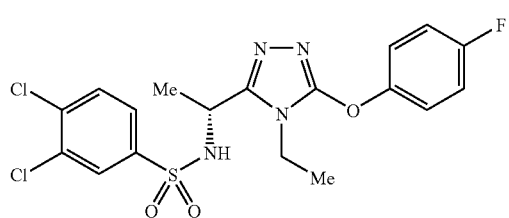

(R)-(1-Hydrazinocarbonyl-2-ethyl)carbamic acid t-butyl ester

[Formula 8]

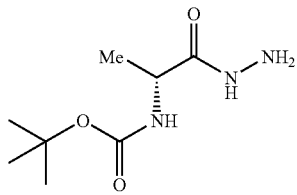

(1) Hydrazine monohydrate (30 ml) was added to a solution of N-(t-butoxycarbonyl)-D-alanine methyl ester (41.8 g) in methanol (180 ml), and the mixture was stirred at room temperature for 12 hours. The reaction solution was concentrated, and the resulting crude crystal was washed with a mixed solvent of hexane and ethyl acetate (1:1, 300 ml) and then dried to give the titled compound as a colorless powder (32.6 g).

$^1$H NMR (300 MHz, DMDO-d6) δ ppm: 1.14 (d, J=7.2 Hz, 3H), 1.37 (s, 9H), 3.30-4.09 (m, 3H), 6.70-6.90 (m, 1H), 8.96 (br s, 1H)

(R)-2-(N-(t-Butoxycarbonyl)amino)propionyl)-N-ethylhydrazinecarbothioamide

[Formula 9]

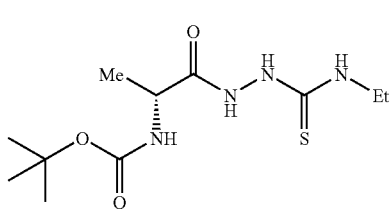

(2) Ethyl isothiocyanate (14.6 ml) was added to a solution of the compound (30.8 g) of Example 1-(1) in ethanol (152 ml), and the mixture was heated under reflux for two hours. Then, the mixture was cooled to room temperature, and the resulting crystal was filtered. The filtrate was concentrated, and the resulting residue was purified by silica-gel chromatography with a mixed solvent of ethyl acetate and chloroform to give the titled compound as a colorless amorphous substance (43.2 g).

$^1$H NMR (300 MHz, DMSO-d6) δ ppm: 0.98-1.28 (m, 6H), 1.40 (s, 9H), 3.25-3.65 (m, 2H), 3.77-3.95 (m, 1H), 7.20-7.39 (m, 1H), 7.45-7.60 (m, 1H), 9.25 (s, 1H), 10.00 (s, 1H)

[(R)-1-(4-Ethyl-5-mercapto-4H-[1,2,4]triazol-3-yl)ethyl]-carbamic acid t-butyl ester

[Formula 10]

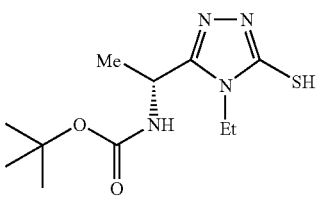

(3) One mol/l aqueous sodium hydroxide (218 ml) was added to a mixed solution of the compound (42.1 g) of Example 1-(2) in methanol (120 ml) and dioxane (240 ml), and the mixture was heated under reflux for three hours. The reaction solution was concentrated, and an aqueous hydrochloric acid (2N, 100 ml) was added. The mixture was extracted with a mixed solution of ethyl acetate, chloroform, and methanol (10:10:1, 500 ml). The organic layer was dried over anhydrous magnesium sulfate and evaporated under reduced pressure to remove the solvent. The resulting residue was washed with a mixed solvent of hexane and ethyl acetate (1:1, 300 ml) and then dried to give the titled compound as a white solid (29.22 g).

¹H NMR (300 MHz, DMSO-d6) δ ppm: 1.21 (t, J=7.1 Hz, 3H), 1.30-1.50 (m, 3H), 1.39 (s, 9H), 3.82-4.05 (m, 2H), 4.72-4.88 (m, 1H), 7.58 (d, J=8.5 Hz, 1H), 13.60 (br s, 1H)

[(R)-1-(4-Ethyl-5-methylsulfanyl-4H-[1,2,4]triazol-3-yl)ethyl]-carbamic acid t-butyl ester

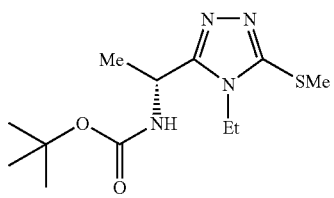

[Formula 11]

(4) Diisopropylamine (17.4 ml) and MeI (7.7 ml) were added to a solution of the compound (28.12 g) of Example 1-(3) in THF (200 ml), and the mixture was stirred at room temperature for one hour. Thereafter, the resulting crystal was filtered. The filtrate was concentrated, and the resulting crude crystal was washed with a mixed solvent of hexane and ethyl acetate (3:1, 200 ml) and then dried to give the titled compound as a white powder (29.5 g).

¹H NMR (300 MHz, DMSO-d6) δ ppm: 1.21 (t, J=7.0 Hz, 3H), 1.38 (s, 9H), 1.45 (t, J=7.0 Hz, 3H), 2.62 (s, 3H), 3.80-4.00 (m, 2H), 4.85-4.92 (m, 1H), 7.52 (d, J=8.5 Hz, 1H)

[(R)-1-(4-Ethyl-5-methanesulfonyl-4H-[1,2,4]triazol-3-yl)ethyl]-carbamic acid t-butyl ester

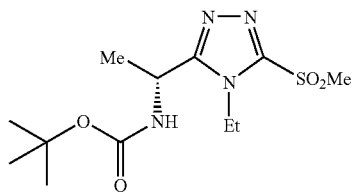

[Formula 12]

(5) With ice cooling, m-chloroperbenzoic acid (43.0 g) was added in four portions to a solution of the compound (21.0 g) of Example 1-(4) in chloroform (293 ml), and the mixture was stirred at room temperature for three hours and thereafter at 40° C. for one hour. Na₂S₂O₃ (12.9 g) and 1 mol/l aqueous sodium hydroxide (300 ml) were added to the reaction solution to separate the organic layer, and the organic layer was washed with saturated aqueous sodium chloride, dried over anhydrous magnesium sulfate, and evaporated under reduced pressure to remove the solvent. The resulting residue was purified by silica-gel flush column chromatography with a mixed solvent of hexane and ethyl acetate, and then recrystallized with hexane and chloroform to give the titled compound as a white powder (17.2 g).

¹H NMR (300 MHz, CDCl₃) δ ppm: 1.44 (s, 9H), 1.49 (t, J=7.1 Hz, 3H), 1.67 (t, J=6.8 Hz, 3H), 3.53 (s, 3H), 4.25-4.59 (m, 2H), 4.92-5.20 (m, 2H)

(R)-1-(4-Ethyl-5-methanesulfonyl-4H-[1,2,4]triazol-3-yl)ethylamine trifluoroacetic acid salts

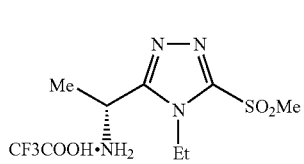

[Formula 13]

(6) Trifluoroacetic acid (121 ml) was added to the compound (100.0 g) obtained in Example 1-(5), and the mixture was stirred at room temperature for two hours. The reaction solution was concentrated under reduced pressure to give the titled compound as a white powder (103.8 g).

¹H NMR (300 MHz, DMSO-d6) δ ppm: 1.37 (t, J=7.2 Hz, 3H), 1.59 (d, J=6.8 Hz, 3H), 3.65 (s, 3H), 4.21-4.50 (m, 2H), 4.72-4.90 (m, 1H), 8.69 (br s, 3H)

(1R)-1-(4-Ethyl-5(4-fluorophenoxy)-4H-[1,2,4]-triazol-3-yl)ethylamine

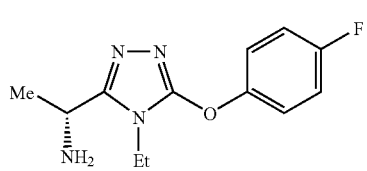

[Formula 14]

(7) In a pressure-resistant screw cap test tube, N,N'-dimethylpropyleneurea (DMPU) (5 mL), 4-fluorophenol (1.01 g) and cesium carbonate (2.94 g) were added to the compound (1.00 g) obtained in Example 1-(6), and the mixture was stirred at 200° C. for one hour. The mixture was brought to room temperature, and saturated aqueous sodium chloride was added. The mixture was extracted with ethyl acetate (100 ml×5). The organic layer was dried over anhydrous sodium sulfate, filtered, and evaporated under reduced pressure to remove the solvent. The resulting crude product was purified by column chromatography (NH SiO₂, hexane/ethyl acetate=50/50 to 20/80, chloroform/methanol=30/1) to give the titled compound (brown oil compound, 0.586 g).

¹H NMR (600 MHz, CDCl₃) δ ppm: 1.41 (t, J=7.3 Hz, 3H), 1.58 (d, J=6.4 Hz, 3H), 3.95-4.23 (m, 3H), 6.90-7.15 (m, 2H), 7.30-7.44 (m, 2H)

3,4-Dichloro-N-{(R)-1-[4-ethyl-5-(4-fluorophenoxy)-4H-[1,2,4]-triazol-3-yl]ethyl}benzenesulfonamide (Compound 12)

[Formula 15]

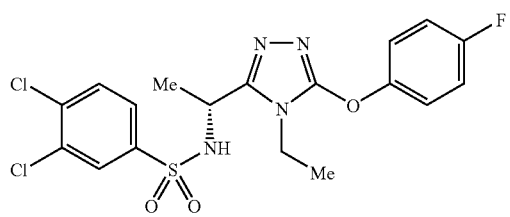

(8) Triethylamine (0.93 mL, 6.64 mmol) and 3,4-dichlorobenzenesulfonyl chloride (0.45 mL, 2.88 mmol) were added at room temperature to a solution of the compound (0.554 g) of Example 1-(7) in THF (10 mL), and the mixture was stirred at room temperature for 2.5 hours. Then, ethyl acetate was added. The organic layer was washed with 1N aqueous hydrochloric acid and thereafter with saturated aqueous sodium chloride, dried over anhydrous magnesium sulfate, filtered, and evaporated under reduced pressure to remove the solvent. The resulting crude product was purified by column chromatography (acidic OH SiO$_2$, hexane/ethyl acetate=50/50 to 10/90) and then recrystallized (ethyl acetate-hexane) to give 0.447 g of the titled compound (Compound 12) as a colorless powder.
Melting point: 190.0° C. to 192.0° C.

Example 2

N-[(1R)-1-(4-Ethyl-5(4-methylphenylamino)-4H-[1,2,4]triazol-3-yl)ethyl]3,4-dichlorobenzenesulfonamide (Compound 61)

[Formula 16]

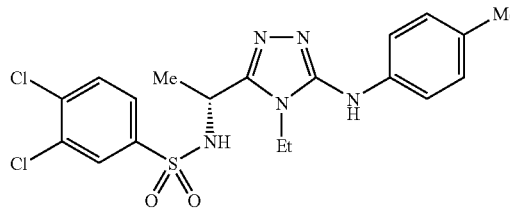

(R)-1-(4-Ethyl-5-methanesulfonyl-4H-[1,2,4]triazol-3-yl)ethylamine

[Formula 17]

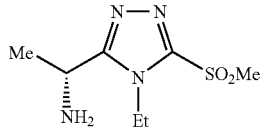

(1) To the compound (4.30 g) obtained in Example 1-(6), n-BuNH$_2$ (20 ml) was added, and the mixture was stirred at room temperature for one hour. The reaction solution was concentrated, and the resulting crude product was purified by NH silica-gel chromatography with a mixed solvent of methanol and chloroform (methanol/chloroform=10%) to give the titled compound as a colorless crystal (2.737 g).
$^1$H NMR (200 MHz, CDCl$_3$) δ ppm: 1.53 (t, J=7.3 Hz, 3H), 1.65 (d, J=6.8 Hz, 3H), 3.53 (s, 3H), 4.14-4.58 (m, 3H)

[5-((R)-1-Aminoethyl)-4-ethyl-4H-[1,2,4]triazol-3-yl]-4-methylphenylamine

[Formula 18]

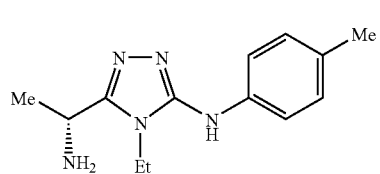

(2) The compound (437 mg) obtained in Example 2-(1), DMPU (2.0 mL), 4-toluidine (257 mg), and NaH (240 mg, 60-72 wt % oily) were put in a pressure-resistant screw cap test tube. The mixture was stirred at 200° C. for 1.0 hour and then brought to room temperature, and 10% methanol/chloroform was added to the reaction solution. The reaction solution was filtered through NH silica gel and then concentrated, and the resulting brown oily substance was purified by column chromatography (NHSiO$_2$, ethyl acetate/hexane=50-99%, methanol/chloroform=5%) to give the titled compound (brown oil compound, 224 mg).
$^1$H NMR (200 MHz, CDCl$_3$) δ ppm: 1.31 (t, J=7.3 Hz, 3H), 1.60 (d, J=6.6 Hz, 3H), 2.28 (5, 3H), 3.60-4.30 (m, 3H), 6.96-7.02 (m, 4H)

N-[(1R)-1-(4-Ethyl-5(4-methylphenylamino)-4H-[1,2,4]triazol-3-yl)ethyl]3,4-dichlorobenzenesulfonamide (Compound 61)

[Formula 19]

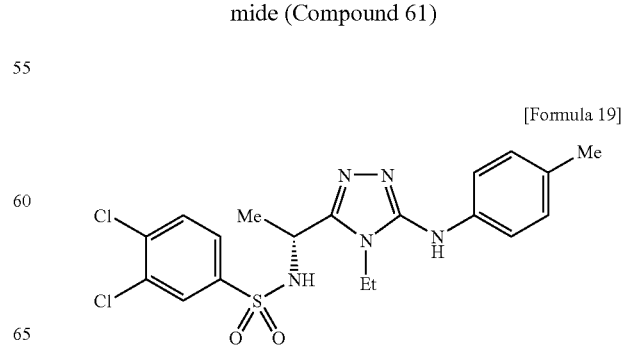

A solution of 3,4-dichlorobenzenesulfonyl chloride (154 μl) in THF (2.0 ml) was added at room temperature to a solution of the compound (220 mg) of Example 2-(2) and triethylamine (0.249 ml) in THF (9.0 ml), and the mixture was stirred at room temperature for five hours. The insoluble matter was filtered off, and the resulting residue was concentrated. The resulting crude product was purified by OH silica-gel column chromatography (elution solvent: ethyl acetate/hexane=50-99%) and then recrystallized (ethyl acetate-hexane) to give 160 mg of the titled compound (Compound 61) as a pale yellow powder.

$^1$H NMR (600 MHz, DMSO-d6) δ ppm 1.18 (t, J=7.1 Hz, 3H), 1.30 (d, J=6.9 Hz, 3H), 2.23 (s, 3H), 3.87-4.03 (m, 2H), 4.63-4.72 (m, 1H), 7.00-7.12 (m, 2H), 7.35-7.45 (m, 2H), 7.74 (dd, J=8.6, 1.9 Hz, 1H), 7.86 (d, J=8.6 Hz, 1H), 7.96 (d, J=1.9 Hz, 1H), 8.27 (s, 1H), 8.57-8.66 (m, 1H)

Melting point: 93.0° C. to 99.0° C.

Example 3

3,4-Dichloro-N-[(R)-1-(4-ethyl-5(4-methylbenzene-sulfanyl)-4H-[1,2,4]triazol-3-yl)-ethyl]-benzene-sulfonamide (Compound 55)

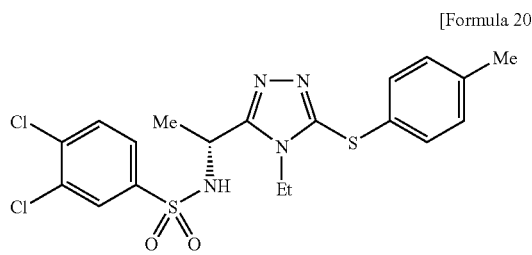

[Formula 20]

(R)-1-(4-Ethyl-5(4-methylphenylsulfanyl)-4H-[1,2,4]triazol-3-yl)-ethylamine

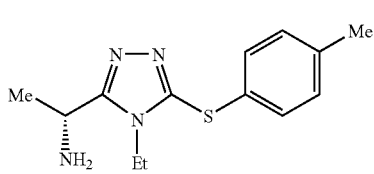

[Formula 21]

(1) The compound (5.00 g, 15.1 mmol) obtained in Example 1-(6), DMF (50 mL), 4-methylbenzenethiol (3.74 g, 30.1 mmol), and cesium carbonate (14.7 g, 45.1 mmol) were put in a pressure-resistant screw cap test tube. The mixture was stirred at 150° C. for four hours and thereafter brought back to room temperature, and a mixed solvent of chloroform/methanol (10/1) was added. The insoluble matter was filtered off. The filtrate was removed by evaporation under reduced pressure, and the resulting crude product was purified by column chromatography (NHSiO$_2$, hexane/ethyl acetate=50/50 to 10/90, chloroform/methanol 40/1) to give 3.01 g of the titled compound (colorless oily compound).

$^1$H NMR (600 MHz, CDCl$_3$) δ ppm 1.21 (t, J=7.3 Hz, 3H), 1.59 (d, J=6.4 Hz, 3H), 2.31 (s, 3H), 4.00-4.18 (m, 3H), 7.06-7.14 (m, 2H), 7.26-7.30 (m, 2H)

3,4-Dichloro-N-[(R)-1-(4-ethyl-5(4-methylbenzene-sulfanyl)-4H-[1,2,4]triazol-3-yl)-ethyl]-benzene-sulfonamide (Compound 55)

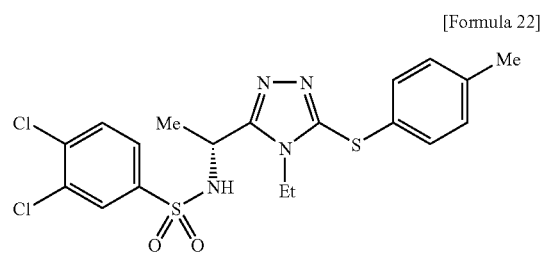

[Formula 22]

(2) Starting from the compound obtained in Example 3-(1), the same procedure as used in Example 1-(8) was repeated to give the titled compound.

$^1$H NMR (600 MHz, DMSO-d6) δ ppm 1.08 (t, J=7.3 Hz, 3H), 1.32 (d, J=6.9 Hz, 3H), 2.28 (s, 3H), 3.90-4.11 (m, 2H), 4.78 (q, J=6.9 Hz, 1H), 7.17-7.23 (m, 4H), 7.67-7.74 (m, 1H), 7.81-7.88 (m, 1H), 7.92-7.94 (m, 1H), 8.77 (s, 1H)

Yield: 46%, Melting point: 141.0° C. to 143.0° C.

Example 4

3,4-Dichloro-N-[(R)-1-[4-ethyl-5(4-methylbenzene-sulfonyl)-4H-[1,2,4]triazol-3-yl]-ethyl]-benzene-sulfonamide (Compound 57)

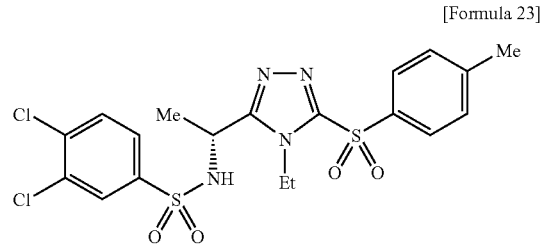

[Formula 23]

To a solution of the compound (0.300 g) of Example 3-(2) in chloroform (6 mL), m-chloroperbenzoic acid (0.329 g) was added, and the mixture was stirred at room temperature for one hour. Then, a further portion of m-chloroperbenzoic acid (0.329 g) was added, and the mixture was stirred at room temperature for 15 hours. Thereafter, a further portion of m-chloroperbenzoic acid (0.329 g) was added, and the mixture was stirred at room temperature for two hours. Then, ethyl acetate was added, and the organic layer was washed with 5% aqueous Na$_2$S$_2$O$_3$ solution and thereafter with saturated aqueous sodium bicarbonate, dried over anhydrous magnesium sulfate, filtered, and evaporated under reduced pressure to remove the solvent. The resulting residue was purified by column chromatography (acidic OH SiO$_2$, hexane/ethyl acetate=70/30 to 40/60) and then recrystallized (ethyl acetate-hexane) to give 0.196 g of the titled compound (Compound 57) (colorless powdered compound).

$^1$H NMR (600 MHz, DMSO-d6) δ ppm 1.25-1.35 (m, 6H), 2.45 (s, 3H), 4.23-4.40 (m, 2H), 4.78-4.86 (m, 1H), 7.52-7.56 (m, 2H), 7.62-7.67 (m, 1H), 7.78-7.82 (m, 1H), 7.86-7.94 (m, 3H)

Melting point: 164.0° C. to 165.0° C.

Example 5

3,4-Dichloro-N-[(R)-1-[4-ethyl-5-(4-methylbenzyl)-4H-[1,2,4]triazol-3-yl]-ethyl]-benzenesulfonamide (Compound 56)

[Formula 24]

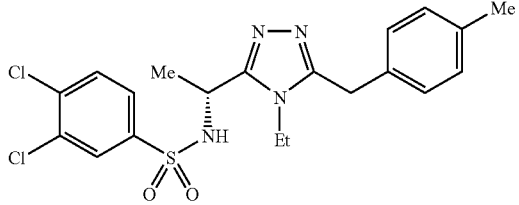

((R)-1-Ethylcarbamoyl-ethyl)-carbamic acid t-butyl ester

[Formula 25]

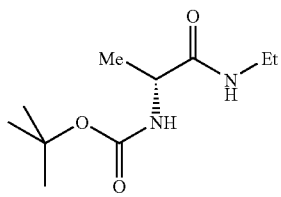

(1) EtNH$_2$ (10 ml, 70% aqueous solution) was added to N-(t-butoxycarbonyl)-D-alanine methyl ester (4.76 g) in methanol (20 ml), and the mixture was stirred at room temperature for 19 hours. The reaction solution was concentrated, and the resulting crude product was purified by column chromatography (acidic OH SiO$_2$, chloroform/ethyl acetate=10-50%) to give 3.96 g of the titled compound (colorless amorphous substance).

$^1$H NMR (200 MHz, CDCl$_3$) δ ppm: 1.12 (t, J=7.2 Hz, 3H), 1.35 (d, J=7.2 Hz, 3H), 1.46 (s, 9H), 3.18-3.37 (m, 2H), 4.00-4.20 (m, 1H), 4.90-5.10 (m, 1H), 6.04-6.22 (m, 1H)

((R)-1-Ethylthiocarbamoyl-ethyl)-carbamic acid t-butyl ester

[Formula 26]

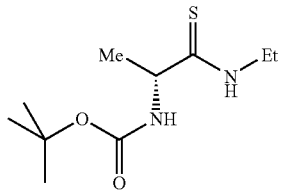

(2) A Lawesson's reagent (8.89 g) was added to a solution of the compound (3.96 g) of Example 5-(1) in THF (92 ml), and the mixture was stirred at room temperature for one hour and thereafter at 50° C. for 30 minutes. The reaction solution was cooled to room temperature, and the insoluble matter was filtered off. Then, the resulting residue was concentrated. The resulting crude product was purified by column chromatography (acidic OH SiO$_2$, chloroform/ethyl acetate=10-50%) and thereafter by NH silica-gel column chromatography (ethyl acetate/hexane=50%) to give the titled compound (3.75 g) as a colorless powder.

$^1$H NMR (200 MHz, CDCl$_3$) δ ppm: 1.26 (t, J=7.2 Hz, 3H), 1.38-1.52 (m, 3H), 1.45 (s, 9H), 3.60-3.77 (m, 2H), 4.36-4.53 (m, 1H), 5.10-5.32 (m, 1H), 7.99-8.24 (m, 1H)

[(R)-1-[4-Ethyl-5-(4-methylbenzyl)-4H-[1,2,4]triazol-3-yl]-ethyl]-carbamic acid t-butyl ester

[Formula 27]

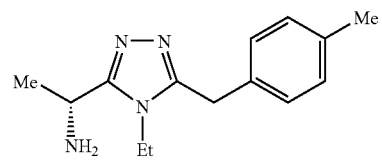

(3) Hg (OAc)$_2$ (2.43 g) was added to a solution of the compound (1.61 g) obtained in Example 5-(2) and 4-methylphenylacetic acid hydrazide (1.25 g) in CH$_3$CN (30 mL), and the mixture was stirred at room temperature for 42 hours. Ethyl acetate was added to the reaction solution, and the insoluble matter was filtered off through celite. The filtrate was washed with 1N aqueous KHSO$_4$ solution and thereafter with saturated aqueous sodium chloride, dried over anhydrous magnesium sulfate, filtered, and evaporated under reduced pressure to remove the solvent. The resulting crude product was purified by column chromatography (acidic OH SiO$_2$, ethyl acetate/hexane=50-100%, methanol/chloroform=1/1) (neutral OH SiO$_2$, methanol/chloroform=1/10) to give 0.530 g of the titled compound (colorless amorphous substance).

$^1$H NMR (600 MHz, CDCl$_3$) δ ppm: 1.04 (t, J=7.3 Hz, 3H), 1.41 (s, 9H), 1.61 (d, J=6.9 Hz, 3H), 2.30 (s, 3H), 3.73-3.90 (m, 2H), 4.06-4.20 (m, 2H), 4.85-4.94 (m, 1H), 5.11-5.17 (m, 1H), 7.09 (s, 4H)

(R)-1-[4-Ethyl-5-(4-methylbenzyl)-4H-[1,2,4]triazol-3-yl]-ethylamine

[Formula 28]

(4) Trifluoroacetic acid (5 mL) was added to a solution of the compound (0.496 g) of Example 5-(3) in chloroform (5 mL), and the mixture was stirred at room temperature for 18 hours. Aqueous sodium hydroxide (1.0N) was added, and the mixture was extracted with ethyl acetate. The organic layer was washed with saturated aqueous sodium chloride, dried over anhydrous sodium sulfate, filtered, and evaporated under reduced pressure to remove the solvent, whereby 0.148 g of the titled compound was obtained as a colorless oily compound.

$^1$H NMR (600 MHz, CDCl$_3$) δ ppm: 1.09 (t, J=7.3 Hz, 3H), 1.57 (d, J=6.9 Hz, 3H), 2.30 (s, 3H), 3.74-3.94 (m, 2H), 4.01-4.20 (m, 3H), 7.10 (s, 4H)

3,4-Dichloro-N-[(R)-1-[4-ethyl-5-(4-methylbenzyl)-4H-[1,2,4]triazol-3-yl]-ethyl]-benzenesulfonamide (Compound 56)

[Formula 29]

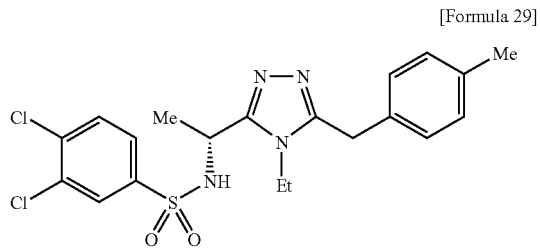

(5) Triethylamine (0.25 mL) and 3,4-dichlorobenzenesulfonyl chloride (0.707 mL) were added to a solution of the compound (0.144 g) of Example 5-(4) in THF (3 mL), and the mixture was stirred at room temperature for 3.5 hours. Then, 2N aqueous hydrochloric acid was added, and the mixture was extracted with ethyl acetate. The organic layer was washed with saturated aqueous sodium chloride, dried over anhydrous magnesium sulfate, filtered, and evaporated under reduced pressure to remove the solvent. The resulting residue was purified by column chromatography (acidic OH SiO$_2$, chloroform/methanol=50/1 to 10/1) and then recrystallized (ethyl acetate-hexane) to give 0.100 g of the titled compound (Compound 56) as a colorless powdered compound.

$^1$H NMR (600 MHz, DMSO-D6) δ ppm: 0.91 (t, J=7.1 Hz, 3H), 1.26 (d, J=6.9 Hz, 3H), 2.23 (s, 3H), 3.77-3.92 (m, 2H), 4.00 (s, 2H), 4.60-4.70 (m, 1H), 7.03-7.12 (m, 4H), 7.64-7.68 (m, 1H), 7.79-7.82 (m, 1H), 7.89-7.91 (m, 1H), 8.64 (s, 1H)

Melting point: 189.0° C. to 191.0° C.

Example 6

3,4-Dichloro-N-[(R)-1-[4-ethyl-5-(4-fluorophenoxy)-4H-[1,2,4]triazol-3-yl]-ethyl]-N-methyl-benzenesulfonamide (Compound 115)

[Formula 30]

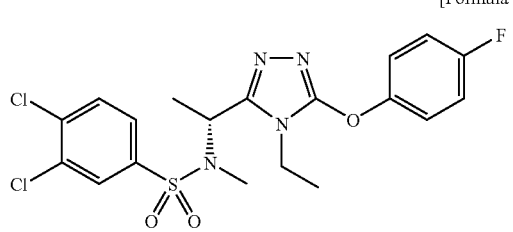

K$_2$CO$_3$ (78 mg) and MeI (0.022 ml) were added at room temperature to a solution of Compound 12 (150 mg) of Example 1 in dimethylformamide (2.0 ml), and the mixture was stirred at room temperature for three hours. Water was added to the reaction solution, and the mixture was extracted with a mixed solution of methanol/chloroform (methanol/chloroform=1/4). The resulting organic layer was washed with saturated aqueous sodium chloride, dried (MgSO$_4$), filtered, and evaporated under reduced pressure to remove the solvent. After eluting the residue with a mixed solvent of ethyl acetate and hexane, the resulting elute was purified by column chromatography (acidic OH SiO$_2$, ethyl acetate/hexane=50-99%, methanol/chloroform=0-10%) and then recrystallized (ethyl acetate-hexane) to give 111 mg of the titled compound as a colorless powdered compound.

Melting point: 125.5° C. to 126.5° C.

Example 7

3,4-Dichloro-N-((R)-1-[5-[3-(1,4-dioxa-8-aza-spiro[4.5]decan-8-yl)-phenoxy]-4-ethyl-4H-[1,2,4]triazol-3-yl]-ethyl)-benzenesulfonamide (Compound 87)

[Formula 31]

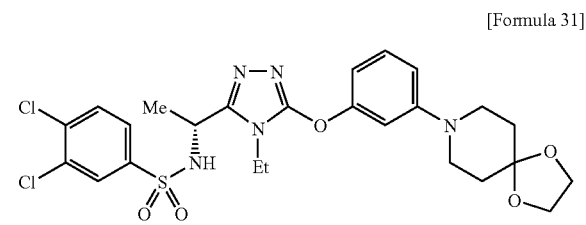

3-(1,4-Dioxa-8-aza-spiro[4.5]decen-8-yl)-phenol

[Formula 32]

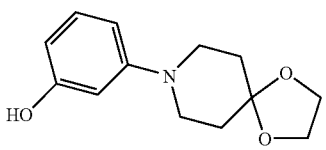

(1) In a pressure-resistant screw cap test tube, 3-bromophenol (1.50 g), 1,4-dioxa-8-azaspiro[4,5]decan (1.49 g), Pd$_2$(dba)$_3$ (0.079 g), (2'-dicyclohexylphosphanyl-biphenyl-2-yl)-dimethylamine (0.082 g), and LiN(TMS)$_2$ (20% in THF, 18 mL) were put, and the mixture was stirred at 65° C. for 7.5 hours. Ethyl acetate was added, and the organic layer was washed with 1N aqueous hydrochloric acid and thereafter with saturated aqueous sodium bicarbonate, dried over anhydrous sodium sulfate, filtered, and evaporated under reduced pressure to remove the solvent. The resulting residue was purified by column chromatography (acidic OH SiO$_2$, hexane/ethyl acetate=70/30 to 60/40) to give 1.96 g of the titled compound (brown oil).

$^1$H NMR (600 MHz, CDCl$_3$) δ ppm: 1.79-1.83 (m, 4H), 3.27-3.35 (m, 4H), 3.98 (s, 4H), 4.86 (s, 1H), 6.28 (dd, J=8.0, 2.5 Hz, 1H), 6.41 (t, J=2.3 Hz, 1H), 6.51 (dd, J=8.5, 2.5 Hz, 1H), 7.08 (t, J=8.3 Hz, 1H)

(R)-1-[5-[3-(1,4-Dioxa-8-aza-spiro[4.5]decan-8-yl)-phenoxy]-4-ethyl-4H-[1,2,4]triazol-3-yl]-ethylamine

[Formula 33]

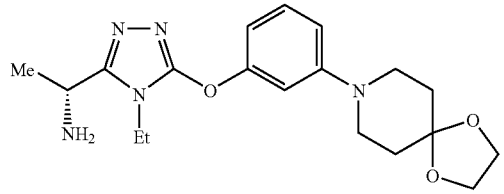

(2) Starting from the compound obtained in Example 7-(1) in place of 4-fluorophenol, the same procedure as used in Example 1-(7) was repeated to give the titled compound (brown oily substance, yield 58%).

$^1$H NMR (600 MHz, CDCl$_3$) δ ppm: 1.38 (t, J=7.3 Hz, 3H), 1.57 (d, J=6.9 Hz, 3H), 1.77-1.83 (m, 4H), 3.27-3.36 (m, 4H), 3.95-4.06 (m, 6H), 4.14 (g, J=6.9 Hz, 1H), 6.70-6.75 (m, 2H), 6.97 (t, J=2.3 Hz, 1H), 7.20 (t, J=8.3 Hz, 1H)

3,4-Dichloro-N-((R)-1-[5-[3-(1,4-dioxa-8-aza-spiro[4.5]decan-8-yl)-phenoxy]-4-ethyl-4H-[1,2,4] triazol-3-yl]-ethyl)-benzenesulfonamide (Compound 87)

[Formula 34]

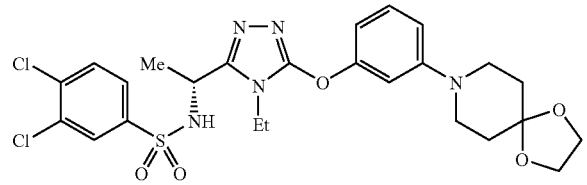

(3) Starting from the compound obtained in Example 7-(2), the same procedure as used in Example 1-(8) was repeated to give the titled compound (colorless powder, yield 64%).

Melting point: 174.0° C. to 179.0° C.

Example 8

3,4-Dichloro-N-((R)-1-[4-ethyl-5-[3-(4-oxo-piperidin-1-yl)-phenoxy]-4H-[1,2,4]triazol-3-yl]-ethyl)-benzenesulfonamide (Compound 88)

[Formula 35]

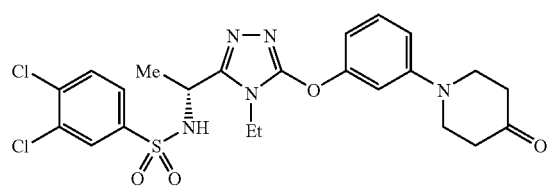

To a solution of the compound (0.981 g) of Example 7 in THF (10 mL), 2N aqueous hydrochloric acid (8.4 mL) was added, and the mixture was stirred at room temperature for one hour. Concentrated hydrochloric acid (2 mL) was added, and the mixture was stirred at 50° C. for six hours. Saturated aqueous sodium bicarbonate was added for neutralization, and the mixture was extracted with ethyl acetate. The organic layer was washed with saturated aqueous sodium chloride, dried over anhydrous magnesium sulfate, filtered, and then evaporated under reduced pressure to remove the solvent. The resulting residue was purified by column chromatography (acidic OH SiO$_2$, ethyl acetate) and then recrystallized (chloroform-hexane) to give the titled compound (0.572 g, colorless powder).

Melting point: 188.5° C. to 190.5° C.

Example 9

3,4-Dichloro-N-((R)-1-[4-ethyl-5-[3-(4-hydroxy-piperidin-1-yl)-phenoxy]-4H-[1,2,4]triazol-3-yl]-ethyl)-benzenesulfonamide (Compound 93)

[Formula 36]

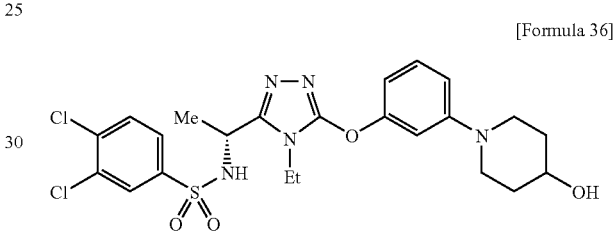

NaBH$_4$ (0.021 g) was added at 0° C. to a solution of the compound (0.150 g) of Example 8 in methanol (3.0 ml), and the mixture was stirred at room temperature for 16 hours. Water was added, and the mixture was extracted with ethyl acetate. The organic layer was washed with saturated aqueous sodium chloride, dried over MgSO$_4$, filtered, and evaporated under reduced pressure to remove the solvent. The resulting crude product was purified by column chromatography (neutral OH SiO$_2$, methanol/chloroform=1/50 to 1/10) and then recrystallized (ethyl acetate-hexane) to give 0.113 g of the titled compound (Compound 93) as a colorless powder.

Melting point: 167.5° C. to 169.5° C.

Example 10

N-[(R)-1-[5-(3-Amino-phenoxy)-4-ethyl-4H-[1,2,4]triazol-3-yl]-ethyl]-3,4-dichlorobenzenesulfonamide (Compound 82)

[Formula 37]

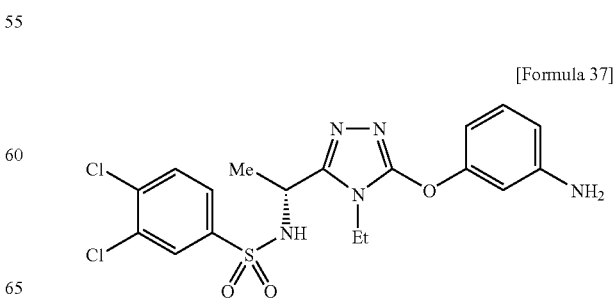

3-[5-((R)-1-Amino-ethyl)-4-ethyl-4H-[1,2,4]triazol-3-yloxy]-phenyl amine

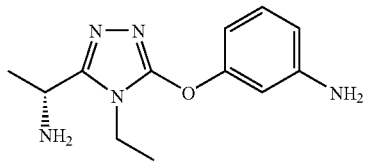

[Formula 38]

(1) Starting from 3-aminophenol in place of 4-fluorophenol, the same procedure as used in Example 1-(7) was repeated to give the titled compound (brown oily substance, yield 99%).

$^1$H NMR (600 MHz, CDCl$_3$) δ ppm; 1.37 (t, J=7.1 Hz, 3H), 1.58 (d, J=6.9 Hz, 3H), 3.96-4.05 (m, 2H), 4.15 (q, J=6.7 Hz, 1H), 6.45-6.50 (m, 1H), 6.62-6.67 (m, 1H), 6.71-6.75 (m, 1H), 7.11 (t, J=8.0 Hz, 1H)

N-[(R)-1-[5-(3-Amino-phenoxy)-4-ethyl-4H-[1,2,4]triazol-3-yl]-ethyl]-3,4-dichlorobenzenesulfonamide (Compound 82)

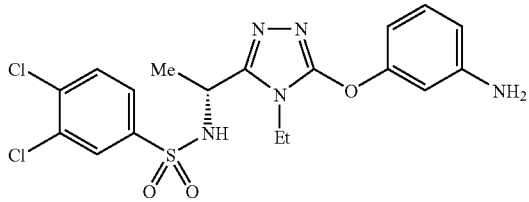

[Formula 39]

(2) Triethylamine (4.16 ml) and 3,4-dichlorobenzenesulfonyl chloride (3.73 g) were added to a solution of the compound (3.69 g) of Example 10-(1) in THF (15 ml), and the mixture was stirred at room temperature overnight. The reaction solution was concentrated, and the resulting crude product was purified by column chromatography (NHSiO$_2$, methanol/chloroform) and recrystallized (ethyl acetate/hexane) to give 3.60 g of the titled compound (Compound 82) (colorless powdered compound).

Melting point: 142.0° C. to 145.0° C.

Example 11

3,4-Dichloro-N-[(R)-1-[4-ethyl-5-(3-pyrrol-1-phenoxy)-4H-[1,2,4]triazol-3-yl]-ethyl]-benzenesulfonamide (Compound 86)

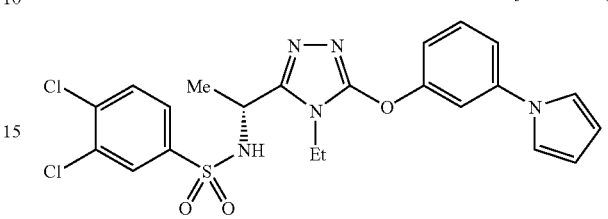

[Formula 40]

To a solution of the compound (700 mg) of Example 10 in AcOH (4.6 ml), 2,5-dimethoxy-tetrahydrofuran (375 μl) was added, and the mixture was stirred at 130° C. for 30 minutes. The reaction solution was cooled to room temperature and concentrated under reduced pressure. Thereafter, water was added, and the mixture was extracted with methanol/chloroform (1/4). Then, the organic layer was washed with saturated aqueous sodium chloride, dried over MgSO$_4$, filtered, and evaporated under reduced pressure to remove the solvent. The resulting residue was purified by column chromatography (acidic OH SiO$_2$, ethyl acetate/hexane=33-100%, methanol/chloroform=5%) and then recrystallized (ethyl acetate-hexane) to give the titled compound (Compound 86) (173 mg, colorless powdered compound).

Melting point: 176.0° C. to 177.0° C.

Example 12

3,4-Dichloro-N-[(R)-1-[4-ethyl-5-(3-formylaminophenoxy)-4H-[1,2,4]triazol-3-yl]-ethyl]-benzenesulfonamide (Compound 90)

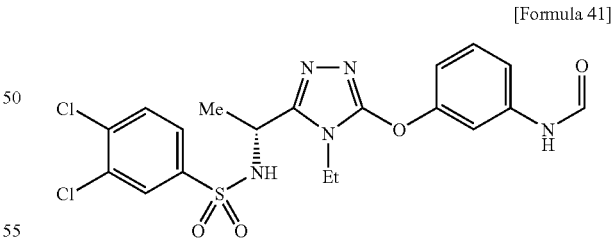

[Formula 41]

A mixture of the compound (300 mg) obtained in Example 10-(2) and ethyl formate (1.1 ml) was stirred at 105° C. for 24 hours. The reaction solution was cooled to room temperature and concentrated under reduced pressure. The resulting crude product was purified by column chromatography (acidic OH SiO$_2$, ethyl acetate/hexane=50-100%, methanol/chloroform=5%) and then recrystallized (ethyl acetate-hexane) to give the titled compound (Compound 90) (81 mg, colorless powder)

Melting point: 168.0° C. to 170.0° C. .

Example 13

3,4-Dichloro-N-[(R)-1-[4-ethyl-5-(3-ureido-phenoxy)-4H-[1,2,4]triazol-3-yl]-ethyl]-benzenesulfonamide (Compound 91)

[Formula 42]

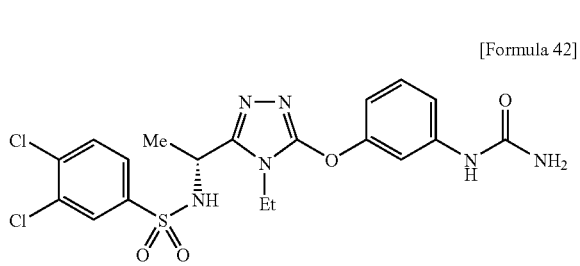

A mixture of the compound (300 mg) obtained in Example 10-(2), potassium cyanate (65 mg), AcOH (1.0 ml), and water (0.5 ml) was stirred at room temperature for one hour. Water was added, and the mixture was extracted with methanol/chloroform (1/4). The organic layer was dried over MgSO$_4$, filtered, and evaporated to remove the solvent. The resulting crude product was purified by column chromatography (acidic OH SiO$_2$, ethyl acetate/hexane=50-99%, methanol/chloroform=0-3%) and then recrystallized (ethyl acetate-hexane) to give the titled compound (Compound 91) (273 mg, colorless powder).

Melting point: 137.0° C. to 138.0° C.

Example 14

3,4-Dichloro-N-((R)-1-[5-[3-(3,3-dimethylureido)-phenoxy]-4-ethyl-4H-[1,2,4]triazol-3-yl]-ethyl)-benzenesulfonamide (Compound 97)

[Formula 43]

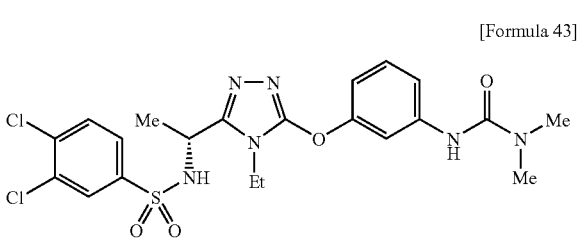

Dimethylcarbamyl chloride (146 μl) was added to a solution of the compound (300 mg) of Example 10-(2) and triethylamine (368 μl) in chloroform (1.1 ml), and the mixture was stirred at room temperature for three hours. The reaction solution was concentrated, and the resulting crude product was purified by column chromatography (neutral OH SiO$_2$, ethyl acetate/hexane=50-99%, methanol/chloroform=0-3%) and then recrystallized (ethyl acetate-hexane) to give the titled compound (Compound 97) (93 mg, colorless powder).

Melting point: 158.0° C. to 159.0° C.

Example 15

3,4-Dichloro-N-((R)-1-[4-ethyl-5-[3-(3-ethylureido)-phenoxy]-4H-[1,2,4]triazol-3-yl]-ethyl)-benzenesulfonamide (Comound 92)

[Formula 44]

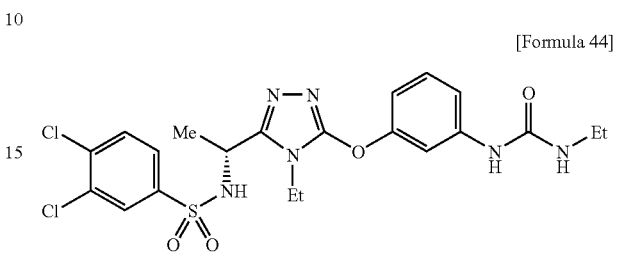

Ethyl isocyanate (63 μl) was added to a solution of the compound (300 mg) of Example 10-(2) in chloroform (1.1 ml), and the mixture was stirred at room temperature for one hour. The reaction solution was concentrated, and the resulting crude product was purified by column chromatography (neutral OH SiO$_2$, ethyl acetate/hexane=50-99%, methanol/chloroform=0-3%) and then recrystallized (ethyl acetate-hexane) to give the titled compound (Compound 92) (228 mg, colorless powder).

Melting point; 118.0° C. to 120.0° C.

Example 16

3,4-Dichloro-N-[(R)-1-[4-ethyl-5-(3-methanesulfonylamino-phenoxy)-4H-[1,2,4]triazol-3-yl]-ethyl]-benzenesulfonamide (Compound 102)

[Formula 45]

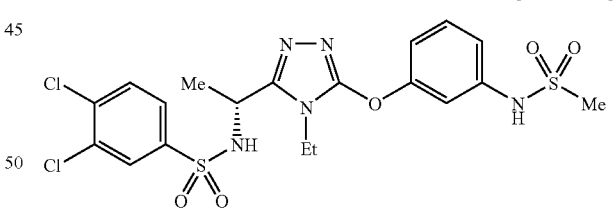

Methanesulfonyl chloride (114 mg) was added to a solution of the compound (300 mg) of Example 10-(2) in pyridine (1.32 ml), and the mixture was stirred at room temperature for three hours. Hydrochloric acid (1.0 N) was added, and the mixture was extracted with methanol/chloroform (1/4). The organic layer was dried over Na$_2$SO$_4$, filtered, and concentrated, and the resulting crude product was purified by column chromatography (neutral OH SiO$_2$, ethyl acetate/hexane=50-99%, methanol/chloroform=0-5%) and then recrystallized (ethyl acetate-hexane) to give the titled compound (Compound 102) (281 mg, colorless powder).

Melting point: 117.0° C. to 118.0° C.

Example 17

3,4-Dichloro-N-[(R)-1-[4-ethyl-5-(3-hydroxyphenoxy)-4H-[1,2,4]triazol-3-yl]-ethyl]-benzenesulfonamide (Compound 114)

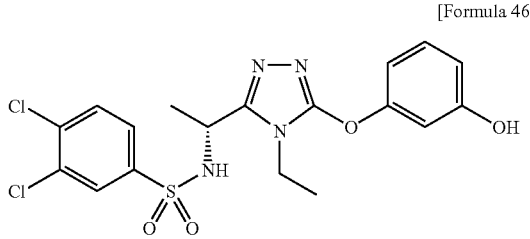
[Formula 46]

(R)-1-[5-(3-Benzyloxy-phenoxy)-4-ethyl-4H-[1,2,4]triazol-3-yl]-ethylamine

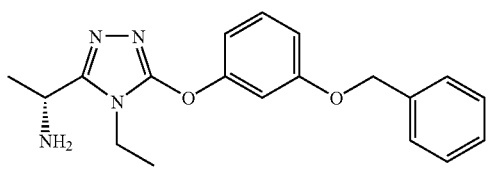
[Formula 47]

(1) Starting from 3-benzyloxyphenol in place of 4-fluorophenol, the same procedure as used in Example 1-(7) was repeated to give the titled compound (brown oily substance, yield 84%).

$^1$H NMR (600 MHz, CDCl$_3$), δ ppm: 1.39 (t, J=7.3 Hz, 3H), 1.60 (d, J=6.4 Hz, 3H), 3.96-4.09 (m, 2H), 4.17 (q, J=6.9 Hz, 1H), 5.06 (s, 2H), 6.79-6.84 (m, 1H), 6.91-6.96 (m, 1H), 7.04-7.08 (m, 1H), 7.22-7.46 (m, 6H)

3-[5-((R)-1-Aminoethyl)-4-ethyl-4H-[1,2,4]triazol-3-yloxy]-phenol

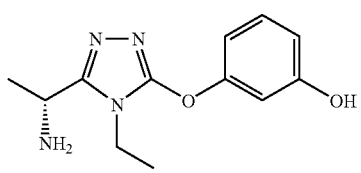
[Formula 48]

(2) A suspension of the compound (1.5 g) of Example 17-(1) and Pd(OH)$_2$/C (150 mg, Pd 20 wt %) in methanol (4.0 ml) was stirred at room temperature for a day under a hydrogen atmosphere (approximately 1 atmospheric pressure). The reaction mixture was filtered through celite and evaporated to remove the solvent. The resulting crude product was purified by column chromatography (NH SiO$_2$, methanol/chloroform=0-25%) to give the titled compound (gray amorphous substance, 323 mg).

$^1$H NMR (600 MHz, DMSO-d6), δ ppm: 1.23 (t, J=7.3 Hz, 3H), 1.54 (d, J=6.9 Hz, 3H), 3.82-4.09 (m, 2H), 4.60 (q, J=6.0 Hz, 1H), 6.61-6.69 (m, 2H), 6.70-6.77 (m, 1H), 7.14-7.21 (m, 1H), 8.28-9.11 (m, 2H), 9.43-10.55 (m, 1H)

3,4-Dichloro-N-[(R)-1-[4-ethyl-5-(3-hydroxyphenoxy)-4H-[1,2,4]triazol-3-yl]-ethyl]-benzenesulfonamide (Compound 114)

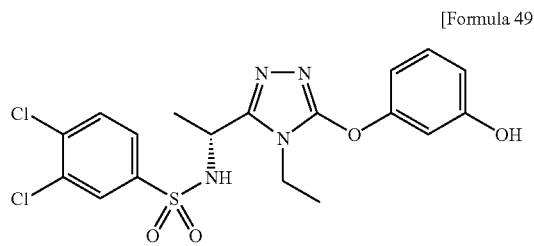
[Formula 49]

(3) Triethylamine (0.225 ml) and 3,4-dichlorobenzenesulfonyl chloride (198 mg) were added at room temperature to a solution of the compound (200 mg) of Example 17-(2) in THF (2.0 ml), and the mixture was stirred at room temperature for 12 hours. The mixture was evaporated to remove the solvent, and KOH (104 mg), ethanol (4.0 ml), and water (4.0 ml) were added to the resulting crude product. The mixture was stirred at 120° C. for 40 minutes, and then cooled to room temperature. HCl (1.0 N) was added, and the mixture was extracted with a mixed solution of methanol/chloroform (methanol/chloroform=1/4), dried (MgSO$_4$), filtered, and evaporated under reduced pressure to remove the solvent. The resulting crude product was purified by column chromatography (acidic OH SiO$_2$, ethyl acetate/hexane=30-70%) and then recrystallized (methanol/chloroform/hexane) to give 37 mg of the titled compound (Compound 114) as a colorless powder.

Melting point: 185.0° C. to 186.0° C.

Example 18

3-[5-[(R)-1-(3,4-Dichlorobenzenesulfonylamino)-ethyl]-4-ethyl-4H-[1,2,4]triazol-3-yloxy]benzoic acid t-butyl ester (Compound 118)

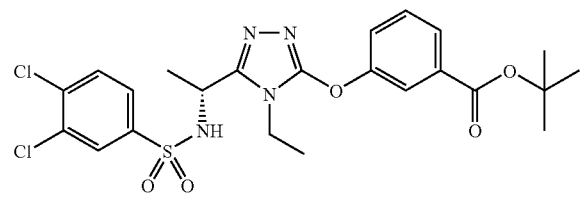
[Formula 50]

3-[5-((R)-1-Aminoethyl)-4-ethyl-4H-[1,2,4]triazol-3-yloxy]-benzoic acid t-butyl ester

[Formula 51]

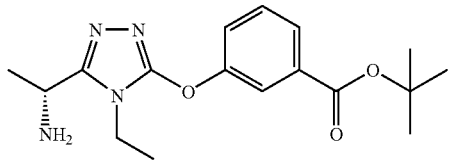

(1) Starting from 3-hydroxybenzoic acid t-butyl ester in place of 4-fluorophenol, the same procedure as used in Example 1-(7) was repeated to give the titled compound (colorless and oily, yield 24%).

$^1$H NMR (600 MHz, CDCl$_3$), b ppm: 1.43 (t, J=7.1 Hz, 3H), 1.58-1.62 (m, 12H), 4.01-4.13 (m, 2H), 4.18 (q, J=6.6 Hz, 1H), 7.42-7.46 (m, 1H), 7.61-7.65 (m, 1H), 7.82-7.85 (m, 1H), 7.87-7.91 (m, 1H)

3-[5-[(R)-1-(3,4-Dichlorobenzenesulfonyamino)-ethyl]-4-ethyl-4H-[1,2,4]triazol-3-yloxy]benzoic acid t-butyl ester (Compound 118)

[Formula 52]

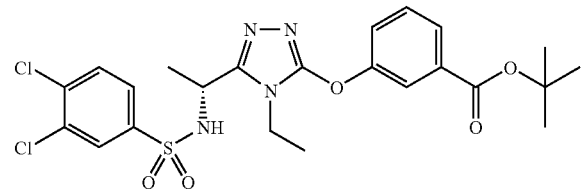

(2) Starting from the compound obtained in Example 18-(1), the same procedure as used in Example 1-(8) was repeated to give the titled compound (colorless powder, yield 68%).

$^1$H NMR (600 MHz, CDCl$_3$), δ ppm: 1.38 (t, J=7.3 Hz, 3H), 1.51 (d, J=6.9 Hz, 3H), 1.58 (s, 9H), 3.93-4.01 (m, 2H), 4.29-4.35 (m, 1H), 7.43-7.48 (m, 1H), 7.50-7.60 (m, 3H), 7.64-7.69 (m, 1H), 7.81-7.89 (m, 2H), 7.90-7.94 (m, 1H)

Example 19

3-[5-[(R)-1-(3,4-Dichlorobenzenesulfonylamino)-ethyl]-4-ethyl-4H-[1,2,4]triazol-3-yloxy]-benzoic acid (Compound 113)

[Formula 53]

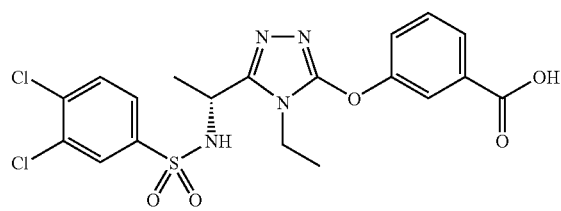

Trifluoroacetic acid (0.12 ml) was added to a solution of the compound (260 mg) of Example 18 in chloroform (12.0 ml), and the mixture was stirred at room temperature for five days. The mixture was evaporated to remove the solvent, and the resulting crude product was purified by column chromatography (neutral OH SiO$_2$, ethyl acetate/hexane=50-99%, methanol/chloroform=0-20%) and then recrystallized (methanol/chloroform/hexane) to give the titled compound (Compound 113) (101 mg, colorless powder).

Melting point: 183.0° C. to 185.0° C.

Example 20

N-[(R)-1-[4-Ethyl-5-(4-fluorophenoxy)-4H-[1,2,4]triazol-3-yl]-ethyl]-4-methoxybenzenesulfonamide (Compound 175)

[Formula 54]

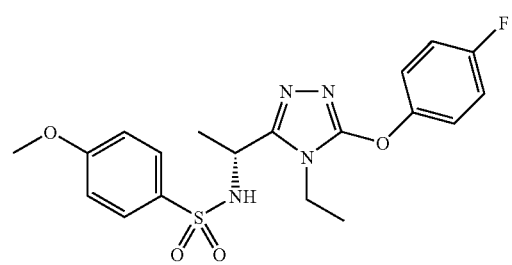

To a solution of the compound (12.5 mg) of Example 1-(7) in THF (0.3 ml), triethylamine (25 µl) was added, and then a solution of 4-methoxybenzenesulfonylchloride (15.5 mg) in THF (0.3 ml) was added. The mixture was stirred at room temperature for two hours. PSA (product name: VARIAN Inc. polymer supported amine, 1.4 meq/g) (75 µl) was added to the reaction mixture, and the mixture was stirred at room temperature for 12 hours. The insoluble matter was filtered off, and the resulting residue was evaporated to remove the solvent. The resulting crude product was purified by silica-gel column chromatography (acidic OH SiO$_2$, ethyl acetate/hexane=50-100%, methanol/chloroform=10%) to give 10.7 mg of the titled compound (Compound 175) as a colorless powder.

APCI MS (M−H)−: 419, APCI MS (M+H)+: 421

Example 21

3,4-Dichloro-N-((R)-1-[4-ethyl-5-[3-(4-methyl-piperazin-1-yl)-phenoxy]-4H-[1,2,4]triazol-3-yl]-ethyl)-benzenesulfonamide (Compound 45)

[Formula 55]

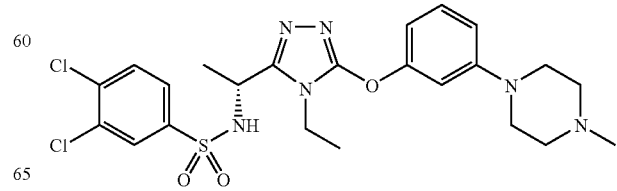

(1) The following compound was obtained by the same procedure as used in Example 1-(7) (the procedure will be specifically described below).

(R)-1-[4-Ethyl-5-[3-(4-methyl-piperazin-1-yl)-phenoxy]-4H-[1,2,4]triazol-3-yl]-ethylamine

[Formula 56]

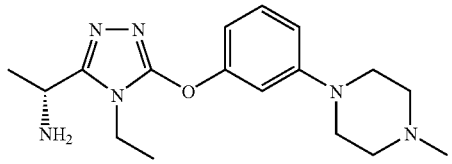

In a pressure-resistant screw cap test tube, N,N'-dimethylpropyleneurea (DMPU) (4.0 ml), 3-(4-methyl-piperazin-1-yl)-phenol (500 mg), and cesium carbonate (2.21 g) were added to the compound (750 mg) obtained in Example 1-(6), and the mixture was stirred at 160° C. for three hours. The mixture was brought to room temperature, and saturated aqueous sodium chloride was added. The mixture was extracted with ethyl acetate. The organic layer was dried over anhydrous sodium sulfate, filtered, and evaporated under reduced pressure to remove the solvent. The resulting crude product was purified by column chromatography (NH SiO$_2$, chloroform/methanol=50/1-30/1) to give the titled compound (yellow oily compound, 427 mg).

$^1$H NMR (600 MHz, CDCl$_3$) δ ppm: 1.40 (t, J=7.3 Hz, 3H), 1.59 (d, J=6.9 Hz, 3H), 2.35 (s, 3H), 2.52-2.61 (m, 4H), 3.22-3.27 (m, 4H), 3.97-4.08 (m, 2H), 4.15 (q, J=6.9 Hz, 1H), 6.71-6.80 (m, 2H), 6.99-7.03 (m, 1H), 7.20-7.25 (m, 1H)

(2) The following compound was obtained by the same procedure as used in Example 1-(8) (the procedure will be specifically described below).

3,4-Dichloro-N-((R)-1-[4-ethyl-5-[3-(4-methyl-piperazin-1-yl)-phenoxy]-4H-[1,2,4]triazol-3-yl]-ethyl)-benzenesulfonamide (Compound 45)

[Formula 57]

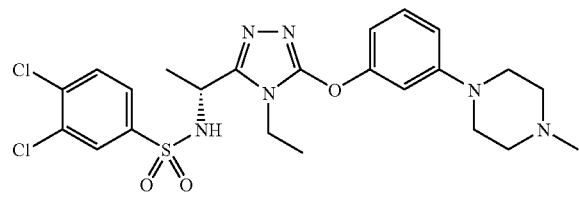

Triethylamine (0.41 mL) and 3,4-dichlorobenzenesulfonyl chloride (0.232 mL) were added at room temperature to a solution of the compound (427 mg) of Example 21-(1) in THF (8.0 mL), and the mixture was stirred at room temperature overnight. The reaction mixture was concentrated, and the resulting residue was purified by column chromatography (NH SiO$_2$, chloroform/methanol=50/1-30/1) and then recrystallized (ethyl acetate-hexane) to give 280 mg of the titled compound (Compound 45) as a colorless powder.

Melting point: 194.0° C. to 196.0° C.

Example 22

3,4-Dichloro-N-[(R)-1-[4-ethyl-5-(1H-indol-6-yloxy)-4H-1,2,4]triazol-3-yl]-ethyl]-benzenesulfonamide (Compound 64)

[Formula 58]

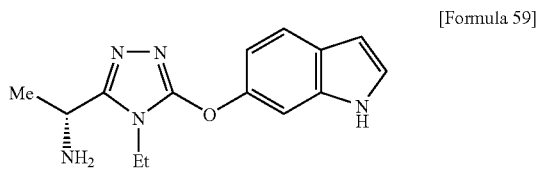

(1) The following compound was obtained by the same procedure as used in Example 1-(7) (the procedure will be specifically described below).

(R)-1-[4-Ethyl-5-(1H-indol-6-yloxy)-4H-[1,2,4]triazol-3-yl]-ethylamine

[Formula 59]

In a pressure-resistant screw cap test tube, N,N'-dimethylpropyleneurea (DMPU) (5.0 ml), 1H-indol-6-ol (601 mg), and cesium carbonate (2.94 g) were added to the compound (1.00 g) obtained in Example 1-(6), and the mixture was stirred at 200° C. for one hour and then brought to room temperature. Saturated aqueous sodium chloride was added, and the mixture was extracted with ethyl acetate. The organic layer was dried (MgSO$_4$), filtered, and evaporated under reduced pressure to remove the solvent. Then, the resulting crude product was purified by column chromatography (NH SiO$_2$, chloroform/methanol=50/1-30/1) to give the titled compound (yellow oily compound, 750 mg).

$^1$H NMR (600 MHz, CDCl$_3$) δ ppm: 1.42 (t, J=7.1 Hz, 3H), 1.58 (d, J=6.4 Hz, 3H), 3.98-4.10 (m, 2H), 4.15 (q, J=6.7 Hz, 1H), 6.30-6.39 (m, 1H), 6.87-7.00 (m, 2H), 7.39-7.52 (m, 2H), 9.55 (s, 1H)

(2) The following compound was obtained by the same procedure as used in Example 1-(8) (the procedure will be specifically described below).

3,4-Dichloro-N-[(R)-1-[4-ethyl-5-(1H-indol-6-yloxy)-4H-1,2,4]triazol-3-yl]-ethyl]-benzenesulfonamide (Compound64)

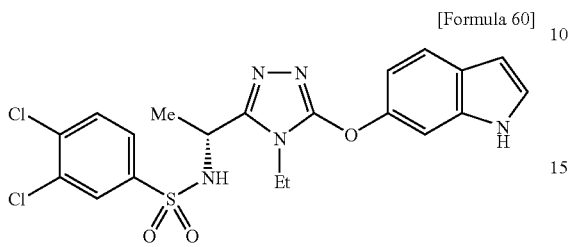

[Formula 60]

Triethylamine (0.77 mL) and 3,4-dichlorobenzenesulfonyl chloride (1.02 g) were added at room temperature to the compound (748 mg) of Example 22-(1) in THF (10.0 mL), and the mixture was stirred at room temperature overnight. The reaction mixture was concentrated, and the resulting residue was purified by column chromatography (NH SiO$_2$, chloroform/methanol=30/1) and then recrystallized (CHCl$_3$/MeOH/hexane) to give 815 mg of the titled compound (Compound 64) as a colorless powder.

Melting point: 223.0° C. to 224.0° C.

Example 23

N-[(S)-2-Benzyloxy-1-[4-ethyl-5-(4-fluorophenoxy)-4H-[1,2,4]triazol-3-yl]-ethyl]-3,4-dichlorobenzenesulfonamide (Compound 695)

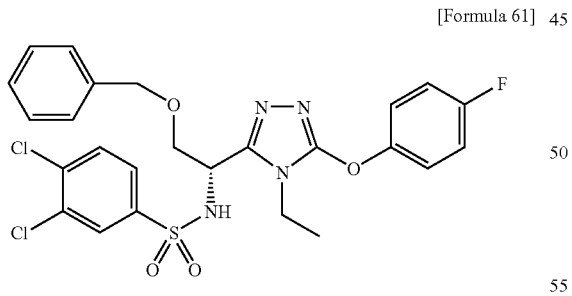

[Formula 61]

Starting from (R)-2-amino-3-benzyloxy-propionic acid methyl ester in place of N-(t-butoxycarbonyl)-D-alanine methyl ester used in Example 1-(1), the same procedure as used in Example 1 was repeated to give the titled compound (Compound 695) as a colorless powder.

$^1$H NMR (200 MHz, CDCl$_3$) δ ppm: 1.31 (t, J=7.3 Hz, 3H), 3.65-4.03 (m, 4H), 4.35 (s, 2H), 4.67 (q, J=7.9 Hz, 1H), 7.03-7.39 (m, 10H), 7.68 (dd, J=8.8, 2.2 Hz, 1H), 7.93 (d, J=2.2 Hz, 1H)

Example 24

3,4-Dichloro-N-[(S)-1-[4-ethyl-5-(4-fluorophenoxy)-4H-[1,2,4]triazol-3-yl]-2-hydroxyethyl]-benzenesulfonamide (Compound 696)

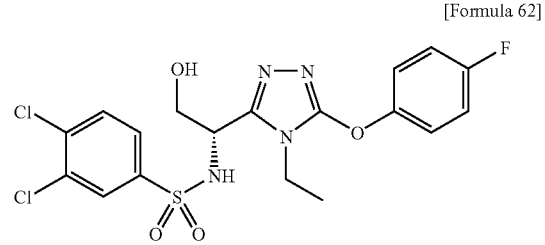

[Formula 62]

AlCl$_3$ (49 mg) and PhNMe$_2$ (148 mg) were added to a solution of the compound (69 mg) of Example 23 in CH$_2$Cl$_2$ (2.0 ml), and the mixture was stirred at room temperature for one hour. Then, AcOEt was added, and the mixture was washed with 1N hydrochloric acid and thereafter with saturated aqueous sodium chloride. The organic layer was dried (Na$_2$SO$_4$), filtered, and evaporated under reduced pressure to remove the solvent. Then, the resulting crude product was purified by column chromatography (OH SiO$_2$, AcOEt/hexane=2/1) to give 54 mg of the titled compound (Compound 696) as a colorless powder.

$^1$H NMR (200 MHz, CDCl$_3$) δ ppm: 1.41 (t, J=7.5 Hz, 3H), 3.62 (dd, J=4.8, 11.8 Hz, 1H), 3.88 (dd, J=4.8, 11.8 Hz, 1H), 4.05 (q, J=7.5 Hz, 2H), 4.51-4.60 (m, 1H), 7.04-7.13 (m, 2H), 7.23-7.31 (m, 3H), 7.53 (d, J=8.8 Hz, 1H), 7.70 (dd, J=8.8, 2.2 Hz, 1H), 7.93 (d, J=2.2 Hz, 1H)

Example 25

3,4-Dichloro-N-[(S)-1-[4-ethyl-5-(4-fluorophenoxy)-4H-[1,2,4]triazol-3-yl]-2-fluoroethyl)]-benzenesulfonamide (Compound 689)

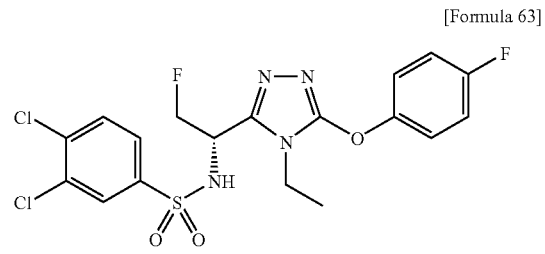

[Formula 63]

A solution of diethylaminosulfurtrifluoride (DAST) (16 mg) in CH$_2$Cl$_2$ (1.0 ml) was added at 0° C. to a solution of the compound (45 mg) of Example 24 in CH$_2$Cl$_2$ (2.0 ml), and the mixture was stirred at the same temperature for one hour. The reaction solution was added to saturated aqueous sodium bicarbonate, and the mixture was extracted with AcOEt. The organic layer was dried (Na$_2$SO$_4$) and filtered evaporated under reduced pressure to remove the solvent. The resulting crude product was purified by column chromatography (OH SiO$_2$, AcOEt/hexane=30-50%) to give 6 mg of the titled compound (Compound 696) as a pale yellow powder.

¹H NMR (200 MHz, CDCl₃) δ ppm 1.39 (t, J=7.5 Hz, 3H), 4.01 (q, J=7.5 Hz, 2H), 4.45-4.86 (m, 3H), 6.98 (br, 1H), 7.05-7.36 (m, 4H), 7.48 (d, J=8.5 Hz, 1H), 7.69 (dd, J=8.5, 2.2 Hz, 1H), 7.93 (d, J=2.2 Hz, 1H)

Example 26

3,4-Dichloro-N-[1-[4-ethyl-5-(4-fluorophenoxy)-4H-[1,2,4]triazol-3-yl]-2,2,2-trifluoroethyl]-benzenesulfonamide (Compound 687)

[Formula 64]

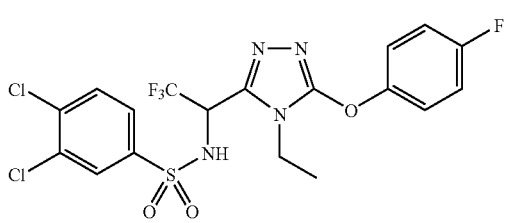

4-Ethyl-5-mercapto-4H-[1,2,4]triazol-3-carboxylic acid ethyl ester

[Formula 65]

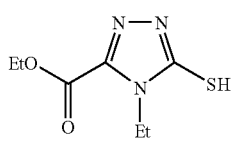

(1) To a solution of diethyl formate (48.64 g) in MeOH (100 ml), a solution of hydrazine monohydrate (16.33 g) in MeOH (100 ml) was added dropwise at −5° C. over 1.5 hours, and ethylisothiocyanate (29.00 g) was added at the same temperature. The mixture was warmed to room temperature and stirred overnight. The insoluble matter was filtered off, and the resulting residue was evaporated to remove the solvent. The resulting solid was washed with a mixed solution of hexane/AcOEt (1/1) and dried, and the resulting white powder (55.30 g) was added to an aqueous solution (228 ml) of NaOH (913 mg). The mixture was stirred at 70° C. for four hours, at room temperature overnight, and then at 100° C. for seven hours. The reaction mixture was concentrated to approximately ⅓, and then a saturated aqueous NH₄Cl solution (300 ml) was added. The resulting white precipitate was filtered and dried to give the titled compound (15.06 g) as a colorless powder.

¹H NMR (200 MHz, CDCl₃) δ ppm 1.38 (t, J=6.6 Hz, 3H), 1.45 (t, J=6.5 Hz, 3H), 4.40-4.57 (m, 4H), 11.58-11.84 (m, 1H)

4-Ethyl-5-methanesulfanyl-4H-[1,2,4]triazol-3-carboxylic acid ethyl ester

[Formula 66]

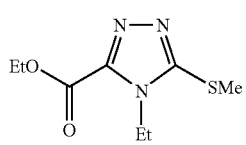

(2) Starting from the compound obtained in Example 26-(1), the same procedure as used in Example 1-(4) was repeated to give the titled compound as a light yellow solid (yield 84%).

¹H NMR (200 MHz, CDCl₃) δ ppm 1.31-1.50 (m, 6H), 2.80 (s, 3H), 4.31 (q, J=7.2 Hz, 2H), 4.47 (q, J=7.1 Hz, 2H)

4-Ethyl-5-methanesulfonyl-4H-[1,2,4]triazol-3-carboxylic acid ethyl ester

[Formula 67]

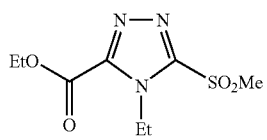

(3) Starting from the compound obtained in Example 26-(2), the same procedure as used in Example 1-(5) was repeated to give the titled compound as a light yellow solid (yield 84%).

¹H NMR (200 MHz, CDCl₃) δ ppm 1.48 (t, J=7.1 Hz, 3H), 1.53 (t, J=7.2 Hz, 3H), 3.60 (s, 3H), 4.53 (q, J=7.1 Hz, 2H), 4.75 (q, J=7.2 Hz, 2H)

4-Ethyl-5-(4-fluorophenoxy)-4H-[1,2,4]triazol-3-carboxylic acid ethyl ester

[Formula 68]

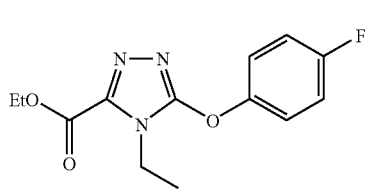

(4) To a suspension of NaH (1.236 g, oil free) in THF (68 ml), 4-fluorophenol (4.62 g) was added at 0° C., and the mixture was warmed to room temperature and stirred for 30 minutes. The reaction mixture was cooled to 0° C., and a solution of the compound (8.49 g) of Example 26-(3) in THF (20 ml) was added. The mixture was stirred at room temperature for 30 minutes and thereafter at 70° C. for 1.5 hours. The temperature was cooled to room temperature, and then the reaction mixture was added to a saturated aqueous NH₄Cl solution (500 ml). The mixture was extracted with AcOEt (500 ml) and washed with saturated aqueous sodium chloride. The organic layer was dried (MgSO₄), filtered, and concentrated, and the resulting crude product was purified by column chromatography (OH acid SiO$_2$, AcOEt/hexane=10-99%) to give the titled compound (5.144 g, light yellow solid).

$^1$H NMR (200 MHz, CDCl$_3$) δ ppm 1.35-1.52 (m, 6H), 4.36 (q, J=7.2 Hz, 2H), 4.48 (q, J=7.2 Hz, 2H), 7.02-7.18 (m, 2H), 7.28-7.48 (m, 2H)

4-Ethyl-5-(4-fluorophenoxy)-4H-[1,2,4]triazol-3-carbaldehyde

[Formula 69]

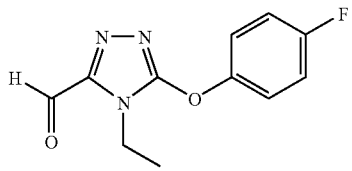

(5) DiBAl-H (0.99 M, toluene solution, 36.1 ml) was added at −5° C. to a solution of the compound (5.00 g) of Example 26-(4) in THF (50 ml), and the mixture was stirred at the same temperature for three hours. Then, 1N-hydrochloric acid was added to the reaction solution, and the mixture was extracted with AcOEt. The organic layer was washed with saturated aqueous sodium chloride, dried (MgSO$_4$), filtered, and concentrated, and the resulting crude product was purified by column chromatography (neutral OH SiO$_2$, AcOEt/hexane=5-40%) to give the titled compound (2.22 g, colorless and oily).

$^1$H NMR (600 MHz, CDCl$_3$) δ ppm ppm 1.44 (t, J=7.3 Hz, 3H), 4.37 (J=7.3 Hz, 2H), 7.10-7.17 (m, 2H), 7.36-7.40 (m, 2H)

4-Methylbenzene sulfonic acid 4-ethyl-5-(4-fluorophenoxy)-4H-[1,2,4]triazol-3-ylmethyleneamide

[Formula 70]

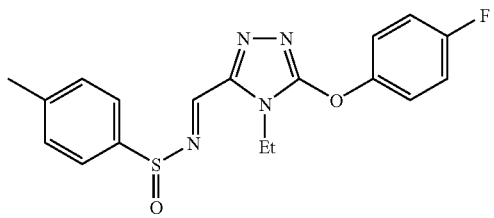

(6) A solution of the compound (1.00 g) obtained in Example 26-(5), 4-methylbenzene sulfonic acid amide (660 mg), and cesium carbonate (1.39 g) in chloroform (21 ml) was stirred at 45° C. for nine hours. The reaction solution was filtered through celite, and the filtrate was concentrated. The resulting residue was purified by silica-gel chromatography (neutral OH silica gel, elution solvent: AcOEt/hexane 0-30%) to give the titled compound (630 mg) as a pale yellow solid.

$^1$H NMR (600 MHz, CDCl$_3$) δ ppm 1.30 (t, J=7.1 Hz, 3H), 2.42 (s, 3H), 4.27-4.43 (m, 2H), 7.07-7.15 (m, 2H), 7.31-7.39 (m, 4H), 7.57-7.62 (m, 2H), 8.85 (s, 1H)

N-[1-[4-Ethyl-5-(4-fluorophenoxy)-4H-[1,2,4]triazol-3-yl]2,2,2-trifluoroethyl]-4-methylbenzamide

[Formula 71]

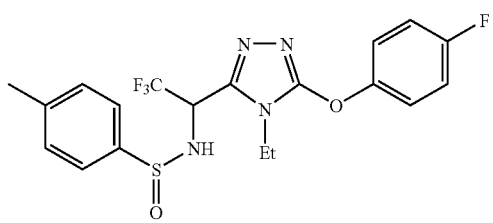

(7) Under an argon atmosphere, a solution of (trifluoromethyl)trimethyl silane (120 μl) in THF (5.0 ml) was added at −35° C. to a suspension of the compound (200 mg) of Example 26-(6) and tetramethylfluoride (60 mg) in THF (5.0 ml), and the mixture was stirred at the same temperature for an hour and a half. A further portion of tetramethylfluoride (60 mg) and thereafter a further portion of (trifluoromethyl)trimethyl silane (60 mg) were added to the reaction solution at the same temperature, and the mixture was stirred at the same temperature for two hours and warmed to −10° C., and a saturated aqueous ammonium chloride solution was added, and the aqueous layer was extracted with ethyl acetate. The and the filtrate was concentrated. The resulting residue was purified by silica-gel column chromatography (neutral —OH silica gel, AcOEt/hexane 0-40%) to give the titled compound (219 mg) as a pale yellow oily substance.

$^1$H NMR (600 MHz, CDCl$_3$) δ ppm 1.32 (t, J=7.3 Hz, 3H), 2.40 (s, 3H), 3.80-3.87 (m, 2H), 4.86-4.92 (m, 1H), 5.59 (d, J=8.3 Hz, 1H), 7.06-7.13 (m, 2H), 7.27-7.31 (m, 2H), 7.32-7.37 (m, 2H), 7.53-7.59 (m, 2H)

1-[4-Ethyl-5-(4-fluorophenoxy)-4H-[1,2,4]triazol-3-yl]-2,2,2,-trifluoroethylamine

[Formula 72]

(8) HCl (4N, dioxane solution, 1.25 ml) was added at room temperature to a solution of the compound (215 mg) of Example 26-(7) in methanol (5.0 ml), and the mixture was stirred at 85° C. for two hours. The reaction solution was concentrated, and the resulting residue was purified by silica-gel column chromatography (NH SiO$_2$, AcOEt/hexane 0-50%) to give the titled compound (82 mg) as a colorless oily substance.

(600 MHz, CDCl$_3$) δ ppm: 1.43 (t, J=7.3 Hz, 3H), 3.97-4.11 (m, 2H), 4.47-4.54 (m, 1H), 7.06-7.12 (m, 2H), 7.35-7.40 (m, 2H)

3,4-Dichloro-N-[1-[4-ethyl-5-(4-fluorophenoxy)-4H-[1,2,4]triazol-3-yl]-2,2,2-trifluoroethyl]-benzenesulfonamide (Compound 687)

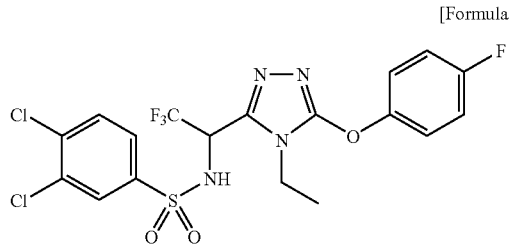

[Formula 73]

(9) Starting from the compound (79 mg) obtained in Example 26-(8), the same procedure as used in Example 1-(8) was repeated to give the titled compound (3 mg) as a light yellow oily substance.

(600 MHz, CDCl$_3$) δ ppm: 1.43 (t, J=7.1 Hz, 3H), 3.91-4.07 (m, 2H), 5.06-5.13 (m, 1H), 7.07-7.16 (m, 2H), 7.29-7.35 (m, 2H), 7.50-7.57 (m, 1H), 7.67-7.74 (m, 1H), 7.90 (s, 1H)

Example 27

N-((R)-1-[5-[3-(4-Acetylpiperazin-1-yl)-phenoxy]-4-ethyl-4H-[1,2,4]triazol-3-yl]-ethyl)-3,4-dichlorobenzenesulfonamide (Compound 697)

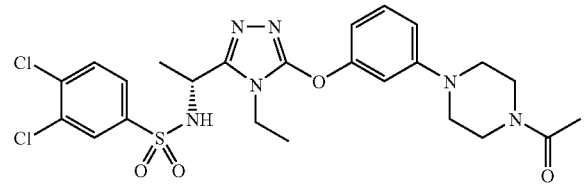

[Formula 74]

(R)-1-[4-Ethyl-5-(3-piperazin-1-yl-phenoxy)-4H-[1,2,4]triazol-3-yl]-ethylamine

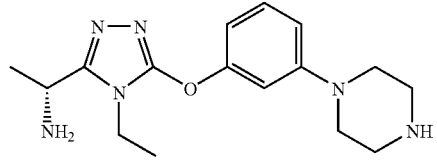

[Formula 75]

(1) In a pressure-resistant screw cap test tube, DMPU (10 ml), 3-piperazinylphenol (1.34 g), and Cs$_2$CO$_3$ (6.13 g) were added to the compound (2.08 g) obtained in Example 1-(6), and the mixture was stirred at 200° C. for 40 minutes. It was cooled to room temperature and then concentrated under reduced pressure, and the resulting crude product was purified by column chromatography (NH SiO$_2$, AcOEt to MeOH/CHCl$_3$=1/50) to give the titled compound (yellow oily compound, 1.17 g).

$^1$H NMR (600 MHz, CDCl$_3$) δ ppm: 1.40 (t, J=7.1 Hz, 3H), 1.59 (d, J=6.9 Hz, 3H), 2.98-3.04 (m, 4H), 3.14-3.19 (m, 4H), 3.97-4.09 (m, 2H), 4.13-4.18 (m, 1H), 6.70-6.80 (m, 2H), 6.97-7.03 (m, 1H), 7.21-7.26 (m, 1H)

1-(4-[3-[5-((R)-1-Aminoethyl)-4-ethyl-4H-[1,2,4]triazol-3-yloxy]-phenyl]-piperazin-1-yl)-ethanone

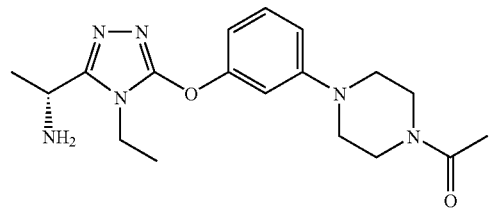

[Formula 76]

(2) AcCl (0.24 ml) was added at −30° C. to a solution of the compound (1.06 g) of Example 27-(1) and Et$_3$N (1.4 ml) in THF (20 ml), and the mixture was stirred at the same temperature for two hours. Then, the mixture was warmed to room temperature and then stirred for another five hours. The reaction mixture was concentrated, and the resulting crude product was purified by column chromatography (neutral OH SiO$_2$, MeOH/CHCl$_3$=1/5) to give a mixture (315 mg, colorless solid) of the titled compound and triethylamine hydrochloride.

$^1$H NMR (600 MHz, CDCl$_3$) δ ppm: 1.35 (t, J=7.3 Hz, 3H), 1.72 (d, J=6.4 Hz, 3H), 2.12 (s, 3H), 3.14-3.23 (m, 4H), 3.57-3.64 (m, 2H), 3.71-3.77 (m, 2H), 3.87-4.10 (m, 2H), 4.57-4.66 (m, 1H), 6.70-6.81 (m, 2H), 6.95-6.99 (m, 1H), 7.21-7.26 (m, 1H)

N-((R)-1-[5-[3-(4-Acetylpiperazin-1-yl)-phenoxy]-4-ethyl-4H-[1,2,4]triazol-3-yl]-ethyl)-3,4-dichlorobenzenesulfonamide (Compound 697)

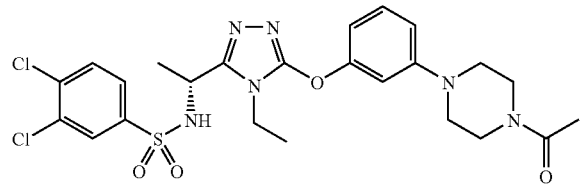

[Formula 77]

(3) Water was added to a mixture (307 mg) of 1-(4-[3-[5-((R)-1-aminoethyl)-4-ethyl-4H-[1,2,4]triazol-3-yloxy]-phenyl]-piperazin-1-yl)-ethanone obtained in Example 27-(2) and triethylamine hydrochloride, 3,4-dichlorobenzenesulfonyl chloride (0.13 ml), and K$_2$CO$_3$ (355 mg). The mixture was stirred at room temperature for 15 hours. The precipitated solid was filtered and purified by column chromatography (NH SiO$_2$, MeOH/CHCl$_3$=1/50) to give the titled compound (Compound 697) (117 mg, colorless syrup).

$^1$H NMR (600 MHz, CDCl$_3$) δ ppm: 1.38 (t, J=7.3 Hz, 3H), 1.52 (d, J=6.9 Hz, 3H), 2.14 (s, 3H), 3.14-3.27 (m, 4H), 3.56-3.64 (m, 2H), 3.72-3.80 (m, 2H), 3.88-4.01 (m, 2H), 4.58-4.68 (m, 1H), 5.98-6.06 (m, 1H), 6.72-6.82 (m, 2H), 6.95-7.01 (m, 1H), 7.25-7.30 (m, 1H), 7.51-7.57 (m, 1H), 7.65-7.73 (m, 1H), 7.89-7.97 (m, 1H)

Example 28

3,4-Dichloro-N-[(R)-1-[4-ethyl-5-(3-piperazin-1-yl-phenoxy)-4H-[1,2,4]triazol-3-yl]-ethyl]-benzene-sulfonamide (Compound 683)

[Formula 78]

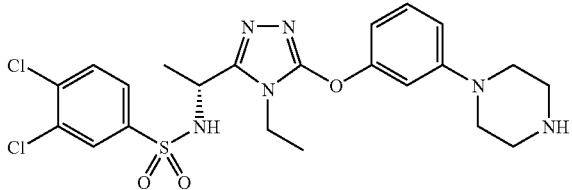

A mixture of the compound (107 mg) obtained in Example 27-(3), NaOH (105 mg), water (2.0 ml), and EtOH (4.0 ml) was stirred at 80° C. for one hour and then stirred at 100° C. for 18 hours. The mixture was cooled to room temperature and then extracted with AcOEt. The organic layer was washed with saturated aqueous sodium chloride, dried (MgSO$_4$), filtered, and concentrated. The resulting crude product was purified by column chromatography (NH SiO$_2$, MeOH/CHCl$_3$=1/30) and then recrystallized (AcOEt/hexane) to give the titled compound (Compound 683) (55 mg, colorless powder).

$^1$H NMR (600 MHz, DMSO-d6) δ ppm: 1.24 (t, J=7.3 Hz, 3H), 1.31 (d, J=6.9 Hz, 3H), 2.77-2.86 (m, 4H), 3.03-3.10 (m, 4H), 3.81-3.99 (m, 2H), 4.67-4.75 (m, 1H), 6.56-6.62 (m, 1H), 6.76-6.85 (m, 2H), 7.19-7.27 (m, 1H), 7.69-7.77 (m, 1H), 7.88 (d, J=8.7 Hz, 1H), 7.93-7.97 (m, 1H)

Melting point: 175.0° C. to 178.0° C.

The compounds shown in Table 1 were obtained using the corresponding starting compounds and the procedures shown in Examples 1 to 28.

The compounds obtained in the Examples above are also shown in Table 1 together with the other compounds.

Test Example 1

S1P$_1$ Binding Assay

Using a human Edg-1 (S1P$_1$) gene transferred HEK-293 cell strain membrane fraction, the Edg-1 (S1P$_1$) binding inhibiting action of the compounds of the present invention was determined in accordance with the method described in the literature (Science. 2002, 296: 346) (showing a binding of Kd=0.15 nM, Bmax=2.5 fmol/μg to [$^{33}$P]-S1P). The membrane fraction was obtained by treating the cells with a solubilizing buffer (1 mM Tris/HCl, pH 7.2) for 10 minutes on ice, centrifuging at 1000×g for 5 minutes to remove insoluble fractions, and then centrifuging at 40000×g for 30 minutes at 4° C. The resulting membrane fraction was dissolved in a binding buffer (20 mM Tris-HCl, pH 7.4, 100 mM NaCl, 15 mM NaF, 2 mM deoxypyridoxine, 4 mg/mL fatty acid-free BSA), and then [$^{33}$P]-S1P (manufactured by ARC, final concentration 0.1 nM) and a DMSO solution (final concentration of the compound 10$^{-5}$M, final concentration of DMSO 0.1%) of the test compound were added. Thereafter, the mixture was stirred and then treated for one hour at 30° C. Using a harvester, the membrane fraction was harvested onto unifilter-96 GF/C filter (manufactured by Perkin Elmer), washing was carried out four times with the binding buffer, and the filter was dried. Twenty five μL Microscint 0 (manufactured by Perkin Elmer) was added, and radioactivity was measured using Top Count NXT (manufactured by Packard) to calculate the amount (A) of [$^{33}$P]-S1P bound to the membrane fraction at the time when the compound was added.

The same procedure was carried out in the absence of the test compound, and the amount (B) of [$^{33}$P]-S1P bound was calculated. Further, the same procedure was carried out in the absence of the test compound by use of HEK-293 cells to which no Edg-1 (S1P$_1$) gene was introduced, and the background amount (C) of [$^{33}$P]-S1P bound was calculated.

The Edg-1 (S1P$_1$) binding inhibition rates of the compound calculated using the following equation are shown in Table 1.

Inhibition rate (%)=[1−(A−C)/(B−C)]×100

Further, concentrations (IC$_{50}$) at the time when binding in the absence of the test compound was inhibited by 50% were calculated. The membrane system binding assay was carried out in the presence of test compounds with various concentrations, and the Edg-1 (S1P$_1$) binding inhibition rates were calculated using the equation above. Then, IC$_{50}$ values were calculated using Origin (Lightstone Corp.), a software for data analysis.

The compounds below each had an IC$_{50}$ value of 35 nM or lower and showed particularly strong activity.

Compounds 5, 13, 16, 18, 21, 23, 25, 26, 32, 35, 37, 43, 46, 64, 69, 76, 101, 102, 109, 122, 123, 125, 131, 134, 141, 142, 145, 665.

The following compounds had an IC$_{50}$ value of 10 nM or below, and showed even stronger activity.

Compounds 24, 39, 40, 70, 75, 87, 93, 94, 107, 111, 112, 121, 132, 133, 137, 138, 139, 140, 147, 151, 663, 666, 667, 669, 671, 681, 683, 690.

Specific IC$_{50}$ values of the individual compounds are as follows (unit: nM).

Compound 3: 4.2. Compound 7: 35.5. Compound 8: 18.5. Compound 10: 17.5. Compound 11: 8.9. Compound 12: 20.0. Compound 14: 6.4. Compound 15: 32.5. Compound 22: 14.0. Compound 28: 3.1. Compound 34: 2.0. Compound 36: 17.5. Compound 38: 11.7. Compound 42: 22.0. Compound 45: 4.2. Compound 46: 28.5. Compound 49: 6.0. Compound 61: 39.0. Compound 73: 2.2. Compound 74: 15.0. Compound 83: 8.1. Compound 88: 5.4. Compound 99: 25.0. Compound 100: 18.5. Compound 105: 2.9. Compound 108: 18.0. Compound 120:1.7. Compound 129: 20.0. Compound 130: 2.9. Compound 136: 8.1. Compound 143: 7.3. Compound 144: 7.9. Compound 146: 12.0. Compound 148: 1.9. Compound 149: 7.8. Compound 670: 5.2. Compound 678: 10.2. Compound 680:1.4. Compound 688: 1.5. Compound 691: 2.6. Compound 692: 5.1. Compound 694: 2.9. Compound 698: 2.3.

TABLE 1

| Compound number | Chemical structure | Melting point (° C.) | Binding assay (membrane) % inhibition (10 μM) |
|---|---|---|---|
| Compound 1 | ABS | 182.0-184.0 | 100.8 |
| Compound 2 | ABS | 134.0-138.0 | 97.8 |
| Compound 3 | ABS | 183.5-187.5 | 98.7 |
| Compound 4 | ABS | 198.5-200.5 | 95.7 |
| Compound 5 | ABS | 160.0-161.0 | 97.3 |
| Compound 6 | ABS | 180.0-190.0 | 98.2 |

TABLE 1-continued

| Compound | ABS | Structure | mp (°C) | Purity |
|---|---|---|---|---|
| Compound 7 | ABS | | 159.5-161.5 | 99.4 |
| Compound 8 | ABS | | 179.0-189.5 | 100.1 |
| Compound 9 | ABS | | 145.0-148.0 | 100.3 |
| Compound 10 | ABS | | 182.5-184.5 | 99.8 |
| Compound 11 | ABS | | 155.0-160.0 | 98.5 |
| Compound 12 | ABS | | 190.0-192.0 | 99.2 |

TABLE 1-continued

| Compound 13 | ABS | [structure: 3,4-dichlorophenyl-SO2-NH-CH(CH3)-triazole(N-Et)-O-3,4-dichlorophenyl] | 152.0-156.0 | 102.0 |
|---|---|---|---|---|
| Compound 14 | ABS | [structure: 3,4-dichlorophenyl-SO2-NH-CH(CH3)-triazole(N-Et)-O-3,4-dimethylphenyl] | 161.0-162.5 | 99.5 |
| Compound 15 | ABS | [structure: 3,4-dichlorophenyl-SO2-NH-CH(CH3)-triazole(N-Et)-O-4-cyclohexylphenyl] | 200.0-205.0 | 102.7 |
| Compound 16 | ABS | [structure: 3,4-dichlorophenyl-SO2-NH-CH(CH3)-triazole(N-Et)-O-3,4-dimethoxyphenyl] | 125.0-127.0 | 101.3 |
| Compound 17 | ABS | [structure: 3,4-dichlorophenyl-SO2-NH-CH(CH3)-triazole(N-Et)-O-3,4,5-trimethoxyphenyl] | 129.5-131.5 | 95.4 |
| Compound 18 | ABS | [structure: 3,4-dichlorophenyl-SO2-NH-CH(CH3)-triazole(N-Et)-O-3,4,5-trimethylphenyl] | 189.0-194.0 | 102.1 |

TABLE 1-continued

| | | | | |
|---|---|---|---|---|
| Compound 19 | ABS | (structure) | 145.0-150.0 | 97.9 |
| Compound 20 | ABS | (structure) | 118.0-120.0 | 97.4 |
| Compound 21 | ABS | (structure) | 146.5-149.5 | 96.7 |
| Compound 22 | ABS | (structure) | 163.0-167.5 | 95.4 |
| Compound 23 | ABS | (structure) | 173.0-176.0 | 96.7 |
| Compound 24 | ABS | (structure) | 172.5-173.0 | 101.0 |

TABLE 1-continued

| | | | | |
|---|---|---|---|---|
| Compound 25 | ABS | (structure) | 155.0-156.0 | 97.5 |
| Compound 26 | ABS | (structure) | 159.0-164.0 | 97.9 |
| Compound 27 | ABS | (structure) | 163.0-168.0 | 100.1 |
| Compound 28 | ABS | (structure) | 165.0-170.0 | 104.4 |
| Compound 29 | ABS | (structure) | 177.0-178.5 | 101.4 |
| Compound 30 | ABS | (structure) | 212.0-216.0 | 100.4 |

TABLE 1-continued

| Compound 31 | ABS | [structure] | 143.0-146.0 | 101.2 |
| Compound 32 | ABS | [structure] | 147.0-148.0 | 104.1 |
| Compound 33 | ABS | [structure] | 173.5-174.5 | 100.8 |
| Compound 34 | ABS | [structure] | 192.5-195.5 | 106.1 |
| Compound 35 | ABS | [structure] | 156.0-159.0 | 100.4 |
| Compound 36 | ABS | [structure] | 125.0-130.0 | 102.2 |

TABLE 1-continued
| Compound | ABS | Structure | mp (°C) | % |
|---|---|---|---|---|
| Compound 37 | ABS | 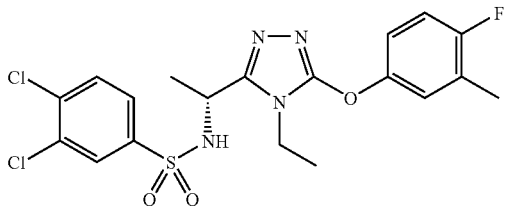 | 145.0-147.0 | 100.3 |
| Compound 38 | ABS | 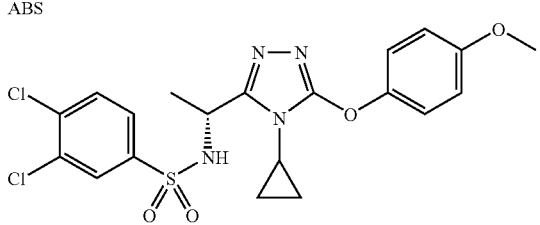 | 148.5-150.0 | 104.8 |
| Compound 39 | ABS | 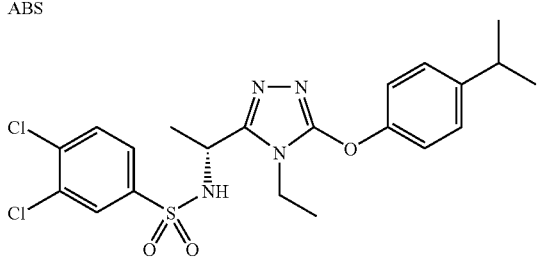 | 176.0-178.0 | 98.5 |
| Compound 40 | ABS | 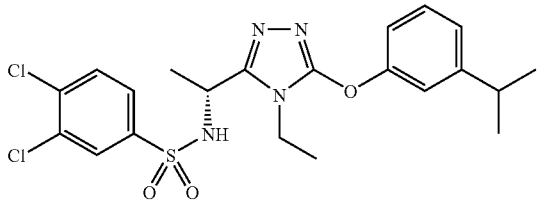 | 155.5-156.5 | 105.6 |
| Compound 41 | ABS | 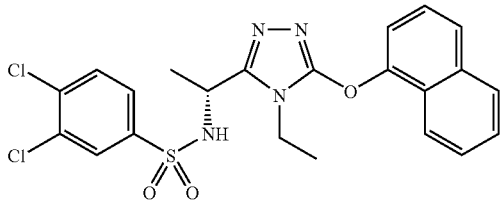 | 166.0-170.0 | 92.0 |
| Compound 42 | ABS | 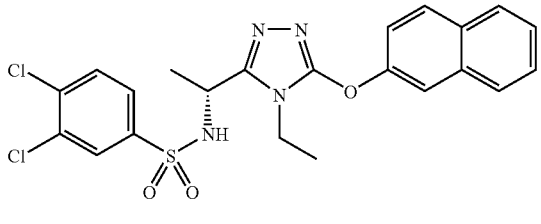 | 176.5-179.5 | 102.4 |

TABLE 1-continued

| Compound 43 | ABS | [structure: 3,4-dichlorophenyl-SO2-NH-CH(CH3)-triazole(N-ethyl)-O-C6H4-N(CH3)2] | 182.5-185.0 | 99.8 |
| Compound 44 | ABS | [structure: 3,4-dichlorophenyl-SO2-NH-CH(CH3)-triazole(N-ethyl)-O-C6H3-3,4-F2] | 140.0-145.5 | 100.1 |
| Compound 45 | ABS | [structure: 3,4-dichlorophenyl-SO2-NH-CH(CH3)-triazole(N-ethyl)-O-C6H4-(4-methylpiperazin-1-yl)] | 194.0-196.0 | 106.0 |
| Compound 46 | ABS | [structure: 3,4-dichlorophenyl-SO2-NH-CH(CH3)-triazole(N-ethyl)-O-(2-methylbenzothiazol-5-yl)] | 247.0-250.0 | 94.6 |
| Compound 47 | ABS | [structure: 3,4-dichlorophenyl-SO2-NH-CH(CH3)-triazole(N-ethyl)-O-C6H4-morpholinyl] | 191.0-192.0 | 102.3 |
| Compound 48 | ABS | [structure: 3,4-dichlorophenyl-SO2-NH-CH(CH3)-triazole(N-ethyl)-O-C6H4-piperidin-1-yl] | 195.5-196.5 | 96.7 |

TABLE 1-continued

| Compound 49 | ABS | | 198.0-199.0 | 102.5 |
|---|---|---|---|---|
| Compound 50 | ABS | | 129.0-130.0 | 92.9 |
| Compound 51 | ABS | | 148.5-150.5 | 99.9 |
| Compound 52 | ABS | | 203.0-205.0 | 100.2 |
| Compound 53 | ABS | | 172.0-173.0 | 86.8 |
| Compound 54 | ABS | | 192.0-193.0 | 104.1 |

TABLE 1-continued

| | | | | |
|---|---|---|---|---|
| Compound 55 | ABS | (structure) | 141.0-143.0 | 80.6 |
| Compound 56 | ABS | (structure) | 189.0-191.0 | 88.3 |
| Compound 57 | ABS | (structure) | 164.0-165.0 | |
| Compound 58 | ABS | (structure) | 181.0-183.0 | 99.7 |
| Compound 59 | ABS | (structure) | 169.5-170.5 | 94.3 |
| Compound 60 | ABS | (structure) | 192.5-195.0 | 98.9 |
| Compound 61 | ABS | (structure) | 93.0-99.0 | 102.2 |

TABLE 1-continued
| Compound | ABS | Structure | mp (°C) | % |
|---|---|---|---|---|
| Compound 62 | ABS | 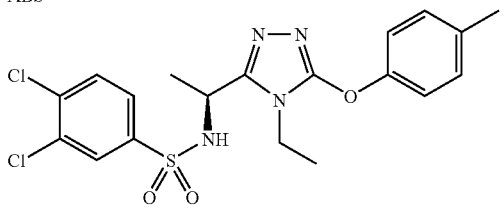 | 186.0-188.5 | 83.5 |
| Compound 63 | ABS | 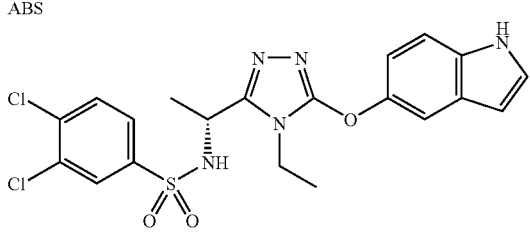 | 216.5-217.5 | 104.7 |
| Compound 64 | ABS | 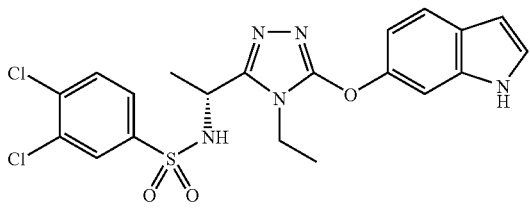 | 223.0-224.0 | 100.8 |
| Compound 65 | ABS | 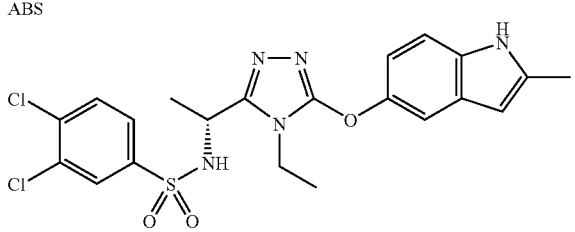 | 201.0-202.0 | 105.3 |
| Compound 66 | ABS | 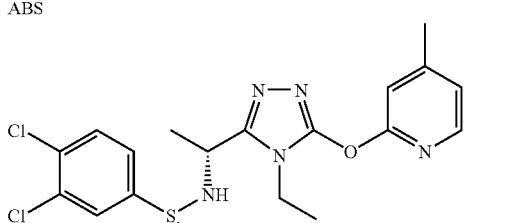 | 183.0-190.0 | 93.4 |
| Compound 67 | ABS | 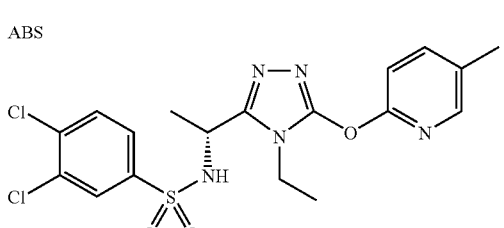 | 182.0-188.0 | 95.5 |

TABLE 1-continued

| Compound | ABS | Structure | mp (°C) | % |
|---|---|---|---|---|
| Compound 68 | ABS | (structure) | 212.0-223.0 | 100.9 |
| Compound 69 | ABS | (structure) | 119.0-120.5 | 103.2 |
| Compound 70 | ABS | (structure) | 144.0-146.0 | 96.5 |
| Compound 71 | ABS | (structure) | 126.0-135.0 | 99.3 |
| Compound 72 | ABS | (structure) | 198.0-200.5 | 99.0 |
| Compound 73 | ABS | (structure) | 185.0-187.0 | 103.3 |

TABLE 1-continued

| Compound 74 | ABS | | 218.5-227.0 | 104.9 |
| --- | --- | --- | --- | --- |
| Compound 75 | ABS | | 177.0-179.0 | 95.0 |
| Compound 76 | ABS | | 151.5-153.5 | 99.2 |
| Compound 77 | ABS | | 123.0-127.0 | 99.7 |
| Compound 78 | ABS | | 178.0-179.0 | 90.7 |
| Compound 79 | ABS | | 190.0-195.0 | 103.7 |

TABLE 1-continued

| Compound 80 | ABS | [structure] | 164.0-165.0 | 87.6 |
| Compound 81 | ABS | [structure] | 160.0-165.0 | 93.2 |
| Compound 82 | ABS | [structure] | 142.0-145.0 | 100.8 |
| Compound 83 | ABS | [structure] | 170.0-173.0 | 100.7 |
| Compound 84 | ABS | [structure] | 160.0-165.0 | 100.5 |
| Compound 85 | ABS | [structure] | 133.0-134.0 | 100.0 |

TABLE 1-continued

| Compound 86 | ABS | (structure) | 176.0-177.0 | 106.7 |
| Compound 87 | ABS | (structure) | 174.0-179.0 | 99.9 |
| Compound 88 | ABS | (structure) | 188.5-190.5 | 99.5 |
| Compound 89 | ABS | (structure) | 101.0-103.0 | 90.3 |
| Compound 90 | ABS | (structure) | 168.0-170.0 | 99.0 |
| Compound 91 | ABS | (structure) | 137.0-138.0 | 90.6 |
| Compound 92 | ABS | (structure) | 118.0-120.0 | 92.1 |

TABLE 1-continued

| Compound | | | | |
|---|---|---|---|---|
| Compound 93 | ABS | (structure) | 167.5-169.5 | 99.9 |
| Compound 94 | ABS | (structure) | 190.0-192.0 | 106.4 |
| Compound 95 | ABS | (structure) | 205.0-208.5 | 92.4 |
| Compound 96 | ABS | (structure) | 191.0-194.0 | 78.7 |
| Compound 97 | ABS | (structure) | 158.0-159.0 | 93.0 |
| Compound 98 | ABS | (structure) | 143.0-144.0 | 100.4 |

TABLE 1-continued

| Compound 99 | ABS | [structure] | 103.0-105.5 | 102.4 |
| Compound 100 | ABS | [structure] | | 109.9 |
| Compound 101 | ABS | [structure] | 142.0-143.0 | 100.9 |
| Compound 102 | ABS | [structure] | 117.0-118.0 | 104.2 |
| Compound 103 | ABS | [structure] | 146.5-147.5 | 91.2 |
| Compound 104 | ABS | [structure] | 187.0-187.5 | 95.2 |

TABLE 1-continued
| | | | | |
|---|---|---|---|---|
| Compound 105 | ABS | 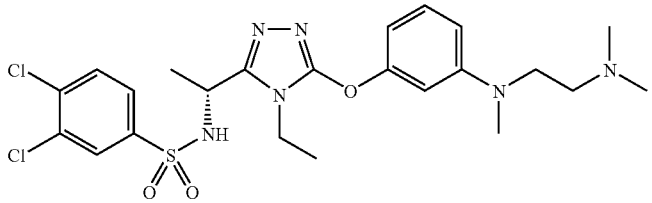 | 121.0-123.0 | 104.4 |
| Compound 106 | ABS | 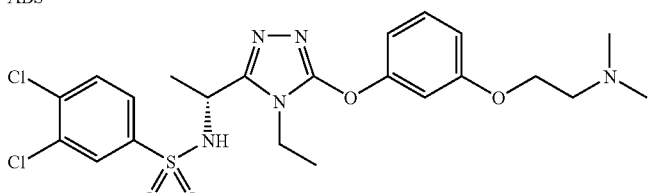 | 132.0-134.0 | 110.2 |
| Compound 107 | ABS | 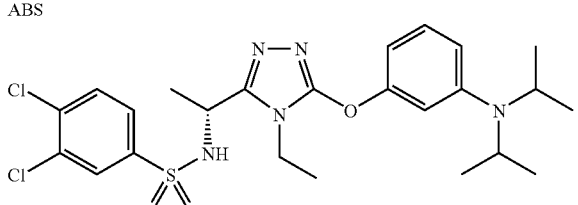 | 159.0-162.0 | 103.8 |
| Compound 108 | ABS | 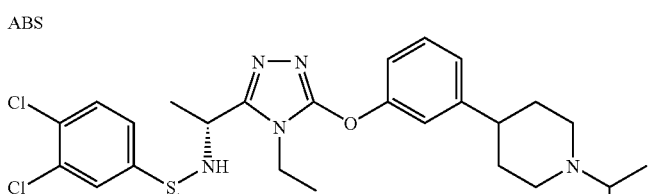 | 175.0-180.0 | 101.3 |
| Compound 109 | ABS | 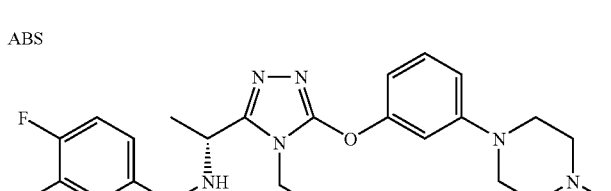 | 152.0-153.0 | 103.5 |
| Compound 110 | ABS | 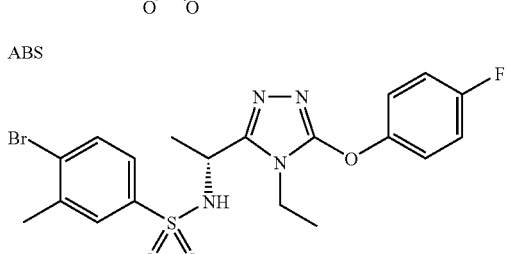 | 187.5-188.5 | 103.6 |
| Compound 111 | ABS | 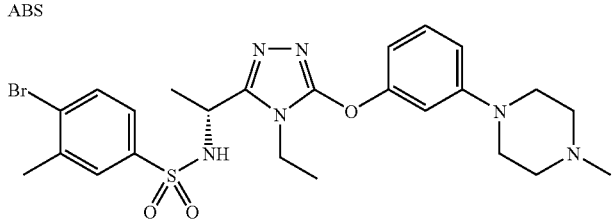 | 204.0-205.0 | 108.7 |

TABLE 1-continued
| Compound 112 | ABS | 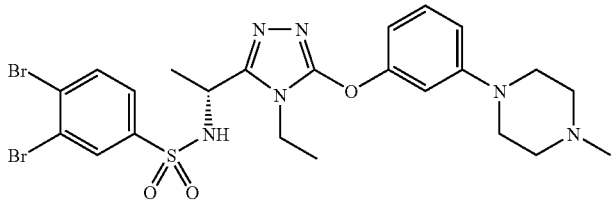 | 171.0-173.0 | 99.2 |
| Compound 113 | ABS | 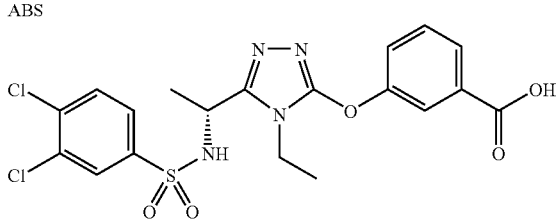 | 183.0-185.0 | 74.2 |
| Compound 114 | ABS | 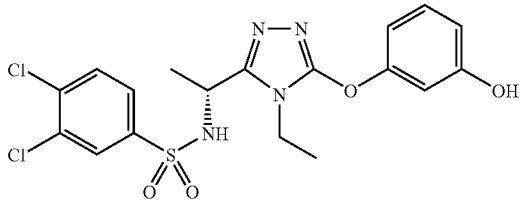 | 185.0-186.0 | 94.5 |
| Compound 115 | ABS | 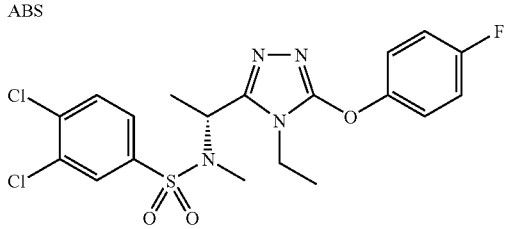 | 125.5-126.5 | 81.8 |
| Compound 116 | ABS | 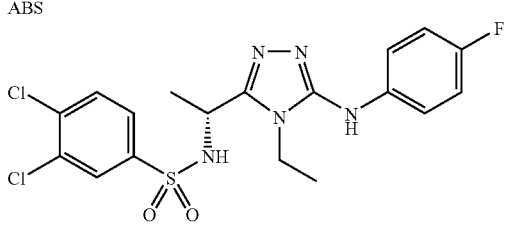 | 192.0-195.0 | 83.1 |
| Compound 117 | ABS | 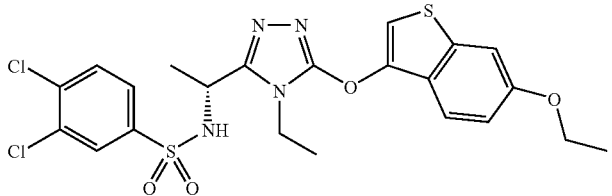 | 153.5-155.5 | 87.1 |

TABLE 1-continued

| | | | | |
|---|---|---|---|---|
| Compound 118 | ABS | [structure] | | |
| Compound 119 | ABS | [structure] | | |
| Compound 120 | ABS | [structure] | 211.5-216.5 | 93.03 |
| Compound 121 | ABS | [structure] | 195.5-198.5 | 103.45 |
| Compound 122 | ABS | [structure] | 167.0-170.0 | 81.93 |
| Compound 123 | ABS | [structure] | 162.0-165.0 | 97.12 |
| Compound 124 | ABS | [structure] | 178.5-180.0 | 97.44 |

TABLE 1-continued

| Compound | ABS | Structure | mp (°C) | % |
|---|---|---|---|---|
| Compound 125 | ABS | (3,4-dichlorophenyl)sulfonyl-NH-CH(CH₃)-[4-cyclopropyl-1,2,4-triazol-3-yl with 5-(1H-indol-6-yloxy)] | 253.5-254.5 | 94.28 |
| Compound 126 | ABS | (3,4-dimethylphenyl)sulfonyl-NH-CH(CH₃)-[4-ethyl-1,2,4-triazol-3-yl with 5-(4-fluorophenoxy)] | 176.5-178.0 | 91.80 |
| Compound 127 | ABS | (3-chloro-4-methylphenyl)sulfonyl-NH-CH(CH₃)-[4-ethyl-1,2,4-triazol-3-yl with 5-(4-fluorophenoxy)] |  | 94.44 |
| Compound 128 | ABS | (4-trifluoromethylphenyl)sulfonyl-NH-CH(CH₃)-[4-ethyl-1,2,4-triazol-3-yl with 5-(4-fluorophenoxy)] | 182.5-183.5 | 90.70 |
| Compound 129 | ABS | (3,4-dimethylphenyl)sulfonyl-NH-CH(CH₃)-[4-ethyl-1,2,4-triazol-3-yl with 5-(1H-indol-6-yloxy)] | 96.0-104.0 | 96.79 |
| Compound 130 | ABS | (2-naphthyl)sulfonyl-NH-CH(CH₃)-[4-ethyl-1,2,4-triazol-3-yl with 5-(1H-indol-6-yloxy)] | 107.0-114.0 | 98.87 |

TABLE 1-continued
| Compound 131 | ABS | 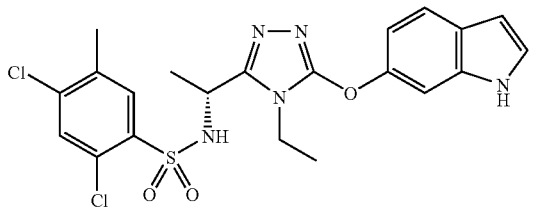 | 102.0-110.5 | 97.35 |
| --- | --- | --- | --- | --- |
| Compound 132 | ABS | 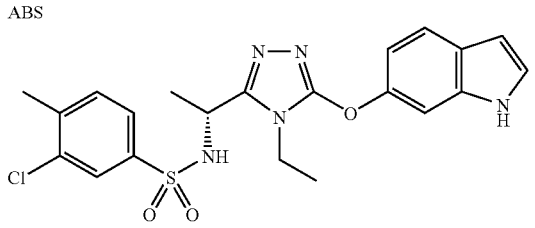 | 95.0-104.0 | 99.52 |
| Compound 133 | ABS | 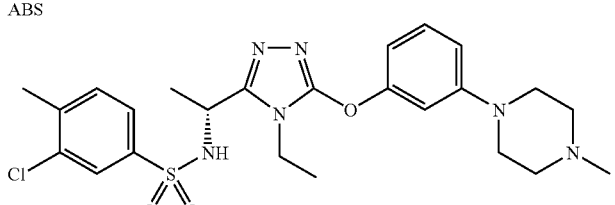 | 164.0-169.5 | 101.11 |
| Compound 134 | ABS | 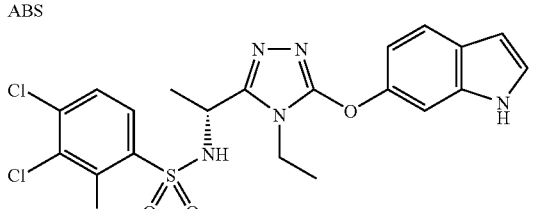 | 108.5-114.5 | 101.47 |
| Compound 135 | ABS | 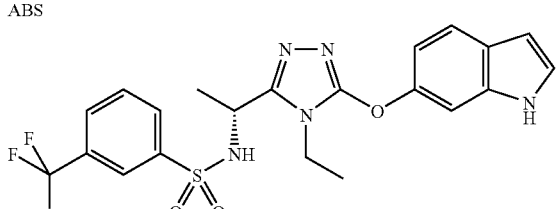 | 188.5-192.0 | 100.63 |
| Compound 136 | ABS | 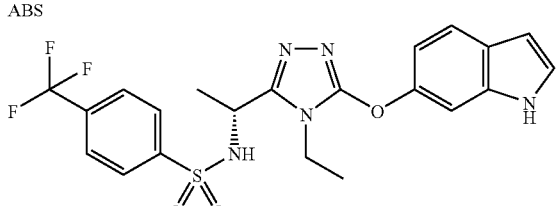 | 100.0-106.0 | 96.51 |

TABLE 1-continued

| Compound 137 | ABS | [structure] | 173.5-177.0 | 101.74 |
| Compound 138 | ABS | [structure] | 167.5-169.0 | 99.58 |
| Compound 139 | ABS | [structure] | 174.0-177.0 | 101.46 |
| Compound 140 | ABS | [structure] | 110.0-119.0 | 101.57 |
| Compound 141 | ABS | [structure] | 169.0-173.0 | 104.70 |
| Compound 142 | ABS | [structure] | 183.0-184.0 | 98.11 |

TABLE 1-continued

| | | | | |
|---|---|---|---|---|
| Compound 143 | ABS | (structure) | 144.0-145.0 | 99.89 |
| Compound 144 | ABS | (structure) | 187.0-188.0 | 99.38 |
| Compound 145 | ABS | (structure) | 150.0-152.0 | 101.30 |
| Compound 146 | ABS | (structure) | 121.0-122.0 | 101.65 |
| Compound 147 | ABS | (structure) | 141.0-143.0 | 102.74 |
| Compound 148 | ABS | (structure) | 154.5-155.5 | 102.47 |
| Compound 149 | | (structure) | 212.0-214.5 | 100.70 |

TABLE 1-continued

| Compound number | Chemical structure | | mp (°C) | Binding assay (membrane) % inhibition (10 μM) |
|---|---|---|---|---|
| Compound 1 | | | 191.5-196.0 | 93.40 |
| Compound 2 | ABS | | 252.0-255.0 | 102.84 |

| Compound number | Chemical structure | APCI MS (M − H)⁻ | APCI MS (M + H)+ | Binding assay (membrane) % inhibition (10 μM) |
|---|---|---|---|---|
| Compound 152 | ABS | 467 | 469 | |
| Compound 153 | ABS | 446 | 448 | |
| Compound 154 | ABS | 431 | 433 | 92.3 |

| | | | | | |
|---|---|---|---|---|---|
| Compound 155 | ABS | 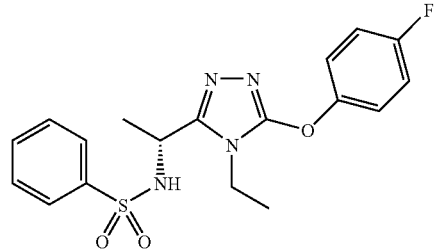 | 389 | 391 | 59.9 |
| Compound 156 | ABS | 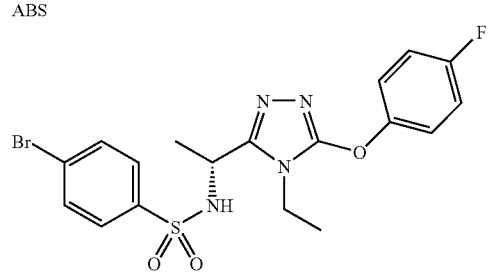 | 467, 469 | 469, 471 | 106.6 |
| Compound 157 | ABS | 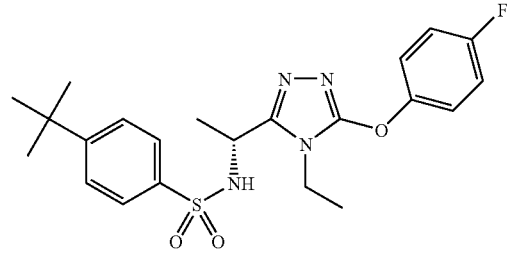 | 445 | 447 | 74.6 |
| Compound 158 | ABS | 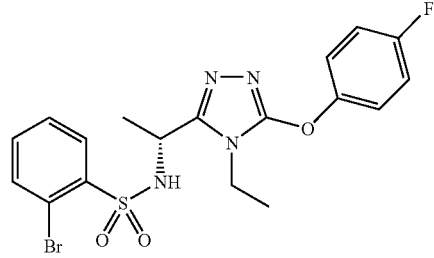 | 467, 469 | 469, 471 | |
| Compound 159 | ABS | 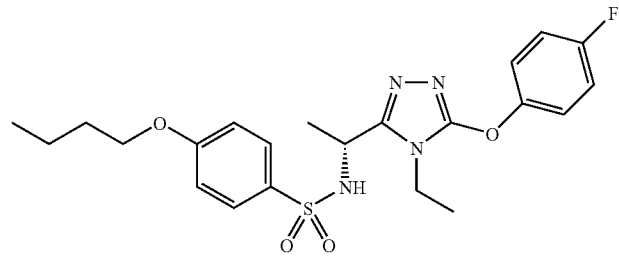 | 461 | 463 | |

TABLE 1-continued

| Compound 160 | ABS | [structure: 3-bromobenzenesulfonamide linked to 1-(4-ethyl-5-(4-fluorophenoxy)-4H-1,2,4-triazol-3-yl)ethyl] | 467, 469 | 469, 471 | 96.9 |
|---|---|---|---|---|---|
| Compound 161 | ABS | [structure: 4-bromo-2-(trifluoromethoxy)benzenesulfonamide linked to 1-(4-ethyl-5-(4-fluorophenoxy)-4H-1,2,4-triazol-3-yl)ethyl] | 551, 553 | 553, 554 | |
| Compound 162 | ABS | [structure: 4-chlorobenzenesulfonamide linked to 1-(4-ethyl-5-(4-fluorophenoxy)-4H-1,2,4-triazol-3-yl)ethyl] | 423 | 425 | 109.3 |
| Compound 163 | ABS | [structure: 2-cyanobenzenesulfonamide linked to 1-(4-ethyl-5-(4-fluorophenoxy)-4H-1,2,4-triazol-3-yl)ethyl] | 414 | 416 | |
| Compound 164 | ABS | [structure: 4-chloro-2,1,3-benzoxadiazole-7-sulfonamide linked to 1-(4-ethyl-5-(4-fluorophenoxy)-4H-1,2,4-triazol-3-yl)ethyl] | 465 | 467 | |

TABLE 1-continued

| Compound 165 | ABS | | 414 | 416 | 72.9 |
|---|---|---|---|---|---|
| Compound 166 | ABS | | 493 | 495 | |
| Compound 167 | ABS | | 451 | 453 | 113.3 |
| Compound 168 | ABS | | 457 | 459 | 68.4 |
| Compound 169 | ABS | | 457 | 459 | |

TABLE 1-continued

| Compound 170 | ABS | [structure] | 449 | 451 | 76.0 |
| Compound 171 | ABS | [structure] | 341 | 343 | |
| Compound 172 | ABS | [structure] | 417 | 419 | 92.0 |
| Compound 173 | ABS | [structure] | 407 | 409 | 97.2 |
| Compound 174 | ABS | [structure] | 431 | 433 | 52.5 |

TABLE 1-continued

| Compound 175 | ABS | [structure] | 419 | 421 | 102.7 |
| Compound 176 | ABS | [structure] | 327 | 329 | |
| Compound 177 | ABS | [structure] | 467 | 469 | 55.3 |
| Compound 178 | ABS | [structure] | 467 | 469 | |
| Compound 179 | ABS | [structure] | 439 | 441 | 83.0 |

TABLE 1-continued
| Compound | ABS | | 467 | 469 | 94.6 |
|---|---|---|---|---|---|
| 180 | | 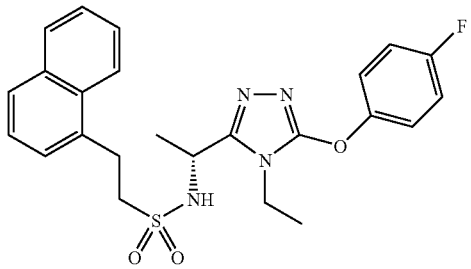 | | | |
| Compound | ABS | | 479 | 481 | 50.4 |
| 181 | | 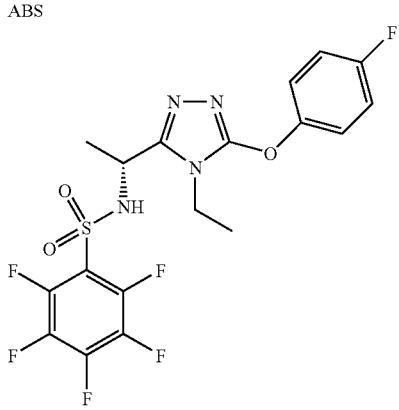 | | | |
| Compound | ABS | | 514 | 517 | 109.3 |
| 182 | | 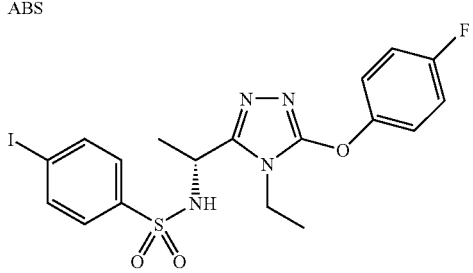 | | | |
| Compound | ABS | | 415 | 417 | 92.8 |
| 183 | | 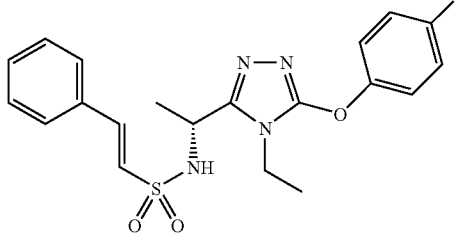 | | | |

TABLE 1-continued
| Compound 184 | ABS | 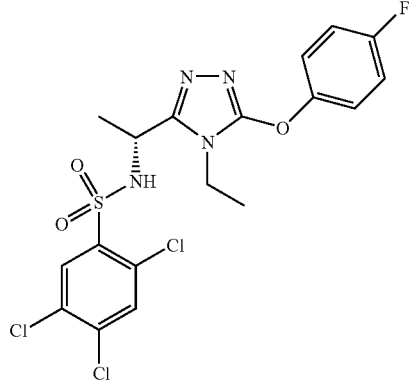 | 491, 493 | 493, 495 | 97.3 |
| Compound 185 | ABS | 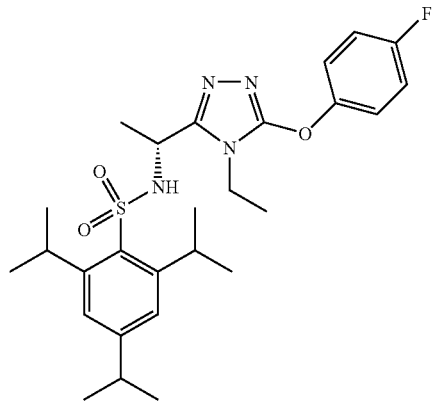 | 515 | 517 | |
| Compound 186 | ABS | 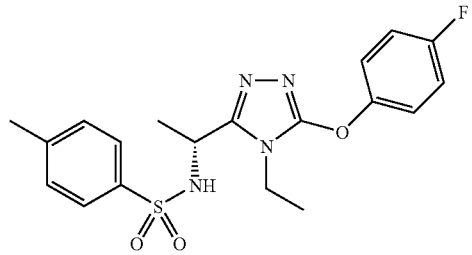 | 403 | 405 | 86.8 |
| Compound 187 | ABS | 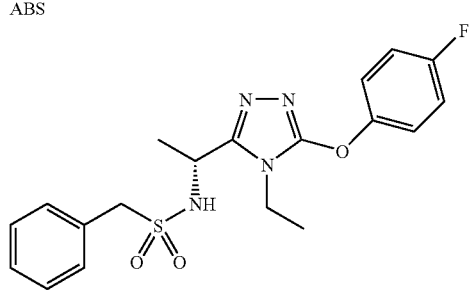 | 403 | 405 | |

TABLE 1-continued

| Compound 188 | ABS | 457 | 459 | 106.6 |
| --- | --- | --- | --- | --- |
| Compound 189 | ABS | 403 | 405 | 99.7 |
| Compound 190 | ABS | 473 | 475 | 87.9 |
| Compound 191 | ABS | 415 | 417 | 969 |
| Compound 192 | ABS | 403 | 405 | 95.2 |

TABLE 1-continued
| | | | | | |
|---|---|---|---|---|---|
| Compound 193 | ABS | 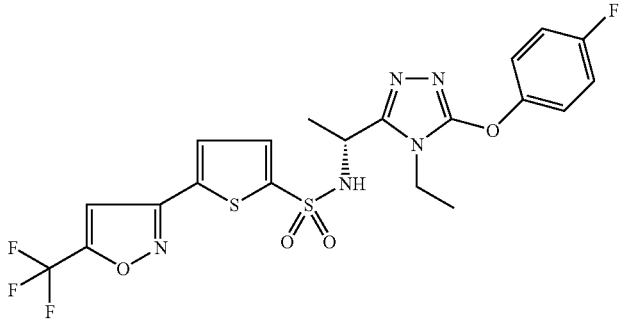 | 530 | 532 | |
| Compound 194 | ABS | 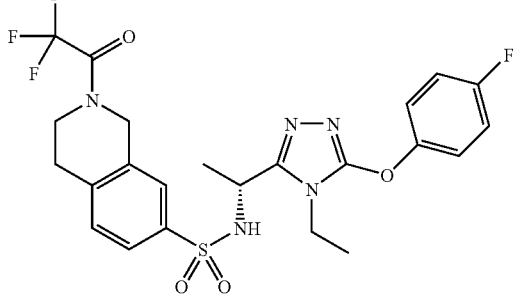 | 540 | 542 | 80.7 |
| Compound 195 | ABS | 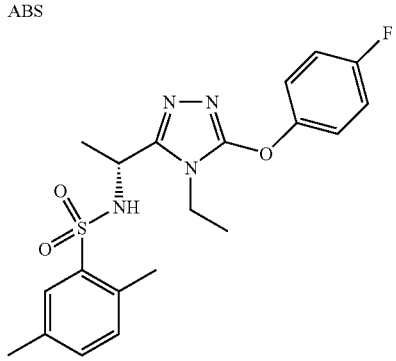 | 417 | 419 | 90.1 |
| Compound 196 | ABS | 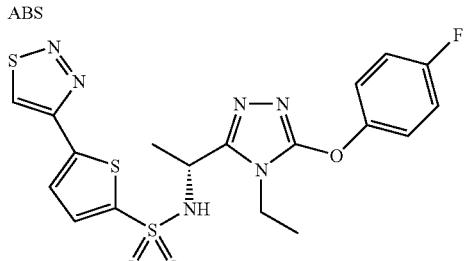 | 479 | 481 | 65.6 |
| Compound 197 | ABS | 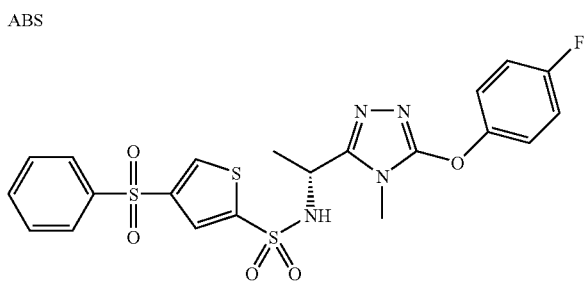 | 535 | 537 | |

TABLE 1-continued

| Compound | ABS | | 441 | 443 | |
|---|---|---|---|---|---|
| 198 | | | | | |
| Compound 199 | ABS | | 408 | 410 | |
| Compound 200 | ABS | | 465 | 467 | |
| Compound 201 | ABS | | 450 | 452 | 84.3 |
| Compound 202 | ABS | | 421 | 42 | |

TABLE 1-continued
| Compound 203 | ABS | 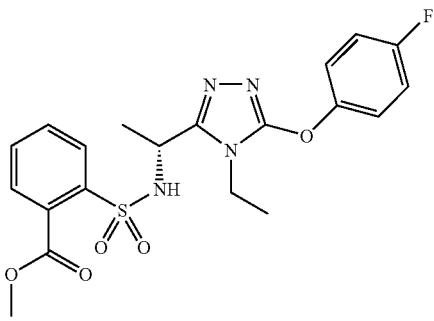 | 447 | 449 | |
| Compound 204 | ABS | 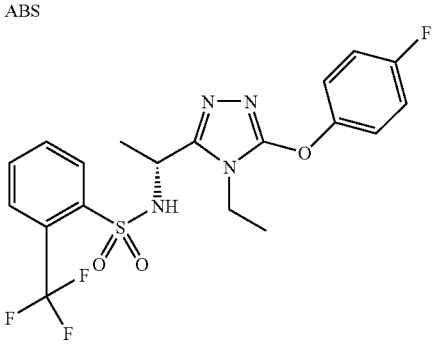 | 457 | 459 | |
| Compound 205 | ABS | 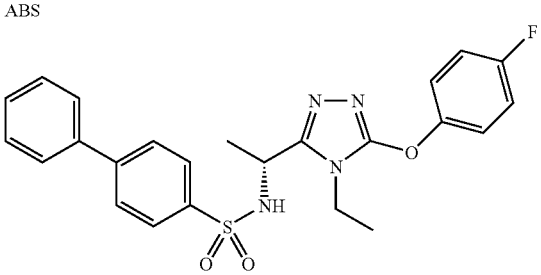 | 465 | 467 | |
| Compound 206 | ABS | 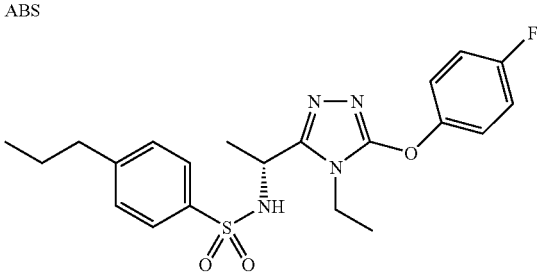 | 431 | 433 | 85.4 |

TABLE 1-continued

| Compound 207 | ABS | | 491, 493 | 493, 495 | 107.7 |
| Compound 208 | ABS | | 445 | 447 | 80.2 |
| Compound 209 | ABS | | 457 | 459 | 91.4 |
| Compound 210 | ABS | | 437 | 439 | |

| | | | | | |
|---|---|---|---|---|---|
| Compound 211 | ABS | 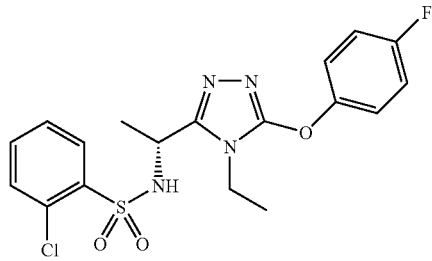 | 423 | 425 | |
| Compound 212 | ABS | 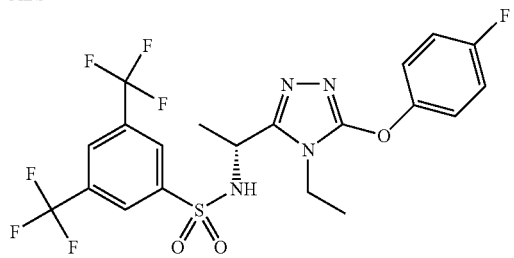 | 525 | 527 | 69.7 |
| Compound 213 | ABS | 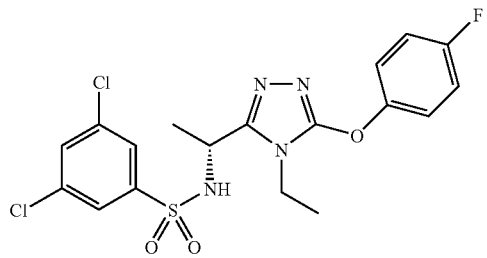 | 457 | 459 | 101.9 |
| Compound 214 | ABS | 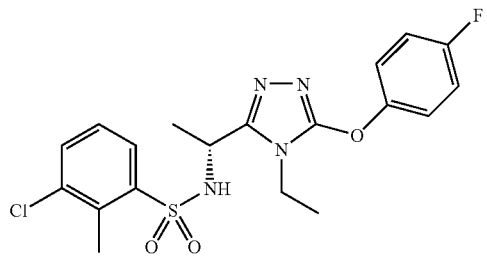 | 437 | 439 | 102.1 |
| Compound 215 | ABS | 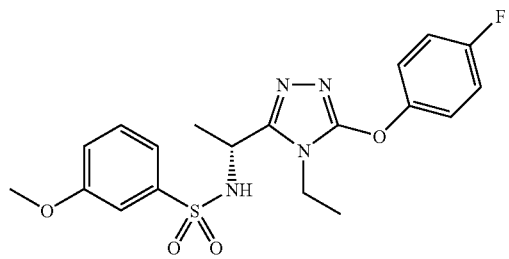 | 419 | 421 | 91.4 |

TABLE 1-continued
| Compound 216 | ABS | 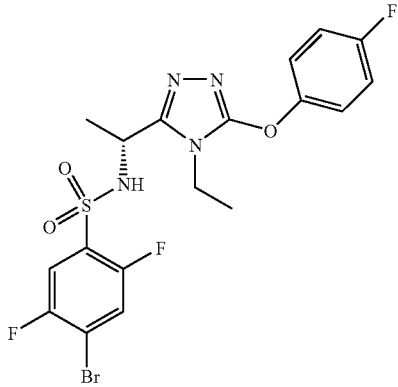 | 503, 505 | 505, 507 | 88 |
| --- | --- | --- | --- | --- | --- |
| Compound 217 | ABS | 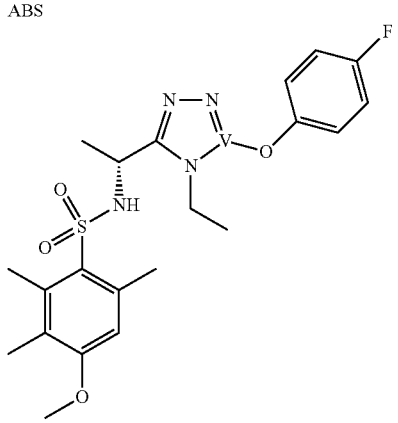 | 461 | 463 | 57.5 |
| Compound 218 | ABS | 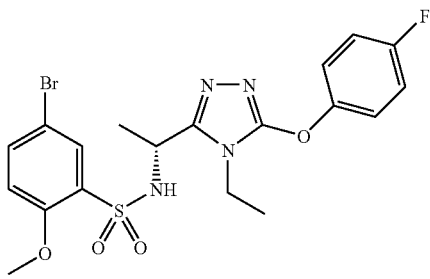 | 497, 499 | 499, 501 | 74.7 |
| Compound 219 | ABS | 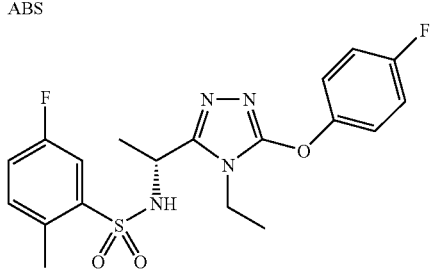 | 421 | 423 | 70.8 |

TABLE 1-continued
| Compound 220 | ABS | 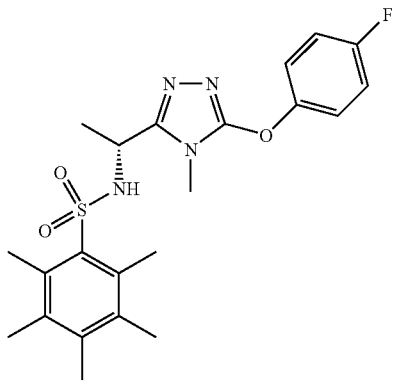 | 459 | 461 | 93.7 |
| Compound 221 | ABS | 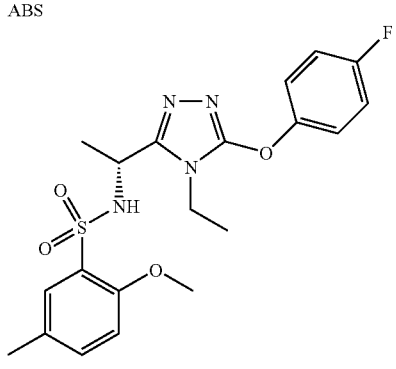 | 433 | 435 | 69.2 |
| Compound 222 | ABS | 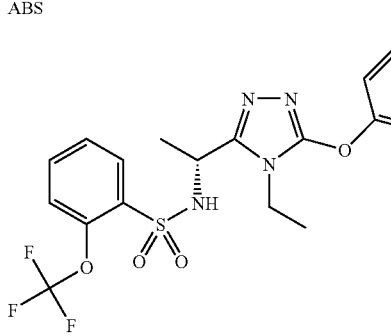 | 473 | 475 | |
| Compound 223 | ABS | 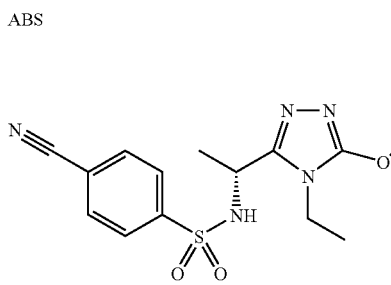 | 414 | 416 | 90.8 |

TABLE 1-continued

| | | Structure | | |
|---|---|---|---|---|
| Compound 224 | ABS | (4-phenoxyphenyl)sulfonyl-N-[(S)-1-(4-ethyl-5-(4-fluorophenoxy)-4H-1,2,4-triazol-3-yl)ethyl] | 481 | 483 |
| Compound 225 | ABS | 2,4,6-trichlorophenylsulfonyl-N-[(S)-1-(4-ethyl-5-(4-fluorophenoxy)-4H-1,2,4-triazol-3-yl)ethyl] | 491, 493 | 493, 495 |
| Compound 226 | ABS | 2,4-dichlorophenylsulfonyl-N-[(S)-1-(4-ethyl-5-(4-fluorophenoxy)-4H-1,2,4-triazol-3-yl)ethyl] | 457 | 459 | 80.4 |
| Compound 227 | ABS | 2,4-difluorophenylsulfonyl-N-[(S)-1-(4-ethyl-5-(4-fluorophenoxy)-4H-1,2,4-triazol-3-yl)ethyl] | 425 | 427 | 51.4 |

TABLE 1-continued

| Compound 228 | ABS | | 449 | 451 | 53.9 |
|---|---|---|---|---|---|
| Compound 229 | ABS | | 441 | 443 | |
| Compound 230 | ABS | | 407 | 409 | |
| Compound 231 | ABS | | 423 | 425 | 65.1 |
| Compound 232 | ABS | | 431 | 433 | 68.7 |

TABLE 1-continued

| Compound | ABS | Structure | | | |
|---|---|---|---|---|---|
| Compound 233 | ABS | | 455 | 457 | 87.1 |
| Compound 234 | ABS | | 495, 497 | 497, 499 | 50.6 |
| Compound 235 | ABS | | 481, 483 | 483, 485 | 82.9 |
| Compound 236 | ABS | | 448 | 450 | |
| Compound 237 | ABS | | 443 | 445 | 64.8 |

TABLE 1-continued
| Compound 238 | ABS | 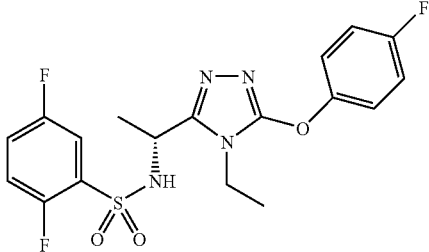 | 425 | 427 | |
| Compound 239 | ABS | 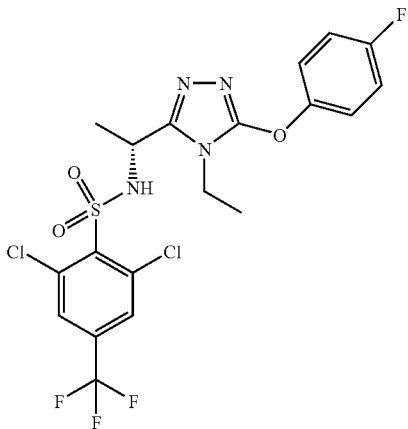 | 525 | 527 | |
| Compound 240 | ABS | 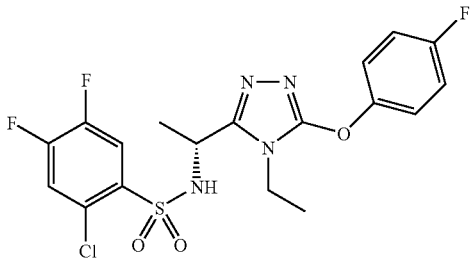 | 459 | 461 | 82.5 |
| Compound 241 | ABS | 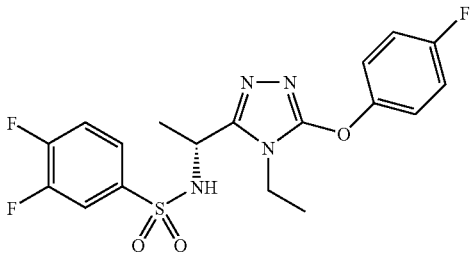 | 425 | 427 | 95.8 |

TABLE 1-continued

| Compound 242 | ABS | *(structure)* | 485, 487 | 487, 489 | 85.9 |
| Compound 243 | ABS | *(structure)* | 459 | 461 | 90.0 |
| Compound 244 | ABS | *(structure)* | 503, 505 | 505, 507 | 94.6 |
| Compound 245 | ABS | *(structure)* | 459 | 461 | 89.3 |
| Compound 246 | ABS | *(structure)* | 471 | 473 | |

TABLE 1-continued
| | | | | | |
|---|---|---|---|---|---|
| Compound 247 | ABS | 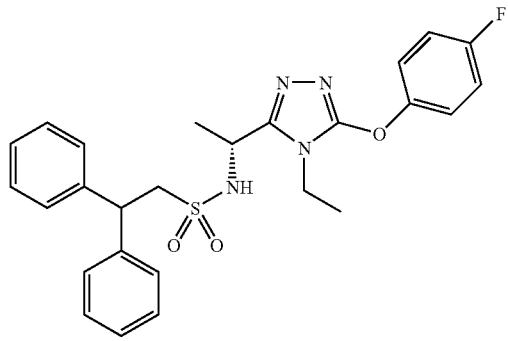 | 493 | 495 | |
| Compound 248 | ABS | 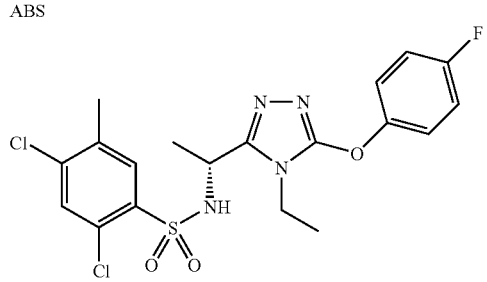 | 471 | 473 | 104.9 |
| Compound 249 | ABS | 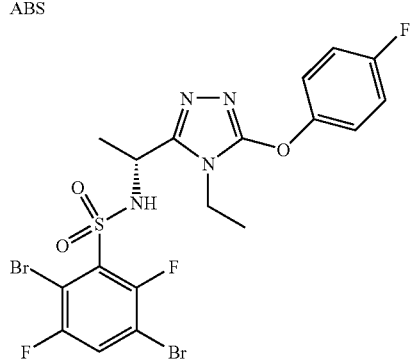 | 581, 583 | 583, 585 | |
| Compound 250 | ABS | 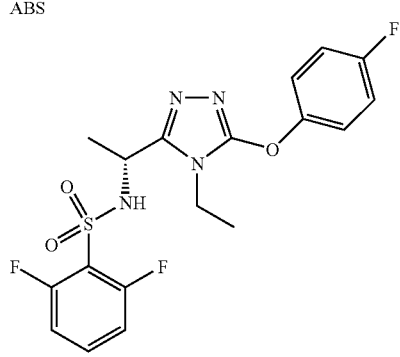 | 425 | 427 | |

TABLE 1-continued

| Compound 251 | ABS | | 491 | 493 | 59.0 |
|---|---|---|---|---|---|
| Compound 252 | ABS | | 407 | 409 | 82.8 |
| Compound 253 | ABS | | 480 | 482 | |
| Compound 254 | ABS | | 453 | 455 | 75.1 |
| Compound 255 | ABS | | 471 | 473 | 86.4 |

TABLE 1-continued

| Compound 256 | ABS | [structure] | 443 | 445 | 85.2 |
| Compound 257 | ABS | [structure] | 545, 547 | 547, 549 | 78.2 |
| Compound 258 | ABS | [structure] | 462 | 464 | 67.9 |
| Compound 259 | ABS | [structure] | 437 | 439 | |
| Compound 260 | ABS | [structure] | 545, 547 | 547, 549 | 74.1 |

TABLE 1-continued

| | | | | | |
|---|---|---|---|---|---|
| Compound 261 | ABS | (structure) | 432 | 434 | 73.6 |
| Compound 262 | ABS | (structure) | 417 | 419 | 79.6 |
| Compound 263 | ABS | (structure) | 455 | 457 | 82.6 |
| Compound 264 | ABS | (structure) | 455 | 457 | 95.9 |
| Compound 265 | ABS | (structure) | 503, 505 | 505, 507 | 59.1 |

TABLE 1-continued
| | | | | | |
|---|---|---|---|---|---|
| Compound 266 | ABS | 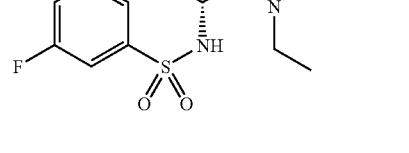 | 425 | 427 | 99.0 |
| Compound 267 | ABS | 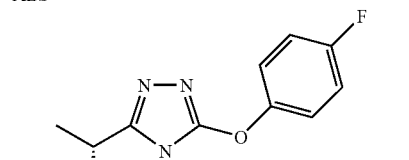 | 441 | 443 | 89.6 |
| Compound 268 | ABS | 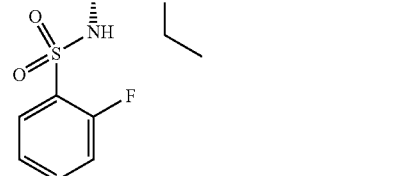 | 443 | 445 | 99.9 |
| Compound 269 | ABS |  | 485, 487 | 487, 489 | 91.5 |
| Compound 270 | ABS | 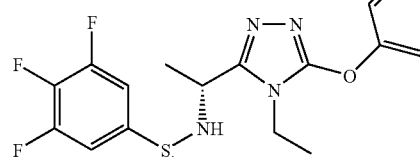 | 535, 537 | 537, 539 | 73.0 |

TABLE 1-continued

| Compound 271 | ABS | [structure] | 535, 537 | 537, 539 | 57.1 |
| Compound 272 | ABS | [structure] | 421 | 423 | 104.3 |
| Compound 273 | ABS | [structure] | 421 | 423 | 71.6 |
| Compound 274 | ABS | [structure] | 441 | 443 | 53.5 |
| Compound 275 | ABS | [structure] | 485, 487 | 487, 489 | 107.1 |

TABLE 1-continued

| Compound 276 | ABS | [structure] | 501, 503 | 503, 505 | 94.4 |
| Compound 277 | ABS | [structure] | 535, 537 | 537, 539 | |
| Compound 278 | ABS | [structure] | 477 | 479 | |
| Compound 279 | ABS | [structure] | 421 | 423 | 79.6 |
| Compound 280 | ABS | [structure] | 441 | 443 | 87.3 |

TABLE 1-continued
| Compound 281 | ABS | 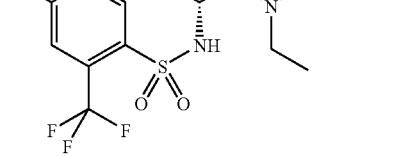 | 475 | 477 |
| Compound 282 | ABS |  | 495 | 497 |
| Compound 283 | ABS | 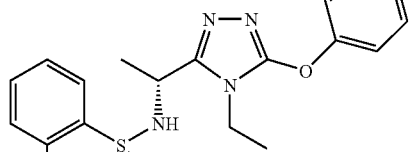 | 482 | 484 |
| Compound 284 | ABS |  | 404 | 406 |

TABLE 1-continued

| Compound 285 | ABS | (structure) | 419 | 421 | |
| Compound 286 | ABS | (structure) | 409 | 411 | 60.6 |
| Compound 287 | ABS | (structure) | 456 | 455 | |
| Compound 288 | ABS | (structure) | 394 | 396 | |
| Compound 289 | ABS | (structure) | 447 | 449 | 105.6 |

TABLE 1-continued

| Compound 290 | ABS | | 424 | 426 | |
|---|---|---|---|---|---|
| Compound 291 | ABS | | 447 | 449 | |
| Compound 292 | ABS | | 447 | 449 | 106.9 |
| Compound 293 | ABS | | 431 | 433 | |
| Compound 294 | ABS | | 395 | 397 | 50.8 |

TABLE 1-continued

| Compound 295 | ABS [structure] | 462 | 464 |
| --- | --- | --- | --- |
| Compound 296 | ABS [structure] | 469 | 471 |
| Compound 297 | ABS [structure] | 478 | 480 |
| Compound 298 | ABS [structure] | 543 | 54 |

TABLE 1-continued
| Compound 299 | ABS | 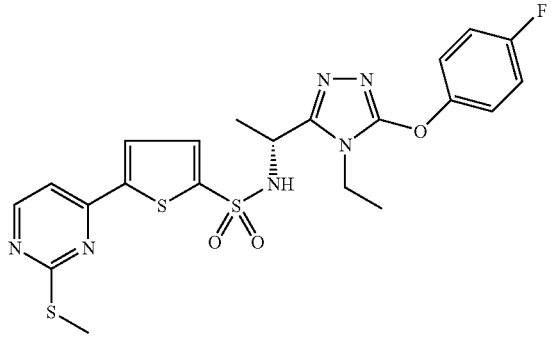 | 519 | 521 | |
| --- | --- | --- | --- | --- | --- |
| Compound 300 | ABS | 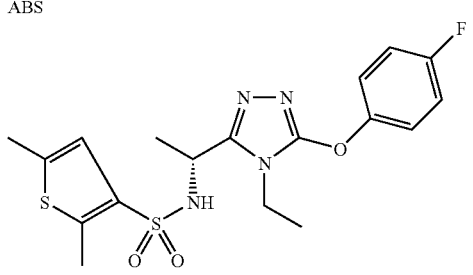 | 423 | 425 | 82.1 |
| Compound 301 | ABS | 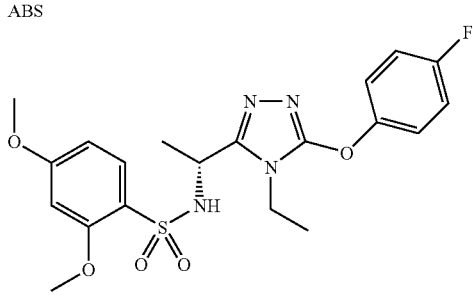 | 449 | 451 | 78.8 |
| Compound 302 | ABS | 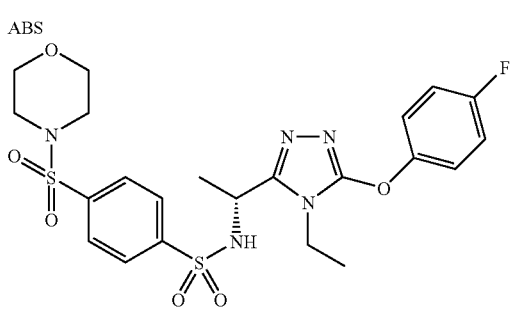 | 538 | 540 | |
| Compound 303 | ABS | 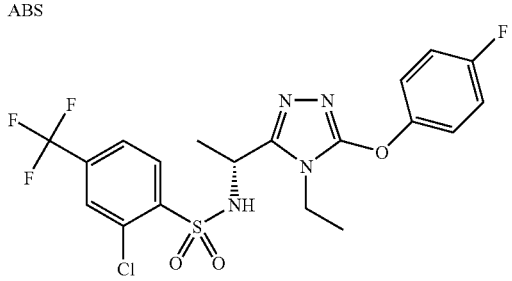 | 491 | 493 | 77. |

TABLE 1-continued

| Compound | ABS | Structure | | | |
|---|---|---|---|---|---|
| Compound 304 | ABS | | 517 | 519 | |
| Compound 305 | ABS | | 561 | 563 | |
| Compound 306 | ABS | | 431 | 433 | 60.2 |
| Compound 307 | ABS | | 457 | 459 | 94.4 |
| Compound 308 | ABS | | 490 | 492 | |

TABLE 1-continued

| | | | | | |
|---|---|---|---|---|---|
| Compound 309 | ABS | | 490 | 492 | |
| Compound 310 | ABS | | 494 | 496 | |
| Compound 311 | ABS | | 447 | 449 | 76.5 |
| Compound 312 | ABS | | 461 | 463 | |
| Compound 313 | ABS | | 437 | 439 | |

TABLE 1-continued

| Compound 314 | ABS | | 502 | 504 | 52.2 |
| --- | --- | --- | --- | --- | --- |
| Compound 315 | ABS | | 440 | 442 | |
| Compound 316 | ABS | | 525 | 527 | |
| Compound 317 | ABS | | 535, 537 | 537, 539 | |
| Compound 318 | ABS | | 535, 537 | 537, 539 | 78.9 |

TABLE 1-continued

| | | | | | |
|---|---|---|---|---|---|
| Compound 319 | ABS | [structure] | 535, 537 | 537, 539 | 61.7 |
| Compound 320 | ABS | [structure] | 390 | 392 | |
| Compound 321 | ABS | [structure] | 475 | 477 | |
| Compound 322 | ABS | [structure] | 539 | 541 | |
| Compound 323 | ABS | [structure] | 445 | 447 | 77.9 |

TABLE 1-continued
| Compound | | | | |
|---|---|---|---|---|
| Compound 324 | ABS 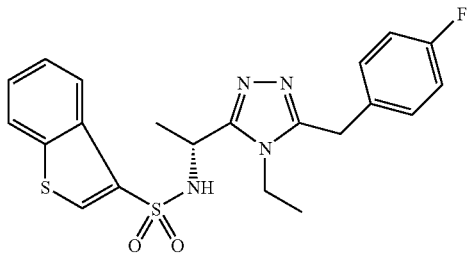 | 445 | 447 | 81.8 |
| Compound 325 | ABS 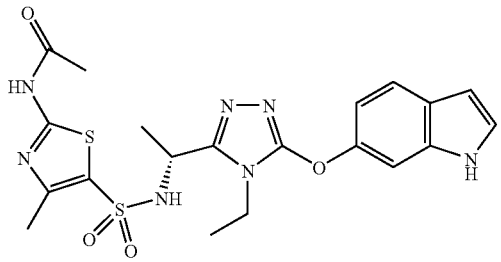 | 488 | 490 | |
| Compound 326 | ABS 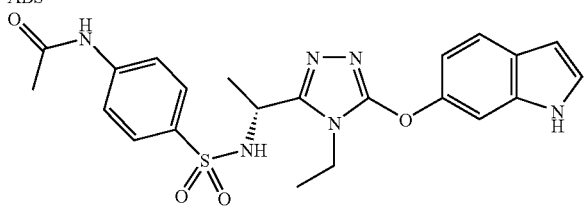 | 467 | 469 | |
| Compound 327 | ABS 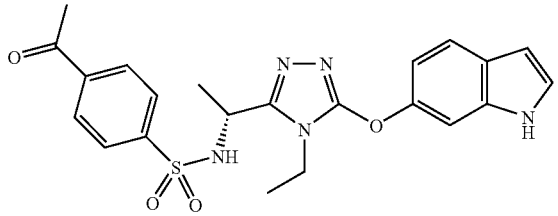 | 452 | 454 | 92.3 |
| Compound 328 | ABS 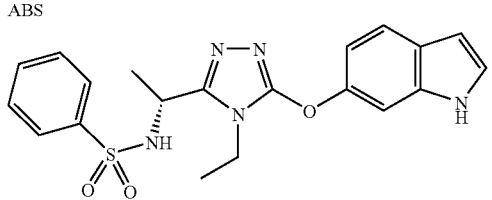 | 410 | 412 | 85.2 |
| Compound 329 | ABS 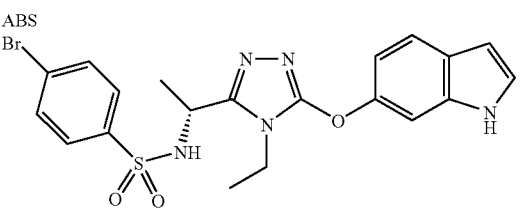 | 488, 490 | 490, 492 | 100.8 |

TABLE 1-continued

| Compound | ABS | | | | |
|---|---|---|---|---|---|
| Compound 330 | ABS | [structure] | 466 | 468 | 81.6 |
| Compound 331 | ABS | [structure] | 488, 490 | 490, 492 | 59.8 |
| Compound 332 | ABS | [structure] | 482 | 484 | |
| Compound 333 | ABS | [structure] | 488, 490 | 490, 492 | 102.2 |
| Compound 334 | ABS | [structure] | 572, 574 | 574, 576 | |
| Compound 335 | ABS | [structure] | 444 | 446 | 106.1 |

TABLE 1-continued

| Compound | | | | |
|---|---|---|---|---|
| Compound 336 | ABS | 435 | 437 | 56.8 |
| Compound 337 | ABS | 486 | 488 | |
| Compound 338 | ABS | 435 | 437 | 69.2 |
| Compound 339 | ABS | 514 | 516 | 62.8 |
| Compound 340 | ABS | 472 | 474 | 100.0 |
| Compound 341 | ABS | 478 | 480 | 92.8 |

TABLE 1-continued

| Compound 342 | ABS | [structure] | 478 | 480 | 53.6 |
| Compound 343 | ABS | [structure] | 470 | 472 | 86.5 |
| Compound 344 | ABS | [structure] | 362 | 364 | |
| Compound 345 | ABS | [structure] | 438 | 440 | 90.4 |
| Compound 346 | ABS | [structure] | 428 | 430 | 89.2 |
| Compound 347 | ABS | [structure] | 452 | 454 | 50.1 |

| Compound 348 | ABS [structure] | 440 | 442 | 109.1 |
| --- | --- | --- | --- | --- |
| Compound 349 | ABS [structure] | 348 | 350 | |
| Compound 350 | ABS [structure] | 488 | 490 | 75.0 |
| Compound 351 | ABS [structure] | 488 | 490 | |
| Compound 352 | ABS [structure] | 460 | 462 | 88.5 |
| Compound 353 | ABS [structure] | 488 | 490 | 92.3 |

TABLE 1-continued

| Compound 354 | ABS | [structure] | 500 | 502 | |
| Compound 355 | ABS | [structure] | 536 | 538 | 98.8 |
| Compound 356 | ABS | [structure] | 436 | 438 | 95.6 |
| Compound 357 | ABS | [structure] | 512, 514 | 514, 516 | 106.1 |
| Compound 358 | ABS | [structure] | 536 | 5 | |

| | | | | | |
|---|---|---|---|---|---|
| Compound 359 | ABS | | 424 | 426 | 95.7 |
| Compound 360 | ABS | | 424 | 426 | |
| Compound 361 | ABS | | 424 | 426 | 96.9 |
| Compound 362 | ABS | | 494 | 496 | 95.1 |
| Compound 363 | ABS | | 436 | 438 | 96.2 |
| Compound 364 | ABS | | 424 | 426 | 87.5 |
| Compound 365 | ABS | | 551 | 553 | |

TABLE 1-continued

| Compound 366 | ABS | [structure] | 561 | 563 | 63.2 |
| --- | --- | --- | --- | --- | --- |
| Compound 367 | ABS | [structure] | 438 | 440 | 94.3 |
| Compound 368 | ABS | [structure] | 500 | 502 | 60.5 |
| Compound 369 | ABS | [structure] | 556 | 55 | |
| Compound 370 | ABS | [structure] | 462 | 464 | |

TABLE 1-continued

| Compound | ABS | Structure | | | |
|---|---|---|---|---|---|
| Compound 371 | ABS | | 429 | 431 | |
| Compound 372 | ABS | | 471 | 473 | 106.3 |
| Compound 373 | ABS | | 442 | 444 | |
| Compound 374 | ABS | | 468 | 470 | |
| Compound 375 | ABS | | 478 | 480 | |
| Compound 376 | ABS | | 486 | 488 | |

TABLE 1-continued

| Compound 377 | ABS | [structure] | 452 | 454 | 73.9 |
| --- | --- | --- | --- | --- | --- |
| Compound 378 | ABS | [structure] | 466 | 468 | 71.6 |
| Compound 379 | ABS | [structure] | 478 | 480 | 89.2 |
| Compound 380 | ABS | [structure] | 458 | 460 | |
| Compound 381 | ABS | [structure] | 444 | 446 | |
| Compound 382 | ABS | [structure] | 546 | 548 | 66.9 |

TABLE 1-continued

| Compound | ABS | Structure | | | |
|---|---|---|---|---|---|
| Compound 383 | ABS | (3,5-dichlorophenyl sulfonamide structure) | 478 | 480 | 83.6 |
| Compound 384 | ABS | (3-chloro-2-methylphenyl sulfonamide structure) | 458 | 460 | 88.1 |
| Compound 385 | ABS | (3-chloro-4-fluorophenyl sulfonamide structure) | 462 | 464 | 98.0 |
| Compound 386 | ABS | (3-methoxyphenyl sulfonamide structure) | 440 | 442 | 84.0 |
| Compound 387 | ABS | (4-bromo-2,5-difluorophenyl sulfonamide structure) | 524, 526 | 526, 528 | 63.5 |
| Compound 388 | ABS | (4-methoxy-2,3-dimethylphenyl sulfonamide structure) | 482 | 484 | 65.8 |

TABLE 1-continued

| Compound | | | | | |
|---|---|---|---|---|---|
| Compound 389 | ABS | | 518, 520 | 520, 522 | 88.0 |
| Compound 390 | ABS | | 442 | 444 | 65.9 |
| Compound 391 | ABS | | 480 | 482 | 80.4 |
| Compound 392 | ABS | | 566, 568 | 568, 570 | 73.6 |
| Compound 393 | ABS | | 454 | 456 | 79.7 |
| Compound 394 | ABS | | 494 | 496 | |

TABLE 1-continued

| Compound | | | | |
|---|---|---|---|---|
| Compound 395 | ABS, structure | 435 | 437 | 79.1 |
| Compound 396 | ABS, structure | 502 | 504 | |
| Compound 397 | ABS, structure | 512, 514 | 514, 516 | |
| Compound 398 | ABS, structure | 478 | 480 | 84.7 |
| Compound 399 | ABS, structure | 446 | 448 | |
| Compound 400 | ABS, structure | 470 | 472 | 75.3 |

TABLE 1-continued

| Compound | | | | |
|---|---|---|---|---|
| Compound 401 | ABS (4-F, 2-Cl phenyl sulfonamide-CH(CH3)-triazole(N-Et)-O-indol-6-yl) | 462 | 464 | |
| Compound 402 | ABS (2-F phenyl sulfonamide-CH(CH3)-triazole(N-Et)-O-indol-6-yl) | 428 | 430 | |
| Compound 403 | ABS (3-Cl phenyl sulfonamide-CH(CH3)-triazole(N-Et)-O-indol-6-yl) | 444 | 446 | 72.5 |
| Compound 404 | ABS (4-iPr phenyl sulfonamide-CH(CH3)-triazole(N-Et)-O-indol-6-yl) | 452 | 454 | 60.2 |
| Compound 405 | ABS (5-F, 3-Cl, 2-Me phenyl sulfonamide-CH(CH3)-triazole(N-Et)-O-indol-6-yl) | 476 | 478 | 61.4 |
| Compound 406 | ABS (4-Br, 2-Et phenyl sulfonamide-CH(CH3)-triazole(N-Et)-O-indol-6-yl) | 516, 518 | 518, 520 | 56.3 |
| Compound 407 | ABS (4-Br, 2-Me phenyl sulfonamide-CH(CH3)-triazole(N-Et)-O-indol-6-yl) | 502, 504 | 504, 506 | 68.2 |

TABLE 1-continued

| Compound | ABS | | | |
|---|---|---|---|---|
| Compound 408 | ABS | | 469 | 471 | |
| Compound 409 | ABS | | 464 | 466 | 74.7 |
| Compound 410 | ABS | | 446 | 448 | |
| Compound 411 | ABS | | 546 | 548 | |
| Compound 412 | ABS | | 480 | 482 | 82.5 |
| Compound 413 | ABS | | 446 | 448 | 95.3 |

TABLE 1-continued

| Compound | ABS | | | | |
|---|---|---|---|---|---|
| Compound 414 | ABS | (structure: 4-bromo-2-fluorophenylsulfonamide linked via NH-CH(CH₃)- to 4-ethyl-1,2,4-triazole-O-indol-6-yl) | 506, 508 | 508, 510 | 92.5 |
| Compound 415 | ABS | (structure: 4-chloro-2,5-difluorophenylsulfonamide linked via NH-CH(CH₃)- to 4-ethyl-1,2,4-triazole-O-indol-6-yl) | 480 | 482 | 91.5 |
| Compound 416 | ABS | (structure: 4-bromo-2,5-difluorophenylsulfonamide linked via NH-CH(CH₃)- to 4-ethyl-1,2,4-triazole-O-indol-6-yl) | 524, 526 | 526, 528 | 83.2 |
| Compound 417 | ABS | (structure: 5-chloro-2,4-difluorophenylsulfonamide linked via NH-CH(CH₃)- to 4-ethyl-1,2,4-triazole-O-indol-6-yl) | 480 | 482 | 90.8 |
| Compound 418 | ABS | (structure: 3,4-dichlorobenzyl sulfonamide linked via NH-CH(CH₃)- to 4-ethyl-1,2,4-triazole-O-indol-6-yl) | 492 | 494 | |
| Compound 419 | ABS | (structure: 2,2-diphenylethylsulfonamide linked via NH-CH(CH₃)- to 4-ethyl-1,2,4-triazole-O-indol-6-yl) | 514 | 516 | |

TABLE 1-continued
| Compound 420 | ABS | 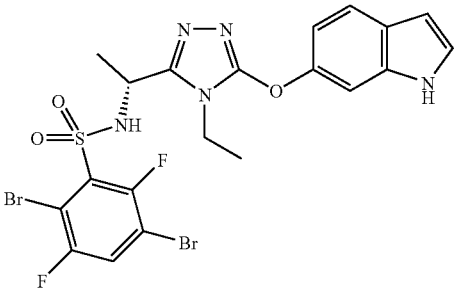 | 602, 604 | 604, 606 | 61.0 |
|---|---|---|---|---|---|
| Compound 421 | ABS | 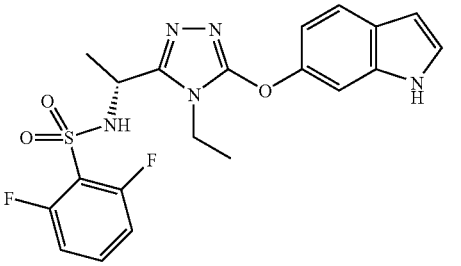 | 446 | 448 | |
| Compound 422 | ABS | 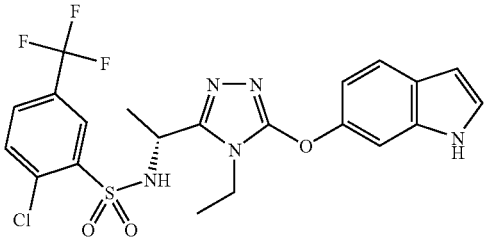 | 512 | 514 | 83.1 |
| Compound 423 | ABS | 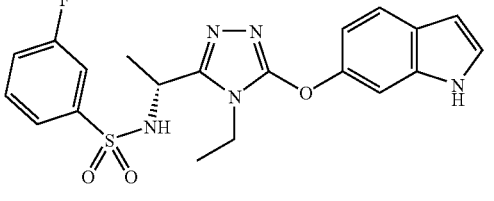 | 428 | 430 | 87.8 |
| Compound 424 | ABS | 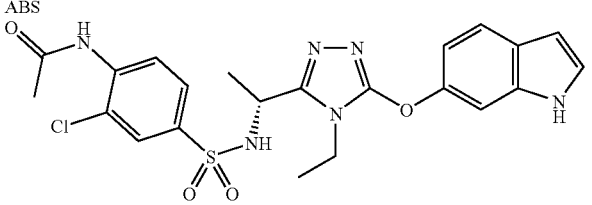 | 501 | 503 | |
| Compound 425 | ABS | 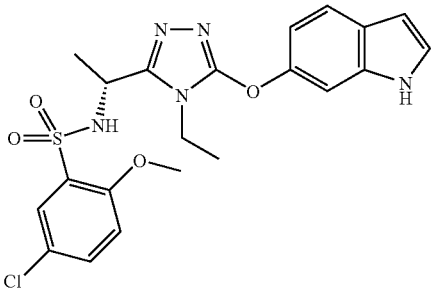 | 474 | 476 | 90.1 |

TABLE 1-continued

| Compound | | | | |
|---|---|---|---|---|
| Compound 426 | ABS | [structure] | 492 | 494 | 92.3 |
| Compound 427 | ABS | [structure] | 464 | 466 | 86.5 |
| Compound 428 | ABS | [structure] | 566, 568 | 568, 570 | 81.4 |
| Compound 429 | ABS | [structure] | 483 | 485 | 71.1 |
| Compound 430 | ABS | [structure] | 458 | 460 | 50.0 |
| Compound 431 | ABS | [structure] | 566, 568 | 568, 570 | |

TABLE 1-continued

| Compound | ABS | Structure | | | |
|---|---|---|---|---|---|
| Compound 432 | ABS | | 453 | 455 | 84.2 |
| Compound 433 | ABS | | 438 | 440 | 93.8 |
| Compound 434 | ABS | | 476 | 478 | 79.5 |
| Compound 435 | ABS | | 476 | 478 | 94.6 |
| Compound 436 | ABS | | 524, 526 | 526, 528 | 67.5 |
| Compound 437 | ABS | | 446 | 448 | 97.3 |

TABLE 1-continued

| Compound | | | | | |
|---|---|---|---|---|---|
| Compound 438 | ABS | [structure: 4-chloro-2-fluorophenylsulfonamide linked to (S)-methyl-triazole-O-indole] | 462 | 464 | 71.6 |
| Compound 439 | ABS | [structure: 3,4,5-trifluorophenylsulfonamide linked to (S)-methyl-triazole-O-indole] | 464 | 466 | 98.1 |
| Compound 440 | ABS | [structure: 4-bromo-3-methylphenylsulfonamide linked to (S)-methyl-triazole-O-indole] | 502, 504 | 504, 506 | 88.4 |
| Compound 441 | ABS | [structure: 2-bromo-4-fluorophenylsulfonamide linked to (S)-methyl-triazole-O-indole] | 506, 508 | 508, 510 | 63.0 |
| Compound 442 | ABS | [structure: 2-bromo-4-trifluoromethylphenylsulfonamide linked to (S)-methyl-triazole-O-indole] | 556, 558 | 558, 560 | 70.1 |
| Compound 443 | ABS | [structure: 2-bromo-5-trifluoromethylphenylsulfonamide linked to (S)-methyl-triazole-O-indole] | 556, 558 | 558, 560 | 55.7 |
| Compound 444 | ABS | [structure: 3-fluoro-4-methylphenylsulfonamide linked to (S)-methyl-triazole-O-indole] | 442 | 444 | 100.2 |

TABLE 1-continued

| Compound | Structure | | | |
|---|---|---|---|---|
| Compound 445 | ABS, 4-F, 2-methyl phenyl sulfonamide linked to (S)-CH(CH3)- triazole (4-ethyl) -O- 1H-indol-6-yl | 442 | 444 | 55.6 |
| Compound 446 | ABS, 5-Cl, 2-F phenyl sulfonamide linked to (S)-CH(CH3)- triazole (4-ethyl) -O- 1H-indol-6-yl | 462 | 464 | 75.8 |
| Compound 447 | ABS, 4-Br, 3-F phenyl sulfonamide linked to (S)-CH(CH3)- triazole (4-ethyl) -O- 1H-indol-6-yl | 506, 508 | 508, 510 | 95.5 |
| Compound 448 | ABS, 4-Br, 2-Cl phenyl sulfonamide linked to (S)-CH(CH3)- triazole (4-ethyl) -O- 1H-indol-6-yl | 522, 524 | 524, 526 | 81.1 |
| Compound 449 | ABS, 4-Br, 2,6-diCl phenyl sulfonamide linked to (S)-CH(CH3)- triazole (4-ethyl) -O- 1H-indol-6-yl | 556, 558 | 558, 560 | |
| Compound 450 | ABS, 4-methoxyphenoxy-propyl sulfonamide linked to (S)-CH(CH3)- triazole (4-ethyl) -O- 1H-indol-6-yl | 498 | 500 | |

TABLE 1-continued

| Compound | | | | |
|---|---|---|---|---|
| Compound 451 | ABS | | 442 | 444 | 76.8 |
| Compound 452 | ABS | | 462 | 464 | 68.9 |
| Compound 453 | ABS | | 496 | 498 | |
| Compound 454 | ABS | | 516 | 518 | |
| Compound 455 | ABS | | 503 | 505 | |
| Compound 456 | ABS | | 425 | 427 | |

TABLE 1-continued

| Compound 457 | ABS | [structure] | 440 | 442 | |
| Compound 458 | ABS | [structure] | 430 | 432 | 83.8 |
| Compound 459 | ABS | [structure] | 474 | 476 | |
| Compound 460 | ABS | [structure] | 482 | 484 | 53.2 |
| Compound 461 | ABS | [structure] | 468 | 470 | 99.7 |
| Compound 462 | ABS | [structure] | 445 | | |

TABLE 1-continued

| Compound | ABS | | | | |
|---|---|---|---|---|---|
| Compound 463 | ABS | | 468 | 470 | |
| Compound 464 | ABS | | 468 | 470 | 87.9 |
| Compound 465 | ABS | | 452 | 454 | |
| Compound 466 | ABS | | 416 | 418 | 511 |
| Compound 467 | ABS | | 483 | 485 | 5.9 |
| Compound 468 | ABS | | 490 | 492 | 56.2 |

TABLE 1-continued

| Compound 469 | ABS | [structure] | 499 | 501 | |
| Compound 470 | ABS | [structure] | 564 | 566 | |
| Compound 471 | ABS | [structure] | 540 | 542 | |
| Compound 472 | ABS | [structure] | 444 | 446 | 55.3 |
| Compound 473 | ABS | [structure] | 470 | 472 | 74.5 |

TABLE 1-continued

| Compound | | | | |
|---|---|---|---|---|
| Compound 474 | ABS [structure] | 559 | 561 | |
| Compound 475 | ABS [structure] | 512 | 514 | 51.8 |
| Compound 476 | ABS [structure] | 482 | 484 | |
| Compound 477 | ABS [structure] | 452 | 454 | 58.1 |
| Compound 478 | ABS [structure] | 478 | 480 | 87.0 |

TABLE 1-continued

| Compound | ABS | | | |
|---|---|---|---|---|
| Compound 479 | ABS | 511 | 513 | |
| Compound 480 | ABS | 511 | 513 | |
| Compound 481 | ABS | 515 | 517 | |
| Compound 482 | ABS | 468 | 470 | 87.4 |
| Compound 483 | ABS | 482 | 484 | |

TABLE 1-continued

| Compound | ABS | Structure | | | |
|---|---|---|---|---|---|
| Compound 484 | ABS | | 523 | 525 | 65.3 |
| Compound 485 | ABS | | 461 | 463 | |
| Compound 486 | ABS | | 546 | 548 | |
| Compound 487 | ABS | | 556, 558 | 558, 560 | |
| Compound 488 | ABS | | 556, 558 | 558, 560 | 62.5 |
| Compound 489 | ABS | | 556, 558 | 558, 560 | |

US 8,022,091 B2

243                                            244

TABLE 1-continued

| Compound | ABS | Structure | | | |
|---|---|---|---|---|---|
| Compound 490 | ABS | | 411 | 413 | |
| Compound 491 | ABS | | 496 | 498 | |
| Compound 492 | ABS | | 560 | 562 | |
| Compound 493 | ABS | | 466 | 468 | 83.1 |
| Compound 494 | ABS | | 456 | 458 | 66.0 |
| Compound 495 | ABS | | 547 | 5 | |

TABLE 1-continued
| Compound | ABS | Structure | | | |
|---|---|---|---|---|---|
| Compound 496 | ABS | 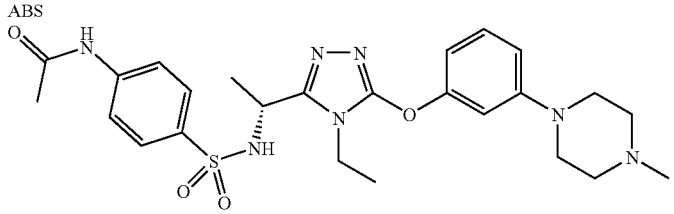 | 526 | 528 | |
| Compound 497 | ABS | 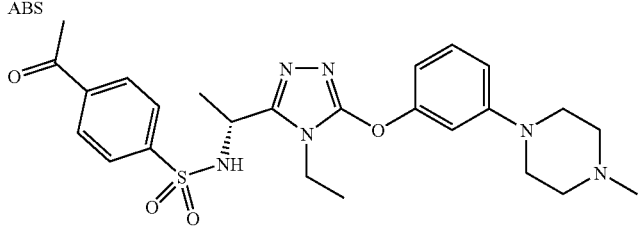 | 511 | 513 | 103.6 |
| Compound 498 | ABS | 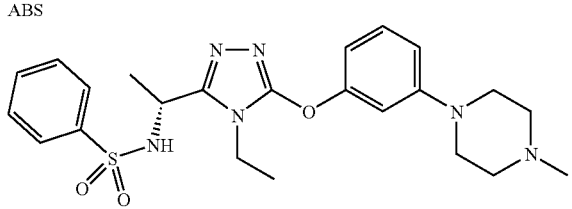 | 469 | 471 | 84.0 |
| Compound 499 | ABS | 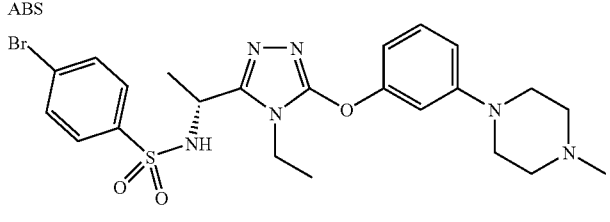 | 547, 549 | 549, 551 | 108.9 |
| Compound 500 | ABS | 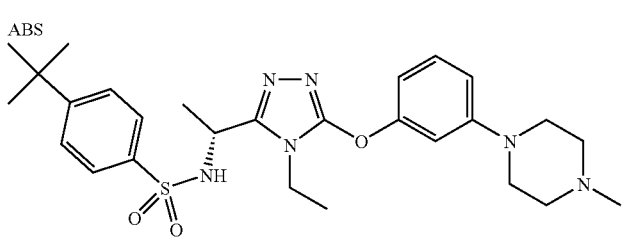 | 525 | 527 | 90.2 |
| Compound 501 | ABS | 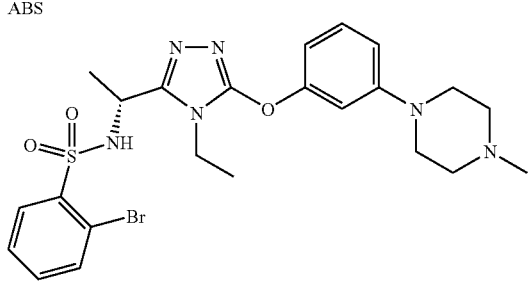 | 547, 549 | 549, 551 | 61.7 |

TABLE 1-continued

| Compound | ABS | Structure | | | |
|---|---|---|---|---|---|
| Compound 502 | ABS | (structure) | 541 | 543 | 75.5 |
| Compound 503 | ABS | (structure) | 547, 549 | 549, 551 | 116.0 |
| Compound 504 | ABS | (structure) | 631, 633 | 633, 635 | 53.5 |
| Compound 505 | ABS | (structure) | 503 | 505 | 108.0 |
| Compound 506 | ABS | (structure) | 494 | 496 | 83.2 |
| Compound 507 | ABS | (structure) | 545 | 547 | 84.8 |

TABLE 1-continued
| Compound | ABS | | | 494 | 496 | |
|---|---|---|---|---|---|---|
| Compound 508 | ABS | 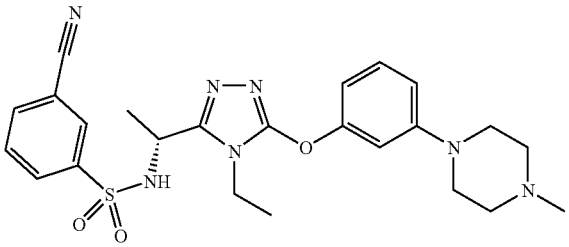 | | 494 | 496 | |
| Compound 509 | ABS | 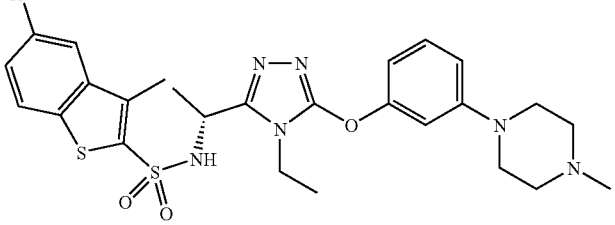 | | 573 | 575 | 87.0 |
| Compound 510 | ABS | 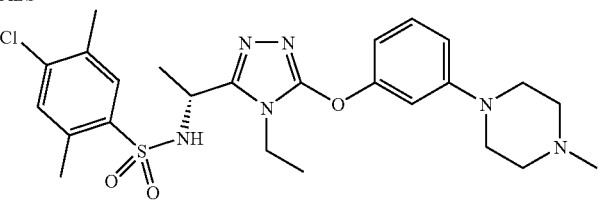 | | 531 | 533 | 113.5 |
| Compound 511 | ABS | 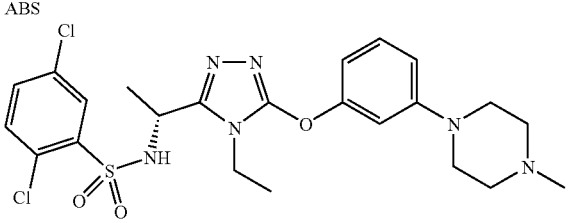 | | 537 | 539 | 98.6 |
| Compound 512 | ABS | 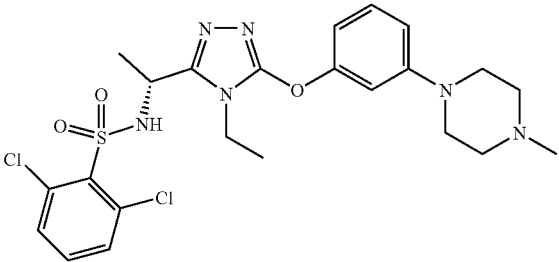 | | 537 | 539 | 60.7 |
| Compound 513 | ABS | 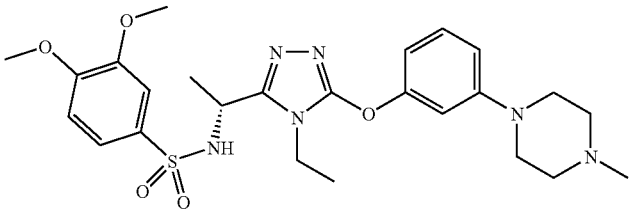 | | 529 | 531 | 96.6 |

TABLE 1-continued

| Compound | | | | |
|---|---|---|---|---|
| Compound 514 | ABS | [structure] | 421 | 423 | |
| Compound 515 | ABS | [structure] | 497 | 499 | 108.9 |
| Compound 516 | ABS | [structure] | 487 | 489 | 106.7 |
| Compound 517 | ABS | [structure] | 511 | 513 | 69.6 |
| Compound 518 | ABS | [structure] | 499 | 501 | 110.8 |
| Compound 519 | ABS | [structure] | 407 | 409 | |

TABLE 1-continued

| Compound 520 | ABS | | 547 | 549 | 69.9 |
|---|---|---|---|---|---|
| Compound 521 | ABS | | 547 | 549 | |
| Compound 522 | ABS | | 519 | 521 | 98.4 |
| Compound 523 | ABS | | 547 | 549 | 113.5 |
| Compound 524 | ABS | | 559 | 561 | 83.0 |
| Compound 525 | ABS | | 595 | 597 | 110.9 |

TABLE 1-continued

| Compound 526 | ABS | [structure: 2,4,5-trichlorophenylsulfonamide triazole] | 571, 573 | 573, 575 | 111.8 |
|---|---|---|---|---|---|
| Compound 527 | ABS | [structure: 2,4,6-triisopropylphenylsulfonamide triazole] | 595 | 597 | 52.1 |
| Compound 528 | ABS | [structure: p-tolylsulfonamide triazole] | 483 | 485 | 106.2 |
| Compound 529 | ABS | [structure: benzylsulfonamide triazole] | 483 | 485 | |
| Compound 530 | ABS | [structure: 3-trifluoromethylphenylsulfonamide triazole] | 537 | 539 | 114.7 |
| Compound 531 | ABS | [structure: 2-methylphenylsulfonamide triazole] | 483 | 485 | 100.1 |

TABLE 1-continued

| Compound | ABS | | | | |
|---|---|---|---|---|---|
| Compound 532 | ABS | | 553 | 555 | 99.2 |
| Compound 533 | ABS | | 495 | 497 | |
| Compound 534 | ABS | | 483 | 485 | 100.8 |
| Compound 535 | ABS | | 610 | 612 | |
| Compound 536 | ABS | | 620 | 622 | 50.3 |
| Compound 537 | ABS | | 497 | 499 | 96.7 |

TABLE 1-continued
| Compound 538 | ABS 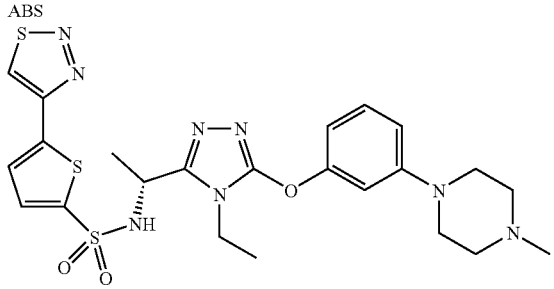 | 559 | 561 | 97.1 |
|---|---|---|---|---|
| Compound 539 | ABS 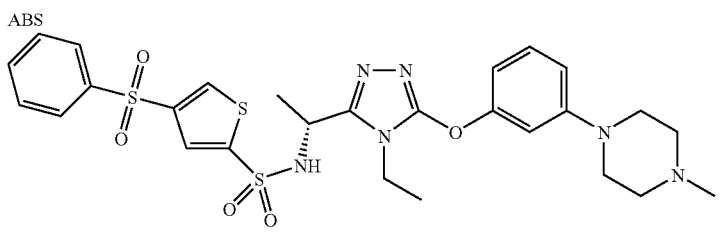 | 615 | 617 | |
| Compound 540 | ABS 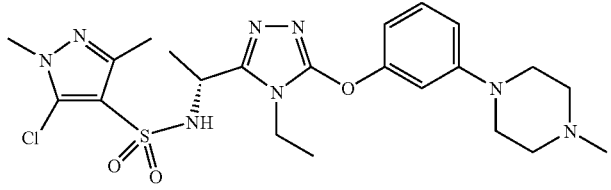 | 521 | 523 | 64.3 |
| Compound 541 | ABS 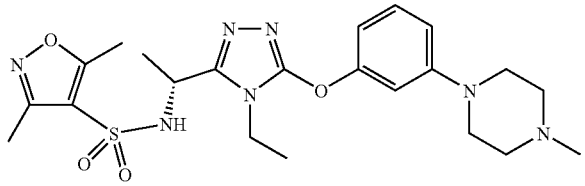 | 488 | 490 | 65.5 |
| Compound 542 | ABS 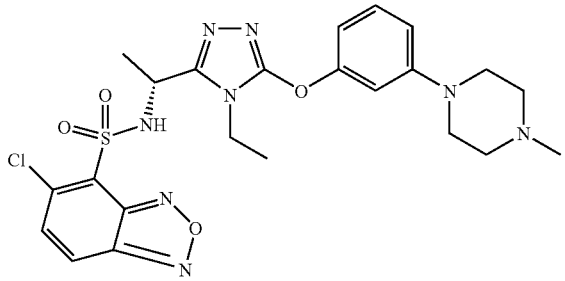 | 545 | 547 | 50. |

TABLE 1-continued

| Compound 543 | ABS | [structure] | 530 | 532 | 111.8 |
| Compound 544 | ABS | [structure] | 501 | 503 | 53.9 |
| Compound 545 | ABS | [structure] | 527 | 529 | 50.7 |
| Compound 546 | ABS | [structure] | 537 | 539 | 55.8 |
| Compound 547 | ABS | [structure] | 545 | 547 | |

TABLE 1-continued

| | | | | | |
|---|---|---|---|---|---|
| Compound 548 | ABS | (structure) | 511 | 513 | 96.7 |
| Compound 549 | ABS | (structure) | 525 | 527 | 89.2 |
| Compound 550 | ABS | (structure) | 537 | 539 | 103.6 |
| Compound 551 | ABS | (structure) | 517 | 519 | 76.1 |
| Compound 552 | ABS | (structure) | 503 | 505 | 67.2 |
| Compound 553 | ABS | (structure) | 605 | 607 | 106.6 |

TABLE 1-continued

| Compound | ABS | Structure | | | |
|---|---|---|---|---|---|
| Compound 554 | ABS | (3,5-dichlorophenyl sulfonamide structure) | 537 | 539 | 116.5 |
| Compound 555 | ABS | (3-chloro-2-methylphenyl sulfonamide structure) | 517 | 519 | 102.0 |
| Compound 556 | ABS | (3-methoxyphenyl sulfonamide structure) | 499 | 501 | 104.8 |
| Compound 557 | ABS | (4-bromo-2,5-difluorophenyl sulfonamide structure) | 583, 585 | 585, 587 | 107.3 |
| Compound 558 | ABS | (2,6-dimethyl-4-methoxy-3-methylphenyl sulfonamide structure) | 541 | 543 | 64.8 |
| Compound 559 | ABS | (5-bromo-2-methoxyphenyl sulfonamide structure) | 577, 579 | 579, 581 | 79.3 |

TABLE 1-continued

| | | | | | |
|---|---|---|---|---|---|
| Compound 560 | ABS | [structure] | 501 | 503 | 74.4 |
| Compound 561 | ABS | [structure] | 539 | 541 | 92.4 |
| Compound 562 | ABS | [structure] | 513 | 515 | 93.3 |
| Compound 563 | ABS | [structure] | 553 | 555 | 64.1 |
| Compound 564 | ABS | [structure] | 494 | 496 | 105.4 |
| Compound 565 | ABS | [structure] | 561 | 563 | |

TABLE 1-continued

| Compound | ABS | Structure | | | |
|---|---|---|---|---|---|
| Compound 566 | ABS | | 571, 573 | 573, 575 | 88.7 |
| Compound 567 | ABS | | 537 | 539 | 101.6 |
| Compound 568 | ABS | | 505 | 507 | 71.1 |
| Compound 569 | ABS | | 529 | 531 | 75.0 |
| Compound 570 | ABS | | 521 | 523 | 77.4 |
| Compound 571 | ABS | | 487 | 489 | 55.7 |

TABLE 1-continued

| Compound | | | | |
|---|---|---|---|---|
| Compound 572 | ABS (3-Cl-phenyl sulfonamide triazole) | 503 | 505 | 96.5 |
| Compound 573 | ABS (4-isopropyl-phenyl sulfonamide triazole) | 511 | 513 | 86.3 |
| Compound 574 | ABS (4-Br-2-ethyl-phenyl sulfonamide triazole) | 575, 577 | 577, 579 | 86.9 |
| Compound 575 | ABS (4-Br-2-methyl-phenyl sulfonamide triazole) | 561, 563 | 563, 565 | 103.7 |
| Compound 576 | ABS (4-CN-2-Cl-phenyl sulfonamide triazole) | 528 | 530 | 81.4 |
| Compound 577 | ABS (2,3,4-triF-phenyl sulfonamide triazole) | 523 | 525 | 92.4 |
| Compound 578 | ABS (2,5-diF-phenyl sulfonamide triazole) | 505 | 507 | |

TABLE 1-continued
| Compound | ABS | Structure | | | |
|---|---|---|---|---|---|
| Compound 579 | ABS | 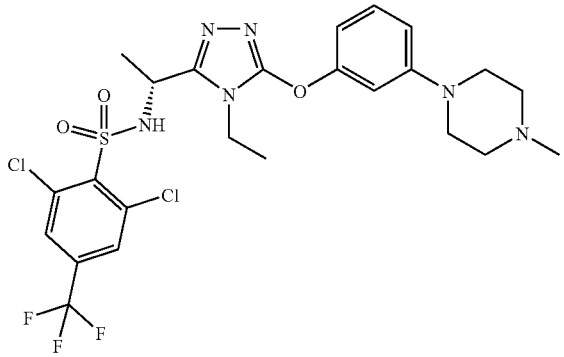 | 605 | 607 | 87.6 |
| Compound 580 | ABS | 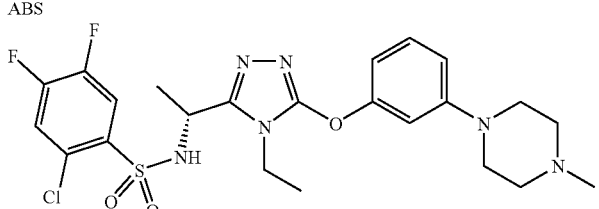 | 539 | 541 | 89.2 |
| Compound 581 | ABS | 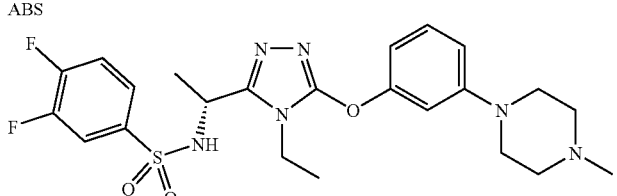 | 505 | 507 | 99.9 |
| Compound 582 | ABS | 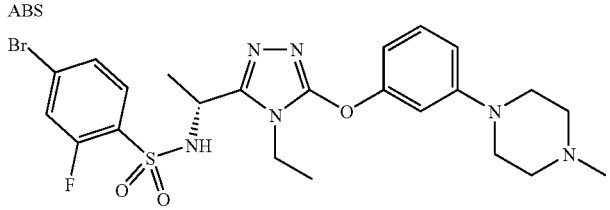 | 565, 567 | 567, 569 | 106.0 |
| Compound 583 | ABS | 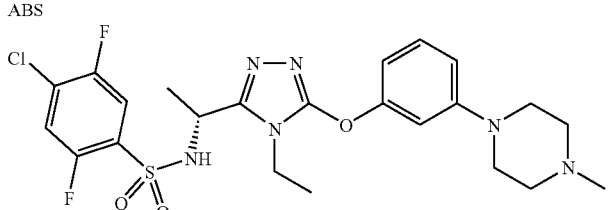 | 539 | 541 | 108.9 |
| Compound 584 | ABS | 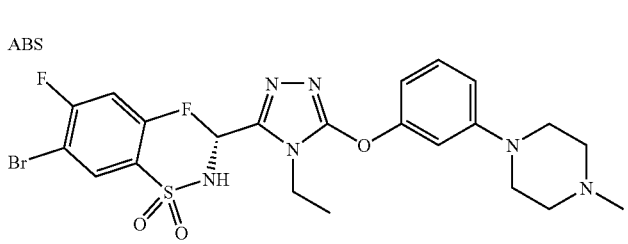 | 583, 585 | 585, 587 | 96.2 |

TABLE 1-continued

| Compound 585 | ABS | [structure] | 539 | 541 | 103.0 |
| Compound 586 | ABS | [structure] | 551 | 553 | 87.9 |
| Compound 587 | ABS | [structure] | 573 | 575 | 60.0 |
| Compound 588 | ABS | [structure] | 551 | 553 | 109.3 |
| Compound 589 | ABS | [structure] | 661, 663 | 663, 665 | 80.2 |
| Compound 590 | ABS | [structure] | 505 | 507 | 62.3 |

TABLE 1-continued

| Compound | ABS | | | | |
|---|---|---|---|---|---|
| Compound 591 | ABS | (structure) | 571 | 573 | 77.5 |
| Compound 592 | ABS | (structure) | 487 | 489 | 95.8 |
| Compound 593 | ABS | (structure) | 560 | 562 | 65.9 |
| Compound 594 | ABS | (structure) | 533 | 535 | 84.0 |
| Compound 595 | ABS | (structure) | 551 | 553 | 93.7 |
| Compound 596 | ABS | (structure) | 523 | 525 | 100.3 |

TABLE 1-continued

| Compound | ABS | | | |
|---|---|---|---|---|
| Compound 597 | ABS (structure) | 625, 627 | 627, 629 | 97.3 |
| Compound 598 | ABS (structure) | 542 | 544 | 89.5 |
| Compound 599 | ABS (structure) | 517 | 519 | 80.6 |
| Compound 600 | ABS (structure) | 625, 627 | 627, 629 | 10.5 |
| Compound 601 | ABS (structure) | 512 | 514 | 100.4 |
| Compound 602 | ABS (structure) | 497 | 499 | 106.7 |

TABLE 1-continued
| Compound | ABS | | | | |
|---|---|---|---|---|---|
| Compound 603 | ABS 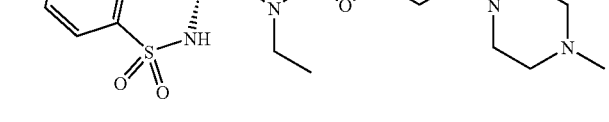 | | 535 | 537 | 106.8 |
| Compound 604 | ABS 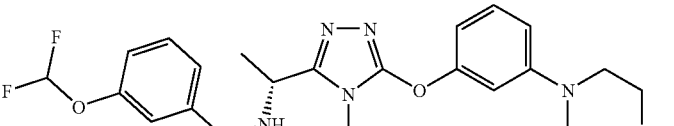 | | 535 | 537 | 109.4 |
| Compound 605 | ABS 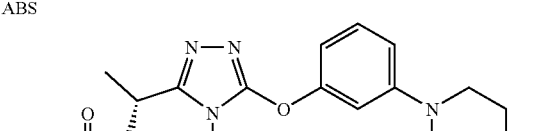 | | 583, 585 | 585, 587 | 83.4 |
| Compound 606 | ABS 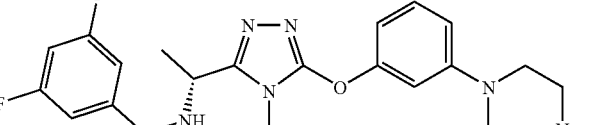 | | 505 | 507 | 107.8 |
| Compound 607 | ABS 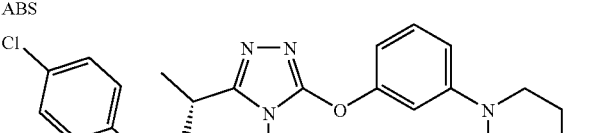 | | 521 | 523 | |
| Compound 608 | ABS 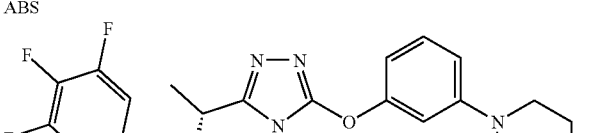 | | 523 | 525 | 108.6 |

TABLE 1-continued

| Compound 609 | ABS | [structure] | 565, 567 | 567, 569 | 93.1 |
| Compound 610 | ABS | [structure] | 615, 617 | 617, 619 | 91.2 |
| Compound 611 | ABS | [structure] | 615, 617 | 617, 619 | 63.9 |
| Compound 612 | ABS | [structure] | 501 | 503 | 114.0 |
| Compound 613 | ABS | [structure] | 501 | 503 | 90.9 |
| Compound 614 | ABS | [structure] | 521 | 523 | |

TABLE 1-continued

| Compound | | | | |
|---|---|---|---|---|
| Compound 615 | ABS (structure) | 565, 567 | 567, 569 | 110.3 |
| Compound 616 | ABS (structure) | 581, 583 | 583, 585 | 99.9 |
| Compound 617 | ABS (structure) | 615, 617 | 617, 619 | 77.5 |
| Compound 618 | ABS (structure) | 557 | 559 | 65.4 |
| Compound 619 | ABS (structure) | 497 | 499 | 114.2 |
| Compound 620 | ABS (structure) | 501 | 503 | 88.4 |

TABLE 1-continued

| Compound | ABS | Structure | | | |
|---|---|---|---|---|---|
| Compound 621 | ABS | | 521 | 523 | 95.4 |
| Compound 622 | ABS | | 555 | 557 | 58.9 |
| Compound 623 | ABS | | 575 | 577 | |
| Compound 624 | ABS | | 562 | 564 | |
| Compound 625 | ABS | | 484 | 486 | |
| Compound 626 | ABS | | 499 | 501 | 61.1 |

TABLE 1-continued

| Compound 627 | ABS | [structure] | 489 | 491 | 90.0 |
| Compound 628 | ABS | [structure] | 533 | 535 | 64.4 |
| Compound 629 | ABS | [structure] | 541 | 543 | 101.1 |
| Compound 630 | ABS | [structure] | 527 | 529 | 107.4 |
| Compound 631 | ABS | [structure] | 504 | 506 | 95.2 |
| Compound 632 | ABS | [structure] | 527 | 529 | 59.9 |

TABLE 1-continued

| Compound | ABS | | | | |
|---|---|---|---|---|---|
| Compound 633 | ABS | | 527 | 529 | 111.2 |
| Compound 634 | ABS | | 511 | 513 | 51.0 |
| Compound 635 | ABS | | 475 | 477 | 68.7 |
| Compound 636 | ABS | | 542 | 544 | 85.7 |
| Compound 637 | ABS | | 549 | 551 | 50.6 |
| Compound 638 | ABS | | 558 | 560 | |

TABLE 1-continued
| Compound 639 | ABS | 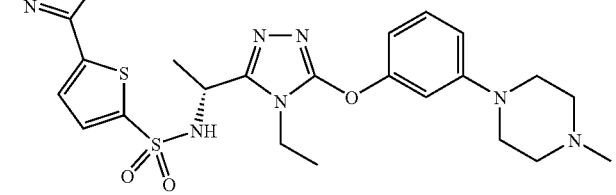 | 623 | 625 | |
| --- | --- | --- | --- | --- | --- |
| Compound 640 | ABS | 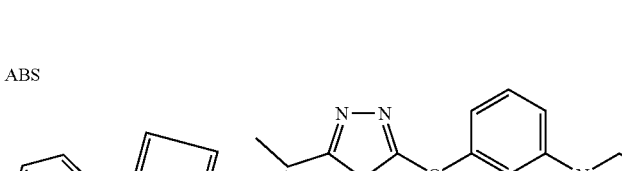 | 599 | 601 | 59.5 |
| Compound 641 | ABS | 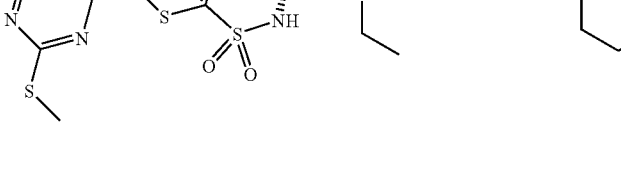 | 503 | 505 | 85.2 |
| Compound 642 | ABS | 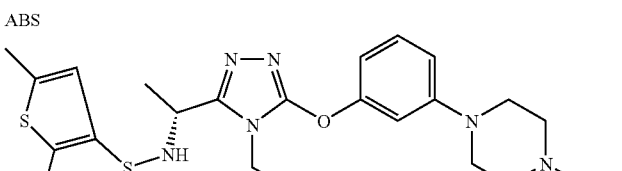 | 529 | 531 | 85.5 |
| Compound 643 | ABS | 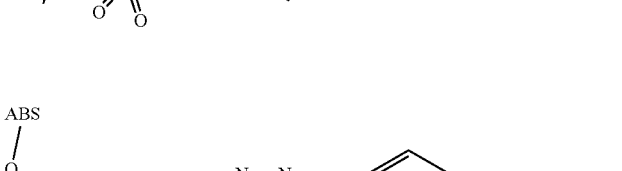 | 618 | 620 | |

TABLE 1-continued

| Compound | ABS | | | |
|---|---|---|---|---|
| Compound 644 | ABS | | 571 | 573 | 93.0 |
| Compound 645 | ABS | | 597 | 599 | |
| Compound 646 | ABS | | 641 | 643 | |
| Compound 647 | ABS | | 511 | 513 | 99.0 |
| Compound 648 | ABS | | 537 | 539 | 107.8 |

TABLE 1-continued

| Compound | ABS | | | | |
|---|---|---|---|---|---|
| Compound 649 | ABS | | 570 | 572 | 64.7 |
| Compound 650 | ABS | | 570 | 572 | |
| Compound 651 | ABS | | 574 | 576 | |
| Compound 652 | ABS | | 527 | 529 | 91.9 |
| Compound 653 | ABS | | 541 | 54 | |

TABLE 1-continued

| Compound 654 | ABS | [structure] | | 582 | 584 | 71.7 |
| --- | --- | --- | --- | --- | --- | --- |
| Compound 655 | ABS | [structure] | | 605 | 607 | |
| Compound 656 | ABS | [structure] | | 615, 617 | 617, 619 | |
| Compound 657 | ABS | [structure] | | 615, 617 | 617, 619 | 94.9 |
| Compound 658 | ABS | [structure] | | 615, 617 | 617, 619 | 80.4 |
| Compound 659 | ABS | [structure] | | 470 | 472 | |

TABLE 1-continued

| Compound number | Chemical structure | | | |
|---|---|---|---|---|
| Compound 660 | ABS | 555 | 557 | |
| Compound 661 | ABS | 619 | 621 | |
| Compound 662 | ABS | 525 | 527 | 95.4 |

| Compound number | Chemical structure | Melting point (° C.) | Binding assay (membrane) % inhibition (10 μM) |
|---|---|---|---|
| Compound 663 | ABS | 210.0-217.0 | 99.5 |
| Compound 664 | ABS | 218.0-221.5 | 85.4 |
| Compound 665 | ABS | 197.0-201.0 | 100.3 |

TABLE 1-continued

| Compound | | | |
|---|---|---|---|
| Compound 666 | ABS | 143.5-144.5 | 97.9 |
| Compound 667 | ABS | 207.0-208.0 | 99.2 |
| Compound 668 | ABS | | 98.6 |
| Compound 669 | ABS | 131.5-132.5 | 100.3 |
| Compound 670 | ABS | 214.5-218.0 | 100.8 |
| Compound 671 | | | 100.6 |
| Compound 672 | ABS | | 102.7 |

TABLE 1-continued

| Compound 673 | ABS | (structure) | 62.0 |
| Compound 674 | ABS | (structure) | 97.0 |
| Compound 675 | ABS | (structure) | 96.6 |
| Compound 676 | ABS | (structure) | 92.6 |
| Compound 677 | ABS | (structure) | 60.8 |
| Compound 678 | ABS | (structure) | 97.4 |

TABLE 1-continued
| Compound 679 | ABS | 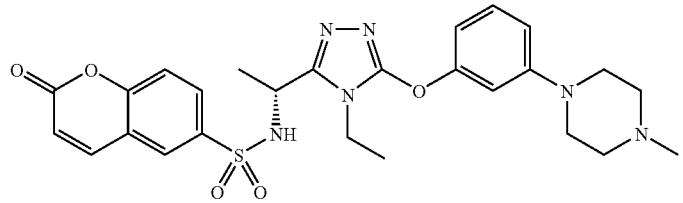 | | 104.0 |
| --- | --- | --- | --- | --- |
| Compound 680 | ABS | 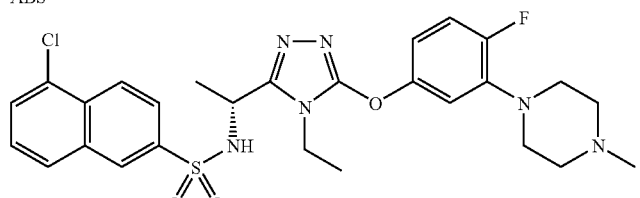 | 169.5-170.5 | 100.1 |
| Compound 681 | ABS | 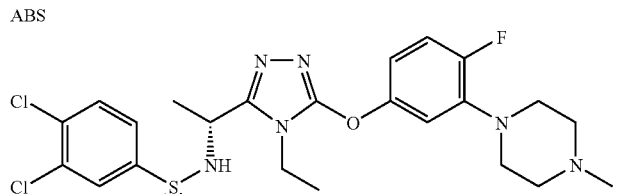 | 189.0-189.5 | 100.2 |
| Compound 682 | | 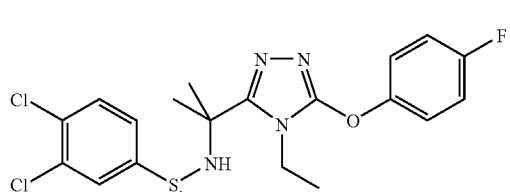 | 228.0-228.5 | 76.6 |
| Compound 683 | ABS | 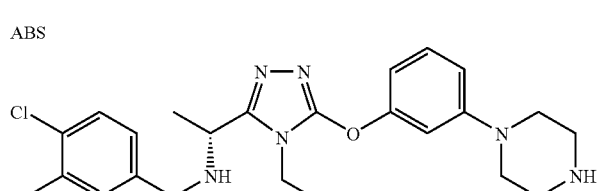 | 175.0-178.0 | 100.5 |
| Compound 684 | ABS | 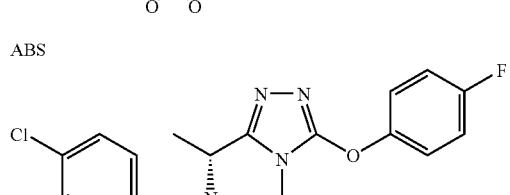 | 169.5-171.5 | |
| Compound 685 | | 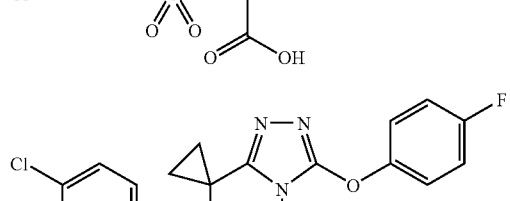 | 255.0-260.0 | 65.1 |

TABLE 1-continued

| | | Mp (°C) | |
|---|---|---|---|
| Compound 686 | [structure] | 220.5-221.0 | 92.7 |
| Compound 687 | [structure] | | 80.1 |
| Compound 688 | ABS [structure] | 192.0-193.0 | 100.5 |
| Compound 689 | ABS [structure] | | 92.7 |
| Compound 690 | ABS [structure] | 198.0-200.0 | 1022 |
| Compound 691 | ABS [structure] | 180.0-182.0 | 9 |

TABLE 1-continued
| Compound 692 | ABS 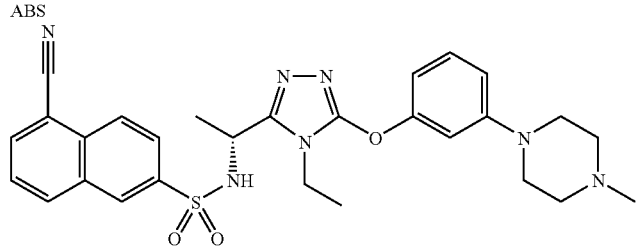 | 227.0-229.0 | 98.5 |
| --- | --- | --- | --- |
| Compound 693 | ABS 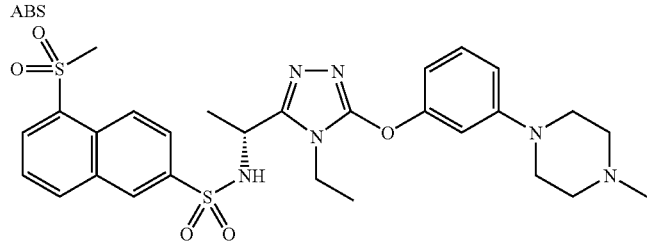 | 158.0-161.0 | 97.7 |
| Compound 694 | ABS 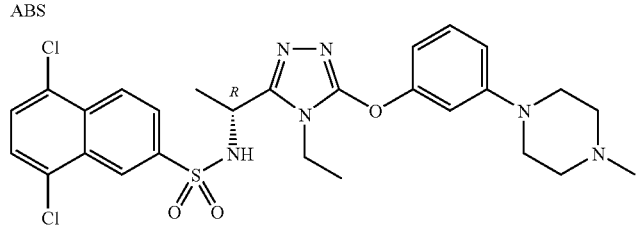 | 189.0-191.0 | 106.0 |
| Compound 695 | ABS 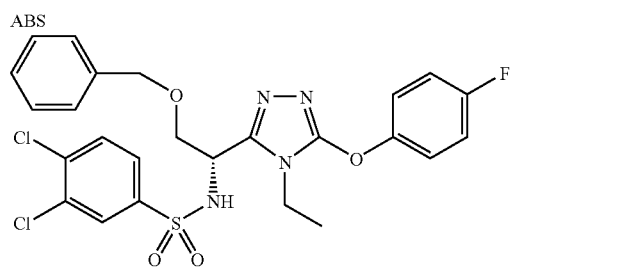 | | |
| Compound 696 | ABS 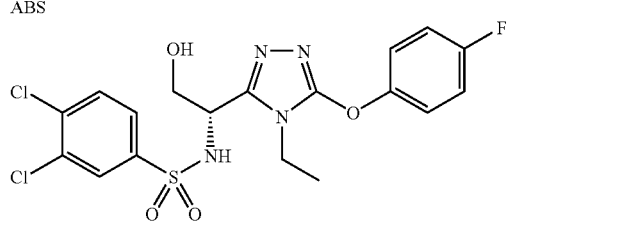 | | |
| Compound 697 | ABS 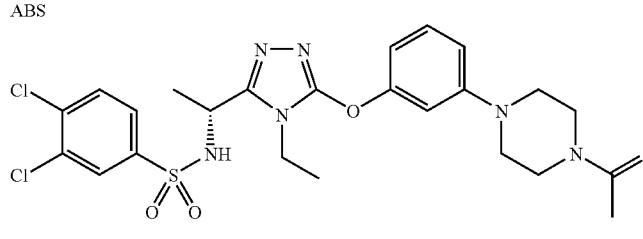 | | |

TABLE 1-continued

Compound 698 ABS

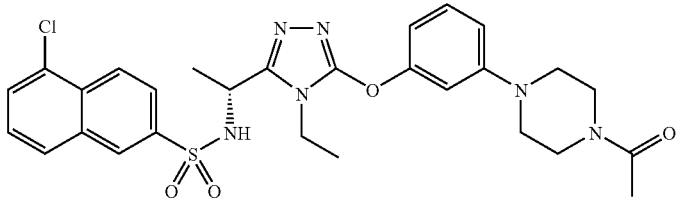

In Table 1, some of the compounds have two data on APCI MS (M−H)− and APCI MS (M+H)+, because two peaks were detected due to isotopes of a chlorine atom or a bromine atom.

For the compounds listed below, $^1$H-NMR data is shown.

Compound 100: (600 MHz, DMSO-d6) δ ppm: 1.21 (t, J=7.1 Hz, 3H) 1.27 (d, J=6.9 Hz, 3H) 3.22 (s, 6H) 3.40-3.50 (m, 8H) 3.77-3.93 (m, 2H) 4.68 (q, J=6.9 Hz, 1H) 6.34 (dd, J=7.3, 2.29 Hz, 1H) 6.52 (dd, J=8.3, 2.29 Hz, 1H) 6.56 (t, J=2.3 Hz, 1H) 7.12 (t, J=8.3 Hz, 1H) 7.70 (dd, J=8.3, 2.3 Hz, 1H) 7.85 (d, J=8.3 Hz, 1H) 7.92 (d, J=1.8 Hz, 1H) 8.66 (s, 1H).

Compound 119: (600 MHz, CDCl$_3$) δ ppm: 1.34 (t, J=7.3 Hz, 3H), 1.50 (d, J=7.3 Hz, 3H), 3.89-3.98 (m, 2H), 4.59-4.65 (m, 1H), 5.06 (s, 2H) 6.37-6.42 (m, 1H), 6.80-6.95 (m, 2H), 7.01-7.04 (m, 1H), 7.24-7.36 (m, 2H), 7.36-7.44 (m, 4H), 7.49-7.53 (m, 1H), 7.67-7.73 (m, 1H), 7.93-7.96 (m, 1H).

Compound 127: (600 MHz, CDCl$_3$) δ ppm: 1.38 (t, J=7.1 Hz, 3H), 1.49 (d, J=6.9 Hz, 3H), 2.41 (s, 3H), 3.93-4.02 (m, 2H), 4.59-4.65 (m, 1H), 5.47 (d, J=9.6 Hz, 1H), 7.05-7.10 (m, 2H), 7.31-7.37 (m, 3H), 7.61-7.64 (m, 1H), 7.80-7.82 (m, 1H).

Compound 129: (600 MHz, DMSO-d6) δ ppm: 1.21-1.29 (m, 6H), 2.29 (s, 6H), 3.83-4.01 (m, 2H), 4.61 (q, J=6.4 Hz, 1H), 6.43-6.47 (m, 1H), 6.89-6.93 (m, 1H), 7.34-7.40 (m, 3H), 7.52-7.60 (m, 3H), 8.24 (s, 1H), 11.18 (s, 1H).

Compound 130: (600 MHz, DMSO-d6) δ ppm: 1.22 (d, J=6.8 Hz, 3H), 1.26 (t, J=7.1 Hz, 3H), 3.87-4.02 (m, 2H), 4.70 (q, J=6.8 Hz, 1H), 6.43-6.45 (m, 1H), 6.77-6.80 (m, 1H), 7.28-7.30 (m, 1H), 7.36-7.38 (m, 1H), 7.50-7.53 (m, 1H), 7.67-7.75 (m, 2H), 7.83-7.86 (m, 1H), 8.04-8.07 (m, 1H), 8.12-8.19 (m, 2H), 8.45-8.47 (m, 1H), 8.52 (s, 1H), 11.16 (s, 1H).

Compound 131: (600 MHz, DMSO-d6) δ ppm: 1.28 (t, J=7.1 Hz, 3H), 1.35 (d, J=6.9 Hz, 3H), 2.36 (s, 3H), 3.89-4.03 (m, 2H), 4.64-4.72 (m, 1H), 6.44-6.46 (m, 1H), 6.87-6.90 (m, 1H), 7.36-7.38 (m, 2H), 7.53-7.57 (m, 1H), 7.82-7.84 (m, 1H), 7.88-7.91 (m, 1H), 8.77 (s, 1H), 11.18 (s, 1H).

Compound 132: (600 MHz, DMSO-d6) δ ppm: 1.23-1.31 (m, 6H), 2.39 (s, 3H), 3.85-4.02 (m, 2H), 4.69 (q, J=6.9 Hz, 1H), 6.43-6.47 (m, 1H), 6.88-6.92 (m, 1H), 7.36-7.39 (m, 2H), 7.53-7.60 (m, 2H), 7.64-7.68 (m, 1H), 7.77-7.80 (m, 1H), 8.51 (s, 1H), 11.18 (s, 1H).

Compound 134: (600 MHz, DMSO-d6) δ ppm: 1.29 (t, J=7.3 Hz, 3H), 1.36 (d, J=6.9 Hz, 3H), 3.89-4.05 (m, 2H), 4.67-4.73 (m, 1H), 6.44-6.46 (m, 1H), 6.86-6.90 (m, 1H), 7.35-7.39 (m, 2H), 7.54-7.57 (m, 1H), 7.83-7.88 (m, 1H), 7.91-7.94 (m, 1H), 9.01 (s, 1H), 11.17 (s, 1H).

Compound 136: (600 MHz, DMSO-d6) δ ppm: 1.23-1.31 (m, 6H), 3.85-4.02 (m, 2H), 4.72 (q, J=6.9 Hz, 1H), 6.44-6.47 (m, 1H), 6.87-6.91 (m, 1H), 7.34-7.39 (m, 2H), 7.52-7.57 (m, 1H), 7.97-8.05 (m, 4H), 8.74 (s, 1H), 11.18 (s, 1H).

Compound 150; (200 MHz, CDCl$_3$) δ ppm: 0.94 (d, J=6.4 Hz, 3H), 0.97 (d, J=6.4 Hz, 3H), 1.30 (t, J=7.3 Hz, 3H), 2.00-2.20 (m, 1H), 2.37 (s, 3H), 3.70-3.88 (m, 2H), 4.10 (dd, J=6.9, 9.4 Hz, 1H), 6.71 (d, J=9.4 Hz, 2H), 7.12-7.22 (m, 4H), 7.40 (d, J=8.4 Hz, 1H), 7.65 (dd, J=2.2, 8.4 Hz, 1H), 7.84 (d, J=2.2 Hz, 1H).

Compound 668: (600 MHz, DMSO-d6) ppm: 1.19-1.25 (m, 6H), 2.22 (s, 3H), 2.41-2.46 (m, 4H), 2.49-2.54 (m, 3H), 3.11-3.17 (m, 4H), 3.83-3.99 (m, 2H), 4.65-4.71 (m, 1H), 6.47-6.51 (m, 1H), 6.77-6.82 (m, 2H), 7.17-7.22 (m, 1H), 7.51-7.55 (m, 1H), 7.77-7.84 (m, 2H), 8.01-8.10 (m, 2H), 8.38-8.51 (m, 2H).

Compound 671: (200 MHz, CDCl$_3$) δ ppm: 0.89 (t, J=7.5 Hz, 3H), 1.23 (t, J=7.3 Hz, 3H), 1.70-2.06 (m, 2H), 2.42 (s, 3H), 2.66 (bs, 4H), 3.29 (t, J=5.1 Hz, 4H), 3.68-3.92 (m, 2H), 4.38 (dd, J=7.0, 15.4 Hz, 1H), 6.50 (bs, 1H), 6.56 (dd, J=2.0, 8.1 Hz, 1H), 6.72 (dd, J=2.0, 8.4 Hz, 1H), 6.89 (t, J=2.0 Hz, 1H), 7.20 (t, J=8.4 Hz, 1H), 7.46 (t, J=8.1 Hz, 1H), 7.69 (d, J=8.0 Hz, 1H), 7.80 (d, J=8.0 Hz, 1H), 7.94 (d, J=2.0, 9.0 Hz, 1H), 8.28 (d, J=9.0 Hz, 1H), 8.4 (d, J=2.0 Hz, 1H).

Compound 672: (200 MHz, CDCl$_3$) δ ppm: 1.33 (t, J=7.3 Hz, 3H), 1.49 (d, J=6.8 Hz, 3H), 2.41 (s, 3H), 2.57-2.70 (m, 4H), 3.16-3.33 (m, 6H), 3.91 (q, J=7.3 Hz, 2H), 4.52-4.69 (m, 3H), 5.08 (d, J=9.0 Hz, 1H), 6.73 (dd, J=2.2, 8.6 Hz, 2H), 6.81 (d, J=9.0 Hz, 1H), 6.97 (t, J=2.2 Hz, 1H), 7.23 (t, J=8.1 Hz, 1H), 7.62-7.68 (m, 2H).

Compound 673: (200 MHz, CDCl$_3$) δ ppm: 1.31 (t, J=7.0 Hz, 3H), 1.33 (s, 6H), 1.49 (d, J=7.0 Hz, 3H), 1.80 (t, J=6.6 Hz, 2H), 2.39 (s, 3H), 2.59 (t, J=5.0 Hz, 4H), 2.79 (t, J=7.0 Hz, 2H), 3.25 (t, J=5.0 Hz, 4H), 3.90 (q, J=7.0 Hz, 2H), 4.48-4.65 (m, 1H), 5.07 (d, J=9.5 Hz, 1H), 6.73 (dd, J=2.4, 8.1 Hz, 2H), 6.82 (d, J=9.2 Hz, 1H), 6.97 (t, J=2.4 Hz, 1H), 7.23 (t, J=8.1 Hz, 1H), 7.51-7.57 (m, 2H).

Compound 674: (200 MHz, CDCl$_3$) δ ppm: 1.34 (t, J=7.3 Hz, 3H), 1.49 (d, J=6.8 Hz, 3H), 2.21 (quint, J=6.0 Hz, 2H), 2.37 (s, 3H), 2.59 (t, J=4.6 Hz, 4H), 3.25 (t, J=4.6 Hz, 4H), 3.93 (q, J=7.3 Hz, 2H), 4.27 (dd, J=6.0, 11.6 Hz, 4H) 4.51-4.66 (m, 1H), 5.15 (d, J=9.5 Hz, 1H), 6.74 (dd, J=2.2, 8.4 Hz, 1H), 7.07-7.13 (m, 2H), 7.23 (t, J=8.1 Hz, 1H), 7.38 (dd, J=2.4, 8.1 Hz, 1H), 7.43 (d, J=2.0 Hz, 1H).

Compound 675: (200 MHz, CDCl$_3$) δ ppm: 1.36 (t, J=7.3 Hz, 3H), 1.49 (d, J=6.8 Hz, 3H), 2.39 (s, 3H), 2.59 (t, J=5.0 Hz, 4H), 3.26 (t, J=5.0 Hz, 4H), 3.95 (q, J=7.3 Hz, 2H), 4.50-4.68 (m, 1H), 5.18 (d, J=9.5 Hz, 1H), 6.05 (s, 2H), 6.74 (dd, J=2.4, 8.1 Hz, 2H), 6.86 (d, J=8.4 Hz, 1H), 6.98 (t, J=2.4 Hz, 1H), 7.19-7.27 (m, 2H), 7.42 (dd, J=1.8, 8.1 Hz, 1H).

Compound 676: (200 MHz, CDCl$_3$) δ ppm: 1.27-1.33 (m, 15H), 1.47 (d, J=6.8 Hz, 3H), 2.43 (s, 3H), 2.61-2.72 (m, 4H), 3.25-3.33 (m, 4H), 3.90 (q, J=7.5 Hz, 2H), 4.57 (dd, J=6.8, 9.2 Hz, 1H), 5.13 (d, J=9.2 Hz, 1H), 6.70-6.79 (m, 2H), 6.99 (t, J=2.2 Hz, 1H), 7.22 (t, J=8.1 Hz, 1H), 7.41 (d, J=8.6 Hz, 1H), 7.57 (dd, J=2.0, 8.1 Hz, 1H), 7.79 (d, J=2.0 Hz, 1H).

Compound 677: (200 MHz, CDCl$_3$) δ ppm: 1.32 (t, J=7.3 Hz, 3H), 1.49 (d, J=6.8 Hz, 3H), 2.22 (s, 3H), 2.38 (s, 3H), 2.56-2.63 (m, 4H), 3.14-3.30 (m, 6H), 3.84-4.10 (m, 4H), 4.53-4.64 (m, 1H), 5.25 (d, J=9.5 Hz, 1H), 6.71-6.79 (m, 2H), 7.01 (t, J=2.4 Hz, 1H), 7.22 (t, J=8.4 Hz, 1H), 7.57 (s, 1H), 7.69 (dd, J=2.0, 8.4 Hz, 1H), 8.27 (d, J=8.4 Hz, 1H).

Compound 678: (200 MHz, CDCl$_3$) δ ppm: 1.32 (t, J=7.3 Hz, 3H), 1.46 (d, J=6.8 Hz, 3H), 2.11 (quint, J=7.5 Hz, 2H), 2.36 (s, 3H), 2.58 (t, J=5.0 Hz, 4H), 2.94 (t, J=7.5 Hz, 4H), 3.25 (t, J=5.0 Hz, 4H), 3.92 (q, J=7.3 Hz, 2H), 4.52-4.67 (m, 1H), 5.15 (d, J=10.0 Hz, 1H), 6.73 (dd, J=2.2, 8.1 Hz, 2H), 6.98 (t, J=2.2 Hz, 1H), 7.22 (t, J=7.9 Hz, 1H), 7.31 (d, J=8.1 Hz, 1H), 7.62 (dd, J=2.2, 7.9 Hz, 1H), 7.67 (s, 1H).

Compound 679: (600 MHz, DMSO-d6) δ ppm; 1.24 (t, J=7.1 Hz, 3H), 1.29 (d, J=6.9 Hz, 3H), 2.22 (s, 3H), 2.40-2.46 (m, 4H), 3.12-3.16 (m, 4H), 3.81-3.97 (m, 2H), 4.64-4.72 (m, 1H), 6.53-6.58 (m, 1H), 6.60-6.65 (m, 1H), 6.77-6.82 (m, 2H), 7.20 (t, J=8.3 Hz, 1H), 7.60 (d, J=8.7 Hz, 1H), 7.94-7.99 (m, 1H), 8.17-8.23 (m, 2H), 8.54-8.61 (m, 1H).

Compound 698: (600 MHz, CDCl$_3$) δ ppm: 1.33 (t, J=7.1 Hz, 3H), 1.43 (d, J=6.9 Hz, 3H), 2.11 (s, 3H), 3.10-3.20 (m, 4H), 3.53-3.59 (m, 2H), 3.67-3.74 (m, 2H), 3.89-4.00 (m, 2H), 4.67 (q, J=7.1 Hz, 1H), 6.65-6.75 (m, 2H), 6.94-6.97 (m, 1H), 7.21-7.25 (m, 1H), 7.46-7.50 (m, 1H), 7.69-7.73 (m, 1H), 7.80-7.84 (m, 1H), 7.95-7.99 (m, 1H), 8.29-8.34 (m, 1H), 8.45-8.47 (m, 1H).

The following describes exemplary methods of preparing starting materials used to produce the compounds of the present application.

Reference Examples 1-3

Starting from the corresponding amine in place of 1,4-dioxa-8-azaspiro[4,5]decane used in Example 7-(1), the same procedure as used in Example 7-(1) was repeated to give the titled compounds.

Reference Example 1

3-((2R,6S)-2,6-Dimethylmorpholine-4-yl)-phenol

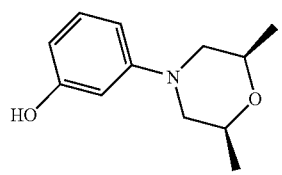

[Formula 79]

Brown oily substance, yield 71%
$^1$H NMR (600 MHz, CDCl$_3$) δ ppm: 1.24 (d, J=6.0 Hz, 6H), 2.36-2.45 (m, 2H), 3.37-3.46 (m, 2H), 3.73-3.83 (m, 2H), 5.01 (s, 1H), 6.28-6.33 (m, 1H), 6.36-6.38 (m, 1H), 6.46-6.51 (m, 1H), 7.10 (t, J=8.0 Hz, 1H)

Reference Example 2

3-[4-(2-Dimethylaminoethyl)-piperazin-1-yl]-phenol

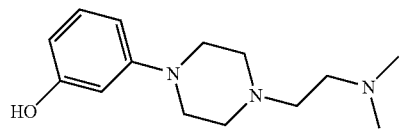

[Formula 80]

Yellow oily substance, yield 12%
$^1$H NMR (600 MHz, CDCl$_3$) δ ppm: 2.29 (s, 6H), 2.48-2.57 (m, 4H), 2.57-2.64 (m, 4H), 3.11-3.16 (m, 4H), 6.24-6.30 (m, 1H), 6.32-6.37 (m, 1H), 6.42-6.49 (m, 1H), 7.04-7.09 (m, 1H)

Reference Example 3

3-[(2-Dimethylaminoethyl)-methyl-amino]-phenol

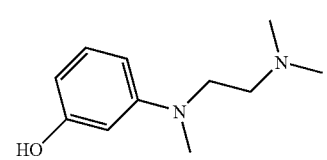

[Formula 81]

Brown oily substance, yield 42%
$^1$H NMR (600 MHz, CDCl$_3$) δ ppm: 2.27 (s, 6H), 2.44-2.50 (m, 2H), 2.87 (s, 3H), 3.37-3.44 (m, 2H), 6.09-6.16 (m, 2H), 6.19-6.24 (m, 1H), 7.01 (t, J=8.0 Hz, 1H)

Reference Example 4

3-(4-Isopropyl-piperazin-1-yl)-phenol

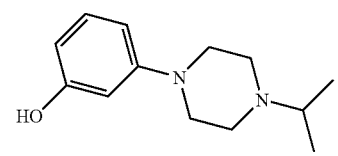

[Formula 82]

Acetone (1.95 g) and NaBH(OAc)$_3$ (7.12 g) were added to a solution of 3-piperazin-1-yl-phenol (2.00 g) in THF (40 ml), and the mixture was stirred at room temperature for 18 hours. Saturated aqueous sodium bicarbonate was added to the reaction solution, and the mixture was extracted with ethyl acetate. The organic layer was dried (MgSO$_4$) and filtered to give the titled compound (1.48 g, colorless powder).
$^1$H NMR (600 MHz, CDCl$_3$) δ ppm: 1.11 (d, J=6.4 Hz, 6H), 2.68-2.72 (m, 4H), 2.71-2.78 (m, 1H), 3.15-3.23 (m, 4H), 6.28-6.32 (m, 1H), 6.36 (t, J=2.3 Hz, 1H), 6.50 (dd, J=8.3, 2.3 Hz, 1H), 7.09 (t, J=8.3 Hz, 1H)

Reference Example 5

3-(1-Isopropylpiperidin-4-yl)-phenol

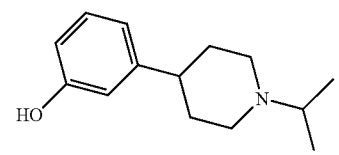

[Formula 83]

Starting from 3-piperidin-4-yl-phenol in place of 3-piperazin-1-yl-phenol used in Reference Example 4, the same procedure as used in Reference Example 4 was repeated to give the titled compound (yield 31%, colorless powder).
$^1$H NMR (600 MHz, CDCl$_3$) δ ppm: 1.16 (d, J=6.4 Hz, 6H), 1.76-1.86 (m, 2H), 1.91-2.01 (m, 2H), 2.31-2.50 (m, 3H), 2.92-3.02 (m, 1H), 3.08-3.19 (m, 2H), 6.66-6.72 (m, 2H), 6.74-6.79 (m, 1H), 7.11 (t, J=7.8 Hz, 1H)

Reference Example 6

4-Fluoro-3-(4-methyl-piperazin-1-yl)-phenol

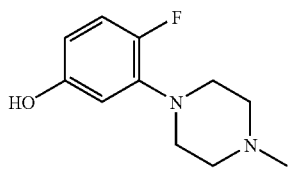

[Formula 84]

4-Benzyloxy-2-chloro-1-fluorobenzene

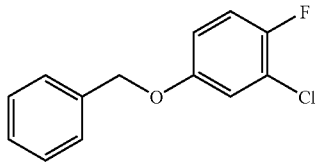

[Formula 85]

(1) A suspension of 3-chloro-4-fluorophenol (2.00 g), benzyl chloride (1.88 ml), and potassium carbonate (2.82 g) in dimethylformamide (10 ml) was stirred at room temperature for three hours. Water was added to the reaction mixture, and the mixture was extracted with ethyl acetate. The organic layer was washed with saturated aqueous sodium chloride, dried (MgSO$_4$), filtered, and concentrated, and the resulting residue was purified by silica-gel column chromatography (OH SiO$_2$, AcOEt/hexane=0-10%) to give the titled compound (2.00 g) as a light yellow oily substance.

$^1$H NMR (600 MHz, CDCl$_3$) δ ppm: 5.01 (s, 2H), 6.77-6.86 (m, 1H), 6.96-7.09 (m, 2H), 7.30-7.46 (m, 5H)

1-(5-Benzyloxy-2-fluorophenyl)-4-methyl-piperazine

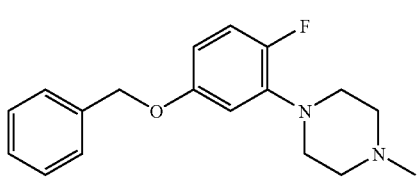

[Formula 86]

(2) Under an argon atmosphere at room temperature, the compound (7.5 g) obtained in Reference Example 6-(1) and thereafter a solution of 2,8,9-triisobutyl-2,5,8,9-tetraaza-1-1 phosphino-bicyclo[3,3,3]-undecane (1.1 g) in toluene (320 ml) were added to tris dibenzylidenedipalladium (1.45 g) and t-butoxysodium (4.26 g). Then, a solution of N-methylpiperazine (1.02 g) in toluene (20 ml) was added at room temperature, and the mixture was stirred at 100° C. for 60 hours. The reaction mixture was concentrated, and the resulting residue was purified by silica-gel column chromatography (NH SiO$_2$, AcOEt/hexane=0-30%) to give the titled compound (2.27 g) as a yellow oily substance.

$^1$H NMR (600 MHz, CDCl$_3$) δ ppm: 2.35 (s, 3H), 2.55-2.63 (m, 4H), 3.06-3.15 (m, 4H), 5.00 (s, 2H), 6.46-6.51 (m, 1H), 6.56-6.59 (m, 1H), 6.89-6.95 (m, 1H), 7.29-7.45 (m, 5H)

4-Fluoro-3-(4-methylpiperazin-1-yl)-phenol

[Formula 87]

(3) A suspension of the compound (2.48 g) obtained in Reference Example 6-(2) and palladium hydroxide (10%, 250 mg) in methanol (30 ml) was stirred under a hydrogen atmosphere at 65° C. for two hours and a half and thereafter at room temperature for overnight. The reaction solution was filtered through celite, and the filtrate was concentrated. The resulting residue was purified by silica-gel column chromatography (NH SiO$_2$, AcOEt/hexane=0-99%, methanol/chloroform=0-10%). Thereafter, the resulting compound was purified again by silica-gel column chromatography (OH SiO$_2$, methanol/chloroform=0-10%) to give the titled compound (877 mg) as an ocher solid.

$^1$H NMR (600 MHz, DMSO-d6) δ ppm: 2.21 (s, 3H), 2.39-2.48 (m, 4H), 2.89-2.99 (m, 4H), 6.26-6.31 (m, 1H), 6.35-6.39 (m, 1H), 6.84-6.91 (m, 1H), 9.20 (s, 1H)

The following describes an exemplary method of producing an intermediate represented by Formula (II) of the present application.

Starting from the corresponding starting materials, the same procedures as shown in Examples 1-(1) to 1-(7), Examples 2-(1) and 2-(2), Examples 7-(1) and 7-(2), Examples 17-(1) and 17-(2), Example 18-(1), Example 21-(1), Example 22-(1), Example 23-(1), and Examples 26-(1) to 26-(8) were repeated, followed by salt formation as needed to obtain compounds or salts of the compounds which are intermediates useful in producing the compound of Formula (I) of the present application. The resulting intermediates are shown in Table 2 together with the intermediates obtained in the Examples above.

TABLE 2

| Compound number | Chemical structure | ¹H NMR |
|---|---|---|
| Intermediate 1 | ABS | (200 MHz, CDCl₃) δ ppm: 1.25 (t, J = 7.3 Hz, 3H), 3.12 (dd, J = 13.3, 8.6 Hz, 1H), 3.38 (dd, J = 13.3, 6.1 Hz, 1H, 3.60-4.30 (m, 3H), 7.10-7.46 (m, 10H) |
| Intermediate 2 | ABS | (600 MHz, DMSO-d6) δ ppm: 1.29 (t, J = 7.3 Hz, 3H), 1.41 (d, J = 6.9 Hz, 3H), 2.30 (s, 3H), 3.96-4.09 (m, 3H), 7.15-7.30 (m, 4H) |
| Intermediate 3 | ABS | (600 MHz, DMSO-d6) δ ppm: 1.33 (t, J = 7.1 Hz, 3H), 1.42 (d, J = 6.4 Hz, 3H), 2.23 (s, 3H), 4.00-4.12 (m, 3H), 7.10-7.40 (m, 4H) |
| Intermediate 4 | ABS | (600 MHz, DMSO-d6) δ ppm: 1.22-1.30 (m, 3H), 1.41-1.48 (m, 3H), 2.33 (s, 3H), 3.83-4.10 (m, 3H), 7.04-7.14 (m, 3H), 7.26-7.37 (m, 1H) |
| Intermediate 5 | ABS | (600 MHz, CDCl₃) δ ppm: 1.46 (t, J = 7.1 Hz, 3H), 1.57 (d, J = 6.9 Hz, 3H), 4.05-4.25 (m, 3H), 6.81-7.32 (m, 4H) |
| Intermediate 6 | ABS | (200 MHz, CDCl₃) δ ppm: 1.41 (t, J = 7.3 Hz, 3H), 1.59 (d, J = 6.6 Hz, 3H), 3.87-4.26 (m, 3H), 7.14-7.26 (m, 1H), 7.30-7.45 (m, 4H) |
| Intermediate 7 | ABS | (600 MHz, CDCl₃) δ ppm: 1.35-1.45 (m, 3H), 1.53-1.62 (m, 3H), 3.95-4.20 (m, 3H), 7.27-7.40 (m, 4H) |

TABLE 2-continued

| Compound number | Chemical structure | $^1$H NMR |
|---|---|---|
| Intermediate 8 | ABS, triazole with 3-chlorophenoxy, 4-ethyl, 5-(1-aminoethyl) | (600 MHz, CDCl$_3$) δ ppm: 1.41 (t, J = 7.1 Hz, 3H), 1.60 (d, J = 6.9 Hz, 3H), 3.90-4.25 (m, 3H), 7.15-7.50 (m, 4H) |
| Intermediate 9 | ABS, triazole with 4-methylphenoxy, 4-ethyl, 5-(1-amino-2-phenylethyl) | (600 MHz, DMSO-d6) δ ppm: 1.14 (t, J = 7.3 Hz, 3H), 2.30 (s, 2H), 3.00 (dd, J = 13.3, 7.3 Hz, 1H), 3.19 (dd, J = 13.3, 6.9 Hz, 1H), 3.77-3.98 (m, 2H), 4.11 (t, J = 7.1 Hz, 1H), 7.13-7.139 (m, 9H) |
| Intermediate 10 | ABS, triazole with 4-methoxyphenoxy, 4-ethyl, 5-(1-aminoethyl) | (600 MHz, CDCl$_3$) δ ppm: 1.41 (t, J = 7.4 Hz, 3H), 1.57 (d, J = 6.8 Hz, 3H), 3.80 (s, 3H), 3.95-4.20 (m, 3H), 6.82-6.97 (m, 2H), 7.21-7.34 (m, 2H) |
| Intermediate 11 | ABS, triazole with 4-fluorophenoxy, 4-ethyl, 5-(1-aminoethyl) | (600 MHz, CDCl$_3$) δ ppm: 1.41 (t, J = 7.3 Hz, 3H), 1.58 (d, J = 6.4 Hz, 3H), 3.95-4.23 (m, 3H), 6.90-7.15 (m, 2H), 7.30-7.44 (m, 2H) |
| Intermediate 12 | ABS, triazole with 3,4-dichlorophenoxy, 4-ethyl, 5-(1-aminoethyl) | (600 MHz, CDCl$_3$) δ ppm: 1.41 (t, J = 7.4 Hz, 3H), 1.60 (d, J = 6.8 Hz, 3H), 3.98-4.21 (m, 3H), 7.26-7.65 (m, 3H) |
| Intermediate 13 | ABS, triazole with 3,4-dimethylphenoxy, 4-ethyl, 5-(1-aminoethyl) | (600 MHz, CDCl$_3$) δ ppm: 1.40 (t, J = 7.1 Hz, 3H), 1.58 (d, J = 6.9 Hz, 3H), 2.24 (s, 3H), 2.25 (s, 3H), 3.95-4.23 (m, 3H), 7.00-7.19 (m, 3H) |

TABLE 2-continued

| Compound number | Chemical structure | $^1$H NMR |
|---|---|---|
| Intermediate 14 | ABS | (200 MHz, CDCl$_3$) δ ppm: 1.05-2.03 (m, 16H), 2.32-2.65 (m, 1H), 3.87-4.29 (m, 3H), 7.00-7.46 (m, 4H) |
| Intermediate 15 | ABS | (200 MHz, CDCl$_3$) δ ppm: 1.43 (t, J = 7.3 Hz, 3H), 1.59 (d, J = 7.0 Hz, 3H), 3.87 (s, 6H), 3.96-4.27 (m, 3H), 6.82-6.88 (m, 2H), 6.97 (d, J = 2.6 Hz, 1H) |
| Intermediate 16 | ABS | (600 MHz, CDCl$_3$) δ ppm: 1.42 (t, J = 7.3 Hz, 3H), 1.59 (d, J = 6.4 Hz, 3H), 3.80 (s, 3H), 3.82 (s, 6H), 3.99-4.12 (m, 2H), 4.13-4.19 (m, 1H), 6.63 (s, 2H) |
| Intermediate 17 | ABS | (600 MHz, CDCl$_3$) δ ppm: 1.39 (t, J = 7.3 Hz, 3H), 1.57 (d, J = 6.9 Hz, 3H), 2.12 (s, 3H), 2.26 (s, 6H), 3.96-4.07 (m, 2H), 4.14 (q, J = 6.6 Hz, 1H), 6.97 (s, 2H) |
| Intermediate 18 | ABS | (600 MHz, CDCl$_3$) δ ppm: 1.38 (t, J = 7.3 Hz, 3H), 1.57 (d, J = 6.9 Hz, 3H), 2.30 (s, 6H), 3.94-4.08 (m, 2H) 4.15 (q, J = 6.9 Hz, 1H), 6.81 (s, 1H), 6.95 (s, 2H) |
| Intermediate 19 | ABS | (600 MHz, CDCl$_3$) δ ppm: 1.43 (t, J = 7.3 Hz, 3H), 1.63 (d, J = 6.9 Hz, 3H), 3.81 (s, 6H), 4.00-4.12 (m, 2H) 4.20 (q, J = 6.7 Hz, 1H), 6.33 (s, 1H), 6.59 (s, 2H) |

TABLE 2-continued

| Compound number | Chemical structure | ¹H NMR |
|---|---|---|
| Intermediate 20 | ABS | (600 MHz, CDCl$_3$) δ ppm: 0.95-0.98 (m, 3H), 1.40 (t, J = 7.3 Hz, 3H), 1.43-1.52 (m, 2H), 1.56 (d, J = 6.9 Hz, 3H), 1.71-1.78 (m, 2H), 3.93 (t, J = 6.4 Hz, 2 H) 3.97-4.08 (m, 2H), 4.15 (q, J = 6.6 Hz, 1H), 6.85-6.89 (m, 2 H) 7.23-7.28 (m, 2H) |
| Intermediate 21 | ABS | (600 MHz, CDCl$_3$) δ ppm: 1.42 (t, J = 7.3 Hz, 3H), 1.59 (d, J = 6.9 Hz, 3H), 3.99-4.13 (m, 2H), 4.17 (q, J = 6.9 Hz, 1H), 6.98-7.05 (m, 4H), 7.07-7.13 (m, 1H), 7.29-7.39 (m, 4H) |
| Intermediate 22 | ABS | (600 MHz, CDCl$_3$) δ ppm: 1.41 (t, J = 7.1 Hz, 3H), 1.58 (d, J = 6.9 Hz, 3H), 3.99-4.10 (m, 2H), 4.16 (q, J = 6.9 Hz, 1H), 5.05 (s, 2H), 6.94-7.00 (m, 2H), 7.25-7.31 (m, 2H), 7.31-7.35 (m, 1H), 7.36-7.41 (m, 2H), 7.41-7.44 (m, 2H) |
| Intermediate 23 | ABS | (600 MHz, CDCl$_3$), δ ppm: 1.23 (t, J = 7.6 Hz, 3H), 1.40 (t, J = 7.3 Hz, 3H), 1.58 (d, J = 6.4 Hz, 3H), 2.64 (q, J = 7.5 Hz, 2H), 3.98-4.11 (m, 2H), 4.16 (q, J = 6.9 Hz, 1H), 7.16-7.31 (m, 4H) |
| Intermediate 24 | ABS | (600 MHz, CDCl$_3$) δ ppm: 0.94 (t, J = 7.3 Hz, 3H), 1.40 (t, J = 7.3 Hz, 3H), 1.54-1.67 (m, 5H), 2.53-2.61 (m, 2H), 3.94-4.10 (m, 2H), 4.17 (q, J = 6.4 Hz, 1 H) 7.12-7.31 (m, 4H) |
| Intermediate 25 | ABS | (600 MHz, CDCl$_3$) δ ppm: 1.39 (t, J = 7.3 Hz, 3H), 1.57 (d, J = 6.9 Hz, 3H), 2.35 (s, 3H), 3.96-4.09 (m, 2H), 4.14 (q, J = 6.6 Hz, 1H), 7.14 (dd, J = 8.7, 3.7 Hz, 1H), 7.27 (d, J = 3.2 Hz, 1H), 7.31 (d, J = 8.7 Hz, 1H) |
| Intermediate 26 | ABS | (600 MHz, CDCl$_3$) δ ppm: 1.40 (t, J = 7.3 Hz, 3H), 1.56 (d, J = 6.9 Hz, 3H), 3.99-4.10 (m, 2H), 4.14 (q, J = 6.7 Hz, 1H), 6.30-6.33 (m, 2H), 6.99-7.03 (m, 2H), 7.34-7.38 (m, 2H), 7.41-7.44 (m, 2H) |

TABLE 2-continued

| Compound number | Chemical structure | ¹H NMR |
|---|---|---|
| Intermediate 27 | ABS | (600 MHz, CDCl₃) δ ppm: 1.38 (t, J = 7.1 Hz, 3H), 1.57 (d, J = 6.9 Hz, 3H), 2.94 (s, 6H), 3.95-4.07 (m, 2H), 4.14 (q, J = 6.9 Hz, 1H), 6.52 (dd, J = 8.7, 2.8 Hz, 1H), 6.60 (dd, J = 8.7, 2.3 Hz, 1H), 6.72 (t, J = 2.3 Hz, 1H), 7.18 (t, J = 8.3 Hz, 1H) |
| Intermediate 28 | ABS | (600 MHz, CDCl₃) δ ppm: 1.43 (t, J = 7.1 Hz, 3H), 1.60 (d, J = 6.9 Hz, 3H), 4.02-4.13 (m, 2H), 4.19 (q, J = 6.9 Hz, 1H), 7.32-7.37 (m, 1H), 7.40-7.48 (m, 4H), 7.55-7.62 (m, 4H) |
| Intermediate 29 | ABS | (600 MHz, CDCl₃) δ ppm: 1.40 (t, J = 7.3 Hz, 3H), 1.61 (d, J = 6.9 Hz, 3H), 4.00-4.12 (m, 2H), 4.17-4.23 (m, 1H), 7.19-7.23 (m, 1H), 7.37-7.42 (m, 2H) |
| Intermediate 30 | ABS | (600 MHz, CDCl₃) δ ppm: 1.42 (t, J = 7.1 Hz, 3H), 1.60 (d, J = 6.4 Hz, 3H), 4.01-4.13 (m, 2H), 4.17 (q, J = 6.4 Hz, 1H), 7.13-7.18 (m, 1H), 7.30-7.54 (m, 1H), 7.51-7.54 (m, 1H) |
| Intermediate 31 | ABS | (600 MHz, CDCl₃) δ ppm: 0.92 (t, J = 7.6 Hz, 3H), 1.30-1.44 (m, 5H), 1.54-1.63 (m, 5H), 2.55-2.64 (m, 2H), 3.97-4.10 (m, 2H), 4.17 (q, J = 6.6 Hz, 1H), 7.15-7.29 (m, 4H) |
| Intermediate 32 | ABS | (600 MHz, CDCl₃) δ ppm: 1.42 (t, J = 7.3 Hz, 3H), 1.60 (d, J = 6.9 Hz, 3H), 4.00-4.15 (m, 2H), 4.18 (q, J = 6.9 Hz, 1H), 7.19-7.28 (m, 2H), 7.39-7.47 (m, 2H) |

TABLE 2-continued

| Compound number | Chemical structure | ¹H NMR |
|---|---|---|
| Intermediate 33 | ABS | (600 MHz, CDCl₃) δ ppm: 1.39 (t, J = 7.3 Hz, 3H), 1.58 (d, J = 6.4 Hz, 3H), 3.12-3.19 (m, 4H), 3.79-3.86 (m, 4H), 3.95-4.09 (m, 2H), 4.14 (q, J = 6.7 Hz, 1H), 6.71 (dd, J = 8.0, 2.1 Hz, 1H), 6.79 (dd, J = 8.3, 2.3 Hz, 1 H) 7.00-7.03 (m, 1H), 7.21-7.25 (m, 1H) |
| Intermediate 34 | ABS | (600 MHz, CDCl₃) δ ppm: 1.39 (t, J = 7.1 Hz, 3H), 1.56 (d, J = 6.9 Hz, 3H), 2.33 (s, 6H), 2.67-2.76 (m, 2H), 3.95-4.08 (m, 4H), 4.14 (q, J = 6.6 Hz, 1H), 6.84-6.93 (m, 2H), 7.19-7.31 (m, 2H) |
| Intermediate 35 | ABS | (600 MHz, CDCl₃) δ ppm: 1.40 (t, J = 7.1 Hz, 3H), 1.56 (d, J = 6.9 Hz, 3H), 2.54-2.59 (m, 4H), 2.78 (t, J = 5.7 Hz, 2H), 3.71-3.75 (m, 4H), 3.98-4.06 (m, 2H), 4.08 (t, J = 5.7 Hz, 2H), 4.14 (q, J = 6.6 Hz, 1H), 6.86-6.90 (m, 2H), 7.24-7.28 (m, 2H) |
| Intermediate 36 | ABS | (600 MHz, CDCl₃) δ ppm: 1.41 (t, J = 7.3 Hz, 3H), 1.59 (d, J = 6.9 Hz, 3H), 2.27 (d, J = 1.8 Hz, 3H), 3.98-4.11 (m, 2H), 4.17 (q, J = 6.9 Hz, 1H), 6.95-7.03 (m, 1H), 7.11-7.16 (m, 1H), 7.21-7.24 (m, 1H) |
| Intermediate 37 | ABS | (200 MHz, CDCl₃) δ ppm: 1.00-1.20 (m, 4H), 1.58 (d, J = 6.6 Hz, 3H), 2.90-3.06 (m, 1H), 3.80 (s, 3H), 4.05-4.32 (m, 1H), 6.38-6.95 (m, 2H), 7.20-7.30 (m, 2H) |
| Intermediate 38 | ABS | (600 MHz, CDCl₃) δ ppm: 1.23 (d, J = 7.3 Hz, 6H), 1.39 (t, J = 7.1 Hz, 3H), 1.57 (d, J = 6.9 Hz, 3H), 2.86-2.93 (m, 1H), 3.97-4.09 (m, 2H), 4.15 (q, J = 6.6 Hz, 1H), 7.19-7.23 (m, 2 H) 7.24-7.27 (m, 2H) |
| Intermediate 39 | ABS | (600 MHz, CDCl₃) δ ppm: 1.25 (d, J = 6.9 Hz, 6H), 1.41 (t, J = 7.3 Hz, 3H), 1.59 (d, J = 6.4 Hz, 3H), 2.85-2.97 (m, 1H), 3.99-4.10 (m, 2H), 4.16 (q, J = 6.7 Hz, 1H), 7.06-7.10 (m, 1H), 7.13-7.18 (m, 1H), 7.20-7.24 (m, 1H), 7.26-7.32 (m, 1H) |

TABLE 2-continued

| Compound number | Chemical structure | ¹H NMR |
|---|---|---|
| Intermediate 40 | ABS | (600 MHz, CDCl$_3$) δ ppm: 1.48 (t, J = 7.3 Hz, 3H), 1.61 (d, J = 6.9 Hz, 3H), 4.09-4.24 (m, 3H), 7.43 (t, J = 8.0 Hz, 1H), 7.51-7.56 (m, 2H), 7.61 (d, J = 6.9 Hz, 1H), 7.68 (d, J = 8.3 Hz, 1H), 7.85-7.90 (m, 1H), 8.11-8.16 (m, 1H) |
| Intermediate 41 | ABS | (600 MHz, CDCl$_3$) δ ppm: 1.43 (t, J = 7.3 Hz, 3H), 1.60 (d, J = 6.4 Hz, 3H), 4.02-4.13 (m, 2H), 4.18 (q, J = 6.6 Hz, 1H), 7.41-7.51 (m, 3H), 7.76-7.92 (m, 4H) |
| Intermediate 42 | ABS | (600 MHz, CDCl$_3$) δ ppm: 1.41 (t, J = 7.1 Hz, 3H), 1.57 (d, J = 6.9 Hz, 3H), 2.93 (s, 6H), 3.96-4.09 (m, 2H), 4.15 (q, J = 6.9 Hz, 1H), 6.66-6.76 (m, 2H), 7.17-7.25 (m, 2H) |
| Intermediate 43 | ABS | (600 MHz, CDCl$_3$) δ ppm: 1.38-1.61 (m, 6H), 4.00-4.19 (m, 3H), 6.69-7.37 (m, 3H) |
| Intermediate 44 | ABS | (600 MHz, CDCl$_3$) δ ppm: 1.40 (t, J = 7.3 Hz, 3H), 1.59 (d, J = 6.9 Hz, 3H), 2.35 (s, 3H), 2.52-2.61 (m, 4H), 3.22-3.27 (m, 4H), 3.97-4.08 (m, 2H), 4.15 (q, J = 6.9 Hz, 1H), 6.71-6.80 (m, 2H), 6.99-7.03 (m, 1H), 7.20-7.25 (m, 1H) |
| Intermediate 45 | ABS | (600 MHz, CDCl$_3$) δ ppm: 1.43 (t, J = 7.1 Hz, 3H), 1.59 (d, J = 6.9 Hz, 3H), 2.82 (s, 3H), 4.02-4.14 (m, 2H), 4.18 (q, J = 6.7 Hz, 1H), 7.42 (dd, J = 8.7, 2.8 Hz, 1H), 7.77 (d, J = 8.7 Hz, 1H), 7.85 (d, J = 2.3 Hz, 1H) |
| Intermediate 46 | ABS | (200 MHz, CDCl$_3$) δ ppm: 1.33-1.47 (m, 3H), 1.57 (d, J = 7.0 Hz, 3H), 3.03-3.19 (m, 4H), 3.78-3.92 (m, 4H), 3.95-4.25 (m, 3H), 6.81-7.00 (m, 2H), 7.18-7.33 (m, 2H) |

TABLE 2-continued

| Compound number | Chemical structure | ¹H NMR |
|---|---|---|
| Intermediate 47 | ABS 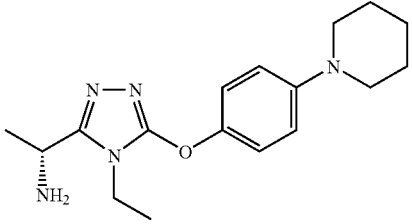 | (200 MHz, CDCl₃) δ ppm: 1.34-1.46 (m, 3H), 1.48-1.82 (m, 9H), 3.02-3.18 (m, 4H), 3.89-4.27 (m, 3H), 6.88-7.00 (m, 2H), 7.16-7.29 (m, 2H) |
| Intermediate 48 | ABS 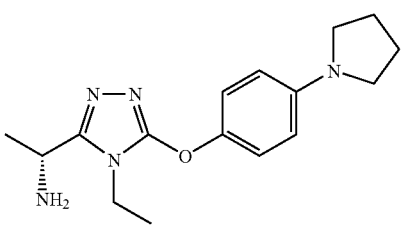 | (600 MHz, CDCl₃) δ ppm: 1.41 (t, J = 7.1 Hz, 3H), 1.57 (d, J = 6.4 Hz, 3H), 1.96-2.03 (m, 4H), 3.23-3.30 (m, 4H), 3.96-4.09 (m, 2H), 4.16 (q, J = 6.6 Hz, 1H), 6.47-6.56 (m, 2H), 7.15-7.22 m, 2H) |
| Intermediate 49 | ABS 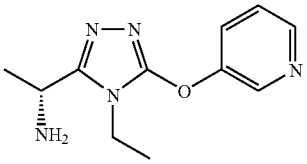 | (600 MHz, CDCl₃) δ ppm: 1.41 (t, J = 7.1 Hz, 3H), 1.57 (d, J = 6.4 Hz, 3H), 1.96-2.03 (m, 4H), 3.23-3.30 (m, 4H), 3.96-4.09 (m, 2H), 4.16 (q, J = 6.6 Hz, 1H), 6.47-6.56 (m, 2H), 7.15-7.22 (m, 2H) |
| Intermediate 50 | ABS 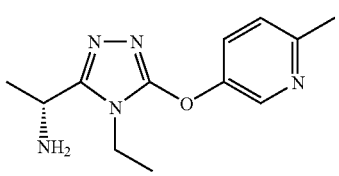 | (600 MHz, CDCl₃) δ ppm: 1.43 (t, J = 7.1 Hz, 3H), 1.59 (d, J = 6.9 Hz, 3H), 2.56 (s, 3H), 4.03-4.14 (m, 2H), 4.17 (q, J = 6.6 Hz, 1H), 7.19 (d, J = 8.7 Hz, 1H), 7.81 (dd, J = 8.7, 2.8 Hz, 1H), 8.52 (d, J = 3.2 Hz, 1H) |
| Intermediate 51 | ABS 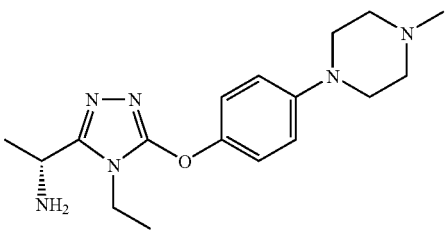 | (600 MHz, CDCl₃) δ ppm: 1.40 (t, J = 7.3 Hz, 3H), 1.59 (d, J = 6.9 Hz, 3H), 2.35 (s, 3H), 2.52-2.61 (m, 4H), 3.22-3.27 (m, 4H), 3.97-4.08 (m, 2H), 4.15 (q, J = 6.9 Hz, 1H), 6.71-6.80 (m, 2H), 6.99-7.03 (m, 1H), 7.20-7.25 (m, 1H) |
| Intermediate 52 | ABS 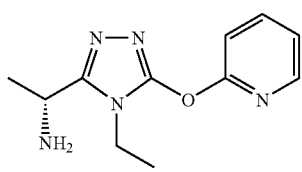 | (600 MHz, CDCl₃) δ ppm: 1.39 (t, J = 7.3 Hz, 3H), 1.63 (d, J = 6.9 Hz, 3H), 3.96-4.09 (m, 2H), 4.20 (q, J = 6.9 Hz, 1H), 7.13-7.17 (m, 1H), 7.30-7.34 (m, 1H), 7.77-7.81 (m, 1H), 8.22-8.25 (m, 1H) |

TABLE 2-continued

| Compound number | Chemical structure | ¹H NMR |
|---|---|---|
| Intermediate 53 | ABS | (600 MHz, CDCl3) δ ppm 1.46 (t, J = 7.3 Hz, 3H), 1.62 (d, J = 6.4 Hz, 3H), 4.06-4.17 (m, 2H), 4.20 (q, J = 6.6 Hz, 1H), 7.64-7.68 (m, 1H), 7.70-7.73 (m, 1H), 7.85-7.90 (m, 1H), 8.10-8.13 (m, 1H), 8.52-8.54 (m, 1H), 9.19-9.25 (m, 1H) |
| Intermediate 54 | ABS | (600 MHz, CDCl$_3$) δ ppm: 1.57 (d, J = 6.9 Hz, 3H), 2.34 (s, 3H), 3.59 (s, 3H), 4.16-4.22 (m, 1H), 7.15-7.18 (m 2H), 7.21-7.25 (m, 2H) |
| Intermediate 55 | ABS | (600 MHz, CDCl$_3$) δ ppm: 0.99 (t, J = 7.3 Hz, 3H), 1.58 (d, J = 6.9 Hz, 3H), 1.77-1.85 (m, 2H), 2.34 (s, 3H), 3.85-3.99 (m, 2H), 4.12 (q, J = 6.9 Hz, 1H), 7.15-7.18 (m, 2H), 7.21-7.24 (m, 2H) |
| Intermediate 56 | ABS | (600 MHz, CDCl$_3$) δ ppm: 1.53-1.58 (m, 9H), 2.34 (s, 3H), 4.20 (q, J = 6.9 Hz, 1H), 4.66-4.72 (m, 1H), 7.15-7.19 (m, 2H), 7.21-7.24 (m, 2H) |
| Intermediate 57 | ABS | (200 MHz, CDCl$_3$) δ ppm: 1.31 (t, J = 7.3 Hz, 3H), 1.60 (d, J = 6.6 Hz, 3H), 2.28 (s, 3H), 3.60-4.30 (m, 3H), 6.96-7.02 (m, 4H) |
| Intermediate 58 | ABS | (600 MHz, CDCl$_3$) δ ppm: 1.40 (t, J = 7.3 Hz, 3H), 1.58 (d, J = 6.4 Hz, 3H), 2.34 (s, 3H), 3.99-4.09 (m, 2H), 4.16 (q, J = 6.4 Hz, 1H), 7.15-7.19 (m, 2H), 7.22-7.25 (m, 2H) |

TABLE 2-continued

| Compound number | Chemical structure | ¹H NMR |
|---|---|---|
| Intermediate 59 | ABS | (600 MHz, CDCl₃) δ ppm: 1.44 (t, J = 7.1 Hz, 3H), 1.59 (d, J = 6.9 Hz, 3H), 4.02-4.13 (m, 2H), 4.17 (q, J = 6.6 Hz, 1H), 6.44-6.47 (m, 1H), 7.04-7.08 (m, 1H), 7.15-7.25 (m, 2H), 7.50-7.57 (m, 1H), 8.72 (s, 1H) |
| Intermediate 60 | ABS | (600 MHz, CDCl₃) δ ppm: 1.42 (t, J = 7.1 Hz, 3H), 1.58 (d, J = 6.4 Hz, 3H), 3.98-4.10 (m, 2H), 4.15 (q, J = 6.7 Hz, 1H), 6.30-6.39 (m, 1H), 6.87-7.00 (m, 2H), 7.39-7.52 (m, 2H), 9.55 (s, 1H) |
| Intermediate 61 | ABS | (600 MHz, CDCl₃), δ ppm: 1.43 (t, J = 7.3 Hz, 3H), 1.59 (d, J = 6.9 Hz, 3H), 2.34 (s, 3H), 3.99-4.12 (m, 2H), 4.16 (q, J = 6.9 Hz, 1H), 6.03-6.13 (m, 1H), 6.86-7.07 (m, 2H), 7.28-7.37 (m, 2H), 8.76 (s, 1H) |
| Intermediate 62 | ABS | (600 MHz, CDCl₃) δ ppm: 1.38 (t, J = 7.1 Hz, 3H), 1.61 (d, J = 6.9 Hz, 3H), 2.40 (s, 3H), 3.96-4.07 (m, 2H), 4.23 (q, J = 6.9 Hz, 1H), 6.95-6.97 (m, 1H), 7.13-7.15 (m, 1H), 8.07-8.09 (m, 1H) |
| Intermediate 63 | ABS | (600 MHz, CDCl₃) δ ppm: 1.36-1.45 (m, 3H), 1.60-1.70 (m, 3H), 2.32 (s, 3H), 3.96-4.10 (m, 2H), 4.16-4.27 (m, 1H), 7.22-7.27 (m, 1H), 7.56-7.66 (m, 1H), 8.02-8.10 (m, 1H) |
| Intermediate 64 | ABS | (600 MHz, CDCl₃) δ ppm: 1.43 (t, J = 7.3 Hz, 3H), 1.59 (d, J = 6.4 Hz, 3H), 2.59-2.63 (m, 2H), 2.92-2.99 (m, 2H), 4.00-4.11 (m, 2H), 4.18 (q, J = 6.4 Hz, 1H), 6.80-6.84 (m, 1H), 7.11-7.16 (m, 1H), 7.21-7.25 (m, 1H), 8.28-8.72 (m, 1H) |
| Intermediate 65 | ABS | (600 MHz, CDCl₃) δ ppm: 1.35 (t, J = 7.3 Hz, 3H), 1.54 (d, J = 6.9 Hz, 3H), 3.76 (s, 3H), 3.93-4.05 (m, 2H), 4.11 (q, J = 6.4 Hz, 1H), 6.69 (dd, J = 8.3, 2.3 Hz, 1H), 6.87 (dd, J = 8.3, 2.3 Hz, 1H), 6.92 (t, J = 2.3 Hz, 1H), 7.18-7.24 (m, 1H) |

TABLE 2-continued

| Compound number | Chemical structure | ¹H NMR |
|---|---|---|
| Intermediate 66 | ABS | (600 MHz, CDCl$_3$) δ ppm: 1.14 (t, J = 7.1 Hz, 6H), 1.38 (t, J = 7.3 Hz, 3H), 1.57 (d, J = 6.9 Hz, 3H), 3.32 (q, J = 6.9 Hz, 4H), 3.95-4.07 (m, 2H), 4.11-4.17 (m, 1H), 6.46 (dd, J = 8.7, 2.3 Hz, 1H), 6.50 (dd, J = 8.0, 2.5 Hz, 1H), 6.67 (t, J = 2.5 Hz, 1H), 7.14 (t, J = 8.3 Hz, 1H) |
| Intermediate 67 | ABS | (600 MHz, CDCl$_3$) δ ppm: 1.39 (t, J = 7.3 Hz, 3H), 1.62 (d, J = 6.4 Hz, 3H), 2.45 (s, 3H), 3.97-4.09 (m, 2H), 4.19 (q, J = 6.4 Hz, 1H), 6.98-7.01 (m, 1H), 7.13-7.16 (m, 1H), 7.64-7.67 (m, 1H) |
| Intermediate 68 | ABS | (600 MHz, CDCl$_3$) δ ppm: 1.45 (t, J = 7.3 Hz, 3H), 1.62 (d, J = 6.9 Hz, 2H), 4.05-4.15 (m, 2H), 4.20 (q, J = 6.9 Hz, 1H), 7.37-7.41 (m, 1H), 7.65-7.68 (m, 1H), 7.84-7.88 (m, 1H), 7.94-7.96 (m, 1H), 8.14-8.19 (m, 1H), 8.90-8.93 (m, 1H) |
| Intermediate 69 | ABS | (600 MHz, CDCl$_3$) δ ppm: 1.38 (t, J = 7.1 Hz, 3H), 1.53-1.60 (m, 5H), 1.64-1.71 (m, 4H), 3.95-4.07 (m, 2H), 4.14 (q, J = 6.7 Hz, 1H), 6.69-6.74 (m, 2H), 6.95 (t, J = 2.5 Hz, 1H), 7.19 (t, J = 8.3 Hz, 1H) |
| Intermediate 70 | ABS | (600 MHz, CDCl$_3$) δ ppm: 1.41 (t, J = 7.1 Hz, 3H), 1.58 (d, J = 6.9 Hz, 3H), 2.57-2.61 (m, 2H), 2.89-2.93 (m, 2H), 3.99-4.11 (m, 2H), 4.17 (q, J = 6.9 Hz, 1H), 6.90-6.97 (m, 2H), 7.11-7.15 (m, 1H), 8.66 (s, 1H) |
| Intermediate 71 | ABS | (600 MHz, CDCl$_3$) δ ppm: 1.38 (t, J = 7.3 Hz, 3H), 1.58 (d, J = 6.9 Hz, 3H), 2.30-2.39 (m, 2H), 3.85-3.89 (m, 4H), 3.94-4.06 (m, 2H), 4.15 (q, J = 6.6 Hz, 1H), 6.22-6.25 (m, 1H), 6.43 (t, J = 2.3 Hz, 1H), 6.59-6.63 (m, 1H), 7.15 (t, J = 8.0 Hz, 1H) |

TABLE 2-continued

| Compound number | Chemical structure | ¹H NMR |
|---|---|---|
| Intermediate 72 | ABS | (600 MHz, CDCl$_3$) δ ppm: 1.24 (d, J = 6.4 Hz, 6H), 1.39 (t, J = 7.3 Hz, 3H), 1.58 (d, J = 6.9 Hz, 3H), 2.39-2.46 (m, 2H), 3.42-3.46 (m, 2H), 3.73-3.81 (m, 2H), 3.97-4.09 (m, 2H), 4.15 (q, J = 6.9 Hz, 1H), 6.71 (dd, J = 8.0, 2.1 Hz, 1H), 6.76 (dd, J = 8.5, 2.1 Hz, 1H), 6.98 (t, J = 2.3 Hz, 1H), 7.22 (t, J = 8.3 Hz, 1H) |
| Intermediate 73 | ABS | (600 MHz, CDCl$_3$) δ ppm: 1.42 (t, J = 7.3 Hz, 3H), 1.59 (d, J = 6.9 Hz, 3H), 3.92 (s, 3H), 4.02-4.13 (m, 2H), 4.16 (q, J = 6.9 Hz, 1H), 6.90 (s, 1H) |
| Intermediate 74 | ABS | (600 MHz, CDCl$_3$) δ ppm: 1.45 (t, J = 7.3 Hz, 3H), 1.63 (d, J = 6.4 Hz, 3H), 4.06-4.17 (m, 2H), 4.18-4.23 (m, 1H), 7.39-7.44 (m, 1H), 7.65-7.71 (m, 1H), 8.02-8.05 (m, 1H), 8.11-8.16 (m, 2H), 8.88-8.91 (m, 1H) |
| Intermediate 75 | ABS | (600 MHz,, CDCl$_3$) δ ppm: 1.38 (t, J = 7.1 Hz, 3H), 1.57 (d, J = 6.4 Hz, 3H), 1.94-2.02 (m, 4H), 3.22-3.29 (m, 4H), 3.95-4.07 (m, 2H), 4.10-4.19 (m, 1H), 6.36 (dd, J = 8.2, 2.3 Hz, 1H), 6.50-6.56 (m, 2H), 7.16 (t, J = 8.3 Hz, 1H) |
| Intermediate 76 | ABS | (600 MHz, CDCl$_3$) δ ppm: 1.38 (t, J = 7.3 Hz, 3H), 1.61 (d, J = 6.9 Hz, 3H), 2.53 (s, 6H), 3.98-4.11 (m, 2H), 4.18 (q, J = 6.9 Hz, 1H), 7.05 (s, 2H) |
| Intermediate 77 | ABS | (600 MHz, CDCl$_3$) δ ppm: 1.46 (t, J = 7.1 Hz, 3H), 1.63 (d, J = 6.9 Hz, 3H), 4.07-4.24 (m, 3H), 7.63-7.65 (m, 1H), 8.00-8.03 (m, 1H), 8.11-8.13 (m, 1H) |

TABLE 2-continued

| Compound number | Chemical structure | ¹H NMR |
| --- | --- | --- |
| Intermediate 78 | ABS | (600 MHz, CDCl₃) δ ppm: 1.37 (t, J = 7.1 Hz, 3H), 1.58 (d, J = 6.9 Hz, 3H), 3.96-4.05 (m, 2H), 4.15 (q, J = 6.7 Hz, 1H), 6.45-6.50 (m, 1H), 6.62-6.67 (m, 1H), 6.71-6.75 (m, 1H), 7.11 (t, J = 8.0 Hz, 1H) |
| Intermediate 79 | ABS | (600 MHz,, CDCl₃) δ ppm: 1.38 (t, J = 7.1 Hz, 3H), 1.58 (d, J = 6.9 Hz, 3H), 2.27 (s, 6H), 2.45-2.56 (m, 4H), 2.58-2.63 (m, 4H), 3.20-3.24 (m, 4H), 3.95-4.07 (m, 2H), 4.11-4.17 (m, 1H), 6.68-6.78 (m, 2H), 6.95-6.98 (m, 1H), 7.21 (t, J = 8.3 Hz, 1H) |
| Intermediate 80 | ABS | (600 MHz, CDCl₃), δ ppm: 1.43 (t, J = 7.1 Hz, 3H), 1.60 (d, J = 6.9 Hz, 3H), 4.02-4.15 (m, 2H), 4.15-4.22 (m, 1H), 7.18-7.20 (m, 1H), 7.22-7.25 (m, 1H), 7.28-7.30 (m, 1H), 7.38-7.41 (m, 1H), 7.46-7.51 (m, 1H), 7.54-7.57 (m, 1H), 7.85-7.89 (m, 1H) |
| Intermediate 81 | ABS | (600 MHz,, CDCl₃) δ ppm: 1.38 (t, J = 7.3 Hz, 3H), 1.57 (d, J = 6.9 Hz, 3H), 1.77-1.83 (m, 4H), 3.27-3.36 (m, 4H), 3.95-4.06 (m, 6H), 4.14 (q, J = 6.9 Hz, 1H), 6.70-6.75 (m, 2H), 6.97 (t, J = 2.3 Hz, 1H), 7.20 (t, J = 8.3 Hz, 1H) |
| Intermediate 82 | ABS | (600 MHz, CDCl3) δ ppm 1.42-1.47 (m, 3 H) 1.62 (dd, J = 6.65, 2.06 Hz, 3 H) 4.05-4.17 (m, 2 H) 4.17-4.22 (m, 1 H) 7.24-7.28 (m, 1 H) 7.48-7.61 (m, 2 H) 7.66 (s, 1 H) 8.52 (s, 2H) |
| Intermediate 83 | ABS | (600 MHz, CDCl₃) δ ppm: 1.07 (d, J = 6.9 Hz, 6H), 1.38 (t, J = 7.3 Hz, 3H), 1.57 (d, J = 6.4 Hz, 3H), 2.62-2.67 (m, 4H), 2.67-2.74 (m, 1H), 3.19-3.24 (m, 4H), 3.96-4.08 (m, 2H), 4.14 (q, J = 6.7 Hz, 1H), 6.71 (dd, J = 8.3, 2.3 Hz, 1H), 6.75 (dd, J = 8.3, 2.3 Hz, 1H), 6.97 (t, J = 2.3 Hz, 1H), 7.21 (t, J = 8.3 Hz, 1H) |

TABLE 2-continued

| Compound number | Chemical structure | ¹H NMR |
|---|---|---|
| Intermediate 84 | ABS | (600 MHz, CDCl₃) δ ppm: 1.38 (t, J = 7.3 Hz, 3H), 1.61 (d, J = 6.9 Hz, 3H), 2.33 (s, 3H), 2.40 (s, 3H), 3.97-4.09 (m, 2H), 4.18 (q, J = 6.9 Hz, 1H), 6.82-6.83 (m, 1H), 6.97-6.98 (m, 1H) |
| Intermediate 85 | ABS | (600 MHz, CDCl₃) δ ppm: 1.30-1.76 (m, 6H), 2.56 (s, 3H), 2.68 (s, 3H), 4.08-4.19 (m, 3H) 6.59 (s, 1H), 6.73 (s, 1H) |
| Intermediate 86 | ABS | (600 MHz, CDCl₃) δ ppm: 1.26 (d, J = 6.9Hz, 6H), 1.40 (t, J = 7.3 Hz, 3H), 1.57 (d, J = 6.9 Hz, 3H), 2.87-2.94 (m, 1H), 3.72 (s, 3H), 3.99-4.11 (m, 2H), 4.14 (q, J = 6.9 Hz, 1H), 6.25 (s, 1H) |
| Intermediate 87 | ABS | (600 MHz,, CDCl₃) δ ppm: 1.39 (t, J = 7.3 Hz, 3H), 1.57 (d, J = 6.9 Hz, 3H), 3.34 (s, 6H), 3.50-3.57 (m, 8H), 3.96-4.07 (m, 2H), 4.15 (q, J = 6.6 Hz, 1H), 6.51 (dd, J = 8.5, 2.5 Hz, 1H), 6.56 (dd, J = 7.8, 2.3 Hz, 1H), 6.69 (t, J = 2.3 Hz, 1H), 7.15 (t, J = 8.3 Hz, 1H) |
| Intermediate 88 | ABS | (600 MHz,, CDCl₃) δ ppm: 1.36-1.41 (m, 3H), 1.57 (d, J = 6.9 Hz, 3H), 2.28 (s, 6H), 2.45-2.50 (m, 2H), 2.94 (s, 3H), 3.39-3.48 (m, 2H), 3.94-4.08 (m, 2H), 4.14 (q, J = 6.9 Hz, 1H), 6.50 (dd, J = 8.3, 2.3 Hz, 1H), 6.58 (dd, J = 8.3, 2.3 Hz, 1H), 6.67 (t, J = 2.5 Hz, 1H), 7.16 (t, J = 8.3 Hz, 1H) |
| Intermediate 89 | ABS | (600 MHz, CDCl₃) δ ppm: 1.39 (t, J = 7.1 Hz, 3H), 1.59 (d, J = 6.4 Hz, 3H), 2.34 (s, 6H), 2.73 (t, J = 5.7 Hz, 2H), 3.98-4.09 (m, 4H), 4.16 (q, J = 6.4 Hz, 1H), 6.75-6.77 (m, 1H), 6.91-6.93 (m, 1H), 6.98-7.00 (m, 1H), 7.24-7.27 (m, 1H) |

TABLE 2-continued

| Compound number | Chemical structure | ¹H NMR |
|---|---|---|
| Intermediate 90 | ABS | (600 MHz, CDCl₃) δ ppm: 1.25 (d, J = 6.9 Hz, 12H), 1.40 (t, J = 7.1 Hz, 3H), 1.58 (d, J = 6.9 Hz, 3H), 3.76-3.85 (m, 2H), 3.96-4.08 (m, 2H), 4.15 (q, J = 6.9 Hz, 1H), 6.57-6.70 (m, 2H), 6.88-6.93 (m, 1H), 7.10-7.17 (m, 1H) |
| Intermediate 91 | ABS | (600 MHz,, CDCl₃) δ ppm: 1.06 (d, J = 6.42 Hz, 6H), 1.39 (t, J = 7.3 Hz, 3H), 1.58 (d, J = 6.9 Hz, 3H), 1.68-1.89 (m, 4H), 2.17-2.25 (m, 2H), 2.44-2.53 (m, 1H), 2.70-2.77 (m, 1H), 2.94-3.03 (m, 2 H) 3.96-4.08 (m, 2H), 4.15 (q, J = 6.6 Hz, 1H), 7.03-7.07 (m, 1H), 7.15-7.22 (m, 2H), 7.28 (t, J = 8.0 Hz, 1H) |
| Intermediate 92 | ABS | (600 MHz, CDCl₃), δ ppm: 1.43 (t, J = 7.1 Hz, 3H), 1.58-1.62 (m, 12H), 4.01-4.13 (m, 2H), 4.18 (q, J = 6.6 Hz, 1H), 7.42-7.46 (m, 1H), 7.61-7.65 (m, 1H), 7.82-7.85 (m, 1H), 7.87-7.91 (m, 1H) |
| Intermediate 93 | ABS | (600 MHz, DMSO-d6), δ ppm: 1.23 (t, J = 7.3 Hz, 3H), 1.54 (d, J = 6.9 Hz, 3H), 3.82-4.09 (m, 2H), 4.60 (q, J = 6.0 Hz, 1H), 6.61-6.69 (m, 2H), 6.70-6.77 (m, 1H), 7.14-7.21 (m, 1H), 8.28-9.11 (m, 2H), 9.43-10.55 (m, 1H) |
| Intermediate 94 | ABS | (600 MHz, CDCl₃), δ ppm: 1.39 (t, J = 7.3 Hz, 3H), 1.60 (d, J = 6.4 Hz, 3H), 3.96-4.09 (m, 2H), 4.17 (q, J = 6.9 Hz, 1H), 5.06 (s, 2H), 6.79-6.84 (m, 1H), 6.91-6.96 (m, 1H), 7.04-7.08 (m, 1H), 7.22-7.46 (m, 6H) |
| Intermediate 95 | ABS | (200 MHz, CDCl₃) δ ppm: 1.34 (t, J = 7.3 Hz, 3H), 1.61 (d, J = 6.8 Hz, 3H), 3.80-4.23 (m, 3H), 5.96 (br s, 1H), 6.88-7.05 (m, 2H), 7.08-7.25 (m, 2H) |

TABLE 2-continued

| Compound number | Chemical structure | ¹H NMR |
|---|---|---|
| Intermediate 96 | ABS | (600 MHz, CDCl₃) δ ppm: 1.42-1.66 (m, 9H), 4.06-4.20 (m, 5H), 7.01-7.05 (m, 1H), 7.24-7.26 (m, 1H), 7.62-7.69 (m, 2H) |
| Intermediate 97 | ABS | (600 MHz, CDCl3) δ ppm: 1.02-1.16 (m, 4H), 1.59 (d, J = 6.9 Hz, 3H), 2.35 (s, 3H), 2.52-2.61 (m, 4H), 2.92-3.01 (m, 1H), 3.21-3.25 (m, 4H), 4.24 (q, J = 6.6 Hz, 1H), 6.68-6.75 (m, 2H), 6.94-6.98 (m, 1H), 7.19-7.25 (m, 1H) |
| Intermediate 98 | ABS | (600 MHz, CDCL3) δ ppm: 1.03-1.18 (m, 4H), 1.59 (d, J = 6.9 Hz, 2H), 2.98-3.04 (m, 1H), 4.25 (q, J = 6.6 Hz, 1H), 7.04-7.10 (m, 2H), 7.30-7.35 (m, 2H) |
| Intermediate 99 | ABS | (600 MHz, CDCl3) δ ppm: 0.98-1.20 (m, 4H), 1.59 (d, J = 6.9 Hz, 3H), 2.93-3.05 (m, 1H), 4.22-4.31 (m, 1H), 6.33-6.44 (m, 1H), 6.90-7.05 (m, 2H), 7.31-7.43 (m, 1H), 7.46-7.55 (m, 1H), 9.08-9.32 (m, 1H) |
| Intermediate 100 | 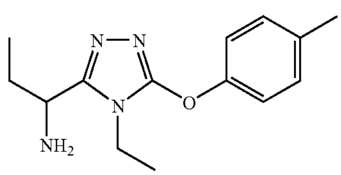 | (CDCl₃, 200 MHz) δ 1.02 (t, J = 7.5 Hz,, 3H), 1.39 (t, J = 7.3 Hz, 3H), 1.68 (bs, 2H), 1.91-2.14 (m, 2H), 2.34 (s, 3H), 3.90 (t, J = 6.4 Hz, 1H), 4.03 (q, J = 7.3 Hz, 2H), 7.16 (d, J = 8.1 Hz, 2H), 7.24 (d, J = 8.1 Hz, 2H) |
| Intermediate 101 | 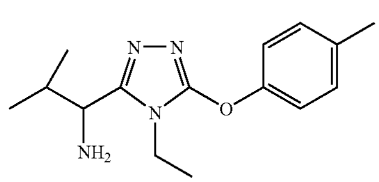 | (CDCl₃, 200 MHz) δ 0.96 (d, J = 6.8 Hz, 3H), 1.07 (d, J = 6.8 Hz, 3H), 1.39 (t, J = 7.3 Hz, 3H), 1.71 (bs, 2H), 2.06-2.24 (m, 1H), 2.34 (s, 3H), 3.69 (d, J = 7.5 Hz, 1H), 4.01 (q, J = 7.3 Hz, 2H), 7.16 (d, J = 8.6 Hz, 2H), 7.25 (d, J = 8.6 Hz, 2H) |
| Intermediate 102 | 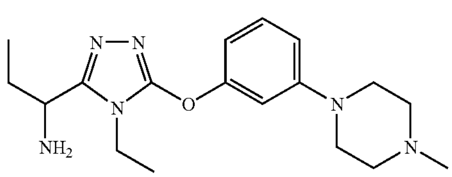 | (200 MHz, CDCl₃) δ ppm: 1.01 (t, J = 7.3 Hz, 3H), 1.39 (t, J = 7.3 Hz, 3H), 1.70-2.11 (m, 2H), 2.35 (s, 3H), 2.56 (t, J = 5.0 Hz, 4H), 3.24 (t, J = 5.0 Hz, 4H), 3.89 (t, J = 7.3 Hz, 1H), 4.02 (q, J = 7.3 Hz, 2H), 6.74 (dt, J = 2.4, 8.4 Hz, 2H), 7.02 (t, J = 2.4 Hz, 1H), 7.22 (t, J = 8.4 Hz, 1H) |

TABLE 2-continued

| Compound number | Chemical structure | $^1$H NMR |
|---|---|---|
| Intermediate 103 | 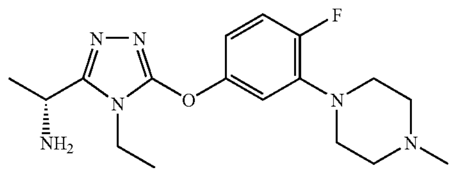 | (600 MHz, CDCl$_3$) δ ppm: 1.41 (t, J = 7.3 Hz, 3H), 1.59 (d, J = 6.4 Hz, 3H), 2.36 (s, 3H), 2.55-2.65 (m, 4H), 3.11-3.19 (m, 4H), 3.98-4.19 (m, 3H), 6.87-6.92 (m, 1H), 6.96-7.04 (m, 2H) |
| Intermediate 104 | 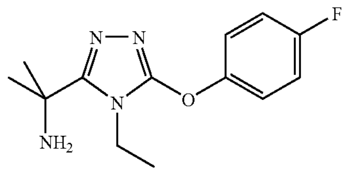 | (600 MHz, CDCl$_3$) δ ppm: 1.42 (t, J = 6.9 Hz, 3H), 1.62 (s, 6H), 4.31 (q, J = 6.9 Hz, 2H), 7.04-7.09 (m, 2H), 7.34-7.40 (m, 2H) |
| Intermediate 105 | 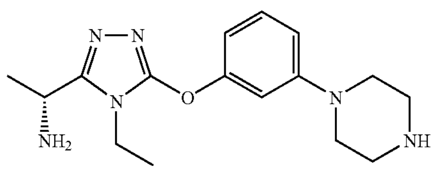 | (600 MHz, CDCl$_3$) δ ppm: 1.40 (t, J = 7.1 Hz, 3H), 1.59 (d, J = 6.9 Hz, 3H), 2.98-3.04 (m, 4H), 3.14-3.19 (m, 4H), 3.97-4.09 (m, 2H), 4.13-4.18 (m, 1H), 6.70-6.80 (m, 2H), 6.97-7.03 (m, 1H), 7.21-7.26 (m, 1H) |
| Intermediate 106 | 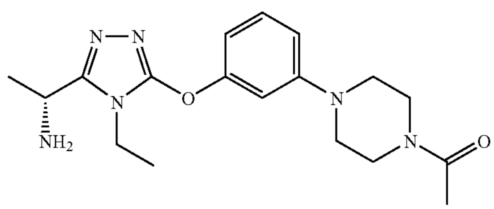 | (600 MHz, CDCl$_3$) δ ppm: 1.35 (t, J = 7.3 Hz, 3H), 1.72 (d, J = 6.4 Hz, 3H), 2.12 (s, 3H), 3.14-3.23 (m, 4H), 3.57-3.64 (m, 2H), 3.71-3.77 (m, 2H), 3.87-4.10 (m, 2H), 4.57-4.66 (m, 1H), 6.70-6.81 (m, 2H), 6.95-6.99 (m, 1H), 7.21-7.26 (m, 1H) |
| Intermediate 107 | 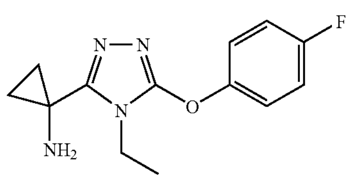 | (200 MHz, CDCl$_3$) δ ppm: 0.94-1.08 (m, 2H), 1.22-1.31 (m, 2H), 1.47 (t, J = 7.1 Hz, 3H), 4.18 (q, J = 7.1 Hz, 2H), 6.98-7.15 (m, 2H), 7.29-7.42 (m, 2H) |
| Intermediate 108 | 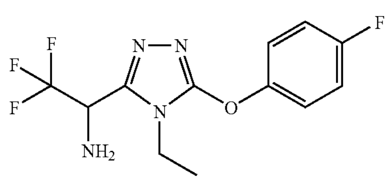 | (600 MHz, CDCl$_3$) δ ppm: 1.43 (t, J = 7.3 Hz, 3H), 3.97-4.11 (m, 2H), 4.47-4.54 (m, 1H), 7.06-7.12 (m, 2H), 7.35-7.40 (m, 2H) |
| Intermediate 109 | 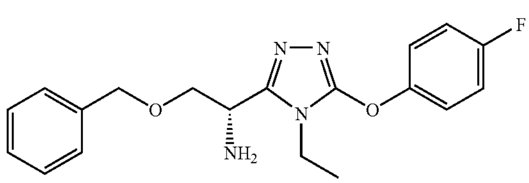 | (200 MHz, CDCl$_3$) δ ppm: 1.41 (t, J = 7.5 Hz, 3H), 3.62 (dd, J = 4.8, 11.8 Hz, 1H), 3.88 (dd, J = 4.8, 11.8 Hz, 1H), 4.05 (q, J = 7.5 Hz, 2H), 4.51-4.60 (m, 1H), 7.04-7.13 (m, 2H), 7.23-7.31 (m, 3H), 7.53 (d, J = 8.8 Hz, 1H), 7.70 (dd, J = 8.8, 2.2 Hz, 1H), 7.93 (d, J = 2.2 Hz, 1H) |

INDUSTRIAL APPLICABILITY

Since the compounds of the present invention are excellent Edg-1($S1P_1$) ligands, they are useful as agents for treating or preventing autoimmune diseases, such as Crohn disease, hypersensitivity colitis, Sjogren's syndrome, multiple sclerosis, and systemic lupus erythematosus, and diseases such as rheumatoid arthritis, asthma, atopic dermatitis, organ transplant rejection, cancer, retinopathy, psoriasis, osteoarthritis, and age-related macular degeneration.

The invention claimed is:
1. A compound represented by Formula (I)

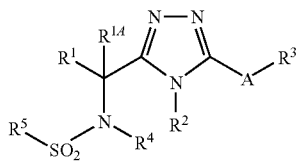

[Formula 1]

or a pharmaceutically acceptable salt thereof, wherein
A represents an oxygen atom;
$R^1$ represents:
  a hydrogen atom,
  an alkyl group having from 1 to 6 carbon atoms and optionally substituted with a substituent(s) selected from the group consisting of:
    a hydroxyl group,
    a halogen atom,
    an alkoxy group having from 1 to 6 carbon atoms, said alkoxy group optionally substituted with a phenyl group, and
    a phenyl group, optionally substituted with a substituent(s) selected from the group consisting of a halogen atom and an alkyl group having from 1 to 6 carbon atoms,
  a cycloalkyl group having from 3 to 8 carbon atoms,
  an alkenyl group having from 2 to 8 carbon atoms,
  an alkynyl group having from 2 to 8 carbon atoms, or
  a phenyl group;
$R^{14}$ represents:
  a hydrogen atom or
  an alkyl group having from 1 to 6 carbon atoms;
$R^1$ and $R^{14}$ optionally form, together with a carbon atom to which said $R^1$ and $R^{14}$ are attached, a cycloalkyl group having from 3 to 6 carbon atoms;
$R^2$ represents:
  a hydrogen atom,
  an alkyl group having from 1 to 6 carbon atoms,
  an alkenyl group having from 2 to 8 carbon atoms,
  an alkynyl group having from 2 to 8 carbon atoms, or
  a cycloalkyl group having from 3 to 6 carbon atoms;
$R^3$ represents a phenyl group substituted at 3 position with a substituent selected from the group consisting of nitrogen-containing groups (i)-(v) below, said phenyl group further optionally substituted at 4 position with a halogen atom:
  (i) a monocylic saturated hydrocarbon group having from 2 to 7 carbon atoms and having a nitrogen atom(s) as a ring atom(s), said saturated hydrocarbon group optionally substituted with an alkyl group(s) having from 1 to 6 carbon atoms,
  (ii) a nitrogen-containing monocylic unsaturated hydrocarbon group,
  (iii) a morpholinyl group optionally substituted with an alkyl group(s) having from 1 to 6 carbon atoms,
  (iv) a piperazino group, optionally substituted with an alkanoyl group having from 2 to 7 carbon atoms or an alkyl group having from 1 to 6 carbon atoms and optionally substituted with a substituent(s) selected from the group consisting of:
    an amino group substituted with two alkyl groups each having from 1 to 4 carbon atoms, and
    a morpholino group, and
  (v) Formula —$NR^7R^8$, wherein:
    $R^7$ and $R^8$ each represent:
      a hydrogen atom,
      an alkyl group having from 1 to 6 carbon atoms, said alkyl group optionally substituted with an amino group optionally substituted with one or two alkyl groups each having from 1 to 6 carbon atoms, a morpholino group, a hydroxyl group, or an alkoxy group having from 1 to 6 carbon atoms,
      an alkanoyl group having from 1 to 6 carbon atoms,
      a carbamoyl group optionally substituted with one or two alkyl groups each having from 1 to 4 carbon atoms,
      a morpholinocarbonyl group,
      an aminosulfonyl group optionally substituted with one or two alkyl groups each having from 1 to 6 carbon atoms, or
      an alkylsulfonyl group having from 1 to 6 carbon atoms, or
    $R^7$ and $R^8$ optionally form, together with the nitrogen atom to which said $R^7$ and $R^8$ are attached, a 3- to 8-membered saturated hydrocarbon ring, said ring optionally substituted with a substituent(s) selected from the group consisting of a dimethylenedioxy group, an oxo group, and a hydroxyl group;
$R^4$ represents:
  a hydrogen atom or
  an alkyl group having from 1 to 6 carbon atoms and optionally substituted with a carboxyl group;
$R^5$ represents:
  (i) an alkyl group having from 1 to 10 carbon atoms,
  (ii) an alkyl group having from 1 to 10 carbon atoms and substituted with 1 to 2 substituents selected from the group consisting of:
    a cycloalkyl group having from 3 to 8 carbon atoms,
    a pyridyl group, and
    a phenyl group, a phenoxy group, and a naphthyl group, each optionally substituted with 1 to 2 substituents selected from the group consisting of a halogen atom and an alkoxy group having from 1 to 6 carbon atoms,
  (iii) a cycloalkyl group having from 3 to 8 carbon atoms,
  (iv) an alkenyl group having from 2 to 8 carbon atoms,
  (v) an alkenyl group having from 2 to 8 carbon atoms and substituted with a phenyl group,
  (vi) an alkynyl group having from 2 to 8 carbon atoms,
  (vii) an alkynyl group having from 2 to 8 carbon atoms and substituted with a phenyl group, or
  (viii) an optionally substituted aryl group.
2. The compound of claim 1, or a pharmaceutically acceptable salt thereof, wherein, in Formula (I):
$R^1$ represents:
  a hydrogen atom,
  an alkyl group having from 1 to 6 carbon atoms,
  an alkyl group having from 1 to 6 carbon atoms and substituted with a phenyl group,
  a cycloalkyl group having from 3 to 8 carbon atoms,
  an alkenyl group having from 2 to 8 carbon atoms,
  an alkynyl group having from 2 to 8 carbon atoms, or
  a phenyl group;

$R^{1A}$ represents a hydrogen atom;

$R^2$ represents:

an alkyl group having from 1 to 6 carbon atoms, an alkenyl group having from 2 to 8 carbon atoms, an alkynyl group having from 2 to 8 carbon atoms, or a cycloalkyl group having from 3 to 6 carbon atoms;

$R^4$ represents:

a hydrogen atom, or an alkyl group having from 1 to 6 carbon atoms;

$R^5$ represents:

(i) an alkyl group having from 1 to 10 carbon atoms, (ii) an alkyl group having from 1 to 10 carbon atoms and substituted with 1 to 2 substituents selected from the group consisting of:

a cycloalkyl group having from 3 to 8 carbon atoms, a phenyl group, a naphthyl group, a pyridyl group, and a phenyl group substituted with 1 to 2 substituents selected from the group consisting of a halogen atom and an alkoxy group having from 1 to 6 carbon atoms, (iii) a cycloalkyl group having from 3 to 8 carbon atoms, (iv) an alkenyl group having from 2 to 8 carbon atoms, (v) an alkenyl group having from 2 to 8 carbon atoms and substituted with a phenyl group, (vi) an alkynyl group having from 2 to 8 carbon atoms, (vii) an alkynyl group having from 2 to 8 carbon atoms and substituted with a phenyl group, or (viii) an optionally substituted aryl group.

3. The compound of claim 1, or a pharmaceutically acceptable salt thereof, wherein:

$R^1$ represents an alkyl group having from 1 to 6 carbon atoms and optionally substituted with a substituent(s) selected from the group consisting of:

a hydroxyl group, a halogen atom, an alkoxy group having from 1 to 6 carbon atoms, said alkoxy group optionally substituted with a phenyl group; and a phenyl group, optionally substituted with a substituent(s) selected from the group consisting of a halogen atom and an alkyl group having from 1 to 6 carbon atoms;

$R^{1A}$ represents:

a hydrogen atom; or an alkyl group having from 1 to 6 carbon atoms; and $R^1$ and $R^{1A}$ optionally form, together with a carbon atom to which said $R^1$ and $R^{1A}$ are attached, a cycloalkyl group having from 3 to 6 carbon atoms.

4. The compound of claim 1, or a pharmaceutically acceptable salt thereof, wherein:

$R^1$ is:

an alkyl group having from 1 to 6 carbon atoms and optionally substituted with a halogen atom(s), or a benzyl group optionally substituted with a substituent(s) selected from the group consisting of a halogen atom and an alkyl group having from 1 to 6 carbon atoms; and $R^{1A}$ is a hydrogen atom.

5. The compound of claim 1, or a pharmaceutically acceptable salt thereof, wherein $R^1$ is a methyl group or an ethyl group, and $R^{1A}$ is a hydrogen atom.

6. The compound of claim 1, or a pharmaceutically acceptable salt thereof, wherein $R^4$ is a hydrogen atom.

7. The compound of claim 1, or a pharmaceutically acceptable salt thereof, wherein $R^2$ is an alkyl group having from 1 to 6 carbon atoms, or a cycloalkyl group having from 3 to 6 carbon atoms.

8. The compound of claim 1, or a pharmaceutically acceptable salt thereof, wherein $R^2$ is an ethyl group or a cyclopropyl group.

9. The compound of claim 1, or a pharmaceutically acceptable salt thereof, wherein $R^5$ is:

(i) an alkyl group having from 1 to 10 carbon atoms, (ii) an alkyl group having from 1 to 10 carbon atoms and substituted with 1 to 2 substituents selected from the group consisting of:

a cycloalkyl group having from 3 to 8 carbon atoms, a pyridyl group, and a phenyl group, a phenoxy group, and a naphthyl group, each optionally substituted with 1 to 2 substituents selected from the group consisting of a halogen atom and an alkoxy group having from 1 to 6 carbon atoms;

(iii) an alkenyl group having from 2 to 8 carbon atoms and, optionally substituted with a phenyl group, or (iv) a phenyl group, a naphthyl group, a thienyl group, a pyrrolyl group, a pyrazolyl group, a pyridyl group, a furanyl group, a benzothienyl group, an isoquinolinyl, an isoxazolyl group, a thiazolyl group, a benzothiadiazolyl group, a benzoxadiazolyl group, a dihydrobenzodioxepinyl group, a dihydrobenzodioxynyl group, a benzodioxolyl group, a dihydrobenzofuranyl group, an indanyl group, an uracil group, a coumaryl group, a chromanyl group, a dihydroindolyl group, a tetrahydronaphthyl group, or a tetrahydroisoquinolinyl group, each optionally substituted with 1 to 5 substituents selected from the group consisting of:

an alkyl group having from 1 to 6 carbon atoms and optionally substituted with a fluorine atom(s), an alkenyl group having from 2 to 8 carbon atoms, a halogen atom, an alkoxy group having from 1 to 6 carbon atoms and optionally substituted with a fluorine atom(s), a pyrazolyl group, an oxazolyl group, an isoxazolyl group, a thiadiazolyl group, and a pyrimidinyl group, each optionally substituted with a substituent(s) selected from Group X consisting of a methyl group, a trifluoromethyl group, a halogen atom, and a methylsulfanyl group, an alkylthio group having from 1 to 6 carbon atoms, an alkylsulfonyl group having from 1 to 6 carbon atoms, a benzenesulfonyl group, a morpholinosulfonyl group, a morpholinocarbonylamino group, an aminosulfonyl group, an alkoxycarbonyl group having from 2 to 10 carbon atoms, a morpholino group optionally substituted with an alkyl group(s) having from 1 to 6 carbon atoms a phenyl group optionally substituted with an alkoxy group(s) having from 1 to 6 carbon atoms, a phenoxy group, a pyridinecarbonyl group, a pyridineoxy group, a cyano group, an alkanoyl group having from 2 to 7 carbon atoms and optionally substituted with a fluorine atom(s), and an alkanoylamino group having from 2 to 7 carbon atoms.

10. The compound of claim 1, or a pharmaceutically acceptable salt thereof, wherein $R^5$ is:

an alkyl group having from 1 to 10 carbon atoms and substituted with a cycloalkyl group having from 3 to 8 carbon atoms, an alkyl group having from 1 to 10 carbon atoms and substituted with a naphthyl group, an alkenyl group having from 2 to 8 carbon atoms and substituted with a phenyl group, a phenyl group or a naphthyl group, each optionally substituted with 1 to 5 substituents selected from the group consisting of:

an alkyl group having from 1 to 6 carbon atoms;

a halogen atom, an alkoxy group having from 1 to 6 carbon atoms;

a trifluoromethoxy group, a difluoromethoxy group, a trifluoromethyl group, an alkenyl group having from 1 to 6 carbon atoms, an alkylsulfonyl group having from 1 to 6 carbon atoms, an alkanoyl group having from 2 to 7 carbon atoms, an alkoxycarbonyl group having from 2 to 7 carbon atoms, and a cyano group, a pyrrolyl group optionally substituted with a substituent(s) selected from the group consisting of an alkyl group having from 1 to 6 carbon atoms and a methoxycarbonyl group;

a furanyl group optionally selected from a substituent(s) selected from the group consisting of an alkyl group having from 1 to 6 carbon atoms, a trifluoromethyl group, and a halogen atom;

a thienyl group optionally substituted with a substituent (s) selected from the group consisting of an alkyl group having from 1 to 6 carbon atoms, a trifluoromethyl group, a thiadiazolyl group, an oxazolyl group, and a halogen atom; or a benzothienyl group, a dihydrobenzodioxepinyl group, a benzodioxolyl group, a dihydrobenzodioxynyl group, a dihydrobenzofuranyl group, a tetrahydronaphthyl group, an indanyl group, a thiadiazolyl group, a benzoxadiazolyl group, or a benzothiadiazolyl group, each optionally substituted with a substituent(s) selected from the group consisting of an alkyl group having from 1 to 6 carbon atoms and a halogen atom.

11. The compound of claim 1, or a pharmaceutically acceptable salt thereof, wherein $R^5$ is:

an alkyl group having from 1 to 6 carbon atoms and substituted with a naphthyl group, an alkenyl group having from 2 to 6 carbon atoms and substituted with a phenyl group;

an unsubstituted phenyl group, a phenyl group substituted with 1 to 5 substituents selected from the group consisting of a methyl group, a methoxy group, and a halogen atom, a phenyl group substituted with 1 to 3 substituents selected from the group consisting of:

an alkyl group having from 1 to 6 carbon atoms, a halogen atom, a methoxy group, a trifluoromethoxy group, a difluoromethoxy group, a trifluoromethyl group, an alkenyl group having from 1 to 6 carbon atoms, a methylsulfonyl group, an acetyl group, a methoxycarbonyl group, and a cyano group, said phenyl group substituted at either 3 or 4 position or both;

a naphthyl group optionally substituted with a substituent(s) selected from the group consisting of:

a halogen atom, an alkyl group having from 1 to 6 carbon atoms, a cyano group, and an alkylsulfonyl group having from 1 to 6 carbon atoms, or a benzothienyl group, a benzoxadiazolyl group, a benzodioxolyl group, a dihydrobenzodioxynyl group, a dihydrobenzofuranyl group, an indanyl group, or a benzothiadiazolyl group, each optionally substituted with a substituent(s) selected from the group consisting of an alkyl group having from 1 to 6 carbon atoms and a halogen atom.

12. The compound of claim 1, or a pharmaceutically acceptable salt thereof, wherein $R^5$ is:

a phenyl group substituted at 3 and 4 positions each with a halogen atom, or a naphthyl group optionally substituted with a substituent(s) selected from the group consisting of a halogen atom, an alkyl group having from 1 to 6 carbon atoms, and a cyano group.

13. The compound of claim 1, or a pharmaceutically acceptable salt thereof, wherein $R^3$ is a phenyl group substituted at 3 position with a substituent (iv) below, said phenyl group further optionally substituted at 4 position with a halogen atom:

(iv) a piperazino group, optionally substituted with an alkanoyl group having from 2 to 7 carbon atoms or an alkyl group having from 1 to 6 carbon atoms and optionally substituted with a substituent(s) selected from the group consisting of:

an amino group substituted with two alkyl groups each having from 1 to 4 carbon atoms, and a morpholino group.

14. A pharmaceutical preparation, comprising the compound of any one of claims 1, 2, 3-12 and 13 or a pharmaceutically acceptable salt thereof.

* * * * *